(12) United States Patent
Tomita et al.

(10) Patent No.: US 9,751,885 B2
(45) Date of Patent: Sep. 5, 2017

(54) CYCLOPROPANAMINE COMPOUND AND USE THEREOF

(71) Applicant: Takeda Pharmaceutical Company Limited, Osaka-shi, Osaka (JP)

(72) Inventors: Naoki Tomita, Tokyo (JP); Daisuke Tomita, Kanagawa (JP); Yusuke Tominari, Kanagawa (JP); Shinichi Imamura, Kanagawa (JP); Shinji Morimoto, Kanagawa (JP); Takuto Kojima, Kanagawa (JP); Masashi Toyofuku, Kanagawa (JP); Yasushi Hattori, Kanagawa (JP); Tomohiro Kaku, Kanagawa (JP); Mitsuhiro Ito, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/435,085

(22) PCT Filed: Oct. 11, 2013

(86) PCT No.: PCT/JP2013/077863
§ 371 (c)(1),
(2) Date: Apr. 10, 2015

(87) PCT Pub. No.: WO2014/058071
PCT Pub. Date: Apr. 17, 2014

(65) Prior Publication Data
US 2015/0266881 A1  Sep. 24, 2015

(30) Foreign Application Priority Data

Oct. 12, 2012 (JP) .................................. 2012-227243
Feb. 7, 2013 (JP) .................................. 2013-022534

(51) Int. Cl.
*C07D 487/04* (2006.01)
*C07C 255/58* (2006.01)
(Continued)

(52) U.S. Cl.
CPC ............ *C07D 487/04* (2013.01); *A61K 45/06* (2013.01); *C07C 237/30* (2013.01); *C07C 237/38* (2013.01); *C07C 237/40* (2013.01); *C07C 255/29* (2013.01); *C07C 255/58* (2013.01); *C07C 255/60* (2013.01); *C07C 317/40* (2013.01); *C07D 207/12* (2013.01); *C07D 207/46* (2013.01); *C07D 211/58* (2013.01); *C07D 213/36* (2013.01); *C07D 213/40* (2013.01); *C07D 223/12* (2013.01); *C07D 231/38* (2013.01); *C07D 231/40* (2013.01); *C07D 241/12* (2013.01);
(Continued)

(58) Field of Classification Search
CPC .. C07D 213/74; C07D 401/12; A61K 31/136; A61K 31/445

USPC .......................................... 514/357; 546/329
See application file for complete search history.

(56) References Cited

U.S. PATENT DOCUMENTS 7,067,507 B2   6/2006  Pulley et al.
9,061,966 B2 *  6/2015  Laria ..................... C07C 211/53
(Continued)

FOREIGN PATENT DOCUMENTS

CN          1882529        12/2006
JP         2012-36124       2/2012
(Continued)

OTHER PUBLICATIONS

Patani et al. "bioisosterism: . . . " Chem. Rev. 96:3147-3176 (1996).*

(Continued)

*Primary Examiner* — Heidi Reese
(74) *Attorney, Agent, or Firm* — Hamre, Schumann, Mueller & Larson, P.C.

(57) ABSTRACT

The present invention provides a compound having a lysine specific demethylase 1 inhibitory action, and useful as a medicament such as a prophylactic or therapeutic agent for schizophrenia, Alzheimer's disease, Parkinson's disease or Huntington's disease, and the like. The present invention relates to a compound represented by the formula (I)

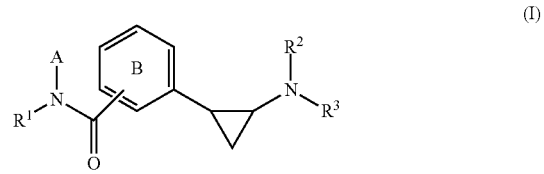

wherein A is a hydrocarbon group optionally having substituent(s), or a heterocyclic group optionally having substituent(s);
B is a benzene ring optionally having further substituent(s);
$R^1$, $R^2$ and $R^3$ are each independently a hydrogen atom, a hydrocarbon group optionally having substituent(s), or a heterocyclic group optionally having substituent(s);
A and $R^1$ are optionally bonded to each other to form, together with the adjacent nitrogen atom, a cyclic group optionally having substituent(s); and
$R^2$ and $R^3$ are optionally bonded to each other to form, together with the adjacent nitrogen atom, a cyclic group optionally having substituent(s), or a salt thereof.

10 Claims, No Drawings

(51) Int. Cl.
| | |
|---|---|
| *C07C 255/60* | (2006.01) |
| *C07D 231/40* | (2006.01) |
| *C07C 317/40* | (2006.01) |
| *C07C 237/30* | (2006.01) |
| *C07C 237/38* | (2006.01) |
| *C07C 237/40* | (2006.01) |
| *C07C 255/29* | (2006.01) |
| *A61K 45/06* | (2006.01) |
| *C07D 309/14* | (2006.01) |
| *C07D 319/18* | (2006.01) |
| *C07D 413/12* | (2006.01) |
| *C07D 241/12* | (2006.01) |
| *C07D 417/12* | (2006.01) |
| *C07D 261/14* | (2006.01) |
| *C07D 207/12* | (2006.01) |
| *C07D 285/135* | (2006.01) |
| *C07D 211/58* | (2006.01) |
| *C07D 295/135* | (2006.01) |
| *C07D 213/40* | (2006.01) |
| *C07D 207/46* | (2006.01) |
| *C07D 213/36* | (2006.01) |
| *C07D 223/12* | (2006.01) |
| *C07D 231/38* | (2006.01) |
| *C07D 241/18* | (2006.01) |
| *C07D 265/36* | (2006.01) |
| *C07D 277/38* | (2006.01) |
| *C07D 333/20* | (2006.01) |
| *C07D 405/12* | (2006.01) |
| *C07D 471/04* | (2006.01) |
| *C07D 513/04* | (2006.01) |

(52) U.S. Cl.
CPC ......... *C07D 241/18* (2013.01); *C07D 261/14* (2013.01); *C07D 265/36* (2013.01); *C07D 277/38* (2013.01); *C07D 285/135* (2013.01); *C07D 295/135* (2013.01); *C07D 309/14* (2013.01); *C07D 319/18* (2013.01); *C07D 333/20* (2013.01); *C07D 405/12* (2013.01); *C07D 413/12* (2013.01); *C07D 417/12* (2013.01); *C07D 471/04* (2013.01); *C07D 513/04* (2013.01); *C07C 2101/02* (2013.01); *C07C 2101/04* (2013.01); *C07C 2101/08* (2013.01); *C07C 2101/14* (2013.01)

(56) References Cited

U.S. PATENT DOCUMENTS

| | | | | |
|---|---|---|---|---|
| 9,278,931 | B2* | 3/2016 | Tomita | .................. C07D 211/98 |
| 2008/0132459 | A1 | 6/2008 | Moradei et al. | |
| 2010/0324147 | A1 | 12/2010 | McCafferty et al. | |
| 2012/0004262 | A1* | 1/2012 | Guibourt | .............. C07C 211/40 514/311 |
| 2014/0228405 | A1 | 8/2014 | Tomita et al. | |

FOREIGN PATENT DOCUMENTS

| | | |
|---|---|---|
| WO | 2005/014552 | 2/2005 |
| WO | 2010/043721 | 4/2010 |
| WO | 2010/084160 | 7/2010 |
| WO | 2010/143582 | 12/2010 |
| WO | 2011/035941 | 3/2011 |
| WO | 2011/042217 | 4/2011 |
| WO | 2011/131576 | 10/2011 |
| WO | 2011/131697 | 10/2011 |
| WO | 2012/013727 | 2/2012 |
| WO | 2012/013728 | 2/2012 |
| WO | 2012/135113 | 10/2012 |
| WO | 2012/156531 | 11/2012 |
| WO | 2012/156537 | 11/2012 |
| WO | 2013/022047 | 2/2013 |
| WO | 2013/057320 | 4/2013 |
| WO | 2013/057322 | 4/2013 |

OTHER PUBLICATIONS

Binda et al., "Biochemical, Structural, and Biological Evaluation of Tranylcypromine Derivatives as Inhibitors of Histone Demethylases LSD1 and LSD2", J. Am. Chem. Soc. 2010, vol. 132, pp. 6827-6833.
Yang et al., "Structurual Basis for the Inhibition of the LSD1 Histone Demethylase by the Antidepressant trans-2-Phenylcyclopropylamine", Biochemistry, vol. 46, 2007, pp. 8058-8065.
Extended European Search Report issued in corresponding European Patent Application No. 12821416.0, Apr. 15, 2015—10 pages.
CAS Registry No. 1026633-98-6, Jun. 8, 2008 ( 1 page).
Huang et al., "Prefrontal Dysfunction in Schizophrenia Involves Mixed-Lineage Leukemia 1-Regulated Histone Methylation at GABAergic Gene Promoters", The Journal of Neuroscience, Oct. 17, 2007, vol. 27, No. 42, pp. 11254-11262.
The Network and Pathway Analysis Subgroup of the Psychiatric Genomics Consortium, "Psychiatric genome-wide association study analyses implicate neuronal, immune and histone pathways", Nature Neuroscience, Feb. 2015, vol. 18, No. 2, pp. 199-209.
Cui et al., "Nuclear Receptors TR2 and TR4 Recruit Multiple Epigenetic Transcriptional Corepressors That Associate Specifically with the Embryonic β-Type Globin Promoters in Differentiated Adult Erythroid Cells", Molecular and Cellular Biology, Aug. 2011, vol. 31, No. 16, p. 3298-3311.
International Search Report, Jul. 14, 2015; PCT/JP2015/061651 (4 pages).
Written Opinion of the International Searching Authority, Jul. 14, 2015; PCT/JP2015/061651 (7 pages).
Gooden et al., "Facile synthesis of substituted trans-2-arylcyclopropylamine inhibitors of the human histone demethylase LSD1 and monoamine oxidases A and B", Bioorganic & Medicinal Chemistry Letters, May 15, 2008, vol. 18, No. 10, pp. 3047-3051.
International Search Report, Nov. 19, 2013; PCT/JP2013/077863 ( 5 pages).
Written Opinion of the International Searching Authority, Nov. 19, 2013; PCT/JP2013/077863 ( 8 pages).
Friedman, et al., "Meeting report on the Alzheimer's Drug Discovery Foundation 1th International Conference on Alzheimer's Drug Discovery", Alzheimer's Research & Therapy 6.2 (2014): 22.
Alzheimer's Disease Fact Sheet, National Institute on Aging, http://www.nia.nih.gov/publication/alzheimers-disease-fact-sheet 2014; p. 1-4; accessed online Aug. 13, 2014.
Damasio, A.R., "Alzheimer's disease and related dementias." Cecil Textbook of Medicine, 2, (1996): 1992-1996.

* cited by examiner

CYCLOPROPANAMINE COMPOUND AND USE THEREOF

TECHNICAL FIELD

The present invention relates to a cyclopropanamine compound having a lysine specific demethylase 1 (sometimes abbreviated as LSD1 in the present specification) inhibitory action and useful as a medicament such as a prophylactic or therapeutic agent for cancer, schizophrenia, Alzheimer's disease, Parkinson's disease or Huntington's disease, and the like.

BACKGROUND OF THE INVENTION

LSD1 is a demethylation enzyme of histone, catalyzes a demethylation reaction of a monomethylated product and a demethylated product of the 4th lysine residue of histone H3 (H3K4me1/2), and forms formaldehyde as a by-product. In addition, LSD1 forms a complex with flavin adenine dinucleotide (FAD) which is a kind of coenzyme, and FAD promotes oxidation of lysine residue by enzymes as a redox mediator.

When a compound having an LSD1 inhibitory activity is allowed to act on a nerve cell, H3K4 methylation, from the methylation modifications of histone H3 (GAD1 gene promoter), is particularly promoted due to the inhibition of LSD1 histone demethylation enzyme activity by the compound (Experimental Example 3 to be mentioned later). There are many reports on the analyses of gene expression level and histone H3K4 methylation state, which conclude that promotion of histone H3K4 methylation at a gene promoter leads to an activated transcription of the gene (Becker et al., Nature 2006, 442: 31-32; Ruthenburg et al., Nature Reviews Molecular Cell Biology 2007, 8: 983-994). Therefore, it is assumed that administration of a compound having an LSD1 inhibitory activity accumulates histone H3K4 methylation in neurons in the brain, which in turn results in the GAD1 mRNA expression in the brain. It is widely known that the induction of GAD1 mRNA expression in the brain is effective for the treatment of central nervous system diseases. For example, intracerebral injection of a GAD1 gene expression vector to Parkinson's disease patients is known to induce GAD1 mRNA expression and improve the symptoms of Parkinson's disease patients (Lewitt et al. Lancet Neurol. 2011, 10: 309-319; Carlson Physiology of Behavior 11th edition 2013). From the above, it is considered that the administration of an LSD1 inhibitor increases the histone H3K4 methylation to increase the GAD1 expression level in the brain, which may be effective for the treatment of central nervous system diseases.

WO 2010/084160 (patent document 1) discloses a compound of the following formula or a pharmaceutically acceptable salt thereof as an LSD1 inhibitor:

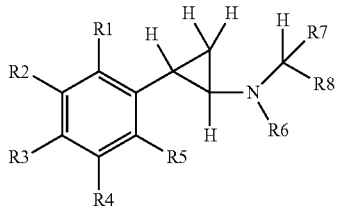

FORMULA I wherein R1-R5 are H, halo and the like; R6 is H or alkyl; R7 is H, alkyl or cycloalkyl; R8 is -L-heterocyclyl or -L-aryl wherein L is —(CH$_2$)$_n$—(CH$_2$)$_n$—, —(CH$_2$)$_n$O(CH$_2$)$_n$— or —(CH$_2$)$_n$S(CH$_2$)$_n$—, and n is 0, 1, 2 or 3.

WO 2010/043721 (patent document 2) discloses a compound of the following formula or a pharmaceutically acceptable salt thereof as an LSD1 inhibitor:

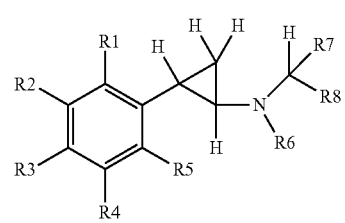

FORMULA I wherein R1-R5 are H, halo and the like; R6 is H or alkyl; R7 is H, alkyl or cycloalkyl; R8 is —C(=O)NRxRy or —C(=O)Rz wherein Rx and Ry are each independently H, alkyl and the like, and Rz is H, alkoxy and the like.

WO 2011/035941 (patent document 3) discloses a compound of the following formula or a pharmaceutically acceptable salt thereof as an LSD1 inhibitor:

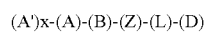

(A')x-(A)-(B)-(Z)-(L)-(D)      I wherein (A') is aryl, arylalkoxy, heterocyclyl and the like; (A) is heteroaryl or aryl; X is 0, 1, 2 or 3; (B) is a cyclopropyl ring; (Z) is —NH—; (L) is —CH$_2$CH$_2$— and the like; (D) is —N(—R1)-R2, —O—R3 or —S—R3 wherein R1 and R2 are each independently H, alkyl and the like; and R3 is H, alkyl and the like.

WO 2011/042217 (patent document 4) discloses a compound of the following formula or a pharmaceutically acceptable salt thereof as an LSD1 inhibitor:

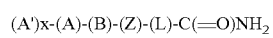

(A')x-(A)-(B)-(Z)-(L)-C(=O)NH$_2$      (I)

wherein (A') is aryl, arylalkoxy, arylalkyl, heterocyclyl and the like; (A) is heteroaryl or aryl; X is 0, 1, 2 or 3; (B) is a cyclopropyl ring; (Z) is —NH—; (L) is —(CH$_2$)$_m$CR1R2- wherein m is 0, 1, 2, 3, 4, 5 or 6; and R1 and R2 are each independently H or C1-6 alkyl.

US2010/0324147 (patent document 5) discloses a compound of the following formula or a salt thereof as an LSD1 inhibitor:

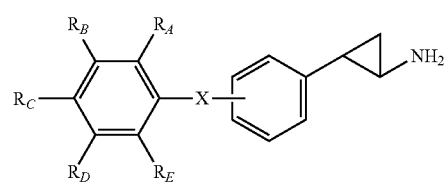

wherein X is a bond, O, S or NH; and R$_A$, R$_B$, R$_C$, R$_D$, and R$_E$ are each independently H, C1-7 alkyl and the like.

WO 2010/143582 (patent document 6) discloses a compound of the following formula or a pharmaceutically acceptable salt thereof as an LSD1 inhibitor:

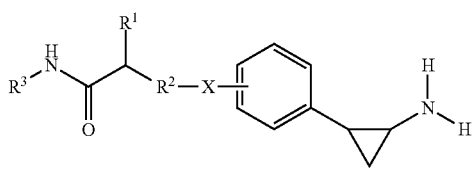

(I)

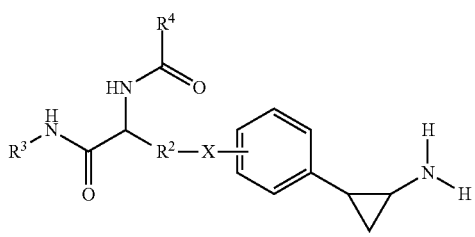

(II)

wherein R¹ is H, an alkyl group optionally having a substituent attached thereto and the like; R² is an alkylene group optionally having a substituent attached thereto; R³ is an alkyl group optionally having a substituent attached thereto, a phenyl group optionally having a substituent attached thereto and the like; R⁴ is an alkyl group optionally having a substituent attached thereto, a phenyl group optionally having a substituent attached thereto and the like; and X is O, NH₂, NHCO, CONH, S or CH₂.

J. Am. Chem. Soc. 2010, 132, 6827-6833 (non-patent document 1) discloses compounds of the following formulas as an LSD 1/2 inhibitor:

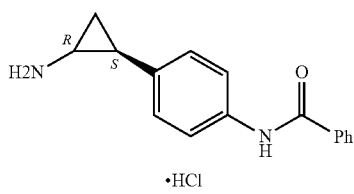

(13b)

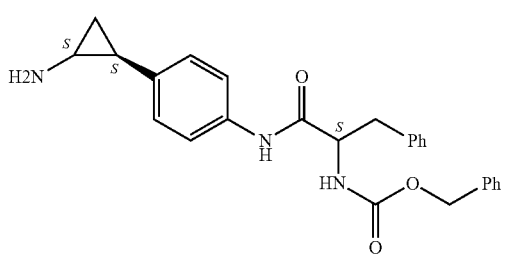

(15e)

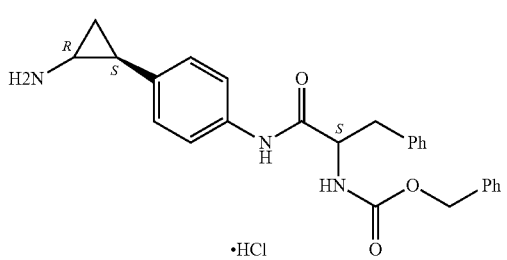

(14e)

WO2012/156531 (patent document 7) discloses use of an LSD1 inhibitor for the prophylaxis or treatment of inflammatory diseases.

WO2012/156537 (patent document 8) discloses use of an LSD1 inhibitor for the prophylaxis or treatment of thrombosis, thrombus formation or circulatory diseases.

WO2012/135113 (patent document 9) discloses, as an LSD1 inhibitor, a compound of the following formula or a pharmaceutically acceptable salt thereof:

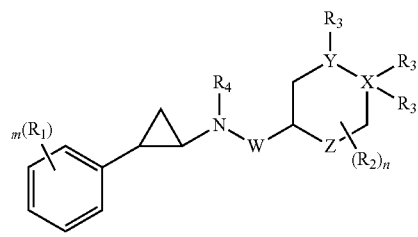

wherein
R₁ is selected from the group consisting of $C_{1-6}$ alkyl, —NSO₂Me, —NSO₂Ph, arylalkoxy, $C_{3-7}$ cycloalkyl, —NC(O)Ra, 1-methyl-1H-pyrazol-4-yl, hydroxy, $C_{1-4}$ alkoxy, halogen, amide, amino, substituted amino and —C(O)ORa;
R₂ is H or COOH;
each R₃ is independently selected from the group consisting of aryl, heteroaryl, H, $C_{1-6}$ alkyl, —SO₂Ra, —NC(O) Ra, —CH₂C(O)ORa, —C(O)ORa, —C(O)Ra, —C(O)NRaRb, substituted amino, amino, urea, amide, sulfonamide, arylalkyl and heteroarylalkyl;
each Ra is independently H, phenyl, phenylmethyl, 3,5-dimethylisoxazol-4-yl, 1,2-dimethyl-1H-imidazol-4-yl, $C_{3-7}$ cycloalkyl, $C_{1-6}$ alkyl, $C_{1-4}$ alkoxy, $C_{1-3}$ alkylamino or —NHPh;
Rb is H or $C_{1-3}$ alkyl, or when attached to the same atom, Ra and Rb together form a 5- or 6-membered heterocycloalkyl ring;
R₄ is $C_{1-4}$ alkyl, acyl, —C(O)CF₃ or H;
W is —(CH₂)₁₋₄ or —CH(Rc) (CH₂)₀₋₃ wherein Rc is CN or $C_{1-4}$ alkyl;
Y is N or C;
X is N or C;
Z is O or (CH₂)$_q$ wherein q is 0-2, and when q is 0, Z is a bond;
m is 0-3, n is 0-3;
provided that when Z is O, Y is N and X is C;
also provided that when X is C, at least one of the R₃ groups attached to X is not H.

The Journal of Neuroscience, Oct. 17, 2007, 27(42): 11254-11262 (non-patent document 2) discloses that a decrease in histone H3K4 methylation and a decrease in Gad1 mRNA expression are observed in the brain of schizophrenia patients.

MOLECULAR AND CELLULAR BIOLOGY, August 2011, 31(16), 3298-3311 (non-patent document 3) discloses that LSD1 contained in a protein complex that regulates transcription of beta globin may be involved in the suppression of transcription of beta globin. Activation of beta globin transcription is known to be useful for the treatment of sickle cell anaemia and beta thalassemia, from which it is assumed that LSD1 inhibition disinhibits beta globin transcription, and provides a treatment effect.

DOCUMENT LIST

Patent Documents patent document 1: WO 2010/084160
patent document 2: WO 2010/043721 patent document 3: WO 2011/035941
patent document 4: WO 2011/042217
patent document 5: US 2010/0324147
patent document 6: WO 2010/143582
patent document 7: WO 2012/156531
patent document 8: WO 2012/156537
patent document 9: WO 2012/135113

Non-Patent Documents non-patent document 1: J. Am. Chem. Soc. 2010, 132, 6827-6833
non-patent document 2: The Journal of Neuroscience, Oct. 17, 2007, 27(42): 11254-11262
non-patent document 3: MOLECULAR AND CELLULAR BIOLOGY, August 2011, 31(16), 3298-3311

SUMMARY OF THE INVENTION

Problems to be Solved by the Invention

An object of the present invention is to provide a cyclopropanamine compound having a superior LSD1 inhibitory action and high LSD1 selectivity, and useful as a medicament such as a prophylactic or therapeutic agent for cancer, schizophrenia, Alzheimer's disease, Parkinson's disease or Huntington's disease.

Means of Solving the Problems

The present inventors have conducted intensive studies in an attempt to solve the aforementioned problems and found that a compound represented by the following formula (I) has a superior LSD1 inhibitory action and high LSD1 selectivity, which resulted in the completion of the present invention.

Accordingly, the present invention relates to the following.

[1] A compound represented by the formula

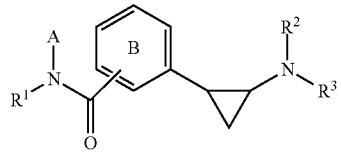

(I)

wherein A is a hydrocarbon group optionally having substituent(s), or a heterocyclic group optionally having substituent(s);
B is a benzene ring optionally having further substituent(s);
$R^1$, $R^2$ and $R^3$ are each independently a hydrogen atom, a hydrocarbon group optionally having substituent(s), or a heterocyclic group optionally having substituent(s);
A and $R^1$ are optionally bonded to each other to form, together with the adjacent nitrogen atom, a cyclic group optionally having substituent(s); and
$R^2$ and $R^3$ are optionally bonded to each other to form, together with the adjacent nitrogen atom, a cyclic group optionally having substituent (s),
or a salt thereof (hereinafter sometimes to be abbreviated as compound (I)).

[2] The compound of [1], wherein A is
(1) a $C_{1-6}$ alkyl group optionally having substituent (s),
(2) a $C_{3-8}$ cycloalkyl group optionally having substituent (s),
(3) a $C_{6-14}$ aryl group optionally having substituent (s),
(4) a $C_{1-6}$ alkyl group having a $C_{6-14}$ aryl group optionally having substituent (s), the $C_{1-5}$ alkyl group optionally further having substituent (s),
(5) a $C_{1-6}$ alkyl group having a heterocyclic group optionally having substituent (s), or
(6) a heterocyclic group optionally having substituent (s),
or a salt thereof.

[3] The compound of [1] or [2], wherein B is a benzene ring optionally further having 1 to 3 substituents selected from
(1) a halogen atom,
(2) a $C_{1-6}$ alkyl group, and
(3) a $C_{1-6}$ alkoxy group,
or a salt thereof.

[3A] The compound of [1], [2] or [3] or a salt thereof, which is a compound represented by the formula

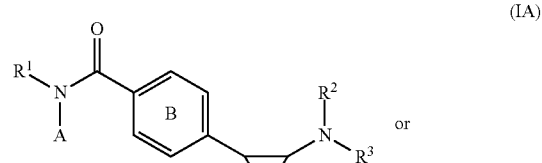

(IA)

or

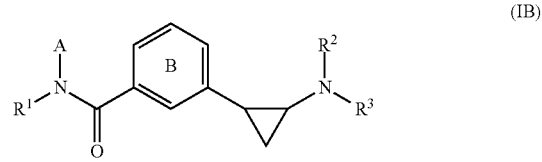

(IB)

or a salt thereof.

[3B] The compound of [1], [2] or [3] or a salt thereof, which is a compound represented by the formula

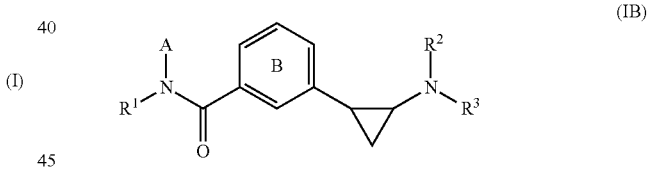

(IB)

or a salt thereof.

[4] The compound of [1], [2] or [3], wherein $R^1$ is a hydrogen atom or a $C_{1-6}$ alkyl group optionally having substituent(s),
or a salt thereof.

[4A] The compound of [1] or [3], wherein A and $R^1$ are optionally bonded to each other to form, together with the adjacent nitrogen atom, a 4- to 10-membered heterocyclic group containing one nitrogen atom as a ring-constituting atom besides carbon atom, and optionally further containing one hetero atom selected from a nitrogen atom, a sulfur atom and an oxygen atom, the heterocyclic group optionally having 1 to 3 substituents selected from a hydroxy group and a cyano group,
or a salt thereof.

[5] The compound of [1], [2], [3], [4] or [4A], wherein $R^2$ is a hydrogen atom, a $C_{1-6}$ alkyl group optionally having substituent(s), or a $C_{3-8}$ cycloalkyl group,
or a salt thereof.

[6] The compound of [1], [2], [3], [4], [4A] or [5], wherein $R^3$ is (1) a hydrogen atom,
(2) a $C_{1-6}$ alkyl group optionally having substituent(s),
(3) a $C_{3-8}$ cycloalkyl group optionally having substituent(s),
(4) a $C_{1-6}$ alkyl group having a $C_{6-14}$ aryl group optionally having substituent(s), the $C_{1-6}$ alkyl group optionally further having substituent(s),
(5) a $C_{3-8}$ cycloalkyl-$C_{1-6}$ alkyl group optionally having substituent(s),
(6) a $C_{1-6}$ alkyl group having a heterocyclic group optionally having substituent(s), or
(7) a heterocyclic group optionally having substituent(s),
or a salt thereof.

[6A] The compound of [1], [2], [3], [4] or [4A], wherein $R^2$ and $R^3$ are optionally bonded to each other to form, together with the adjacent nitrogen atom, a 4- to 10-membered heterocyclic group containing one nitrogen atom as a ring-constituting atom besides carbon atom, and optionally further containing one hetero atom selected from a nitrogen atom, a sulfur atom and an oxygen atom, the heterocyclic group optionally having 1 to 3 oxo groups,
or a salt thereof.

[6B] The compound of [1] or [3A], wherein A is
(1) a $C_{1-6}$ alkyl group optionally having a $C_{3-8}$ cycloalkyl group optionally having 1 to 5 halogen atoms,
(2) a $C_{3-8}$ cycloalkyl group optionally having 1 to 5 halogen atoms,
(3) a $C_{6-14}$ aryl group optionally having 1 to 3 substituents selected from
    (a) a halogen atom,
    (b) a $C_{1-6}$ alkyl group optionally having 1 to 5 substituents selected from a halogen atom, a $C_{6-14}$ aryl group and a 5- to 7-membered nonaromatic heterocyclic group optionally having 1 to 3 oxo groups,
    (c) a $C_{1-6}$ alkylsulfonyl group,
    (d) a $C_{1-6}$ alkylsulfonylamino group,
    (e) a $C_{1-6}$ alkoxy group optionally having 1 to 5 halogen atoms,
    (f) a $C_{6-14}$ aryl group,
    (g) a 4- to 10-membered heterocyclic group containing, as a ring-constituting atom besides carbon atom, 1 to 4 hetero atoms selected from a nitrogen atom, a sulfur atom and an oxygen atom, the heterocyclic group optionally having 1 to 3 substituents selected from a $C_{1-6}$ alkyl group, a $C_{1-6}$ alkoxy group and an oxo group, and
    (h) a pyrimidinylsulfanyl group optionally having 1 to 3 $C_{1-6}$ alkyl groups,
(4) a $C_{1-6}$ alkyl group having a $C_{6-14}$ aryl group optionally having 1 to 3 substituents selected from
    (a) a cyano group,
    (b) a 4- to 10-membered heterocyclic group containing, as a ring-constituting atom besides carbon atom, 1 to 4 hetero atoms selected from a nitrogen atom, a sulfur atom and an oxygen atom, the heterocyclic group optionally having 1 to 3 oxo groups,
    (c) a $C_{6-14}$ aryloxy group, and
    (d) a heterocyclyloxy group, said heterocyclyl moiety is a 4- to 10-membered heterocyclic group containing, as a ring-constituting atom besides carbon atom, 1 to 4 hetero atoms selected from a nitrogen atom, a sulfur atom and an oxygen atom, the $C_{1-6}$ alkyl group optionally further having a morpholinyl group,
(5) a $C_{1-6}$ alkyl group containing a 4- to 10-membered heterocyclic group containing, as a ring-constituting atom besides carbon atom, 1 to 4 hetero atoms selected from a nitrogen atom, a sulfur atom and an oxygen atom, the heterocyclic group optionally having 1 to 3 substituents selected from $C_{1-6}$ alkyl groups optionally having 1 to 5 halogen atoms, or
(6) a 4- to 14-membered heterocyclic group containing, as a ring-constituting atom besides carbon atom, 1 to 4 hetero atoms selected from a nitrogen atom, a sulfur atom and an oxygen atom, the heterocyclic group optionally having 1 to 3 substituents selected from
    (a) a $C_{1-6}$ alkyl group optionally having 1 to 5 substituents selected from a halogen atom, a $C_{3-8}$ cycloalkyl group, and a $C_{6-14}$ aryl group optionally having 1 to 5 halogen atoms,
    (b) a $C_{6-14}$ aryl group optionally having 1 to 5 halogen atoms,
    (c) an oxo group,
    (d) a hydroxy group,
    (e) a $C_{6-14}$ aryloxy group optionally having 1 to 5 halogen atoms, and
    (f) a 5- to 7-membered heterocyclic group;

B is a benzene ring optionally further having 1 to 3 substituents selected from
(1) a halogen atom,
(2) a $C_{1-6}$ alkyl group, and
(3) a $C_{1-6}$ alkoxy group;

$R^1$ is a hydrogen atom or a $C_{1-6}$ alkyl group optionally having 1 to 3 cyano groups;

$R^2$ is a hydrogen atom, a $C_{1-6}$ alkyl group, or a $C_{3-8}$ cycloalkyl group;

$R^3$ is
(1) a hydrogen atom,
(2) a $C_{1-6}$ alkyl group optionally having 1 to 3 cyano groups,
(3) a $C_{3-8}$ cycloalkyl group optionally having 1 to 3 halogen atoms,
(4) a $C_{1-6}$ alkyl group having a $C_{6-14}$ aryl group optionally having 1 to 3 substituents selected from
    (a) a halogen atom,
    (b) a cyano group,
    (c) a $C_{1-6}$ alkyl group optionally having 1 to 5 halogen atoms,
    (d) a $C_{1-6}$ alkoxy group,
    (e) a mono- or di-$C_{1-5}$ alkylamino group,
    (f) a 4- to 10-membered heterocyclic group containing, as a ring-constituting atom besides carbon atom, 1 to 4 hetero atoms selected from a nitrogen atom, a sulfur atom and an oxygen atom, and
    (g) a heterocyclylgroup, said heterocyclyl moiety is a 4- to 10-membered heterocyclic group containing, as a ring-constituting atom besides carbon atom, 1 to 4 hetero atoms selected from a nitrogen atom, a sulfur atom and an oxygen atom,
(5) a $C_{3-8}$ cycloalkyl-$C_{1-6}$ alkyl group optionally having 1 to 3 cyano groups,
(6) a $C_{1-6}$ alkyl group having 1 to 3 substituents selected from 4- to 10-membered heterocyclic groups containing, as a ring-constituting atom besides carbon atom, 1 to 4 hetero atoms selected from a nitrogen atom, a sulfur atom and an oxygen atom, each of the heterocyclic groups optionally has 1 to 3 substituents selected from a $C_{1-6}$ alkyl group and an oxo group, or
(7) a 4- to 10-membered heterocyclic group containing, as a ring-constituting atom besides carbon atom, 1 to 4 hetero atoms selected from a nitrogen atom, a sulfur atom and an oxygen atom, the heterocyclic group optionally having 1 to 3 substituents selected from
    (a) a $C_{1-6}$ alkyl group optionally having 1 to 5 halogen atoms,
    (b) a $C_{3-8}$ cycloalkyl group, (c) a $C_{6-14}$ aryl-$C_{1-5}$ alkyl group,
(d) a $C_{1-6}$ alkyl-carbonyl group, and
(e) an oxo group;

A and $R^1$ are optionally bonded to each other to form, together with the adjacent nitrogen atom, a 4- to 10-membered heterocyclic group containing one nitrogen atom as a ring-constituting atom besides carbon atom, and optionally further containing one hetero atom selected from a nitrogen atom, a sulfur atom and an oxygen atom, the heterocyclic group optionally having 1 to 3 substituents selected from a hydroxy group and a cyano group; and $R^2$ and $R^3$ are optionally bonded to each other to form, together with the adjacent nitrogen atom, a 4- to 10-membered heterocyclic group containing one nitrogen atom as a ring-constituting atom besides carbon atom, and optionally further containing one hetero atom selected from a nitrogen atom, a sulfur atom and an oxygen atom, the heterocyclic group optionally having 1 to 3 oxo groups, or a salt thereof.

[7] The compound of [1] or [3A], wherein A is
(1) a $C_{1-6}$ alkyl group optionally having a $C_{3-8}$ cycloalkyl group optionally having 1 to 5 halogen atoms,
(2) a $C_{3-8}$ cycloalkyl group optionally having 1 to 5 halogen atoms,
(3) a phenyl group optionally having 1 to 3 substituents selected from
  (a) a halogen atom,
  (b) a $C_{1-6}$ alkyl group optionally having 1 to 3 substituents selected from a halogen atom, a phenyl group, and a thiomorpholinyl group optionally having 1 to 3 oxo groups,
  (c) a $C_{1-6}$ alkylsulfonyl group,
  (d) a $C_{1-6}$ alkoxy group optionally having 1 to 5 halogen atoms,
  (e) a phenyl group,
  (f) a pyrimidinyl group, a piperazinyl group, a pyrrolidinyl group, a morpholinyl group, a dihydroimidazo[2,1-b][1,3]thiazolyl group, a thiazolyl group or a 6,7,8,9-tetrahydro-5H-[1,2,4]triazolo[4,3-a]azepinyl group, each optionally having 1 to 3 substituents selected from a $C_{1-6}$ alkyl group, a $C_{1-6}$ alkoxy group and an oxo group, and
  (g) a pyrimidinylsulfanyl group optionally having 1 to 3 $C_{1-6}$ alkyl groups,
(4) a methyl group or an ethyl group, each having a phenyl group optionally having 1 to 3 substituents selected from
  (a) a cyano group,
  (b) a morpholinyl group or a pyrrolidinyl group, each optionally having 1 to 3 oxo groups,
  (c) a phenoxy group, and
  (d) a pyrazinyloxy group, the methyl group or the ethyl group each optionally further having a morpholinyl group,
(5) a $C_{1-6}$ alkyl group having a heterocyclic group optionally having 1 to 3 substituents selected from $C_{1-6}$ alkyl groups optionally having 1 to 5 halogen atoms, said heterocyclic group is selected from a pyridinyl group, a dihydro-1,4-benzodioxinyl group and a pyrazinyl group, or (6) a pyrrolidinyl group, a piperidinyl group, a pyridinyl group, a pyrazolyl group, an isoxazolyl group, an oxazolyl group, an indazolyl group, a thiazolyl group, an isothiazolyl group, a thiadiazolyl group, a tetrahydropyranyl group, a tetrahydrothiopyranyl group, an azepanyl group, a benzothiazolyl group, a dihydrobenzothiazolyl group, a dihydrobenzoxazinyl group, a benzimidazolyl group, a quinoxalinyl group, a 7,8,9,10-tetrahydro-6H-azepino[1, 2-a]benzimidazolyl group, or a tetrahydroquinazolinyl group, each optionally having 1 to 3 substituents selected from
  (a) a $C_{1-6}$ alkyl group optionally having 1 to 5 substituents selected from a halogen atom, a $C_{3-8}$ cycloalkyl group, and a phenyl group optionally having 1 to 5 halogen atoms,
  (b) a phenyl group optionally having 1 to 5 halogen atoms,
  (c) an oxo group,
  (d) a hydroxy group,
  (e) a phenoxy group optionally having 1 to 5 halogen atoms, and
  (f) a morpholinyl group or a thienyl group;

B is a benzene ring optionally further having 1 to 3 substituents selected from
(1) a halogen atom,
(2) a $C_{1-6}$ alkyl group, and
(3) a $C_{1-6}$ alkoxy group;

$R^1$ is a hydrogen atom or a $C_{1-6}$ alkyl group optionally having 1 to 3 cyano groups;

$R^2$ is a hydrogen atom or a $C_{3-8}$ cycloalkyl group;

$R^3$ is
(1) a hydrogen atom,
(2) a $C_{1-6}$ alkyl group,
(3) a $C_{3-8}$ cycloalkyl group optionally having 1 to 3 halogen atoms,
(4) a methyl group having a phenyl group optionally having 1 to 3 substituents selected from
  (a) a halogen atom,
  (b) a cyano group,
  (c) a $C_{1-6}$ alkyl group optionally having 1 to 5 halogen atoms,
  (d) a $C_{1-6}$ alkoxy group,
  (e) a di-$C_{1-6}$ alkylamino group, and
  (f) a pyrazinyl group,
(5) a $C_{3-8}$ cycloalkyl-$C_{1-6}$ alkyl group,
(6) a $C_{1-6}$ alkyl group having 1 to 3 substituents selected from a 3,4-dihydro-2H-1,4-benzoxazinyl group, a thienyl group and a tetrahydropyranyl group, each optionally having 1 to 3 substituents selected from a $C_{1-6}$ alkyl group and an oxo group, or
(7) a piperidinyl group, a tetrahydropyranyl group, or a tetrahydrothiopyranyl group, each optionally having 1 to 3 substituents selected from
  (a) a $C_{1-6}$ alkyl group optionally having 1 to 5 halogen atoms,
  (b) a $C_{3-8}$ cycloalkyl group,
  (c) a $C_{1-6}$ alkyl-carbonyl group, and
  (d) an oxo group; and A and $R^1$ are optionally bonded to each other to form, together with the adjacent nitrogen atom, a pyrrolidinyl group, a piperidinyl group, a 5,7-dihydro-6H-pyrrolo[3,4-b]pyridinyl group, or a 1,3-dihydro-2H-isoindolyl group, or a salt thereof.

[7A] The compound of [1] or [3A], wherein A is
(1) a $C_{1-6}$ alkyl group optionally having a cyclobutyl group optionally having 1 to 5 halogen atoms,
(2) a cyclobutyl group, a cyclopentyl group or a cyclohexyl group, each optionally having 1 to 5 halogen atoms,
(3) a phenyl group optionally having 1 to 3 substituents selected from
  (a) a halogen atom,
  (b) a $C_{1-6}$ alkyl group optionally having 1 to 3 substituents selected from a halogen atom, a phenyl group, and a thiomorpholinyl group optionally having 1 to 3 oxo groups, (c) a $C_{1-6}$ alkylsulfonyl group,
(d) a $C_{1-6}$ alkoxy group optionally having 1 to 5 halogen atoms,
(e) a phenyl group,
(f) a pyrimidinyl group, a piperazinyl group, a pyrrolidinyl group, a morpholinyl group, a dihydroimidazo[2,1-b][1,3]thiazolyl group, a thiazolyl group or a 6,7,8,9-tetrahydro-5H-[1,2,4]triazolo[4,3-a]azepinyl group, each optionally having 1 to 3 substituents selected from a $C_{1-6}$ alkyl group, a $C_{1-6}$ alkoxy group and an oxo group, and
(g) a dimethylpyrimidinylsulfanyl group,
(4) a methyl group or an ethyl group, each having a phenyl group optionally having 1 to 3 substituents selected from
(a) a cyano group,
(b) a morpholinyl group or a pyrrolidinyl group, each optionally having 1 to 3 oxo groups,
(c) a phenoxy group, and
(d) a pyrazinyloxy group, the methyl group or the ethyl group each optionally further having a morpholinyl group,
(5) a $C_{1-6}$ alkyl group having a heterocyclic group optionally having 1 to 3 substituents selected from $C_{1-6}$ alkyl groups optionally having 1 to 5 halogen atoms, said heterocyclic group is selected from a pyridinyl group, a dihydro-1,4-benzodioxinyl group and a pyrazinyl group, or
(6) a pyrrolidinyl group, a piperidinyl group, a pyridinyl group, a pyrazolyl group, an isoxazolyl group, an oxazolyl group, an indazolyl group, a thiazolyl group, an isothiazolyl group, a thiadiazolyl group, a tetrahydropyranyl group, a tetrahydrothiopyranyl group, an azepanyl group, a benzothiazolyl group, a dihydrobenzothiazolyl group, a dihydrobenzoxazinyl group, a benzimidazolyl group, a quinoxalinyl group, a 7,8,9,10-tetrahydro-6H-azepino[1,2-a]benzimidazolyl group, or a tetrahydroquinazolinyl group, each optionally having 1 to 3 substituents selected from
(a) a $C_{1-6}$ alkyl group optionally having 1 to 5 substituents selected from a halogen atom, a cyclopropyl group, and a phenyl group optionally having 1 to 5 halogen atoms,
(b) a phenyl group optionally having 1 to 5 halogen atoms,
(c) an oxo group,
(d) a hydroxy group,
(e) a phenoxy group optionally having 1 to 5 halogen atoms, and
(f) a morpholinyl group or a thienyl group;
B is a benzene ring optionally further having 1 to 3 substituents selected from
(1) a halogen atom,
(2) a $C_{1-6}$ alkyl group, and
(3) a $C_{1-6}$ alkoxy group;
$R^1$ is a hydrogen atom or a $C_{1-6}$ alkyl group optionally having 1 to 3 cyano groups;
$R^2$ is a hydrogen atom or a cyclobutyl group;
$R^3$ is
(1) a hydrogen atom,
(2) a $C_{1-6}$ alkyl group,
(3) a cyclohexyl group, a cyclopentyl group, or a cyclobutyl group, each optionally having 1 to 3 halogen atoms,
(4) a methyl group having a phenyl group optionally having 1 to 3 substituents selected from
(a) a halogen atom,
(b) a cyano group,
(c) a $C_{1-6}$ alkyl group optionally having 1 to 5 halogen atoms,
(d) a $C_{1-6}$ alkoxy group,
(e) a di-$C_{1-6}$ alkylamino group, and
(f) a pyrazinyl group,
(5) a cyclopropylmethyl group,
(6) a $C_{1-6}$ alkyl group having one substituent selected from a 3,4-dihydro-2H-1,4-benzoxazinyl group, a thienyl group and a tetrahydropyranyl group, each optionally having 1 to 3 substituents selected from a $C_{1-6}$ alkyl group and an oxo group, or
(7) a piperidinyl group, a tetrahydropyranyl group, or a tetrahydrothiopyranyl group, each optionally having 1 to 3 substituents selected from
(a) a $C_{1-6}$ alkyl group optionally having 1 to 5 halogen atoms,
(b) a cyclopropyl group,
(c) an acetyl group, and
(d) an oxo group; and
A and $R^1$ are optionally bonded to each other to form, together with the adjacent nitrogen atom, a pyrrolidinyl group, a piperidinyl group, a 5,7-dihydro-6H-pyrrolo[3,4-b]pyridinyl group, or a 1,3-dihydro-2H-isoindolyl group,
or a salt thereof.
[7B] The compound of [1] or [3A], wherein A is
(1) a $C_{1-6}$ alkyl group optionally having a cyclobutyl group optionally having 1 or 2 halogens atoms,
(2) a cyclobutyl group, a cyclopentyl group, or a cyclohexyl group, each optionally having 1 or 2 halogen atoms,
(3) a phenyl group optionally having one substituent selected from
(a) a halogen atom,
(b) a $C_{1-6}$ alkyl group optionally having 1 to 3 substituents selected from a halogen atom, a phenyl group, and a thiomorpholinyl group optionally having 1 or 2 oxo groups,
(c) a $C_{1-6}$ alkylsulfonyl group,
(d) a $C_{1-6}$ alkoxy group optionally having 1 to 3 halogen atoms,
(e) a phenyl group,
(f) a pyrimidinyl group, a piperazinyl group, a pyrrolidinyl group, a morpholinyl group, a dihydroimidazo[2,1-b][1,3]thiazolyl group, a thiazolyl group or a 6,7,8,9-tetrahydro-5H-[1,2,4]triazolo[4,3-a]azepinyl group, each optionally having 1 or 2 substituents selected from a $C_{1-6}$ alkyl group, a $C_{1-6}$ alkoxy group and an oxo group, and
(g) a dimethylpyrimidinylsulfanyl group,
(4) a methyl group or an ethyl group, each having a phenyl group optionally having one substituent selected from
(a) a cyano group,
(b) a morpholinyl group or a pyrrolidinyl group, each optionally having one oxo group,
(c) a phenoxy group, and
(d) a pyrazinyloxy group, the methyl group or the ethyl group each optionally further having a morpholinyl group,
(5) a $C_{1-6}$ alkyl group having a heterocyclic group optionally having one substituent selected from $C_{1-6}$ alkyl groups optionally having 1 to 3 halogen atoms,
said heterocyclic group is selected from a pyridinyl group, a dihydro-1,4-benzodioxinyl group and a pyrazinyl group, or
(6) a pyrrolidinyl group, a piperidinyl group, a pyridinyl group, a pyrazolyl group, an isoxazolyl group, an oxazolyl group, an indazolyl group, a thiazolyl group, an isothiazolyl group, a thiadiazolyl group, a tetrahydropyranyl group, a tetrahydrothiopyranyl group, an azepanyl group, a benzothiazolyl group, a dihydrobenzothiazolyl group, a dihydrobenzoxazinyl group, a benzimidazolyl group, a quinoxalinyl group, a 7,8,9,10-tetrahydro-6H-azepino[1,2-a]benzimidazolyl group, or a tetrahydroquinazolinyl group, each optionally having 1 or 2 substituents selected from
  (a) a $C_{1-6}$ alkyl group optionally having 1 to 3 substituents selected from a halogen atom, a cyclopropyl group, and a phenyl group optionally having one halogen atom,
  (b) a phenyl group optionally having one halogen atom,
  (c) an oxo group,
  (d) a hydroxy group,
  (e) a phenoxy group optionally having one halogen atom, and
  (f) a morpholinyl group or a thienyl group;
B is a benzene ring optionally further having one substituent selected from
(1) a halogen atom,
(2) a $C_{1-6}$ alkyl group, and
(3) a $C_{1-6}$ alkoxy group;
$R^1$ is a hydrogen atom or a $C_{1-6}$ alkyl group optionally having one cyano group;
$R^2$ is a hydrogen atom or a cyclobutyl group;
$R^3$ is
(1) a hydrogen atom,
(2) a $C_{1-6}$ alkyl group,
(3) a cyclohexyl group, a cyclopentyl group, or a cyclobutyl group, each optionally having 1 or 2 halogen atoms,
(4) a methyl group having a phenyl group optionally having 1 or 2 substituents selected from
  (a) a halogen atom,
  (b) a cyano group,
  (c) a $C_{1-6}$ alkyl group optionally having 1 to 3 halogen atoms,
  (d) a $C_{1-6}$ alkoxy group,
  (e) a di-$C_{1-6}$ alkylamino group, and
  (f) a pyrazinyl group,
(5) a cyclopropylmethyl group,
(6) a $C_{1-6}$ alkyl group having one substituent selected from a 3,4-dihydro-2H-1,4-benzoxazinyl group, a thienyl group and a tetrahydropyranyl group, each optionally having one substituent selected from a $C_{1-6}$ alkyl group and an oxo group, or
(7) a piperidinyl group, a tetrahydropyranyl group, or a tetrahydrothiopyranyl group, each optionally having 1 or 2 substituents selected from
  (a) a $C_{1-6}$ alkyl group optionally having 1 to 3 halogen atoms,
  (b) a cyclopropyl group,
  (c) an acetyl group, and
  (d) an oxo group; and
A and $R^1$ are optionally bonded to each other to form, together with the adjacent nitrogen atom, a pyrrolidinyl group, a piperidinyl group, a 5,7-dihydro-6H-pyrrolo[3,4-b]pyridinyl group, or a 1,3-dihydro-2H-isoindolyl group,
or a salt thereof.
[8] The compound of [1] or [3A], wherein A is
(1) a $C_{3-8}$ cycloalkyl group optionally having 1 to 5 halogen atoms,
(2) a phenyl group optionally having one pyrimidinyl group, or
(3) a piperidinyl group, a pyrazolyl group, an isoxazolyl group, a thiazolyl group, a thiadiazolyl group, or a tetrahydropyranyl group, each optionally having 1 to 3 substituents selected from $C_{1-6}$ alkyl groups optionally having 1 to 5 substituents selected from a halogen atom and a $C_{3-8}$ cycloalkyl group; B is a benzene ring optionally further having one substituent selected from
(1) a halogen atom,
(2) a $C_{1-6}$ alkyl group, and
(3) a $C_{1-6}$ alkoxy group;
$R^1$ is a hydrogen atom;
$R^2$ is a hydrogen atom; and
$R^3$ is
(1) a $C_{3-8}$ cycloalkyl group optionally having 1 to 3 halogen atoms,
(2) a $C_{3-8}$ cycloalkyl-$C_{1-6}$ alkyl group,
(3) a $C_{1-6}$ alkyl group having one tetrahydropyranyl group, or
(4) a piperidinyl group or a tetrahydropyranyl group, each optionally having one substituent selected from
  (a) a $C_{1-6}$ alkyl group optionally having 1 to 5 halogen atoms, and
  (b) a $C_{3-8}$ cycloalkyl group,
or a salt thereof.
[8A] The compound of [1] or [3A], wherein A is
(1) a cyclobutyl group, a cyclopentyl group, or a cyclohexyl group, each optionally having 1 to 5 halogen atoms,
(2) a phenyl group optionally having one pyrimidinyl group, or
(3) a piperidinyl group, a pyrazolyl group, an isoxazolyl group, a thiazolyl group, a thiadiazolyl group, or a tetrahydropyranyl group, each optionally having 1 to 3 substituents selected from C1-6 alkyl groups optionally having 1 to 5 substituents selected from a halogen atom and a cyclopropyl group;
B is
a benzene ring optionally further having one substituent selected from
(1) a halogen atom,
(2) a $C_{1-6}$ alkyl group, and
(3) a $C_{1-6}$ alkoxy group;
$R^1$ is a hydrogen atom;
$R^2$ is a hydrogen atom; and
$R^3$ is
(1) a cyclohexyl group, a cyclopentyl group, or a cyclobutyl group, each optionally having 1 to 3 halogen atoms,
(2) a cyclopropylmethyl group,
(3) a $C_{1-6}$ alkyl group having one tetrahydropyranyl group, or
(4) a piperidinyl group or a tetrahydropyranyl group, each optionally having one substituent selected from
  (a) a $C_{1-6}$ alkyl group optionally having 1 to 5 halogen atoms, and
  (b) a cyclopropyl group,
or a salt thereof.
[8B] The compound of [1] or [3A], wherein A is
(1) a cyclobutyl group, a cyclopentyl group, or a cyclohexyl group, each optionally having 1 or 2 halogen atoms,
(2) a phenyl group optionally having one pyrimidinyl group, or
(3) a piperidinyl group, a pyrazolyl group, an isoxazolyl group, a thiazolyl group, a thiadiazolyl group, or a tetrahydropyranyl group, each optionally having 1 or 2 substituents selected from $C_{1-6}$ alkyl groups optionally having 1 to 3 substituents selected from a halogen atom and a cyclopropyl group;
B is
a benzene ring optionally further having one substituent selected from
(1) a halogen atom,
(2) a $C_{1-6}$ alkyl group, and
(3) a $C_{1-6}$ alkoxy group;

R¹ is a hydrogen atom;
R² is a hydrogen atom; and
R³ is
(1) a cyclohexyl group, a cyclopentyl group, or a cyclobutyl group, each optionally having 1 or 2 halogen atoms,
(2) a cyclopropylmethyl group,
(3) a $C_{1-6}$ alkyl group having one tetrahydropyranyl group, or
(4) a piperidinyl group or a tetrahydropyranyl group, each optionally having one substituent selected from
  (a) a $C_{1-6}$ alkyl group optionally having 1 to 3 halogen atoms, and
  (b) a cyclopropyl group,
or a salt thereof.

[9] The compound of [1] or [3A], wherein A is
(1) a $C_{3-8}$ cycloalkyl group optionally having 1 to 5 halogen atoms, or
(2) a piperidinyl group, an isoxazolyl group, a thiadiazhlyl group, or a tetrahydropyranyl group, each optionally having one $C_{1-6}$ alkyl group optionally having 1 to 5 halogen atoms;
B is a benzene ring;
R¹ is a hydrogen atom;
R² is a hydrogen atom; and
R³ is
(1) a $C_{3-8}$ cycloalkyl group optionally having 1 to 3 halogen atoms,
(2) a $C_{3-8}$ cycloalkyl-$C_{1-6}$ alkyl group, or
(3) a piperidinyl group or a tetrahydropyranyl group, each optionally having one $C_{3-8}$ cycloalkyl group,
or a salt thereof.

[9A] The compound of [1] or [3A], wherein A is
(1) a cyclopentyl group or a cyclohexyl group, each optionally having 1 to 5 halogen atoms, or
(2) a piperidinyl group, an isoxazolyl group, a thiadiazolyl group, or a tetrahydropyranyl group, each optionally having one $C_{1-6}$ alkyl group optionally having 1 to 5 halogen atoms;
B is a benzene ring;
R¹ is a hydrogen atom;
R² is a hydrogen atom; and
R³ is
(1) a cyclohexyl group or a cyclobutyl group, each optionally having 1 to 3 halogen atoms,
(2) a cyclopropylmethyl group, or
(3) a piperidinyl group or a tetrahydropyranyl group, each optionally having one cyclopropyl group,
or a salt thereof.

[9B] The compound of [1] or [3A], wherein A is
(1) a cyclopentyl group or a cyclohexyl group, each optionally having 1 or 2 halogen atoms, or
(2) a piperidinyl group, an isoxazolyl group, a thiadiazolyl group, or a tetrahydropyranyl group, each optionally having one C1-6 alkyl group optionally having 1 to 3 halogen atoms;
B is a benzene ring;
R¹ is a hydrogen atom;
R² is a hydrogen atom; and
R³ is
(1) a cyclohexyl group or a cyclobutyl group, each optionally having 1 or 2 halogen atoms,
(2) a cyclopropylmethyl group, or
(3) a piperidinyl group or a tetrahydropyranyl group, each optionally having one cyclopropyl group,
or a salt thereof.

[9C] The compound of [1], [2], [3], [4], [4A], [5], [6], [6A], [6B], [7], [7A], [7B], [8], [8A], [8B], [9], [9A] or [9B], wherein the compound represented by the formula (I) is a compound represented by the formula (IB)

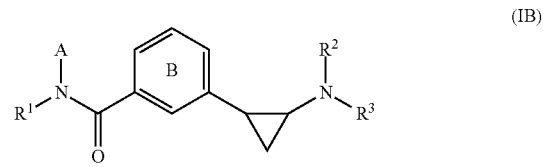

or a salt thereof.

[10] 3-(trans-2-((cyclopropylmethyl)amino)cyclopropyl)-N-(5-methyl-1,2-oxazol-3-yl)benzamide or a salt thereof.
[10A] (+)-3-(trans-2-((cyclopropylmethyl)amino)cyclopropyl)-N-(5-methyl-1,2-oxazol-3-yl)benzamide or a salt thereof.
[10B] (−)-3-(trans-2-((cyclopropylmethyl)amino)cyclopropyl)-N-(5-methyl-1,2-oxazol-3-yl)benzamide or a salt thereof.
[11] 3-(trans-2-((1-cyclopropylpiperidin-4-yl)amino)cyclopropyl)-N-(5-methyl-1,3,4-thiadiazol-2-yl)benzamide or a salt thereof.
[11A] (+)-3-(trans-2-((1-cyclopropylpiperidin-4-yl)amino)cyclopropyl)-N-(5-methyl-1,3,4-thiadiazol-2-yl)benzamide or a salt thereof.
[11B] (−)-3-(trans-2-((1-cyclopropylpiperidin-4-yl)amino)cyclopropyl)-N-(5-methyl-1,3,4-thiadiazol-2-yl)benzamide or a salt thereof.
[12] 3-(trans-2-(cyclobutylamino)cyclopropyl)-N-(tetrahydro-2H-pyran-4-yl)benzamide or a salt thereof.
[12A] (+)-3-(trans-2-(cyclobutylamino)cyclopropyl)-N-(tetrahydro-2H-pyran-4-yl)benzamide or a salt thereof.
[12B] (−)-3-(trans-2-(cyclobutylamino)cyclopropyl)-N-(tetrahydro-2H-pyran-4-yl)benzamide or a salt thereof.
[12a] 3-(trans-2-((cyclopropylmethyl)amino)cyclopropyl)-N-(5-methyl-1,2-oxazol-3-yl)benzamide or a salt thereof (optical isomer, retention time short, see Example 105 for the measurement conditions of retention time).
[12b] 3-(trans-2-((cyclopropylmethyl)amino)cyclopropyl)-N-(5-methyl-1,2-oxazol-3-yl)benzamide or a salt thereof (optical isomer, retention time long, see Example 105 for the measurement conditions of retention time).
[12c] 3-(trans-2-((1-cyclopropylpiperidin-4-yl)amino)cyclopropyl)-N-(5-methyl-1,3,4-thiadiazol-2-yl)benzamide or a salt thereof (optical isomer, retention time long, see Example 257 for the measurement conditions of retention time).
[12d] 3-(trans-2-((1-cyclopropylpiperidin-4-yl)amino)cyclopropyl)-N-(5-methyl-1,3,4-thiadiazol-2-yl)benzamide or a salt thereof (optical isomer, retention time short, see Example 257 for the measurement conditions of retention time).
[12e] 3-(trans-2-(cyclobutylamino)cyclopropyl)-N-(tetrahydro-2H-pyran-4-yl)benzamide or a salt thereof (optical isomer, retention time long, see Example 261 for the measurement conditions of retention time).
[12f] 3-(trans-2-(cyclobutylamino)cyclopropyl)-N-(tetrahydro-2H-pyran-4-yl)benzamide or a salt thereof (optical isomer, retention time short, see Example 261 for the measurement conditions of retention time).
[12C] N-cyclopentyl-3-(trans-2-(tetrahydro-2H-pyran-4-ylamino)cyclopropyl)benzamide or a salt thereof.
[12D] (+)-N-cyclopentyl-3-(trans-2-(tetrahydro-2H-pyran-4-ylamino)cyclopropyl)benzamide or a salt thereof.

[12E] (−)-N-cyclopentyl-3-(trans-2-(tetrahydro-2H-pyran-4-ylamino)cyclopropyl)benzamide or a salt thereof.

[12F] 3-(trans-2-((cyclopropylmethyl)amino)cyclopropyl)-N-(5-methyl-1,3,4-thiadiazol-2-yl)benzamide or a salt thereof.

[12G] (+)-3-(trans-2-((cyclopropylmethyl)amino)cyclopropyl)-N-(5-methyl-1,3,4-thiadiazol-2-yl)benzamide or a salt thereof.

[12H] (−)-3-(trans-2-((cyclopropylmethyl)amino)cyclopropyl)-N-(5-methyl-1,3,4-thiadiazol-2-yl)benzamide or a salt thereof.

[12I] N-(4,4-difluorocyclohexyl)-3-(trans-2-(tetrahydro-2H-pyran-4-ylamino)cyclopropyl)benzamide or a salt thereof

[12J] (+)-N-(4,4-difluorocyclohexyl)-3-(trans-2-(tetrahydro-2H-pyran-4-ylamino)cyclopropyl)benzamide or a salt thereof.

[12K] (−)-N-(4,4-difluorocyclohexyl)-3-(trans-2-(tetrahydro-2H-pyran-4-ylamino)cyclopropyl)benzamide or a salt thereof.

[12L] 3-(trans-2-(cyclobutylamino)cyclopropyl)-N-(5-methyl-1,3,4-thiadiazol-2-yl)benzamide or a salt thereof.

[12M] (+)-3-(trans-2-(cyclobutylamino)cyclopropyl)-N-(5-methyl-1,3,4-thiadiazol-2-yl)benzamide or a salt thereof.

[12N] (−)-3-(trans-2-(cyclobutylamino)cyclopropyl)-N-(5-methyl-1,3,4-thiadiazol-2-yl)benzamide or a salt thereof.

[12O] 3-(trans-2-((cyclopropylmethyl)amino)cyclopropyl)-N-(4,4-difluorocyclohexyl)benzamide or a salt thereof.

[12P] (+)-3-(trans-2-((cyclopropylmethyl)amino)cyclopropyl)-N-(4,4-difluorocyclohexyl)benzamide or a salt thereof.

[12Q] (−)-3-(trans-2-((cyclopropylmethyl)amino)cyclopropyl)-N-(4,4-difluorocyclohexyl)benzamide or a salt thereof.

[12R] 3-(trans-2-((4,4-difluorocyclohexyl)amino)cyclopropyl)-N-(tetrahydro-2H-pyran-4-yl)benzamide or a salt thereof.

[12S] (+)-3-(trans-2-((4,4-difluorocyclohexyl)amino)cyclopropyl)-N-(tetrahydro-2H-pyran-4-yl)benzamide or a salt thereof.

[12T] (−)-3-(trans-2-((4,4-difluorocyclohexyl)amino)cyclopropyl)-N-(tetrahydro-2H-pyran-4-yl)benzamide or a salt thereof.

[12U] 3-(trans-2-((cyclopropylmethyl)amino)cyclopropyl)-N-(1-(2,2,2-trifluoroethyl)piperidin-4-yl)benzamide or a salt thereof.

[12V] (+)-3-(trans-2-((cyclopropylmethyl)amino)cyclopropyl)-N-(1-(2,2,2-trifluoroethyl)piperidin-4-yl)benzamide or a salt thereof.

[12W] (−)-3-(trans-2-((cyclopropylmethyl)amino)cyclopropyl)-N-(1-(2,2,2-trifluoroethyl)piperidin-4-yl)benzamide or a salt thereof.

[12X] 3-(trans-2-((cyclopropylmethyl)amino)cyclopropyl)-N-(5-methyl-1,2-oxazol-3-yl)benzamide, (+)-3-(trans-2-((cyclopropylmethyl)amino)cyclopropyl)-N-(5-methyl-1,2-oxazol-3-yl)benzamide, (−)-3-(trans-2-((cyclopropylmethyl)amino)cyclopropyl)-N-(5-methyl-1,2-oxazol-3-yl)benzamide, 3-(trans-2-((1-cyclopropylpiperidin-4-yl)amino)cyclopropyl)-N-(5-methyl-1,3,4-thiadiazol-2-yl)benzamide, (+)-3-(trans-2-((1-cyclopropylpiperidin-4-yl)amino)cyclopropyl)-N-(5-methyl-1,3,4-thiadiazol-2-yl)benzamide, (−)-3-(trans-2-((1-cyclopropylpiperidin-4-yl)amino)cyclopropyl)-N-(5-2-mthyl-1,3,4-thiadiazol-2-yl)benzamide, 3-(trans-2-(cyclobutylamino)cyclopropyl)-N-(tetrahydro-2H-pyran-4-yl)benzamide, (+)-3-(trans-2-(cyclobutylamino)cyclopropyl)-N-(tetrahydro-2H-pyran-4-yl)benzamide, or (−)-3-(trans-2-(cyclobutylamino)cyclopropyl)-N-(tetrahydro-2H-pyran-4-yl)benzamide or a salt thereof.

[12Y] 3-(trans-2-((cyclopropylmethyl)amino)cyclopropyl)-N-(5-methyl-1,2-oxazol-3-yl)benzamide, (+)-3-(trans-2-((cyclopropylmethyl)amino)cyclopropyl)-N-(5-methyl-1,2-oxazol-3-yl)benzamide, (−)-3-(trans-2-((cyclopropylmethyl)amino)cyclopropyl)-N-(5-methyl-1,2-oxazol-3-yl)benzamide, 3-(trans-2-((1-cyclopropylpiperidin-4-yl)amino)cyclopropyl)-N-(5-methyl-1,3,4-thiadiazol-2-yl)benzamide, (+)-3-(trans-2-((1-cyclopropylpiperidin-4-yl)amino)cyclopropyl)-N-(5-methyl-1,3,4-thiadiazol-2-yl)benzamide, (−)-3-(trans-2-((1-cyclopropylpiperldin-4-yl)amino)cyclopropyl)-N-(5-methyl-1,3,4-thiadiazol-2-yl)benzamide, 3-(trans-2-(cyclobutylamino)cyclopropyl)-N-(tetrahydro-2H-pyran-4-yl)benzamide, (+)-3-(trans-2-(cyclobutylamino)cyclopropyl)-N-(tetrahydro-2H-pyran-4-yl)benzamide, (−)-3-(trans-2-(cyclobutylamino)cyclopropyl)-N-(tetrahydro-2H-pyran-4-yl)benzamide, N-cyclopentyl-3-(trans-2-(tetrahydro-2H-pyran-4-ylamino)cyclopropyl)benzamide, (+)-N-cyclopentyl-3-(trans-2-(tetrahydro-2H-pyran-4-ylamino)cyclopropyl)benzamide, (−)-N-cyclopentyl-3-(trans-2-(tetrahydro-2H-pyran-4-ylamino)cyclopropyl)benzamide, 3-(trans-2-((cyclopropylmethyl)amino)cyclopropyl)-N-(5-methyl-1,3,4-thiadiazol-2-yl)benzamide, (+)-3-(trans-2-((cyclopropylmethyl)amino)cyclopropyl)-N-(5-methyl-1,3,4-thiadiazol-2-yl)benzamide, (−)-3-(trans-2-((cyclopropylmethyl)amino)cyclopropyl)-N-(5-methyl-1,3,4-thiadiazol-2-yl)benzamide, N-(4,4-difluorocyclohexyl)-3-(trans-2-(tetrahydro-2H-pyran-4-ylamino) cyclopropyl)benzamide, (+)-N-(4,4-difluorocyclohexyl)-3-(trans-2-(tetrahydro-2H-pyran-4-ylamino)cyclopropyl)benzamide, (−)-N-(4,4-difluorocyclohexyl)-3-(trans-2-(tetrahydro-2H-pyran-4-ylamino)cyclopropyl)benzamide, 3-(trans-2-(cyclobutylamino)cyclopropyl)-N-(5-methyl-1,3,4-thiadiazol-2-yl)benzamide, (+)-3-(trans-2-(cyclobutylamino)cyclopropyl)-N-(5-methyl-1,3,4-thiadiazol-2-yl)benzamide, (−)-3-(trans-2-(cyclobutylamino)cyclopropyl)-N-(5-methyl-1,3,4-thiadiazol-2-yl)benzamide, 3-(trans-2-((cyclopropylmethyl)amino)cyclopropyl)-N-(4,4-difluorocyclohexyl)benzamide, (+)-3-(trans-2-((cyclopropylmethyl)amino)cyclopropyl)-N-(4,4-difluorocyclohexyl) benzamide, (−)-3-(trans-2-((cyclopropylmethyl)amino)cyclopropyl)-N-(4,4-difluorocyclohexyl)benzamide, 3-(trans-2-((4,4-difluorocyclohexyl)amino)cyclopropyl)-N-(tetrahydro-2H-pyran-4-yl)benzamide, (+)-3-(trans-2-((4,4-difluorocyclohexyl)amino)cyclopropyl)-N-(tetrahydro-2H-pyran-4-yl)benzamide, (−)-3-(trans-2-((4,4-difluorocyclohexyl)amino)cyclopropyl)-N-(tetrahydro-2H-pyran-4-yl)benzamide, 3-(trans-2-((cyclopropylmethyl)amino)cyclopropyl)-N-(1-(2,2,2-trifluoroethyl)piperidin-4-yl)benzamide, (+)-3-(trans-2-((cyclopropylmethyl)amino)cyclopropyl)-N-(1-(2,2,2-trifluoroethyl)piperidin-4-yl)benzamide, or (−)-3-(trans-2-((cyclopropylmethyl)amino)cyclopropyl)-N-(1-(2,2,2-trifluoroethyl)piperidin-4-yl)benzamide or a salt thereof.

[13] A medicament containing the compound of [1] or a salt thereof.

[14] The medicament of [13], which is an LSD1 inhibitor.

[15] The medicament of [13], which is a prophylactic or therapeutic agent for schizophrenia, Alzheimer's disease, Parkinson's disease or Huntington's disease.

[16] The compound of [1] or a salt thereof for use in the prophylaxis or treatment of schizophrenia, Alzheimer's disease, Parkinson's disease or Huntington's disease.

[17] A method of inhibiting LSD1 in a mammal, comprising administering an effective amount of the compound of [1] or a salt thereof to the mammal.
[18] A method for the prophylaxis or treatment of schizophrenia,
Alzheimer's disease, Parkinson's disease or Huntington's disease in a mammal, comprising administering an effective amount of the compound of [1] or a salt thereof to the mammal.
[19] Use of the compound of [1] or a salt thereof for producing a prophylactic or therapeutic agent for schizophrenia, Alzheimer's disease, Parkinson's disease or Huntington's disease.

The definition of each symbol used in the present specification is described in detail in the following.

Examples of the "halogen atom" include fluorine, chlorine, bromine and iodine.

Examples of the "hydrocarbon group" in the "hydrocarbon group optionally having substituent(s)" for A, $R^1$, $R^2$ or $R^3$ include (1) a $C_{1-20}$ alkyl group (e.g., methyl, ethyl, propyl, isopropyl, butyl, isobutyl, sec-butyl, tert-butyl, pentyl, hexyl, heptyl, octyl, nonyl, decyl, undecyl, dodecyl), preferably, a $C_{1-6}$ alkyl group (e.g., methyl, ethyl, propyl, isopropyl, butyl, isobutyl, sec-butyl, tert-butyl, pentyl, hexyl),
(2) a $C_{2-6}$ alkenyl group (e.g., vinyl, allyl, isopropenyl, 2-butenyl),
(3) a $C_{2-6}$ alkynyl group (e.g., ethynyl, propargyl, 2-butynyl),
(4) a $C_{3-8}$ cycloalkyl group (e.g., cyclopropyl, cyclobutyl, cyclopentyl, cyclohexyl, cycloheptyl, cyclooctyl),
(5) a $C_{3-8}$ cycloalkenyl group (e.g., cyclopropenyl, cyclobutenyl, cyclopentenyl, cyclohexenyl, cycloheptenyl, cyclooctenyl),
(6) a $C_{3-8}$ cycloalkyl-$C_{1-6}$ alkyl group (e.g., cyclopropylmethyl, cyclobutylmethyl, cyclopentylmethyl, cyclohexylmethyl, cycloheptylmethyl, cyclooctylmethyl),
(7) a $C_{6-14}$ aryl group (e.g., phenyl, 1-naphthyl, 2-naphthyl, 2-anthryl, biphenylyl),
(8) a $C_{6-14}$ aryl-$C_{1-6}$ alkyl group (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl), and
(9) a $C_{10-14}$ cyclic hydrocarbon group (e.g., tetrahydronaphthyl).

Examples of the substituent of the aforementioned "hydrocarbon group optionally having substituent(s)" include substituents selected from the following substituent group A and the like.
[Substituent Group A]
(1) a halogen atom (e.g., fluorine, chlorine, bromine, iodine),
(2) a nitro group,
(3) a cyano group,
(4) a hydroxy group,
(5) an optionally halogenated $C_{1-6}$ alkoxy group,
(6) an optionally halogenated $C_{1-6}$ alkylthio group,
(7) a $C_{6-14}$ aryloxy group (e.g., phenoxy, naphthoxy),
(8) a $C_{6-14}$ aryl-$C_{1-6}$ alkyloxy group (e.g., benzyloxy),
(9) a heterocyclyloxy group,
(10) an amino group,
(11) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(12) a heterocyclic group optionally having substituent(s),
(13) a formyl group,
(14) a carboxy group,
(15) a carbamoyl group,
(16) a thiocarbamoyl group,
(17) an optionally halogenated $C_{1-6}$ alkyl-carbonyl group,
(18) a $C_{1-6}$ alkoxy-carbonyl group,
(19) a $C_{6-14}$ aryl-carbonyl group (e.g., benzoyl, 1-naphthoyl, 2-naphthoyl),
(20) a heterocyclylcarbonyl group optionally having substituent(s),
(21) a $C_{6-14}$ aryloxy-carbonyl group (e.g., phenyloxycarbonyl, 1-naphthyloxycarbonyl, 2-naphthyloxycarbonyl),
(22) a $C_{6-14}$ aryl-$C_{1-6}$ alkyloxy-carbonyl group (e.g., benzyloxycarbonyl, phenethyloxycarbonyl),
(23) a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl),
(24) a carbamoyl-$C_{1-6}$ alkyl-carbamoyl group (e.g., carbamoylmethylcarbamoyl, carbamoylethylcarbamoyl),
(25) a $C_{6-14}$ aryl-carbamoyl group (e.g., phenylcarbamoyl),
(26) a heterocyclylcarbamoyl group optionally having substituent(s),
(27) an optionally halogenated $C_{1-6}$ alkylsulfonyl group,
(28) a $C_{6-14}$ arylsulfonyl group (e.g., phenylsulfonyl, 1-naphthylsulfonyl, 2-naphthylsulfonyl),
(29) a formylamino group,
(30) an optionally halogenated $C_{1-6}$ alkyl-carbonylamino group,
(31) a $C_{6-14}$ aryl-$C_{1-6}$ alkylamino group (e.g., benzylamino),
(32) a $C_{6-14}$ aryl-carbonylamino group (e.g., phenylcarbonylamino, naphthylcarbonylamino),
(33) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(34) a $C_{6-14}$ aryl-$C_{1-6}$ alkyloxy-carbonylamino group (e.g., benzyloxycarbonylamino),
(35) a $C_{1-6}$ alkylsulfonylamino group (e.g., methylsulfonylamino, ethylsulfonylamino),
(36) a $C_{1-6}$ alkyl-carbonyloxy group (e.g., acetoxy, propanoyloxy),
(37) a $C_{6-14}$ aryl-carbonyloxy group (e.g., benzoyloxy, 1-naphthoyloxy, 2-naphthoyloxy),
(38) a $C_{1-6}$ alkoxy-carbonyloxy group (e.g., methoxycarbonyloxy, ethoxycarbonyloxy, propoxycarbonyloxy, butoxycarbonyloxy),
(39) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(40) a $C_{6-14}$ aryl-carbamoyloxy group (e.g., phenylcarbamoyloxy, naphthylcarbamoyloxy),
(41) a 5- or 6-membered heterocyclylcarbonyloxy group (e.g., nicotinoyloxy),
(42) a sulfamoyl group,
(43) an oxo group,
(44) a $C_{3-8}$ cycloalkyl group, and
(45) a $C_{6-14}$ aryl group (e.g., phenyl) optionally having 1 to 3 substituents selected from a halogen atom and a $C_{1-6}$ alkyl group.

The number of the substituents is, for example, 1 to 5, preferably 1 to 3. When the number of the substituents is two or more, the respective substituents may be the same or different.

When the "hydrocarbon group" in the aforementioned "hydrocarbon group optionally having substituent(s)" is a $C_{3-8}$ cycloalkyl group, a $C_{3-8}$ cycloalkenyl group, a $C_{3-8}$ cycloalkyl-$C_{1-6}$ alkyl group, a $C_{6-14}$ aryl group or a $C_{6-14}$ aryl-$C_{1-6}$ alkyl group, examples of the substituent of the "hydrocarbon group optionally having substituent(s)" include (1) the aforementioned substituent group A,
(2) a $C_{1-3}$ alkylenedioxy group (e.g., methylenedioxy, ethylenedioxy),
(3) a $C_{1-6}$ alkyl group optionally having 1 to 5 halogen atoms, and
(4) a $C_{1-6}$ alkyl group optionally having a 5-membered heterocyclic group (e.g., imidazolyl, triazolyl) containing 2 or 3 nitrogen atoms as a ring-constituting atom besides carbon atom, and the like.

The number of, the substituents is, for example, 1 to 5, preferably 1 to 3. When the number of the substituents is two or more, the respective substituents may be the same or different.

Examples of the aforementioned "optionally halogenated $C_{1-6}$ alkoxy group" include a $C_{1-6}$ alkoxy group (e.g., methoxy, ethoxy, propoxy, butoxy, pentyloxy) optionally having 1 to 5, preferably 1 to 3, halogen atoms (e.g., fluorine, chlorine, bromine, iodine) and the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

Examples of the aforementioned "optionally halogenated $C_{1-6}$ alkylthio group" include a $C_{1-6}$ alkylthio group (e.g., methylthio, ethylthio, propylthio, isopropylthio, butylthio, sec-butylthio, tert-butylthio) optionally having 1 to 5, preferably 1 to 3, halogen atoms (e.g., fluorine, chlorine, bromine, iodine) and the like. Specific examples include methylthio, difluoromethylthio, trifluoromethylthio, ethylthio, propylthio, isopropylthio, butylthio, 4,4,4-trifluorobutylthio, pentylthio, hexylthio and the like.

Examples of the "heterocyclic group" in the aforementioned "heterocyclic group optionally having substituent(s)" and the heterocyclyl moiety of the aforementioned "heterocyclyloxy group" include a 4- to 10-membered (preferably, 4- to 7-membered, more preferably, 5- to 7-membered) heterocyclic group containing, as a ring-constituting atom besides carbon atom, 1 to 4 hetero atoms selected from a nitrogen atom, a sulfur atom and an oxygen atom and the like. Preferable examples of the 4- to 10-membered heterocyclic group include 4- to 10-membered (preferably, 4- to 7-membered, more preferably, 5- to 7-membered) nonaromatic heterocyclic groups such as pyrrolidinyl (e.g., 1-, 2- or 3-pyrrolidinyl); imidazolidinyl (e.g., 1-, 2-, 4- or 5-imidazolidinyl); imidazolinyl (e.g., 2- or 4-imidazolinyl); pyrazolidinyl (e.g., 2-, 3- or 4-pyrazolidinyl); piperidyl (e.g., 1-, 2-, 3- or 4-piperidyl); piperazinyl (e.g., 1- or 2-piperazinyl); tetrahydropyranyl; morpholinyl; thiomorpholinyl; dihydropyrazolyl; 2,3-dihydro-1,4-benzodioxinyl; 3,4-dihydro-2H-1,4-benzoxazinyl and the like; and 5- to 10-membered (preferably, 5- to 7-membered) aromatic heterocyclic groups such as thienyl (e.g., 2- or 3-thienyl); furyl (e.g., 2- or 3-furyl); pyrrolyl (e.g., 1-, 2- or 3-pyrrolyl); imidazolyl (e.g., 1-, 2- or 4-imidazolyl); thiazolyl (e.g., 2-, 4- or 5-thiazolyl); oxazolyl (e.g., 2-, 4- or 5-oxazolyl); isothiazolyl (e.g., 3-isothiazolyl); isoxazolyl (e.g., 3-isoxazolyl); pyridyl (e.g., 2-, 3- or 4-pyridyl); pyrazolyl (e.g., 1-, 3- or 4-pyrazolyl); pyrazinyl (e.g., 2-pyrazinyl); pyrimidinyl (e.g., 2-, 4- or 5-pyrimidinyl); pyridazinyl (e.g., 3- or 4-pyridazinyl); oxadiazolyl (e.g., 1,2,4-oxadiazol-5-yl; 1,2,4-oxadiazol-3-yl); thiadiazolyl (e.g., 1,2,4-thiadiazol-5-yl; 1,2,4-thiadiazol-3-yl); triazolyl (e.g., 1,2,3-triazol-1-yl; 1,2,3-triazol-4-yl; 1,2,4-triazol-1-yl; 1,2,4-triazol-3-yl); tetrazolyl (e.g., 1- or 5-tetrazolyl); pyranyl (e.g., 2-, 3- or 4-pyranyl); benzoxazolyl and the like.

Examples of the aforementioned "optionally halogenated $C_{1-6}$ alkyl-carbonyl group" include a $C_{1-6}$ alkyl-carbonyl group (e.g., acetyl, propanoyl, butanoyl, pentanoyl, hexanoyl) optionally having 1 to 5, preferably 1 to 3, halogen atoms (e.g., fluorine, chlorine, bromine, iodine) and the like. Specific examples include acetyl, monochloroacetyl, trifluoroacetyl, trichloroacetyl, propanoyl, butanoyl, pentanoyl, hexanoyl and the like.

Examples of the aforementioned "$C_{1-6}$ alkoxy-carbonyl group" include methoxycarbonyl, ethoxycarbonyl, propoxycarbonyl, tert-butoxycarbonyl and the like.

Examples of the "heterocyclylcarbonyl group" of the aforementioned "heterocyclylcarbonyl group optionally having substituent(s)" include nicotinoyl, isonicotinoyl, thenoyl (e.g., 2-thenoyl, 3-thenoyl), furoyl (e.g., 2-furoyl, 3-furoyl), morpholinocarbonyl, piperidinocarbonyl, pyrrolidin-1-ylcarbonyl, indolylcarbonyl and the like.

Examples of the "heterocyclylcarbamoyl group" of the aforementioned "heterocyclylcarbamoyl group optionally having substituent(s)" include morpholinocarbamoyl, piperidinocarbamoyl, pyridylcarbamoyl (e.g., 2-pyridylcarbamoyl, 3-pyridylcarbamoyl, 4-pyridylcarbamoyl), thienylcarbamoyl (e.g., 2-thienylcarbamoyl, 3-thienylcarbamoyl), indolylcarbamoyl and the like.

Examples of the aforementioned "optionally halogenated $C_{1-6}$ alkylsulfonyl group" include a $C_{1-6}$ alkylsulfonyl group (e.g., methylsulfonyl, ethylsulfonyl, propylsulfonyl, isopropylsulfonyl, butylsulfonyl, sec-butylsulfonyl, tert-butylsulfonyl) optionally having 1 to 5, preferably 1 to 3, halogen atoms (e.g., fluorine, chlorine, bromine, iodine) and the like. Specific examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl and the like.

Examples of the aforementioned "optionally halogenated $C_{1-6}$ alkyl-carbonylamino group" include a $C_{1-6}$ alkyl-carbonylamino group (e.g., acetylamino, propanoylamino, butanoylamino) optionally having 1 to 5, preferably 1 to 3, halogen atoms (e.g., fluorine, chlorine, bromine, iodine) and the like. Specific examples include acetylamino, trifluoroacetylamino, propanoylamino, butanoylamino and the like.

Examples of the substituent of the aforementioned "heterocyclic group optionally having substituent(s)", "heterocyclylcarbonyl group optionally having substituent(s)" and "heterocyclylcarbamoyl group optionally having substituent(s)" include a substituent selected from the following substituent group B and the like.

[Substituent group B]
(1) a halogen atom (e.g., fluorine, chlorine, bromine, iodine),
(2) a $C_{1-3}$ alkylenedioxy group (e.g., methylenedioxy, ethylenedioxy),
(3) a nitro group,
(4) a cyano group,
(5) an oxo group,
(6) an optionally halogenated $C_{1-6}$ alkyl group,
(7) a carbamoyl-$C_{1-6}$ alkyl group (e.g., carbamoylmethyl),
(8) an optionally halogenated $C_{3-8}$ cycloalkyl group,
(9) a $C_{6-14}$ aryl group (e.g., phenyl, naphthyl),
(10) a $C_{6-14}$ aryl-$C_{1-6}$ alkyl group (e.g., benzyl, phenethyl),
(11) an optionally halogenated $C_{1-6}$ alkoxy group,
(12) an optionally halogenated $C_{1-6}$ alkylthio group,
(13) a hydroxy group,
(14) an amino group,
(15) a mono- or di-$C_{1-6}$ alkylamino group (e.g., methylamino, ethylamino, propylamino, isopropylamino, butylamino, dimethylamino, diethylamine, dipropylamino, dibutylamino, N-ethyl-N-methylamino),
(16) a formyl group,
(17) a carboxy group,
(18) a carbamoyl group,
(19) a thiocarbamoyl group,
(20) an optionally halogenated $C_{1-6}$ alkyl-carbonyl group,
(21) a $C_{1-6}$ alkoxy-carbonyl group,
(22) a $C_{2-6}$ alkenyloxy-carbonyl group (e.g., allyloxycarbonyl),
(23) a $C_{6-14}$ aryl-carbonyl group (e.g., benzoyl, 1-naphthoyl, 2-naphthoyl),
(24) a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl),
(25) a mono- or di-$C_{6-14}$ aryl-$C_{1-6}$ alkyl-carbamoyl group (e.g., benzylcarbamoyl),
(26) an optionally halogenated $C_{1-6}$ alkylsulfonyl group,
(27) a $C_{6-14}$ arylsulfonyl group (e.g., phenylsulfonyl),
(28) a sulfamoyl group,
(29) a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl),
(30) a formylamino group,
(31) an optionally halogenated $C_{1-6}$ alkyl-carbonylamino group,
(32) a $C_{1-6}$ alkoxy-carbonylamino group (e.g., methoxycarbonylamino, ethoxycarbonylamino, propoxycarbonylamino, butoxycarbonylamino),
(33) a $C_{1-6}$ alkylsulfonylamino group (e.g., methylsulfonylamino, ethylsulfonylamino),
(34) a $C_{1-6}$ alkyl-carbonyloxy group (e.g., acetoxy, propanoyloxy),
(35) a $C_{1-6}$ alkoxy-carbonyloxy group (e.g., methoxycarbonyloxy, ethoxycarbonyloxy, propoxycarbonyloxy, butoxycarbonyloxy),
(36) a 5- or 6-membered aromatic heterocyclic group (e.g., tetrazolyl, thiazolyl, oxazolyl, furyl, thienyl, pyrazolyl, pyrrolyl, imidazolyl, pyridyl, pyrimidinyl, thiadiazolyl) optionally having 1 to 3 $C_{1-6}$ alkyl groups,
(37) a dihydropyrazolyl group optionally having 1 to 3 substituents selected from a $C_{1-6}$ alkyl group and an oxo group,
(38) a piperazinyl group having 1 to 3 $C_{1-6}$ alkyl groups,
(39) a piperidyl group optionally having one oxo group,
(40) a $C_{1-6}$ alkyl group optionally having 1 to 3 substituents selected from a halogen atom, a phenyl group, an imidazolyl group and a triazolyl group,
(41) a $C_{1-6}$ alkoxy group optionally having 1 to 3 substituents selected from a halogen atom and a phenyl group,
(42) a phenyl group optionally having 1 to 3 substituents selected from a halogen atom and a $C_{1-6}$ alkyl group,
(43) a phenoxy group,
(44) a phenylcarbonylamino group,
(45) a benzyloxycarbonylamino group, and
(46) a benzylamino group.

The number of the substituents is, for example, 1 to 3. When the number of the substituents is two or more, the respective substituents may be the same or different.

Examples of the aforementioned "optionally halogenated $C_{1-6}$ alkyl group" include a $C_{1-6}$ alkyl group (e.g., methyl, ethyl, propyl, isopropyl, butyl, isobutyl, sec-butyl, tert-butyl, pentyl, hexyl) optionally having 1 to 5, preferably 1 to 3, halogen atoms (e.g., fluorine, chlorine, bromine, iodine). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the aforementioned "optionally halogenated $C_{3-8}$ cycloalkyl group" include a $C_{3-8}$ cycloalkyl group (e.g., cyclopropyl, cyclobutyl, cyclopentyl, cyclohexyl) optionally having 1 to 5, preferably 1 to 3, halogen atoms (e.g., fluorine, chlorine, bromine, iodine) and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

Examples of each of the aforementioned "optionally halogenated $C_{1-6}$ alkoxy group", "optionally halogenated $C_{1-6}$ alkylthio group", "optionally halogenated $C_{1-6}$ alkyl-carbonyl group", "$C_{1-6}$ alkoxy-carbonyl group", "optionally halogenated $C_{1-6}$ alkylsulfonyl group" and "optionally halogenated $C_{1-6}$ alkyl-carbonylamino group" include those exemplified as the "substituent" of the aforementioned "hydrocarbon group optionally having substituents)".

Examples of the "heterocyclic group" of the "heterocyclic group optionally having substituent(s)" for A, $R^1$, $R^2$ or $R^3$, include (i) an aromatic heterocyclic group, (ii) a nonaromatic heterocyclic group and (iii) a 7- to 10-membered bridged heterocyclic group, each of which contains, as a ring-constituting atom besides carbon atom, 1 to 4 hetero atoms selected from a nitrogen atom, a sulfur atom and an oxygen atom.

Here, examples of the "aromatic heterocyclic group" include a 4- to 14-membered (preferably 4- to 10-membered) aromatic heterocyclic group containing, as a ring-constituting atom besides carbon atom, 1 to 4 hetero atoms selected from a nitrogen atom, a sulfur atom and an oxygen atom, and the like. Preferable examples of the "aromatic heterocyclic group" include monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like; fused polycyclic (preferably bicyclic or tricyclic) aromatic heterocyclic groups such as benzothiophenyl, benzofuranyl, benzimidazolyl, benzoxazolyl, benzothiazolyl, benzisothiazolyl, naphtho[2,3-b]thiophenyl, phenoxathiinyl, indolyl, isoindolyl, 1H-indazolyl, purinyl, 4H-quinolizinyl, isoquinolyl, quinolyl, phthalazinyl, naphthyridinyl (e.g., 1,8-naphthyridinyl), quinoxalinyl, quinazolinyl, cinnolinyl, carbazolyl, β-carbolinyl, phenanthridinyl, acridinyl, phenazinyl, phenothiazinyl, phenoxazinyl, phthalimido, imidazopyridyl, imidazothiazolyl, thienopyridyl etc., and the like.

Examples of the "nonaromatic heterocyclic group" include a 4- to 14-membered (preferably 4- to 10-membered) nonaromatic heterocyclic group containing, as a ring-constituting atom besides carbon atom, 1 to 4 hetero atoms selected from a nitrogen atom, a sulfur atom and an oxygen atom and the like. Preferable examples of the "nonaromatic heterocyclic group" include monocyclic nonaromatic heterocyclic groups such as azetidinyl, tetrahydrothiophenyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydrothiazolyl, tetrahydroisothiazolyl, tetrahydrooxazolyl, tetrahydroisoxazolyl, piperidyl, piperazinyl, tetrahydropyridinyl, dihydropyridinyl, tetrahydropyrimidinyl, tetrahydropyridazinyl, tetrahydropyranyl, tetrahydrothiopyranyl, azepanyl, morpholinyl, thiomorpholinyl, diazepanyl, azepinyl, azocanyl, diazocanyl and the like; fused polycyclic (preferably bicyclic or tricyclic) nonaromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thiophenyl, tetrahydroisoquinolyl, tetrahydroquinolyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl, dihydrobenzoxazinyl, 7,8,9,10-tetrahydro-6H-azepino[1,2-a]benzimidazolyl, 5,7-dihydro-6H-pyrrolo[3,4-b]pyridinyl and the like.

Preferable examples of the "7- to 10-membered bridged heterocyclic group" include quinuclidinyl, 7-azabicyclo[2.2.1]heptanyl and the like.

Examples of the substituent of the "heterocyclic group optionally having substituent(s)" include substituents selected from the aforementioned substituent group B and the like.

The number of the substituents is, for example, 1 to 3. When the number of the substituents is two or more, the respective substituents may be the same or different.

Examples of the "substituent" of the "benzene ring optionally further having substituent(s)" for B include a halogen atom, a cyano group, a nitro group, a hydrocarbon group optionally having substituent(s), a heterocyclic group optionally having substituent(s), an acyl group optionally having substituent(s), an amino group optionally having substituent(s), a carbamoyl group optionally having substituent(s), a sulfamoyl group optionally having substituent(s), a hydroxy group optionally having a substituent, a sulfanyl(SH) group optionally having a substituent and the like.

Examples of the aforementioned "hydrocarbon group optionally having substituent(s)" include those similar to the "hydrocarbon group optionally having substituent(s)" for A, $R^1$, $R^2$ or $R^3$.

Examples of the aforementioned "heterocyclic group optionally having substituent(s)" include those similar to the "heterocyclic group optionally having substituent(s)" for A, $R^1$, $R^2$ or $R^3$.

Examples of the acyl group of the aforementioned "acyl group optionally having substituent(s)" include —$COR^{1A}$, —CO—$OR^{1A}$, —$SO_2R^{1A}$, —$SOR^{1A}$, —$PO(OR^{1A})(OR^{2A})$ wherein $R^{1A}$ and $R^{2A}$ are each independently a hydrogen atom, a hydrocarbon group or a heterocyclic group, and the like.

Examples of the "hydrocarbon group" for $R^{1A}$ or $R^{2A}$ include the "hydrocarbon groups" exemplified for the "hydrocarbon group optionally having substituent(s)" exemplified as the substituent for A, $R^1$, $R^2$ or $R^3$. The hydrocarbon group is preferably a $C_{1-6}$ alkyl group, a $C_{2-6}$ alkenyl group, a $C_{3-8}$ cycloalkyl group, a $C_{3-8}$ cycloalkenyl group, a $C_{6-14}$ aryl group, a $C_{6-14}$ aryl-$C_{1-6}$ alkyl group and the like.

Examples of the "heterocyclic group" for $R^{1A}$ or $R^{2A}$ include the "heterocyclic groups" exemplified for the "heterocyclic group optionally having substituent(s)" exemplified as the substituent for A, $R^1$, $R^2$ or $R^3$. The heterocyclic group is preferably thiazolyl, oxazolyl, isothiazolyl, isoxazolyl, pyrazolyl, pyridyl, pyrazinyl, benzoxazolyl, benzothiazolyl, quinolyl, isoquinolyl, pyrrolidinyl, piperidyl, piperazinyl and the like.

The acyl group optionally has 1 to 3 substituents at substitutable position(s). Examples of such substituent include an optionally halogenated $C_{1-6}$ alkyl group (e.g., methyl, ethyl); an optionally halogenated $C_{1-6}$ alkoxy group (e.g., methoxy, ethoxy); a halogen atom (e.g., fluorine, chlorine, bromine, iodine); a nitro group; a hydroxy group; an amino group (e.g., methylamino, dimethylamino) optionally mono- or di-substituted by a $C_{1-6}$ alkyl group (e.g., methyl, ethyl); a $C_{1-6}$ alkoxy-carbonylamino group (e.g., tert-butoxycarbonylamino) and the like.

Preferable examples of the acyl group include a formyl group, a carboxyl group, a $C_{1-6}$ alkyl-carbonyl group (e.g., acetyl, propionyl, butyryl, isobutyryl, valeryl, isovaleryl, pivaloyl, hexanoyl), a $C_{2-6}$ alkenyl-carbonyl group (e.g., crotonoyl), a $C_{3-8}$ cycloalkyl-carbonyl group (e.g., cyclobutanecarbonyl, cyclopentanecarbonyl, cyclohexanecarbonyl, cycloheptanecarbonyl), a $C_{3-8}$ cycloalkenyl-carbonyl group (e.g., 2-cyclohexenecarbonyl), a $C_{6-14}$ aryl-carbonyl group (e.g., benzoyl, 1-naphthoyl, 2-naphthoyl), a $C_{6-14}$ aryl-$C_{1-6}$ alkyl-carbonyl group (e.g., benzylcarbonyl, phenethylcarbonyl), an aromatic heterocyclylcarbonyl group (e.g., nicotinoyl, isonicotinoyl), a nonaromatic heterocyclylcarbonyl group (e.g., pyrrolidinylcarbonyl, piperidylcarbonyl), a $C_{1-6}$ alkoxy-carbonyl group (e.g., methoxycarbonyl, ethoxycarbonyl, propoxycarbonyl, butoxycarbonyl, tert-butoxycarbonyl), a $C_{6-14}$ aryloxy-carbonyl group (e.g., phenyloxycarbonyl, naphthyloxycarbonyl), a $C_{6-14}$ aryl-$C_{1-6}$ alkyloxycarbonyl group (e.g., benzyloxycarbonyl, phenethyloxycarbonyl), a $C_{1-6}$ alkylsulfinyl group (e.g., methylsulfinyl, ethylsulfinyl), a $C_{1-6}$ alkylsulfonyl group (e.g., methylsulfonyl, ethylsulfonyl), a $C_{6-14}$ arylsulfonyl group (e.g., phenylsulfonyl), a phosphono group, a mono- or di-$C_{1-6}$ alkylphosphono group (e.g., dimethylphosphono, diethylphosphono, diisopropylphosphono, dibutylphosphono) and the like.

Examples of the aforementioned "amino group optionally having substituent(s)", "carbamoyl group optionally having substituent(s)" and "sulfamoyl group optionally having substituent(s)" include an amino group, a carbamoyl group and a sulfamoyl group, each optionally having 1 or 2 substituents selected from (1) the "hydrocarbon group optionally having substituent(s)" and "heterocyclic group optionally having substituent(s)" for A, $R^1$, $R^2$ or $R^3$;

(2) the aforementioned "acyl group optionally having substituent(s)";

(3) a carbamoyl group optionally having 1 or 2 substituents selected from a $C_{1-6}$ alkyl group (e.g., methyl, ethyl), a $C_{3-8}$ cycloalkyl group (e.g., cyclopropyl, cyclohexyl), a $C_{6-14}$ aryl group (e.g., phenyl) and a $C_{6-14}$ aryl-$C_{1-6}$ alkyl group (e.g., benzyl). When the nitrogen atom constituting the amino group, carbamoyl group and sulfamoyl group is substituted by two substituents, the substituents may form, together with the adjacent nitrogen atom, a nitrogen-containing heterocycle. Examples of the "nitrogen-containing heterocycle" include a 5- to 7-membered nitrogen-containing heterocycle containing one nitrogen atom as a ring-constituting atom besides carbon atom, and optionally further containing 1 or 2 hetero atoms selected from a nitrogen atom, a sulfur atom and an oxygen atom. Preferable examples of the nitrogen-containing heterocycle include pyrrolidine, imidazolidine, pyrazolidine, piperidine, piperazine, morpholine, thiomorpholine and the like.

The "amino group optionally having substituent(s)", "carbamoyl group optionally having substituent(s)" and "sulfamoyl group optionally having substituent(s)" are preferably an amino group, a carbamoyl group and a sulfamoyl group, respectively, each of which optionally has "1 or 2 substituents selected from a $C_{1-6}$ alkyl group, a $C_{2-6}$ alkenyl group, a $C_{3-8}$ cycloalkyl group, a $C_{6-14}$ aryl group, a $C_{6-14}$ aryl-$C_{1-6}$ alkyl group, a $C_{1-6}$ alkyl-carbonyl group, a $C_{6-14}$ aryl-carbonyl group, a $C_{6-14}$ aryl-$C_{1-6}$ alkyl-carbonyl group, an aromatic heterocyclylcarbonyl group, a nonaromatic heterocyclylcarbonyl group, a $C_{1-6}$ alkoxy-carbonyl group, an aromatic heterocyclic group, a carbamoyl group, a mono- or di-$C_{1-6}$ alkyl-carbamoyl group and a mono- or di-$C_{6-14}$ aryl $C_{1-6}$ alkyl-carbamoyl group, each of which optionally has 1 to 3 substituents selected from a halogen atom (e.g., fluorine, chlorine, bromine, iodine), an optionally halogenated $C_{1-6}$ alkoxy group, a hydroxy group, a nitro group, an amino group and a carbamoyl group".

Preferable examples of the amino group optionally having substituent(s) include an amino group, a mono- or di-$C_{1-6}$ alkylamino group (e.g., methylamino, dimethylamino, ethylamino, diethylamino, propylamino, dibutylamino), a mono- or di-$C_{2-6}$ alkenylamino group (e.g., diallylamino), a mono- or di-$C_{3-8}$ cycloalkylamino group (e.g., cyclopropylamino, cyclohexylamino), a mono- or di-$C_{6-14}$ arylamino group (e.g., phenylamino), a mono- or di-$C_{6-14}$ aryl-$C_{1-6}$ alkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{6-14}$ aryl-$C_{1-6}$ alkyl-carbonylamino group (e.g., benzylcarbonylamino), a mono- or di-aromatic heterocyclylcarbonylamino group (e.g., nicotinoylamino, isonicotinoylamino), a mono- or di-nonaromatic heterocyclylcarbonylamino group (e.g., piperidylcarbonylamino), a mono- or di-$C_{1-6}$ alkoxy-carbonylamino group (e.g., tert-butoxycarbonylamino), an aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{6-14}$ aryl-$C_{1-6}$ alkyl-carbamoyl)amino group (e.g., benzylcarbamoylamino) and the like.

Preferable examples of the carbamoyl group optionally having substituent(s) include a carbamoyl group, a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl), a mono- or di-$C_{2-6}$ alkenyl-carbamoyl group (e.g., diallylcarbamoyl), a mono- or di-$C_{3-8}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{6-14}$ aryl-$C_{1-6}$ alkyl-carbamoyl group (e.g., benzylcarbamoyl, phenethylcarbamoyl), a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl), an aromatic heterocyclylcarbamoyl group (e.g., pyridylcarbamoyl), and a nitrogen-containing heterocyclylcarbonyl group (e.g., morpholinocarbonyl).

Preferable examples of the sulfamoyl group optionally having substituent(s) include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., dialkylsulfamoyl), a mono- or di-$C_{3-8}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{6-14}$ aryl-$C_{1-6}$ alkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl), an aromatic heterocyclylsulfamoyl group (e.g., pyridylsulfamoyl) and the like.

Examples of the "hydroxy group optionally having a substituent" and "sulfanyl group optionally having a substituent" include a hydroxy group and a sulfanyl group, each optionally having substituent selected from the "hydrocarbon group optionally having substituent(s)", "heterocyclic group optionally having substituent(s)", and the aforementioned "optionally having substituent(s) acyl group" for A, $R^1$, $R^2$ or $R^3$.

The "hydroxy group optionally having a substituent" and "sulfanyl group optionally having a substituent" are preferably a hydroxy group and a sulfanyl group, each optionally having the "substituent selected from a $C_{1-6}$ alkyl group, a $C_{2-6}$ alkenyl group, a $C_{3-8}$ cycloalkyl group, a $C_{6-14}$ aryl group, a $C_{6-14}$ aryl-$C_{1-6}$ alkyl group, a $C_{1-6}$ alkyl-carbonyl group, a $C_{6-14}$ aryl-carbonyl group and an aromatic heterocyclic group, each of which optionally has 1 to 3 substituents selected from a halogen atom (e.g., fluorine, chlorine, bromine, iodine), an optionally halogenated $C_{1-6}$ alkoxy group, a hydroxy group, a nitro group, an amino group and a carbamoyl group".

Preferable examples of the hydroxy group optionally having a substituent include a hydroxy group, a $C_{1-6}$ alkoxy group (e.g., methoxy, ethoxy, propoxy, isopropoxy, butoxy, isobutoxy, sec-butoxy, tert-butoxy, pentyloxy, isopentyloxy, neopentyloxy, hexyloxy), a $C_{2-6}$ alkenyloxy group (e.g., allyloxy, 2-butenyloxy, 2-pentenyloxy, 3-hexenyloxy), a $C_{3-8}$ cycloalkyloxy group (e.g., cyclohexyloxy), a $C_{6-14}$ aryloxy group (e.g., phenoxy, naphthyloxy), a $C_{6-14}$ aryl-$C_{1-6}$ alkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), an aromatic heterocyclyloxy group (e.g., pyridyloxy) and the like.

Preferable examples of the sulfanyl group optionally having a substituent include a sulfanyl group, a $C_{1-6}$ alkylthio group (e.g., methylthio, ethylthio, propylthio, isopropylthio, butylthio, isobutylthio, sec-butylthio, tert-butylthio, pentylthio, isopentylthio, neopentylthio, hexylthio), a $C_{2-6}$ alkenylthio group (e.g., allylthio, 2-butenylthio, 2-pentenylthio, 3-hexenylthio), a $C_{3-8}$ cycloalkylthio group (e.g., cyclohexylthio), a $C_{6-14}$ arylthio group (e.g., phenylthio, naphthylthio), a $C_{6-14}$ aryl-$C_{1-6}$ alkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), an aromatic heterocyclylthio group (e.g., pyridylthio) and the like.

Examples of the "cyclic group" of the "cyclic group optionally having substituent(s)", which is optionally formed by A and $R^1$, bonded to each other, together with the adjacent nitrogen atom include a 4- to 10-membered heterocyclic group containing one nitrogen atom as a ring-constituting atom besides carbon atom, and optionally further containing one hetero atom selected from a nitrogen atom, a sulfur atom and an oxygen atom, and the like. Examples of the "4- to 10-membered heterocyclic group" include azetidin-1-yl, pyrrolidin-1-yl, pyrrolin-1-yl, pyrazolin-1-yl, imidazolin-1-yl, thiazolidin-3-yl, oxazolidin-3-yl, isothiazolidin-2-yl, isoxazolidin-2-yl, thiazolin-3-yl, oxazolin-3-yl, isothiazolin-2-yl, isoxazolin-2-yl, piperidin-1-yl, piperazin-1-yl, morpholin-4-yl, thiomorpholin-4-yl, azepan-1-yl, diazepan-1-yl, 1,4-oxazepan-4-yl, 1,4-thiazepan-4-yl, 5,7-dihydro-6H-pyrrolo[3,4-b]pyridin-6-yl, 1,3-dihydro-2H-isoindol-2-yl and the like.

Examples of the substituent of the "cyclic group optionally having substituent(s)", which is optionally formed by A and $R^1$, bonded to each other, include substituents selected from the aforementioned substituent group B and the like.

The number of the substituents is, for example, 1 to 3. When the number of the substituents is two or more, the respective substituents may be the same or different.

Examples of the "cyclic group" of the "cyclic group optionally having substituent(s)", which is optionally formed by $R^2$ and $R^3$, bonded to each other, together with the adjacent nitrogen atom include a 4- to 10-membered heterocyclic group containing one nitrogen atom as a ring-constituting atom besides carbon atom, and optionally further containing one hetero atom selected from a nitrogen atom, a sulfur atom and an oxygen atom, and the like. Examples of the "4- to 10-membered heterocyclic group" include azetidin-1-yl, pyrrolidin-1-yl, pyrrolin-1-yl, pyrazolin-1-yl, imidazolin-1-yl, thiazolidin-3-yl, oxazolidin-3-yl, isothiazolidin-2-yl, isoxazolidin-2-yl, thiazolin-3-yl, oxazolin-3-yl, isothiazolin-2-yl, isoxazolin-2-yl, piperidin-1-yl, piperazin-1-yl, morpholin-4-yl, thiomorpholin-4-yl, azepan-1-yl, diazepan-1-yl, 1,4-oxazepan-4-yl, 1,4-thiazepan-4-yl, 5,7-dihydro-6H-pyrrolo[3,4-b]pyridin-6-yl, 1,3-dihydro-2H-isoindol-2-yl and the like.

Examples of the substituent of the "cyclic group optionally having substituent(s)", which is optionally formed by $R^2$ and $R^3$, bonded to each other, include substituents selected from the aforementioned substituent group B and the like.

The number of the substituents is, for example, 1 to 3. When the number of the substituents is two or more, the respective substituents may be the same or different.

A is a hydrocarbon group optionally having substituent(s), or a heterocyclic group optionally having substituent(s).

A is preferably
(1) a $C_{1-6}$ alkyl group optionally having substituent(s),
(2) a $C_{3-8}$ cycloalkyl group optionally having substituent(s),
(3) a $C_{6-14}$ aryl group optionally having substituent(s),
(4) a $C_{1-6}$ alkyl group having a $C_{6-14}$ aryl group optionally having substituent(s), the $C_{1-6}$ alkyl group optionally further having substituent(s),
(5) a $C_{1-6}$ alkyl group having a heterocyclic group optionally having substituent(s), or
(6) a heterocyclic group optionally having substituent(s).

A is more preferably
(1) a $C_{3-8}$ cycloalkyl group optionally having substituent(s),
(2) a $C_{6-14}$ aryl group optionally having substituent(s),
(3) a $C_{1-6}$ alkyl group having a $C_{6-14}$ aryl group optionally having substituent(s), the $C_{1-6}$ alkyl group optionally further having substituent(s),
(4) a $C_{1-6}$ alkyl group having a heterocyclic group optionally having substituent(s), or
(5) a heterocyclic group optionally having substituent(s).

A is further preferably
(1) a $C_{3-8}$ cycloalkyl group (e.g., cyclopentyl, cyclohexyl),
(2) a $C_{6-14}$ aryl group (e.g., phenyl) optionally having 1 to 3 substituents selected from
 (a) a $C_{1-6}$ alkyl group optionally having 1 to 5 halogen atoms,
 (b) a $C_{1-6}$ alkylsulfonyl group,
 (c) a $C_{1-6}$ alkylsulfonylamino group, and
 (d) a heterocyclic group optionally having 1 to 3 substituents selected from a $C_{1-6}$ alkyl group and an oxo group (preferably a 4- to 10-membered heterocyclic group containing, as a ring-constituting atom besides carbon atom, 1 to 4 hetero atoms selected from a nitrogen atom, a sulfur atom and an oxygen atom, for example, piperazinyl, dihydropyrazolyl, tetrazolyl, pyrimidinyl, oxazolyl),
(3) a $C_{1-6}$ alkyl group having a $C_{6-14}$ aryl group (e.g., benzyl, phenethyl) optionally having 1 to 3 substituents selected from
 (a) a cyano group,
 (b) a heterocyclic group optionally having 1 to 3 oxo groups (preferably a 4- to 10-membered heterocyclic group containing, as a ring-constituting atom besides carbon atom, 1 to 4 hetero atoms selected from a nitrogen atom, a sulfur atom and an oxygen atom, for example, morpholinyl, pyrrolidinyl),
 (c) a $C_{6-14}$ aryloxy group (e.g., phenoxy), and
 (d) a heterocyclyloxy group (preferably, a heterocyclyloxy group wherein the heterocyclyl moiety is a 4- to 10-membered heterocyclic group containing, as a ring-constituting atom besides carbon atom, 1 to 4 hetero atoms selected from a nitrogen atom, a sulfur atom and an oxygen atom, for example, pyrazinyloxy), the $C_{1-6}$ alkyl group optionally further having a heterocyclic group (e.g., morpholinyl),
(4) a $C_{1-6}$ alkyl group having a heterocyclic group (preferably, the heterocyclic group is a 4- to 10-membered heterocyclic group containing, as a ring-constituting atom besides carbon atom, 1 to 4 hetero atoms selected from a nitrogen atom, a sulfur atom and an oxygen atom, for example, pyridyl, 2,3-dihydro-1,4-benzodioxinyl, benzoxazolyl, pyrazinyl) optionally having 1 to 3 substituents selected from $C_{1-6}$ alkyl groups optionally having 1 to 5 halogen atoms, or
(5) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, pyrazolyl, isoxazolyl, indolyl) optionally having 1 to 3 substituents selected from
 (a) a $C_{1-6}$ alkyl group optionally having 1 to 5 halogen atoms, and
 (b) a $C_{6-14}$ aryl group (e.g., phenyl).

A is further more preferably
(1) a $C_{6-14}$ aryl group (e.g., phenyl) optionally having 1 to 3 substituents selected from $C_{1-6}$ alkyl groups optionally having 1 to 5 halogen atoms, or
(2) a $C_{6-14}$ aryl-$C_{1-6}$ alkyl group (e.g., benzyl).

B is a benzene ring optionally further having substituent(s).

B is preferably a benzene ring optionally further having 1 to 3 substituents selected from
(1) a halogen atom,
(2) a $C_{1-6}$ alkyl group, and
(3) a $C_{1-6}$ alkoxy group.

B is more preferably a benzene ring optionally further having 1 to 3 (preferably 1) $C_{1-6}$ alkyl groups, further more preferably a benzene ring.

$R^1$, $R^2$ and $R^3$ are each independently a hydrogen atom, a hydrocarbon group optionally having substituent(s), or a heterocyclic group optionally having substituent(s).

$R^1$ is preferably a hydrogen atom or a $C_{1-6}$ alkyl group optionally having substituent(s), more preferably a hydrogen atom or a $C_{1-6}$ alkyl group optionally having 1 to 3 cyano groups, further preferably a hydrogen atom or a $C_{1-6}$ alkyl group, particularly preferably a hydrogen atom.

A and $R^1$ are optionally bonded to each other to form, together with the adjacent nitrogen atom, a cyclic group optionally having substituent(s).

Preferable examples of the "cyclic group optionally having substituent(s)", which is formed by A and $R^1$, bonded to each other, together with the adjacent nitrogen atom include a 4- to 10-membered heterocyclic group containing one nitrogen atom as a ring-constituting atom besides carbon atom, and optionally further containing one hetero atom selected from a nitrogen atom, a sulfur atom and an oxygen atom (e.g., azetidin-1-yl, pyrrolidin-1-yl, piperidin-1-yl, 5,7-dihydro-6H-pyrrolo[3,4-b]pyridin-6-yl, 1,3-dihydro-2H-isoindol-2-yl), the heterocyclic group optionally having 1 to 3 substituents selected from a hydroxy group and a cyano group.

$R^2$ is preferably a hydrogen atom, a $C_{1-6}$ alkyl group optionally having substituent(s), or a $C_{3-8}$ cycloalkyl group.

$R^2$ is more preferably a hydrogen atom or a $C_{1-6}$ alkyl group optionally having substituent(s), further preferably a hydrogen atom or a $C_{1-6}$ alkyl group, particularly preferably a hydrogen atom.

$R^3$ is preferably
(1) a hydrogen atom,
(2) a $C_{1-6}$ alkyl group optionally having substituent(s),
(3) a $C_{3-8}$ cycloalkyl group optionally having substituent(s),
(4) a $C_{1-6}$ alkyl group having a $C_{6-14}$ aryl group optionally having substituent(s), the $C_{1-6}$ alkyl group optionally further having substituent(s),
(5) a $C_{3-8}$ cycloalkyl-$C_{1-6}$ alkyl group optionally having substituent (s),
(6) a $C_{1-6}$ alkyl group having a heterocyclic group optionally having substituent(s), or
(7) a heterocyclic group optionally having substituent(s).

$R^3$ is more preferably
(1) a hydrogen atom,
(2) a $C_{1-6}$ alkyl group optionally having 1 to 3 cyano groups,
(3) a $C_{3-8}$ cycloalkyl group (e.g., cyclohexyl) optionally having 1 to 3 halogen atoms,
(4) a $C_{1-6}$ alkyl group having a $C_{6-14}$ aryl group (e.g., benzyl, phenethyl, 3-phenylpropyl) optionally having 1 to 3 substituents selected from
  (a) a halogen atom,
  (b) a cyano group,
  (c) a $C_{1-6}$ alkyl group optionally having 1 to 5 halogen atoms,
  (d) a $C_{1-6}$ alkoxy group,
  (e) a mono- or di-$C_{1-6}$ alkylamino group,
  (f) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, morpholinyl, pyrazinyl), and
  (g) a heterocyclyloxy group (preferably, a heterocyclyloxy group wherein the heterocyclyl moiety is a O- to 10-membered heterocyclic group containing, as a ring-constituting atom besides carbon atom, 1 to 4 hetero atoms selected from a nitrogen atom, a sulfur atom and an oxygen atom, for example, pyrazinyloxy), the $C_{1-6}$ alkyl group optionally further having a heterocyclic group (e.g., morpholinyl),
(5) a $C_{3-8}$ cycloalkyl-$C_{1-6}$ alkyl group (e.g., cyclopropylmethyl) optionally having 1 to 3 cyano groups,
(6) a $C_{1-6}$ alkyl group having a heterocyclic group (preferably, the heterocyclic group is a 4- to 10-membered heterocyclic group containing, as a ring-constituting atom besides carbon atom, 1 to 4 hetero atoms selected from a nitrogen atom, a sulfur atom and an oxygen atom, for example, 3,4-dihydro-2H-1,4-benzoxazinyl, thienyl) optionally having 1 to 3 substituents selected from a $C_{1-6}$ alkyl group and an oxo group, or (7) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, piperidyl, tetrahydropyranyl, tetrahydrothiopyranyl) optionally having 1 to 3 substituents selected from
  (a) a $C_{1-6}$ alkyl group,
  (b) a $C_{3-8}$ cycloalkyl group (e.g., cyclopropyl),
  (c) a $C_{6-14}$ aryl-$C_{1-6}$ alkyl group (e.g., benzyl),
  (d) a $C_{1-6}$ alkyl-carbonyl group (e.g., acetyl), and
  (e) an oxo group.

$R^3$ is more preferably a hydrogen atom or a $C_{3-8}$ cycloalkyl-$C_{1-6}$ alkyl group (e.g., cyclopropylmethyl).

$R^2$ and $R^3$ are optionally bonded to each other to form, together with the adjacent nitrogen atom, a cyclic group optionally having substituent(s).

Preferable examples of the "cyclic group optionally having substituent(s)", which is formed by $R^2$ and $R^3$, bonded to each other, together with the adjacent nitrogen atom include a 4- to 10-membered heterocyclic group containing one nitrogen atom as a ring-constituting atom besides carbon atom, optionally further containing one hetero atom selected from a nitrogen atom, a sulfur atom and an oxygen atom (e.g., pyrrolidin-1-yl, piperidin-1-yl, morpholin-4-yl, thiomorpholin-4-yl), the heterocyclic group optionally having 1 to 3 oxo groups.

The compound represented by the formula (I) includes compounds represented by the following formulas (IA) and (IB).

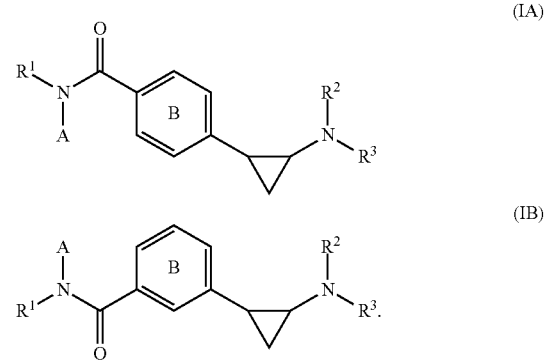

A preferable example of the compound represented by the formula (I) is a compound represented by the formula (IA).

Another preferable example of the compound represented by the formula (I) is a compound represented by the formula (IB).

In the formula (I), the configuration of the substituent represented by the formula

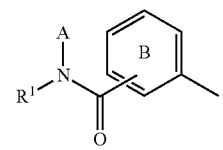

and the substituent represented by the formula —$N(R^2)(R^3)$ on the cyclopropane ring is more preferably a trans form than a cis form.

A compound of the formula (I) having a preferable relative configuration is shown by the following formula (IAA) or (IBB).
relative configuration

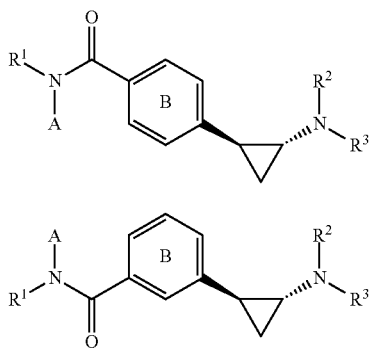

Preferable examples of compound (I) include the following compounds.
[Compound A]
Compound (I) wherein
A is
(1) a $C_{3-8}$ cycloalkyl group (e.g., cyclopentyl, cyclohexyl),
(2) a $C_{6-14}$ aryl group (e.g., phenyl) optionally having 1 to 3 substituents selected from
  (a) a $C_{1-6}$ alkyl group optionally having 1 to 5 halogen atoms,
  (b) a $C_{1-6}$ alkylsulfonyl group,
  (c) a $C_{1-6}$ alkylsulfonylamino group, and
  (d) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, piperazinyl, dihydropyrazolyl, tetrazolyl, pyrimidinyl, oxazolyl) optionally having 1 to 3 substituents selected from a $C_{1-6}$ alkyl group and an oxo group,
(3) a $C_{6-14}$ aryl-$C_{1-6}$ alkyl group (e.g., benzyl, phenethyl) optionally having 1 to 3 substituents selected from
  (a) a cyano group,
  (b) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, morpholinyl, pyrrolidinyl) optionally having 1 to 3 oxo groups,
  (c) a $C_{6-14}$ aryloxy group (e.g., phenoxy), and
  (d) a heterocyclyloxy group (preferably, a heterocyclyloxy group wherein the heterocyclyl moiety is a 4- to 10-membered heterocyclic group containing, as a ring-constituting atom besides carbon atom, 1 to 4 hetero atoms selected from a nitrogen atom, a sulfur atom and an oxygen atom, for example, pyrazinyloxy),
(4) a $C_{1-6}$ alkyl group having a heterocyclic group (preferably, the heterocyclic group is a 4- to 10-membered heterocyclic group containing, as a ring-constituting atom besides carbon atom, 1 to 4 hetero atoms selected from a nitrogen atom, a sulfur atom and an oxygen atom, for example, pyridyl, 2,3-dihydro-1,4-benzodioxinyl, benzoxazolyl, pyrazinyl) optionally having 1 to 3 substituents selected from $C_{1-6}$ alkyl groups optionally having 1 to 5 halogen atoms, or (5) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, pyrazolyl, isoxazolyl, indolyl) optionally having 1 to 3 substituents selected from
  (a) a $C_{1-6}$ alkyl group optionally having 1 to 5 halogen atoms, and
  (b) a $C_{6-14}$ aryl group (e.g., phenyl);
B is a benzene ring optionally further having 1 to 3 $C_{1-6}$ alkyl groups;
$R^1$ is a hydrogen atom or a $C_{1-6}$ alkyl group optionally having 1 to 3 cyano groups;
$R^2$ is a hydrogen atom or a $C_{1-6}$ alkyl group;
$R^3$ is
(1) a hydrogen atom,
(2) a $C_{1-6}$ alkyl group optionally having 1 to 3 cyano groups,
(3) a $C_{3-8}$ cycloalkyl group (e.g., cyclohexyl) optionally having 1 to 3 halogen atoms,
(4) a $C_{6-14}$ aryl-$C_{1-6}$ alkyl group (e.g., benzyl, phenethyl, 3-phenylpropyl) optionally having 1 to 3 substituents selected from
  (a) a halogen atom,
  (b) a cyano group,
  (c) a $C_{1-6}$ alkyl group optionally having 1 to 5 halogen atoms,
  (d) a $C_{1-6}$ alkoxy group,
  (e) a mono- or di-$C_{1-6}$ alkylamino group,
  (f) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, morpholinyl, pyrazinyl), and
  (g) a heterocyclyloxy group (preferably, a heterocyclyloxy group wherein the heterocyclyl moiety is a 4- to 10-membered heterocyclic group containing, as a ring-constituting atom besides carbon atom, 1 to 4 hetero atoms selected from a nitrogen atom, a sulfur atom and an oxygen atom, for example, pyrazinyloxy),
(5) a $C_{3-8}$ cycloalkyl-$C_{1-6}$ alkyl group (e.g., cyclopropylmethyl) optionally having 1 to 3 cyano groups,
(6) a $C_{1-6}$ alkyl group having a heterocyclic group (preferably, the heterocyclic group is a 4- to 10-membered heterocyclic group containing, as a ring-constituting atom besides carbon atom, 1 to 4 hetero atoms selected from a nitrogen atom, a sulfur atom and an oxygen atom, for example, 3,4-dihydro-2H-1,4-benzoxazinyl, thienyl) optionally having 1 to 3 substituents selected from a $C_{1-6}$ alkyl group and an oxo group, or
(7) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, piperidyl, tetrahydropyranyl, tetrahydrothiopyranyl) optionally having 1 to 3 substituents selected from
  (a) a $C_{1-6}$ alkyl group,
  (b) a $C_{3-8}$ cycloalkyl group (e.g., cyclopropyl),
  (c) a $C_{6-14}$ aryl-$C_{1-6}$ alkyl group (e.g., benzyl),
  (d) a $C_{1-6}$ alkyl-carbonyl group (e.g., acetyl), and
  (e) an oxo group;
A and $R^1$ are optionally bonded to each other to form, together with the adjacent nitrogen atom, a 4- to 10-membered heterocyclic group containing one nitrogen atom as a ring-constituting atom besides carbon atom, optionally further containing one hetero atom selected from a nitrogen atom, a sulfur atom and an oxygen atom (e.g., azetidin-1-yl, pyrrolidin-1-yl, piperidin-1-yl, 5,7-dihydro- 6H-pyrrolo[3,4-b]pyridin-6-yl), the heterocyclic group optionally having 1 to 3 substituents selected from a hydroxy group and a cyano group; and $R^2$ and $R^3$ are optionally bonded to each other to form, together m with the adjacent nitrogen atom, a 4- to 10-membered heterocyclic group containing one nitrogen atom as a ring-constituting atom besides carbon atom, optionally further containing one hetero atom selected from a nitrogen atom, a sulfur atom and an oxygen atom (e.g., pyrrolidin-1-yl, piperidin-1-yl, morpholin-4-yl, thiomorpholin-4-yl), the heterocyclic group optionally having 1 to 3 oxo groups.

[Compound B]

Compound (I) wherein

A is (1) a $C_{3-8}$ cycloalkyl group (e.g., cyclohexyl),
(2) a $C_{6-14}$ aryl group (e.g., phenyl) optionally having 1 to 3 substituents selected from $C_{1-6}$ alkyl groups optionally having 1 to 5 halogen atoms,
(3) a $C_{6-14}$ aryl-$C_{1-6}$ alkyl group (e.g., benzyl), or
(4) a heterocyclic group (preferably a 4- to 10-membered heterocyclic group containing, as a ring-constituting atom besides carbon atom, 1 to 4 hetero atoms selected from a nitrogen atom, a sulfur atom and an oxygen atom, for example, pyrazolyl);

B is a benzene ring;

$R^1$ is a hydrogen atom or a $C_{1-6}$ alkyl group;

$R^2$ is a hydrogen atom;

$R^3$ is a hydrogen atom or a $C_{3-8}$ cycloalkyl-$C_{1-6}$ alkyl group (e.g., cyclopropylmethyl);

A and $R^1$ are optionally bonded to each other to form, together with the adjacent nitrogen atom, a 4- to 10-membered heterocyclic group containing one nitrogen atom as a ring-constituting atom besides carbon atom, optionally further containing one hetero atom selected from a nitrogen atom, a sulfur atom and an oxygen atom (e.g., piperidin-1-yl).

[Compound C]

A compound represented by the formula (IA)

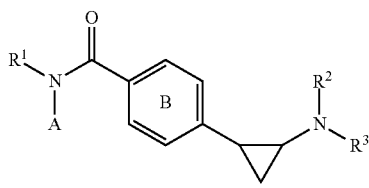

(IA)

wherein A, B, $R^1$, $R^2$ and $R^3$ are as defined for compound A, or a salt thereof.

[Compound D]

A compound represented by the formula (IA)

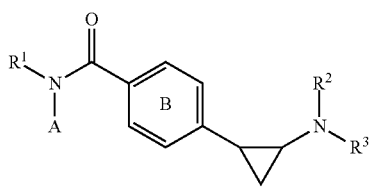

(IA)

wherein A, B, $R^1$, $R^2$ and $R^3$ are as defined for compound B, or a salt thereof.

[Compound E]

A compound represented by the formula (IB)

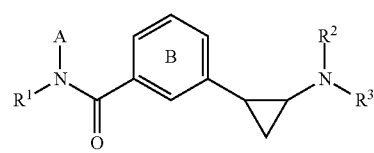

(IB)

wherein A, B, $R^1$, $R^2$ and $R^3$ are as defined for compound A, or a salt thereof.

[Compound F]

A compound represented by the formula (IB)

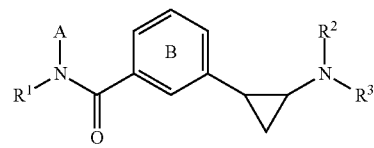

(IB)

wherein A, B, $R^1$, $R^2$ and $R^3$ are as defined for compound B, or a salt thereof.

[Compound G]

A compound represented by the formula (IAA)

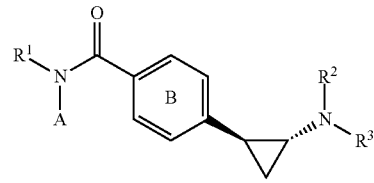

(IAA)

wherein A, B, $R^1$, $R^2$ and $R^3$ are as defined for compound A, and the steric configuration shows a relative configuration, or a salt thereof.

[Compound H]

A compound represented by the formula (IAA)

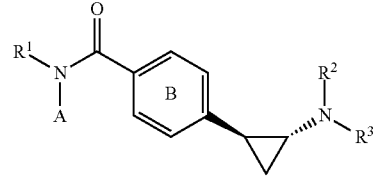

(IAA)

wherein A, B, $R^1$, $R^2$ and $R^3$ are as defined for compound B, and the steric configuration shows a relative configuration, or a salt thereof.

[Compound I]
A compound represented by the formula (IBB)

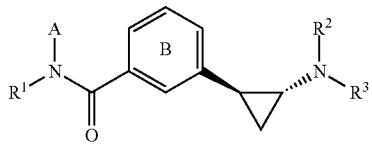

wherein A, B, R$^1$, R$^2$ and R$^3$ are as defined for compound A, and the steric configuration shows a relative configuration, or a salt thereof.

[Compound J]
A compound represented by the formula (IBB)

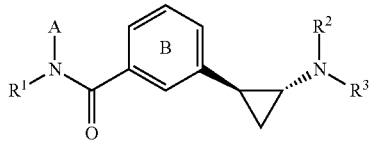

wherein A, B, R$^1$, R$^2$ and R$^3$ are as defined for compound B, and the steric configuration shows a relative configuration, or a salt thereof.

Preferable specific examples of the compound represented by the formula (I) include the following compounds, Example compounds to be mentioned later, an optically active form thereof, and a mixture of the optical isomers thereof.

4-(trans-2-aminocyclopropyl)-N-phenylbenzamide
4-(trans-2-aminocyclopropyl)-N-benzylbenzamide
4-(trans-2-aminocyclopropyl)-N-methyl-N-phenylbenzamide
4-(trans-2-aminocyclopropyl)-N-(3-(trifluoromethyl)phenyl)benzamide
4-(trans-2-aminocyclopropyl)-N-(1H-pyrazol-4-yl)benzamide
4-(trans-2-aminocyclopropyl)-N-cyclohexylbenzamide (4-(trans-2-aminocyclopropyl)phenyl)(piperidin-1-yl)methanone
4-(trans-2-((cyclopropylmethyl)amino)cyclopropyl)-N-phenylbenzamide
4-(trans-2-aminocyclopropyl)-N-benzyl-N-methylbenzamide N-benzyl-4-(trans-2-((cyclopropylmethyl)amino)cyclopropyl)-N-methylbenzamide
3-(trans-2-aminocyclopropyl)-N-phenylbenzamide
3-(trans-2-aminocyclopropyl)-N-benzylbenzamide
3-(trans-2-((cyclopropylmethyl)amino)cyclopropyl)-N-phenylbenzamide
N-benzyl-3-(trans-2-((cyclopropylmethyl)amino)cyclopropyl)benzamide
4-(trans-2-((cyclopropylmethyl)amino)cyclopropyl)-N-(4-(methylsulfonyl)phenyl) benzamide
4-(trans-2-((cyclopropylmethyl)amino)cyclopropyl)-N-(4-(4-methylpiperazin-1-yl) phenyl) benzamide
4-(trans-2-((cyclopropylmethyl)amino)cyclopropyl)-N-(pyridin-3-ylmethyl)benzamide
4-(trans-2-((cyclopropylmethyl)amino)cyclopropyl)-N-(pyridin-2-ylmethyl)benzamide
4-(trans-2-((cyclopropylmethyl)amino)cyclopropyl)-N-(pyridin-4-ylmethyl)benzamide
N-(3-cyanobenzyl)-4-(trans-2-((cyclopropylmethyl)amino)cyclopropyl)benzamide
4-(trans-2-((cyclopropylmethyl)amino)cyclopropyl)-N-(4-(morpholin-4-yl)benzyl)benzamide
4-(trans-2-((cyclopropylmethyl)amino)cyclopropyl)-N-((3-(trifluoromethyl)pyridin-2-yl)methyl)benzamide
4-(trans-2-((cyclopropylmethyl)amino)cyclopropyl)-N-(4-(2-oxopyrrolidin-1-yl)benzyl)benzamide
4-(trans-2-((cyclopropylmethyl)amino)cyclopropyl)-N-(2,3-dihydro-1,4-benzodioxin-5-ylmethyl)benzamide
N-benzyl-N-(cyanomethyl)-4-(trans-2-((cyclopropylmethyl)amino)cyclopropyl)benzamide
(4-(trans-2-((cyclopropylmethyl)amino)cyclopropyl)phenyl) (5,7-dihydro-6H-pyrrolo[3,4-b]pyridin-6-yl)methanone
N-(1,3-benzoxazol-2-ylmethyl)-4-(trans-2-((cyclopropylmethyl)amino)cyclopropyl)benzamide
4-(trans-2-((cyclopropylmethyl)amino)cyclopropyl)-N-(2-(morpholin-4-yl)-2-phenylethyl)benzamide
4-(trans-2-((cyclopropylmethyl)amino)cyclopropyl)-N-(2-(pyridin-2-yl)ethyl)benzamide
4-(trans-2-((cyclopropylmethyl)amino)cyclopropyl)-N-((5-methylpyrazin-2-yl)methyl)benzamide
4-(trans-2-((cyclopropylmethyl)amino)cyclopropyl)-N-(3-(pyrazin-2-yloxy)benzyl)benzamide
4-(trans-2-((cyclopropylmethyl)amino)cyclopropyl)-N-(3-phenyl-1,2-oxazol-5-yl)benzamide
4-(trans-2-((cyclopropylmethyl)amino)cyclopropyl)-N-(3-phenoxybenzyl)benzamide
4-(trans-2-((cyclopropylmethyl)amino)cyclopropyl)-N-(1H-pyrazol-4-yl)benzamide
4-(trans-2-((cyclopropylmethyl)amino)cyclopropyl)-N-(1-methyl-1H-pyrazol-4-yl)benzamide
N-(1-tert-butyl-1H-pyrazol-4-yl)-4-(trans-2-((cyclopropylmethyl)amino)cyclopropyl)benzamide
N-benzyl-4-(trans-2-((cyclopropylmethyl)amino)cyclopropyl)benzamide
N-benzyl-4-(trans-2-((2,2-dimethylpropyl)amino)cyclopropyl)benzamide
4-(trans-2-((1-acetylpiperidin-4-yl)amino)cyclopropyl)-N-benzylbenzamide
N-benzyl-4-(trans-2-((1-methylpiperidin-4-yl) amino) cyclopropyl) benzamide
N-benzyl-4-(trans-2-((1-benzylpiperidin-4-yl)amino)cyclopropyl)benzamide
N-benzyl-4-(trans-2-(tetrahydro-2H-pyran-4-ylamino)cyclopropyl)benzamide
N-benzyl-4-(trans-2-((1,1-dioxidotetrahydro-2H-thiopyran-4-yl)amino)cyclopropyl)benzamide
N-benzyl-4-(trans-2-((1-cyclopropylpiperidin-4-yl)amino)cyclopropyl)benzamide
N-benzyl-4-(trans-2-((4,4-difluorocyclohexyl)amino)cyclopropyl)benzamide
N-benzyl-4-(trans-2-((4-tert-butylbenzyl)amino)cyclopropyl)benzamide
N-benzyl-4-(trans-2-(benzylamino)cyclopropyl)benzamide
N-benzyl-4-(trans-2-((2-methoxybenzyl)amino)cyclopropyl)benzamide
N-benzyl-4-(trans-2-((4-methoxybenzyl)amino)cyclopropyl)benzamide
N-benzyl-4-(trans-2-((4-cyanobenzyl)amino)cyclopropyl) benzamide
N-benzyl-4-(trans-2-((3-methoxybenzyl) amino) cyclopropyl)benzamide
N-benzyl-4-(trans-2-((4-(trifluoromethyl)benzyl)amino)cyclopropyl)benzamide N-benzyl-4-(trans-2-((2-chlorobenzyl)amino)cyclopropyl) benzamide
N-benzyl-4-(trans-2-((2-fluorobenzyl)amino)cyclopropyl) benzamide
N-benzyl-4-(trans-2-((2-fluoro-5-methoxybenzyl)amino) cyclopropyl)benzamide
N-benzyl-4-(trans-2-((2-chloro-5-cyanobenzyl)amino)cyclopropyl)benzamide
N-benzyl-4-(trans-2-((4-chloro-2-methoxybenzyl)amino) cyclopropyl)benzamide
N-benzyl-4-(trans-2-((2-(dimethylamino)benzyl)amino)cyclopropyl)benzamide
N-benzyl-4-(trans-2-((3-cyanobenzyl)amino)cyclopropyl) benzamide
N-benzyl-4-(trans-2-((2-cyanobenzyl)amino)cyclopropyl) benzamide
N-benzyl-4-(trans-2-(((3-oxo-3,4-dihydro-2H-1,4-benzoxazin-6-yl)methyl)amino)cyclopropyl)benzamide
N-benzyl-4-(trans-2-((4-(morpholin-4-yl)benzyl)amino)cyclopropyl)benzamide
N-benzyl-4-(trans-2-((2-(pyrazin-2-yloxy)benzyl)amino) cyclopropyl)benzamide
N-benzyl-4-(trans-2-((2-(pyrazin-2-yl)benzyl)amino)cyclopropyl)benzamide
N-benzyl-4-(trans-2-(((4-methyl-3,4-dihydro-2H-1,4-benzoxazin-7-yl)methyl)amino)cyclopropyl)benzamide
N-benzyl-4-(trans-2-((2-thienylmethyl)amino)cyclopropyl) benzamide
N-benzyl-4-(trans-2-(((3-methyl-2-thienyl)methyl) amino) cyclopropyl)benzamide
N-benzyl-4-(trans-2-(((5-methyl-2-thienyl)methyl)amino) cyclopropyl)benzamide
N-benzyl-4-(trans-2-((3-phenylpropyl)amino)cyclopropyl) benzamide
N-benzyl-4-(trans-2-((2-phenylethyl)amino)cyclopropyl) benzamide
(4-(trans-2-((cyclopropylmethyl)amino)cyclopropyl)phenyl)(3-hydroxyazetidin-1-yl)methanone
(4-(trans-2-((cyclopropylmethyl)amino)cyclopropyl)phenyl)(4-hydroxypiperidin-1-yl)methanone
1-(4-(trans-2-((cyclopropylmethyl)amino)cyclopropyl)benzoyl)piperidine-4-carbonitrile
1-(4-(trans-2-((cyclopropylmethyl)amino)cyclopropyl)benzoyl)azetidine-3-carbonitrile
4-(trans-2-((cyclopropylmethyl)amino)cyclopropyl)-N-(1-methyl-3-(trifluoromethyl)-1H-pyrazol-4-yl)benzamide
4-(trans-2-((cyclopropylmethyl)amino)cyclopropyl)-N-(1-methyl-5-(trifluoromethyl)-1H-pyrazol-4-yl)benzamide
4-(trans-2-((1,1-dioxidotetrahydro-2H-thiopyran-4-yl) amino)cyclopropyl)-N-(3-(trifluoromethyl)phenyl)benzamide
4-(trans-2-((cyclopropylmethyl)amino)cyclopropyl)-N-(1, 5-dimethyl-1H-pyrazol-3-yl)benzamide
4-(trans-2-((cyclopropylmethyl)amino)cyclopropyl)-N-(4-((methylsulfonyl)amino)phenyl)benzamide
4-(trans-2-((cyclopropylmethyl)amino)cyclopropyl)-N-(4-(3-methyl-5-oxo-4,5-dihydro-1H-pyrazol-1-yl)phenyl) benzamide
4-(trans-2-((cyclopropylmethyl)amino)cyclopropyl)-N-(4-(1H-tetrazol-5-yl)phenyl)benzamide
N-methyl-4-(trans-2-((1-methylpiperidin-4-yl)amino)cyclopropyl)-N-(3-(trifluoromethyl)phenyl)benzamide
4-(trans-2-((cyclopropylmethyl)amino)cyclopropyl)-N-(4-(pyrimidin-2-yl)phenyl)benzamide
4-(trans-2-((cyclopropylmethyl)amino)cyclopropyl)-2-methyl-N-phenylbenzamide
4-(trans-2-((cyclopropylmethyl)amino)cyclopropyl)-N-(4-(1,3-oxazol-5-yl)phenyl)benzamide
4-(trans-2-((cyclopropylmethyl)amino)cyclopropyl)-N-(1H-indol-6-yl)benzamide
4-(trans-2-((cyclopropylmethyl)amino)cyclopropyl)-N-(4-(4-methylpiperazin-1-yl)phenyl)benzamide
4-(trans-2-((1-methylpiperidin-4-yl)amino)cyclopropyl)-N-(3-(trifluoromethyl)phenyl)benzamide
4-(trans-2-((cyclopropylmethyl)amino)cyclopropyl)-N-(1H-indol-3-yl)benzamide
N-benzyl-4-(trans-2-((cyanomethyl)amino)cyclopropyl) benzamide
N-benzyl-4-(trans-2-((cyano(cyclopropyl)methyl)amino) cyclopropyl)benzamide
N-benzyl-4-(trans-2-((cyano(phenyl)methyl)amino)cyclopropyl)benzamide
N-benzyl-4-(trans-2-(pyrrolidin-1-yl)cyclopropyl)benzamide
N-benzyl-4-(trans-2-(piperidin-1-yl)cyclopropyl)benzamide
N-benzyl-4-(trans-2-(morpholin-4-yl)cyclopropyl)benzamide
N-benzyl-4-(trans-2-(1,1-dioxidothiomorpholin-4-yl)cyclopropyl)benzamide
N-benzyl-4-(trans-2-((cyclopropylmethyl)(methyl)amino) cyclopropyl)benzamide
N-benzyl-4-(trans-2-((1,1-dioxidotetrahydro-2H-thiopyran-4-yl)amino)cyclopropyl)-N-methylbenzamide
4-(trans-2-((1,1-dioxidotetrahydro-2H-thiopyran-4-yl) amino)cyclopropyl)-N-phenylbenzamide
4-(trans-2-((1,1-dioxidotetrahydro-2H-thiopyran-4-yl) amino)cyclopropyl)-N-methyl-N-phenylbenzamide
N-benzyl-4-(trans-2-((2-methylbenzyl) amino) cyclopropyl) benzamide
N-benzyl-4-(trans-2-((4-methylbenzyl)amino)cyclopropyl) benzamide
N-benzyl-4-(trans-2-((4-(pyrazin-2-yl)benzyl)amino)cyclopropyl)benzamide
N-benzyl-4-(trans-2-(((4-methyl-2-thienyl)methyl)amino) cyclopropyl)benzamide
4-(trans-2-aminocyclopropyl)-N-(4-(pyrimidin-2-yl) phenyl) benzamide
4-(trans-2-aminocyclopropyl)-N-(1-methyl-1H-pyrazol-4-yl)benzamide
3-(trans-2-aminocyclopropyl)-N-(4-(pyrimidin-2-yl)phenyl)benzamide
3-(trans-2-aminocyclopropyl)-N-(1-methyl-1H-pyrazol-4-yl)benzamide
3-(trans-2-aminocyclopropyl)-N-cyclopentylbenzamide
(3-(trans-2-aminocyclopropyl)phenyl)(pyrrolidin-1-yl) methanone
3-(trans-2-((cyclopropylmethyl)amino)cyclopropyl)-N-(4-(pyrimidin-2-yl)phenyl)benzamide
3-(trans-2-((cyclopropylmethyl)amino)cyclopropyl)-N-(1-methyl-1H-pyrazol-4-yl)benzamide
N-cyclopentyl-3-(trans-2-((cyclopropylmethyl)amino)cyclopropyl)benzamide
(3-(trans-2-((cyclopropylmethyl)amino)cyclopropyl)phenyl)(pyrrolidin-1-yl)methanone The salt of compound (I) is preferably a pharmacologically acceptable salt. Examples of such salt include salts with inorganic bases, salts with organic bases, salts with inorganic acids, salts with organic acids, and salts with basic or acidic amino acids.

Preferable examples of salts with inorganic bases include alkali metal salts such as sodium salts, potassium salts and the like; alkali earth metal salts such as calcium salts, magnesium salts and the like; aluminum salts; and ammonium salts.

Preferable examples of salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of salts with inorganic acids include salts with hydrochloric acid, hydrobromic acid, nitric acid, sulfuric acid, phosphoric acid and the like.

Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of salts with basic amino acids include salts with arginine, lysine, ornithine and the like.

Preferable examples of salts with acidic amino acids include salts with aspartic acid, glutamic acid and the like.

The salt of compound (I) is preferably a salt with an inorganic acid (preferably, hydrochloric acid) or an organic acid (preferably, trifluoroacetic acid, fumaric acid).

Compound (I) may also be used as a prodrug. A prodrug of compound (I) means a compound which is converted to compound (I) due to a reaction due to an enzyme, gastric acid, etc. under the physiological condition in the living body, that is, a compound which is converted to compound (I) with oxidation, reduction, hydrolysis, and the like according to an enzyme; a compound which is converted to compound (I) by hydrolysis etc. due to gastric acid, and the like. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation and dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation) and the like. Any of these compounds can be produced from compound (I) by a method known per se.

The prodrug of compound (I) may be a compound that converts to compound (I) under physiological conditions as described in Development of Pharmaceutical Products, vol. 7, Molecular Design, 163-198, Hirokawa Shoten (1990).

Compound (I) may be labeled with an isotope (e.g., $^{2}$H, $^{3}$H, $^{14}$C, $^{35}$S, $^{125}$I, $^{11}$C, $^{18}$F) and the like.

Compound (I) labeled with or substituted by an isotope can be used, for example, as a tracer used for Positron Emission Tomography (PET) (PET tracer), and is useful in the field of medical diagnosis and the like.

Compound (I) may be an anhydrate or a hydrate. Compound (I) may be a solvate or a non-solvate. Furthermore, compound (I) may be a deuterated compound.

Compound (I) may be a crystal, and both a single crystal and crystal mixtures are encompassed in compound (I). Crystals can be produced by crystallization according to crystallization methods known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, and stability). The cocrystal and cocrystal salt can be produced by cocrystallization method known per se.

When compound (I) includes isomers such as optical isomers, stereoisomers, regioisomers, rotational isomers, geometrical isomers, and the like, one of the isomers and mixture are also encompassed in compound (I).

Compound (I) or a prodrug thereof (hereinafter sometimes to be simply abbreviated as the compound of the present invention) has low toxicity (e.g., acute toxicity, chronic toxicity, genetic toxicity, reproductive toxicity, cardiotoxicity, carcinogenicity), and can be used as it is or in the form of a pharmaceutical composition (in the present specification, sometimes to be abbreviated as "medicament of the present invention") after mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As a pharmaceutical acceptable carrier here, common organic or inorganic carrier substances are used as formulation raw materials. Carriers are added as vehicles, lubricants, binders and disintegrants in the solid formulations; and as solvents, solubilizing agents, suspending agents, isotonization agents, buffering agents, soothing agents etc. in the liquid formulations. If desired, formulation additives such as preservatives, antioxidants, colorants, sweeteners, etc. can be used.

Preferable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light anhydrous silicic acid, synthetic aluminum silicate, and magnesium metasilicic aluminate.

Preferable examples of the lubricant include magnesium stearate, calcium stearate, talc, colloidal silica, and the like.

Preferable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methylcellulose, and polyvinylpyrrolidone.

Preferable examples of the disintegrants are as follows: lactose, sucrose, starch, carboxymethylcellulose, calcium carboxymethylcellulose, croscarmellose sodium, sodium carboxymethyl starch, light anhydrous silicic acid, and low-substituted hydroxypropylcellulose.

Preferable examples of the solvents are as follows: water for injection, physiological saline, Linger solution, alcohol, propylene glycol, polyethylene glycol, sesame oil, corn oil, olive oil, and cottonseed oil.

Preferable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Preferable examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, and polyoxyethylene hydrogenated castor oil.

Preferable examples of the isotonization agents include sodium chloride, glycerin, D-mannitol, D-sorbitol, and glucose.

Preferable examples of the buffering agent include buffer solutions such as phosphates, acetates, carbonates, and citrates.

Preferable examples of the soothing agent include benzyl alcohol.

Preferable examples of the preservative include p-hydroxybenzoates, chlorobutanol, benzyl alcohol, phenethyl alcohol, dehydroacetic acid, and sorbic acid.

Preferable examples of antioxidants include sulfites and ascorbates.

Preferable examples of the colorants include water soluble edible tar dyes (e.g., edible dyes such as Food Red No. 2 and No. 3, Food Yellow No. 4 and No. 5, Food Blue No. 1 and 2, etc.); water insoluble lake dyes (e.g., aluminum salts of the aforementioned water soluble edible tar dyes), and natural dyes (e.g., β-carotene, chlorophyll, ferric oxide red).

Preferable examples of the sweeteners include sodium saccharin, dipotassium glycyrrhizinate, aspartame and stevia.

Examples of the dosage form of the medicament of the present invention include oral preparations such as tablet (including sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or parenterally.

These preparations may be a release control preparation (e.g., sustained-release microcapsule) such as an immediate-release preparation, a sustained-release preparation and the like.

The medicament of the present invention can be manufactured by the common methods in the field of formulation technology, for example, methods listed in the Japanese Pharmacopoeia, and the like.

The content of the compound of the present invention in the medicament of the present invention varies based on the dosage forms, dosages of the compound of the present invention, and the like. For example, it is approximately about 0.1 to 100 wt %.

The compound of the present invention has a superior LSD1 inhibitory action and can be used as a prophylactic or therapeutic agent for various diseases in mammals (e.g., human, mouse, rat, rabbit, dog, cat, bovine, horse, swine, monkey). Moreover, since the compound of the present invention shows low monoamine oxidase A (MAO-A) and monoamine oxidase B (MAO-B) inhibitory activity and high LSD1 selectivity, it causes fewer side effects.

In addition, the compound of the present invention is expected to show, after transfer into the brain, suppression of a decrease in histone H3K4 methylation and suppression of a decrease in Gad1 mRNA expression, which are derived from the inhibition of LSD1. As a result, it is also useful as a medicament based on superior actions of neuronal function, enhancement of neural plasticity, promotion of neurogenesis, and promotion of BDNF production.

The compound of the present invention can be used as a prophylactic or therapeutic agent for cancer. Examples of the cancer include breast cancer, prostate cancer, pancreatic cancer, gastric cancer, lung cancer, colorectal cancer, rectal cancer, esophagus cancer, duodenal cancer, tongue cancer, pharyngeal cancer, brain tumor, schwannoma, non-small cell lung cancer, small cell lung cancer, liver cancer, kidney cancer, bile duct cancer, uterine body cancer, cervical cancer, ovarian cancer, urinary bladder cancer, skin cancer, hemangioma, malignant lymphoma, malignant melanoma, thyroid cancer, bone tumor, angiofibroma, retinoblastoma, penile cancer, childhood solid cancer, Kaposi's sarcoma, AIDS-related Kaposi's sarcoma, tumor of maxillary sinus, fibrous histiocytoma, leiomyosarcoma, rhabdomyosarcoma, and leukemia. Among these, the compound can be preferably used for prostate cancer, leukemia, and malignant lymphoma.

The compound of the present invention can be used as a therapeutic agent for anemia. As anemia, sickle cell anemia and beta thalassemia can be mentioned.

The compound of the present invention can be used as a therapeutic agent for virus infections. Examples of the virus infection include influenza, viral hepatitis, viral meningitis, acquired immunodeficiency syndrome (AIDS), adult T-cell leukemia, Ebola hemorrhagic fever, yellow fever, cold syndrome, rabies, simple herpes virus (HSV1, HSV2) infections, vesicular stomatitis virus (VSV) infections, cytomegalovirus (CMV) infections, severe acute respiratory syndrome (SARS), progressive multifocal leukoencephalopathy, varicella, herpes zoster, hand, foot and mouth disease, dengue fever, erythema infectiosum, infectious mononucleosis, smallpox, rubella, acute poliomyelitis (polio), measles, pharyngoconjunctival fever (swimming pool fever), Marburg hemorrhagic fever, Hantavirus hemorrhagic fever, Lassa fever, epidemic parotitis, West Nile fever, herpangina, and chikungunya fever. Among these, the compound can be preferably used for simple herpes virus (HSV1, HSV2) infections, vesicular stomatitis virus (VSV) infections, and cytomegalovirus (CMV) infections.

It is known that the level of H3K4me2, which is a substrate of LSD1, and memory improvement are correlated (Nature 2007, Vol. 447, page 175), and the compound of the present invention having a superior LSD1 inhibitory action can also be used as a prophylactic or therapeutic agent for neurodegenerative diseases.

The compound of the present invention can be used as a prophylactic or therapeutic agent for central nervous system diseases. It is useful as a prophylactic or therapeutic agent for diseases such as (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, mood disorder, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety symptom, anxious mental state, emotional abnormality, cyclothymia, nervous erethism, faint, addiction, low sex drive, attention deficit hyperactivity disorder (ADHD), psychotic major depression, refractory major depression, treatment-resistant depression, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], (2) neurodegenerative diseases [e.g., Alzheimer's disease, Alzheimer-type senile dementia, Parkinson's disease, Huntington's disease, multi-infarct dementia, frontotemporal dementia, frontotemporal dementia with Parkinsonism, progressive supranuclear palsy, Pick's syndrome, Niemann-Pick syndrome, corticobasal degeneration, Down's syndrome, vascular dementia, postencephalitic parkinsonism, dementia with Lewy body, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neuromyopathy], (3) age-related cognition and memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake disorder and the like), parasomnia, sleep disorders associated with internal medical or psychiatric disorder (e.g., chronic obstructive pulmonary disease, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol intoxication, alcoholic jealousy, alcoholic mania, alcohol-dependent psychiatric disorder, alcoholic insanity, pharmacophilia, pharmacophobia, pharmacomania, drug abuse, drug dependence, drug withdrawal, migraine, stress headache, catatonic headache, diabetic neuropathy, obesity, diabetes, muscular spasm, Meniere's disease, autonomic ataxia, alopecia, glaucoma, hearing loss, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, and the like.

The compound of the present invention is particularly useful as a prophylactic or therapeutic agent for diseases such as schizophrenia, Alzheimer's disease, Parkinson's disease, Huntington's disease, fragile X syndrome and the like.

The compound of the present invention is particularly useful as a prophylactic or therapeutic agent for diseases such as schizophrenia, Alzheimer's disease, Parkinson's disease, Huntington's disease and the like.

Since the compound of the present invention has a superior LSD1 inhibitory activity and action, it is expected to show a superior treatment effect for the above-mentioned diseases.

The dosage of the compound of the present invention varies depending on the administration subjects, administration routes, target diseases, symptoms, and the like. For example, for oral administration to adult patients with cancer, generally a single dose is about 0.01 to 100 mg/kg body weight, preferably 0.1 to 50 mg/kg body weight, further preferably 0.5 to 20 mg/kg body weight, and this dosage is preferably administered 1 to 3 times daily.

The compound of the present invention can be used in combination with a medicament such as chemotherapeutic agent, immunotherapeutic agent, medicament inhibiting actions of cell growth factor and receptor thereof (hereinafter to be abbreviated as a concomitant drug).

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of such administration mode include the following methods:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

Examples of the chemotherapeutic agent include alkylating agents (e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin), metabolic antagonists (e.g., mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine), antitumor antibiotics (e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride), plant-derived antitumor agents (e.g., etoposide, etoposide phosphate, vinblastine sulfate, vincristine sulfate, vindesine sulfate, teniposide, paclitaxel, docetaxel, vinorelbine), HDAC (histone deacetylase) inhibitor and DNMT (DNA methyltransferase) inhibitor.

Examples of the immunotherapeutic agent include picibanil, krestin, schizophyllan, lentinan, ubenimex, interferon, interleukin, macrophage colony stimulating factor, granulocyte colony stimulating factor, erythropoietin, lymphotoxin, BCG vaccine, corynebacterium parvum, levamisole, polysaccharide K, procodazole and anti-CTLA4 antibody.

Examples of the "medicament inhibiting actions of cell growth factor and receptor thereof" include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino[quinazolin-7-yloxy]propyl]-N-ethylaminoethyl phosphate (AZD-1152), 4-[9-chloro-7-(2,6-difluorophenyl)-5H-primido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and everolimus (RAD001).

Examples of the concomitant drug for the central nervous system diseases include the following.

benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT$_{1A}$ agonist, (buspirone hydrochloride, tandospirone citrate, osemozotan hydrocloride etc.), 5-HT$_3$ antagonist (cyamemazine etc.), non-cardioselective βblocker (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), HDAC (histone deacetylase) inhibitor, DNMT (DNA methyltransferase) inhibitor, antibody medicament, nucleic acid or nucleic acid derivative, aptamer drug, and the like.

The above-mentioned concomitant drug may be used in a combination of two or more kinds at an appropriate ratio.

When the compound of the present invention is used in combination with a concomitant drug, the respective dosages can be reduced within a safe range in consideration of the opposite effects of the respective drugs. As a result, the opposite effect caused by these agents can be prevented safely.

The compound of the present invention can also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; (7) radiation therapy; and (8) immunotherapy.

[Production Method]

The production method of compound (I) of the present invention is shown in the following.

Compound (I) of the present invention can be produced, for example, according to the method shown in the following reaction scheme or a method analogous thereto and the like. The compounds in the schemes may form a salt, and examples of such salt include those similar to the aforementioned salts of compound (I). When the compound obtained in each step is a free compound, it can be converted to a desired salt by a method known per se. Conversely, when the compound obtained in each step is a salt, it can be converted to a free form or a desired other kind of salt by a method known per se. While the compounds obtained in each step can be directly used for the next reaction in the form of a reaction mixture or as a crude product, they can be isolated and purified from a reaction mixture according to a conventionally known method such as concentration, extraction, recrystallization, distillation, chromatography and the like. In addition, the compound obtained in each step may be used after optical resolution by a known means such as chiral column chromatography, optical fractional crystallization, diastereomer derivatization and the like. When the starting material or a reagent compound for each step is commercially available, the commercially available product can be directly used.

The reaction schemes are shown below. In the schemes, is an alkyl group such as a methyl group, an ethyl group and the like, and other symbols are each as defined above. Compound (Ia) and compound (Ib) are encompassed in the aforementioned compound (I), and they show a compound group of compound (I) wherein $R^3$=H, and a compound group of compound (I) wherein $R^2$ and $R^3$ are bonded to each other to form a cyclic group together with the adjacent nitrogen atom, respectively.

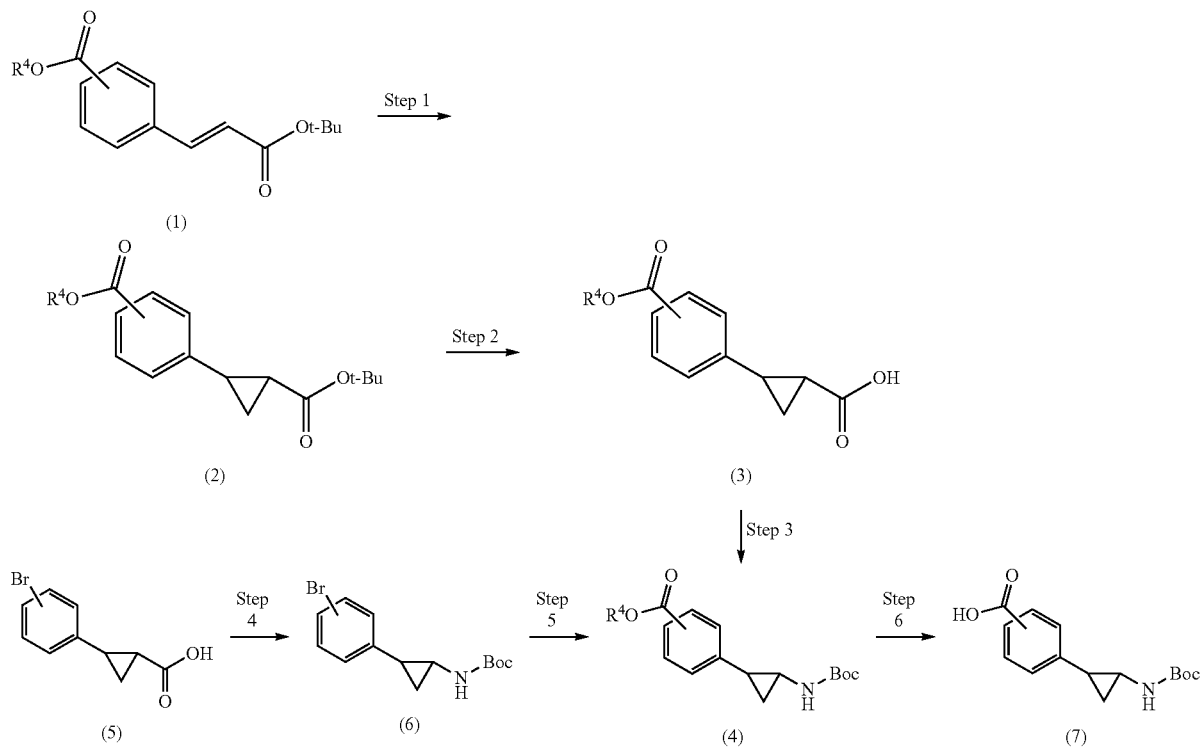

<Reaction scheme 1>

[Step 1]

In this step, compound (2) is produced by reacting trimethylsulfoxonium iodide with a base, and reacting same with compound (1). Compound (1) may be a commercially available product, or can be produced by a method known per se (e.g., J. Org. Chem., 2011, 76, 5061-5073; Org. Biomol. Chem., 2009, 7, 2110-2119) or a method analogous thereto. This reaction is generally performed in an inert solvent and, where necessary, may be performed under an inert gas atmosphere of nitrogen, argon and the like.

Examples of the base include sodium hydride, potassium tert-butoxide, lithium bis(trimethylsilyl)amide, sodium bis (trimethylsilyl)amide, potassium bis(trimethylsilyl)amide, sodium methoxide, sodium ethoxide and the like.

The amount of trimethylsulfoxonium iodide and the base to be used is generally 1-10 molar equivalents relative to compound (1).

Examples of the inert solvent include dimethyl sulfoxide, tetrahydrofuran, dimethoxyethane, 1,4-dioxane, diethyl ether, N,N-dimethylformamide, N,N-dimethylacetamide, acetonitrile, methylene chloride and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 2]

In this step, compound (3) is produced by subjecting compound (2) to a tert-butyl(-t-Bu) group-removal reaction. This reaction is generally performed in the presence of an acid and in an inert solvent. Alternatively, it may be performed using a solvent amount of an acid itself and, where necessary, under an inert gas atmosphere of nitrogen, argon and the like.

As the acid, trifluoroacetic acid, hydrochloric acid, hydrobromic acid, sulfuric acid and hydrofluoric acid can be used. Among these, hydrochloric acid and trifluoroacetic acid are preferable.

The amount of the acid to be used is generally not less than 1 molar equivalent relative to compound (2).

Examples of the inert solvent include methanol, ethanol, isopropanol, ethyl acetate, water, methylene chloride, toluene, benzene, xylene, cyclopentyl methyl ether, tetrahydrofuran, 1,4-dioxane, N,N-dimethylformamide, N,N-dimethylacetamide, acetonitrile and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 3]

In this step, compound (4) is produced by reacting compound (3) with diphenylphosphoryl azide and tert-butyl alcohol. This reaction is generally performed in the presence of a base and in an inert solvent or a solvent amount of tert-butyl alcohol, and may be performed, where necessary, under an inert gas atmosphere of nitrogen, argon and the like.

As the base, triethylamine, diisopropylethylamine, 1,8-diazabicyclo[5.4.0]undec-7-ene, potassium carbonate, cesium carbonate, potassium Cert-butoxide and the like can be used. Among these, triethylamine and diisopropylethylamine are preferable.

The amount of diphenylphosphoryl azide and the base to be used is generally 1-10 molar equivalents relative to compound (3), and the amount of tert-butyl alcohol to be used is generally not less than 1 molar equivalent relative to compound (3).

Examples of the inert solvent include toluene, benzene, xylene, tetrahydrofuran, 1,4-dioxane, N,N-dimethylformamide, N,N-dimethylacetamide, acetonitrile and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 4]

In this step, compound (6) is produced from compound (5) in the same manner as in step 3. Compound (5) may be a commercially available product, or can be produced by a method known per se (e.g., J. Am. Chem. Soc., 2010, 132, 6827-6833; J. Med. Chem., 2009, 52, 1885-1902) or a method analogous thereto.

[Step 5]

In this step, compound (4) is produced by subjecting compound (6) to a carbon monoxide insertion reaction using a palladium catalyst and a subsequent nucleophilic substitution reaction by alcohol. This reaction is performed using a base and a palladium catalyst, and phosphine ligand may be used where necessary. This reaction is generally performed in an inert solvent under a carbon monoxide atmosphere from normal pressure to about 10 atm.

Examples of the palladium catalyst include tetrakis(triphenylphosphine)palladium(O), bis(triphenylphosphine)palladium(II) dichloride, tris(dibenzylideneacetone)dipalladium(O), trans-dichlorobis(tri-o-tolylphosphine)palladium(II), palladium(II) trifluoroacetate, palladium(II) acetate and the like.

Examples of the phosphine ligand include triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like.

Examples of the base include sodium hydroxide, potassium hydroxide, sodium carbonate, potassium carbonate, cesium carbonate, tripotassium phosphate, sodium methoxide, sodium ethoxide, triethylamine, diisopropylethylamine, pyridine, 1,8-diazabicyclo[5.4.0]undec-7-ene and the like.

Examples of the alcohol include methanol, ethanol, 2-propanol, benzyl alcohol and the like.

The amount of the palladium catalyst and phosphine ligand to be used is generally 0.01-2 molar equivalents relative to compound (6), the amount of the base to be used is generally 1-10 molar equivalents relative to compound (6), and the amount of the alcohol to be used is generally not less than 1 molar equivalent relative to compound (6).

Examples of the inert solvent include tetrahydrofuran, dimethoxyethane, 1,4-dioxane, N,N-dimethylformamide, N,N-dimethylacetamide, acetonitrile and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 6]

In this step, compound (7) is produced by subjecting compound (4) to hydrolysis. This reaction is generally performed in the presence of a base and in water or a water-containing solvent, and may be performed, where necessary, under an inert gas atmosphere of nitrogen, argon and the like.

Examples of the base include sodium hydroxide, lithium hydroxide, potassium hydroxide, barium hydroxide, sodium ethoxide, sodium methoxide, sodium hydroperoxide and the like.

The amount of the base to be used is generally 1-1000 molar equivalents relative to compound (4).

Examples of the solvent to be used as the water-containing solvent include tetrahydrofuran, methanol, ethanol, isopropanol, 1,4-dioxane, N,N-dimethylformamide, N,N-dimethylacetamide, acetonitrile, dimethyl sulfoxide, acetone and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

<Reaction scheme 2>

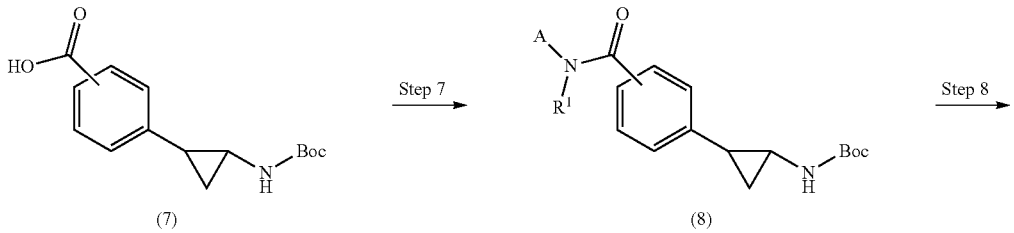

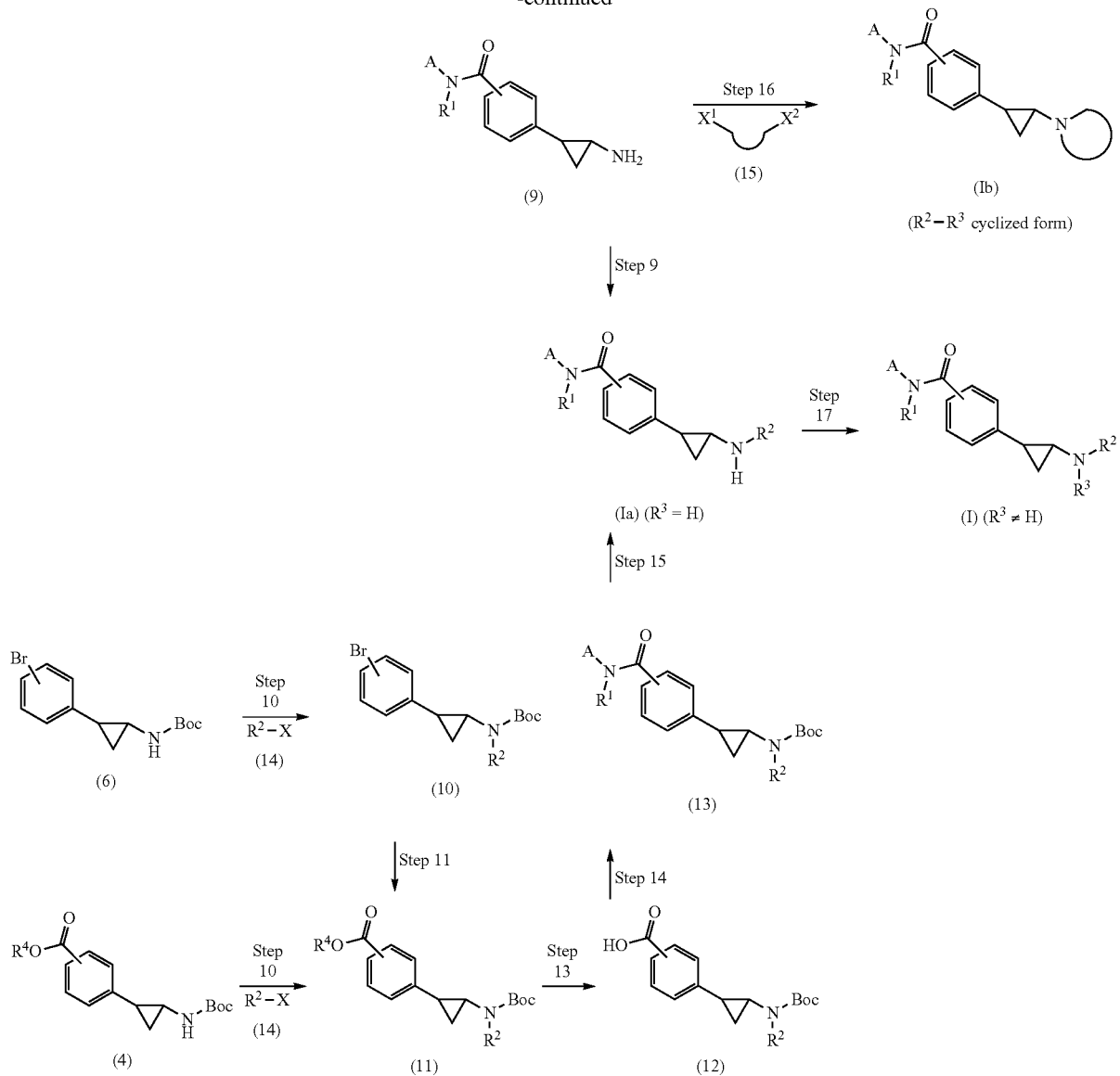

[Step 7]

In this step, compound (8) is produced by reacting compound (7) with amine (AR$^1$NH) and a condensing agent. This reaction is generally performed in the presence of a base and in an inert solvent, and may be performed, where necessary, under an inert gas atmosphere of nitrogen, argon and the like.

As the base, triethylamine, diisopropylethylamine, pyridine, N,N-dimethylaniline, 1,8-diazabicyclo[5.4.0]undec-7-ene and the like can be used. Among these, triethylamine and diisopropylethylamine are preferable.

Examples of the inert solvent include N,N-dimethylformamide, N,N-dimethylacetamide, acetonitrile, ethyl acetate, methylene chloride and the like. Two or more kinds of these solvents may be used in an appropriate ratio.

Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, 0-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like.

The amount of the amine, base and condensing agent to be used is generally 1-10 molar equivalents relative to compound (7).

In this reaction, a suitable condensation accelerator (e.g., 1-hydroxybenzotriazole, N-hydroxysuccinimide, N,N-dimethyl-4-aminopyridine etc.) can be used as necessary. The amount of the condensation accelerator to be used is generally 0.1-10 molar equivalents relative to compound (7).

The reaction temperature is generally about 0-150° C. While the reaction time is not particularly limited, it is generally 0.1-100 hr, preferably 0.5-72 hr.

[Step 8]

In this step, compound (9) is produced by subjecting compound (8) to a tert-butoxycarbonyl group (-Boc)-removal reaction in the same manner as in step 2.

[Step 9]

In this step, compound (Ia) (R$^3$=H) is produced by reacting compound (9) with aldehyde or ketone in the presence of a reducing agent. This reaction is generally performed in the presence of a reducing agent and in an inert solvent, and may be performed, where necessary, under an inert gas atmosphere of nitrogen, argon and the like.

Examples of the reducing agent include sodium triacetoxyborohydride, sodium cyanoborohydride, sodium borohydride, 2-picoline borane complex and the like.

The amount of aldehyde or ketone, and the reducing agent to be used is generally 1-10 molar equivalents relative to compound (9).

Examples of the inert solvent include tetrahydrofuran, methanol, ethanol, isopropanol, 1,4-dioxane, N,N-dimethylformamide, N,N-dimethylacetamide, acetonitrile, methylene chloride, acetic acid, water and the like. Two or more kinds of these solvents may be used in an appropriate ratio.

The reaction temperature is generally about 0-100° C. While the reaction time is not particularly limited, it is generally 0.1-100 hr, preferably 0.5-72 hr.

[Step 10]

In this step, compound (10) is produced by reacting compound (6) with compound (14) ($R^2X$; X is a leaving group such as a halogen atom, a methanesulfonyloxy group, a trifluoromethanesulfonyloxy group and the like) under basic conditions. This reaction is generally performed in the presence of a base and in an inert solvent, and may be performed, where necessary, under an inert gas atmosphere of nitrogen, argon and the like.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and potassium carbonate are preferable.

The amount of compound (14) to be used is generally not less than 1 molar equivalent relative to compound (6), and the amount of the base to be used is generally 0.1-10 molar equivalents relative to compound (6).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 11]

In this step, compound (11) is produced from compound (10) in the same manner as in step 5.

[Step 12]

In this step, compound (11) is produced from compound (4) in the same manner as in step 10.

[Step 13]

In this step, compound (12) is produced from compound (11) in the same manner as in step 6.

[Step 14]

In this step, compound (13) is produced from compound (12) in the same manner as in step 7.

[Step 15]

In this step, compound (Ia) ($R^3$=H) is produced by subjecting compound (13) to a tert-butoxycarbonyl group (-Boc)-removal reaction in the same manner as in step 2.

[Step 16]

In this step, compound (Ib) (wherein $R^2$ and $R^3$ are optionally bonded to each other to form a cyclic group together with the adjacent nitrogen atom) is produced by reacting compound (9) with compound (15) ($X^1$ and $X^2$ are each independently a leaving group such as a halogen atom, a methanesulfonyloxy group, a trifluoromethanesulfonyloxy group and the like) under basic conditions. This reaction is generally performed in the presence of a base and in an inert solvent, and may be performed, where necessary, under an inert gas atmosphere of nitrogen, argon and the like.

As the base, for example, triethylamine, diisopropylethylamine, 1,8-diazabicyclo[5.4.0]undec-7-ene, potassium carbonate, sodium carbonate, cesium carbonate, potassium tert-butoxide, sodium hydroxide and the like can be used. Among these, triethylamine, diisopropylethylamine, potassium carbonate and sodium hydroxide are preferable.

The amount of compound (15) to be used is generally 0.1-10 molar equivalents relative to compound (9), and the amount of the base to be used is generally 1 or more molar equivalents relative to compound (9).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

[Step 17]

In this step, compound (I) ($R^3$=H) is produced from compound (Ia) ($R^3$=H) in the same manner as in step 9 or step 10.

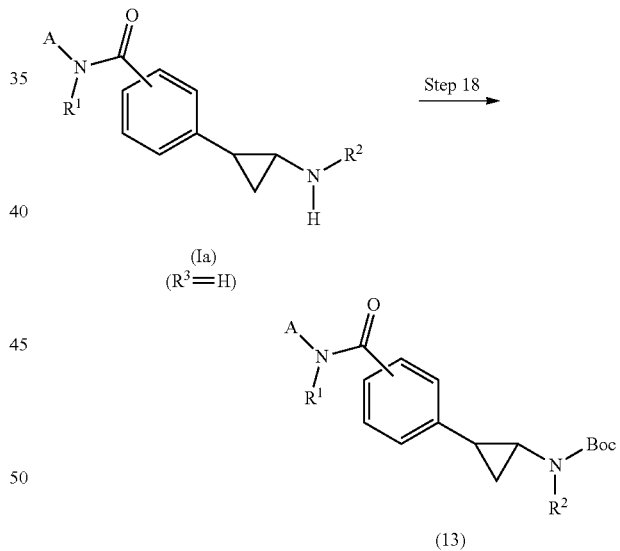

[Step 18]

In this step, compound (13) is produced by reacting compound (Ia) ($R^3$=H) with di-tert-butyl dicarbonate under basic conditions. This reaction is generally performed in the presence of a base and in an inert solvent, and may be performed, where necessary, under an inert gas atmosphere of nitrogen, argon and the like.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine, and potassium carbonate are preferable.

The amount of the di-tert-butyl dicarbonate to be used is generally not less than 1 molar equivalent relative to compound (Ia), and the amount of the base to be used is generally 0.1-10 molar equivalents relative to compound (Ia).

Examples of the inert solvent include tetrahydrofuran, methanol, ethanol, isopropanol, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C. While the reaction time is not particularly limited, it is generally 0.1-100 hr, preferably 0.5-72 hr.

<Reaction scheme 4>

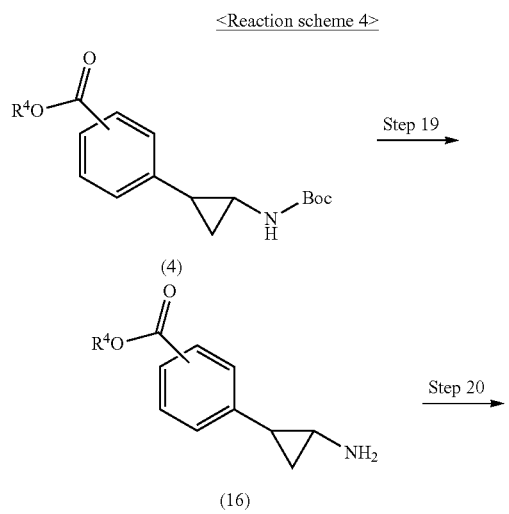

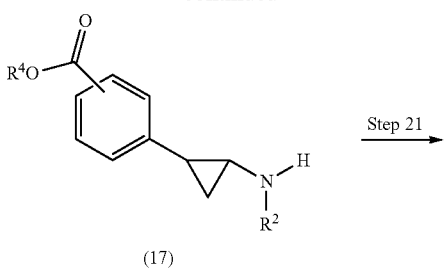

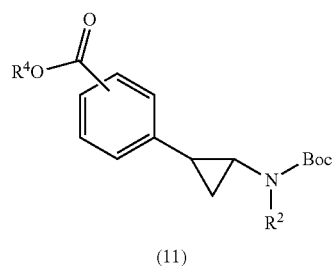

[Step 19]

In this step, compound (16) is produced by subjecting compound (4) to a tert-butoxycarbonyl group (-Boc)-removal reaction in the same manner as in step 2.

[Step 20]

In this step, compound (17) is produced from compound (16) in the same manner as in step 9.

[Step 21]

In this step, compound (11) is produced from compound (17) in the same manner as in step 18.

<Reaction scheme 5>

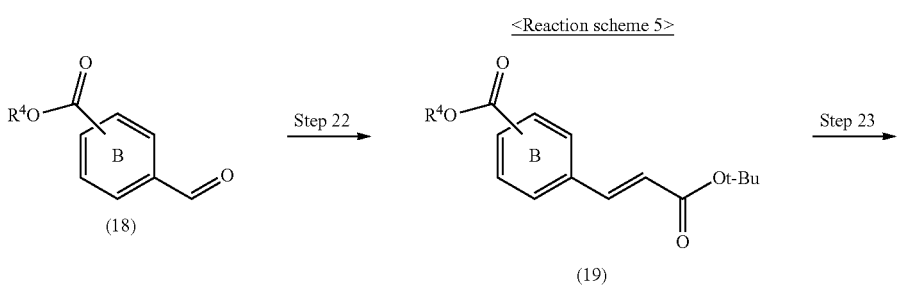

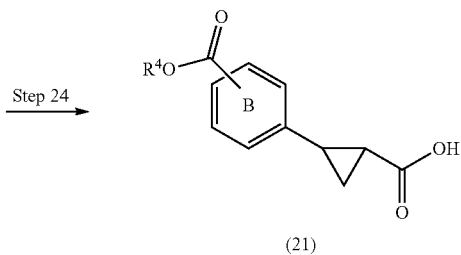

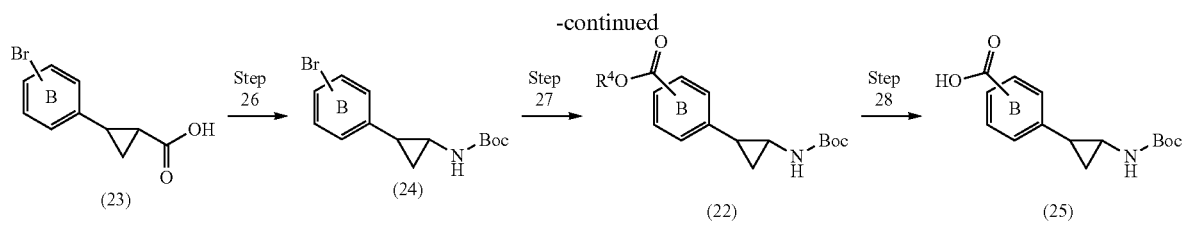

[Step 22]

In this step, compound (19) is produced by reacting compound (18) with tert-butyl diethylphosphonoacetate. This reaction is generally performed in the presence of a base and in an inert solvent, and may be performed, where necessary, under an inert gas atmosphere of nitrogen, argon and the like.

As the base, triethylamine, diisopropylethylamine, 1,8-diazabicyclo[5.4.0]undec-7-ene, potassium carbonate, cesium carbonate, sodium hydride, sodium methoxide, potassium tert-butoxide and the like can be used. Among these, 1,8-diazabicyclo[5.4.0]undec-7-ene and triethylamine are preferable, and lithium chloride may be used in combination.

The amount of tert-butyl diethylphosphonoacetate and the base to be used is generally 1-10 molar equivalents relative to compound (18), and the amount of lithium chloride to be used is generally not less than 1 molar equivalent relative to compound (18).

Examples of the inert solvent include methanol, ethanol, isopropanol, tetrahydrofuran, 1,2-dimethoxyethane, dimethyl sulfoxide and the like. Two or more kinds of these solvents may be used in an appropriate ratio.

The reaction temperature is generally about 0-100° C. While the reaction time is not particularly limited, it is generally 0.1-100 hr, preferably 0.5-24 hr.

[Step 23] In this step, compound (20) is produced from compound (19) in the same manner as in step 1.

[Step 24]

In this step, compound (21) is produced from compound (20) in the same manner as in step 2.

[Step 25]

In this step, compound (22) is produced from compound (21) in the same manner as in step 3.

[Step 26]

In this step, compound (24) is produced from compound (23) in the same manner as in step 4.

[Step 27]

In this step, compound (22) is produced from compound (24) in the same manner as in step 5.

[Step 28] In this step, compound (25) is produced from compound (22) in the same manner as in step 6.

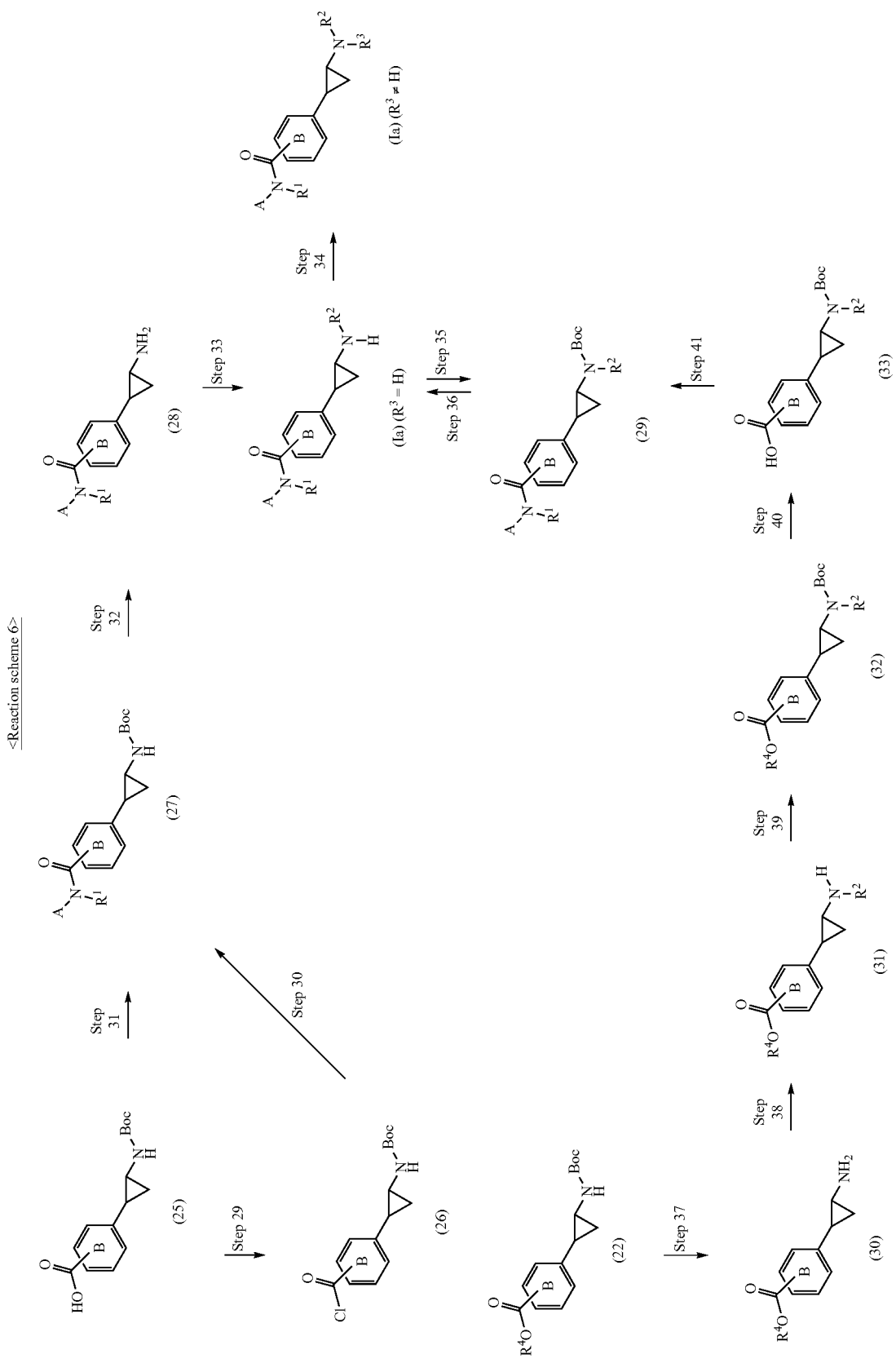

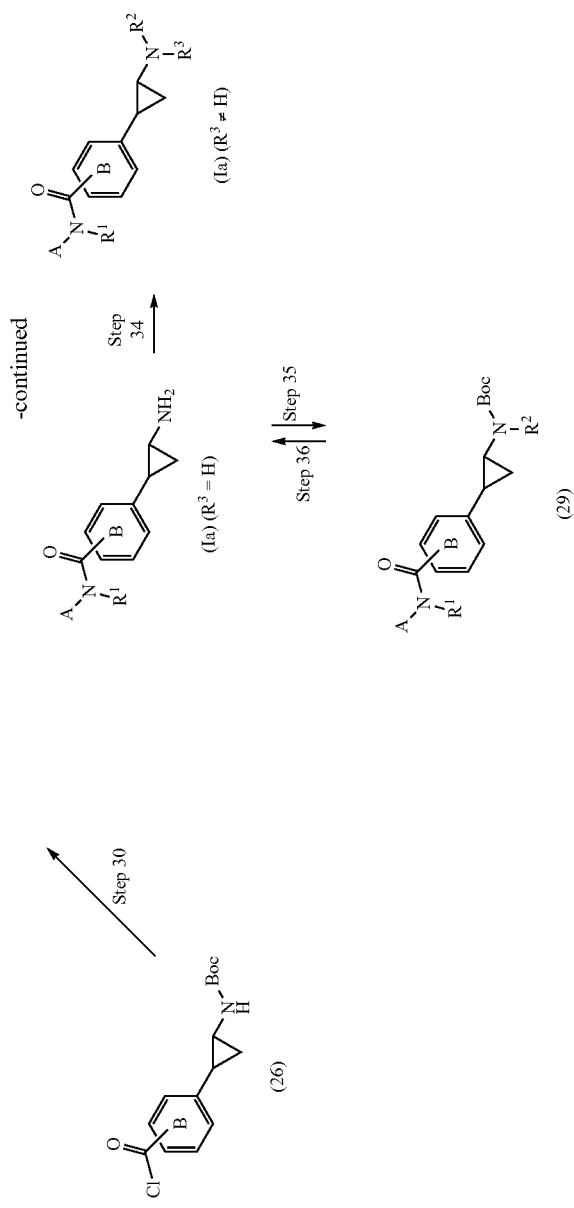

[Step 29]

In this step, compound (26) is produced by chlorinating compound (25). This reaction is generally performed in an inert solvent, and may be performed, where necessary, under an inert gas atmosphere of nitrogen, argon and the like.

As the chlorinating reagent, thionyl chloride, phosphorus trichloride, phosphorus pentachloride, sulfuryl chloride, oxalyl chloride and the like can be used. Among these, thionyl chloride and oxalyl chloride are preferable, and N,N-dimethylformamide can be used as a catalyst.

The amount of the chlorinating reagent to be used is generally 1-10 molar equivalents relative to compound (25).

Examples of the inert solvent include tetrahydrofuran, methylene chloride, toluene and the like. Two or more kinds of these solvents may be used in an appropriate ratio.

The reaction temperature is generally about 0-100° C. While the reaction time is not particularly limited, it is generally 0.1-100 hr, preferably 0.1-24 hr.

[Step 30]

In this step, compound (27) is produced by reacting compound (26) with amine (AR$^1$NH). This reaction is generally performed in the presence of a base and in an inert solvent, and may be performed, where necessary, under an inert gas atmosphere of nitrogen, argon and the like.

As the base, triethylamine, diisopropylethylamine, pyridine, N,N-dimethylaniline, 1,8-diazabicyclo[5.4.0]undec-7-ene and the like can be used. Among these, triethylamine and diisopropylethylamine are preferable.

Examples of the inert solvent include N,N-dimethylformamide, N,N-dimethylacetamide, acetonitrile, ethyl acetate, tetrahydrofuran, methylene chloride, toluene and the like. Two or more kinds of these solvents may be used in an appropriate ratio.

The amount of the amine and base to be used is generally 1-10 molar equivalents relative to compound (26).

The reaction temperature is generally about 0-150° C. While the reaction time is not particularly limited, it is generally 0.1-100 hr, preferably 0.5-72 hr.

[Step 31]

In this step, compound (27) is produced from compound (25) in the same manner as in step 7.

[Step 32]

In this step, compound (28) is produced from compound (27) in the same manner as in step 8.

[Step 33]

In this step, compound (Ia) (R$^3$=H) is produced from compound (28) in the same manner as in step 9.

[Step 34]

In this step, compound (I) (R$^3$≠H) is produced from compound (Ia) (R$^3$=H) in the same manner as in step 9.

[Step 35]

In this step, compound (29) is produced from compound (Ia) (R$^3$=H) in the same manner as in step 18.

[Step 36]

In this step, compound (Ia) (R$^3$=H) is produced by subjecting compound (29) to a tert-butoxycarbonyl group (-Boc)-removal reaction in the same manner as in step 2.

[Step 37]

In this step, compound (30) is produced by subjecting compound (22) to a tert-butoxycarbonyl group (-Boc)-removal reaction in the same manner as in step 2.

[Step 38]

In this step, compound (31) is produced from compound (30) in the same manner as in step 9.

[Step 39]

In this step, compound (32) is produced from compound (31) in the same manner as in step 18.

[Step 40]

In this step, compound (33) is produced from compound (32) in the same manner as in step 6.

[Step 41] In this step, compound (29) is produced from compound (33) in the same manner as in step 7.

It is also possible to produce a compound encompassed in the present invention by further applying substituent introduction or functional group conversion to compound (I) according to a means known per se. Substituent introduction and functional group conversion are performed according to known conventional methods such as conversion to carboxy group by ester hydrolysis, conversion to carbamoyl group by amidation of carboxy group, conversion to hydroxymethyl group by reduction of carboxy group, conversion to alcohol compound by reduction or alkylation of carbonyl group, reductive amination of carbonyl group, oximation of carbonyl group, acylation, ureation, sulfonylation or alkylation of amino group, amination of activated halogen with amine, conversion to amino group by reduction of nitro group, and acylation, carbamation, sulfonylation or alkylation of hydroxy group. When a reactive substituent causing an unintended reaction during substituent introduction and functional group conversion is present, a protecting group may be introduced in advance into the reactive substituent as necessary according to a means known per se, the object reaction is performed and the protecting group is removed according to a means known per se, whereby compounds encompassed in the present invention can be produced.

In each of the above-mentioned reactions, when the starting compounds have an amino group, a carboxyl group, a hydroxy group or a carbonyl group as a substituent, such groups may be protected with the protecting groups generally used in peptide chemistry, etc. In such case, if necessary, such protecting groups can be removed after the reactions to obtain the objective compounds.

Examples of the amino-protecting group include formyl, and $C_{1-6}$ alkylcarbonyl (e.g., acetyl, ethylcarbonyl etc.), phenylcarbonyl, $C_{1-6}$ alkoxy-carbonyl (e.g., methoxycarbonyl, ethoxycarbonyl, tert-butoxycarbonyl etc.), phenyloxycarbonyl, $C_{7-10}$ aralkyl-carbonyl (e.g., benzylcarbonyl etc.), trityl, phthaloyl, N,N-dimethylaminomethylene and the like, each of which optionally has substituent(s). Examples of the substituent of the "amino-protecting group" include a halogen atom (e.g., fluorine, chlorine, bromine, iodine), $C_{1-6}$ alkyl-carbonyl (e.g., methylcarbonyl, ethylcarbonyl, butylcarbonyl etc.), a nitro group and the like, wherein the number of the substituents is 1 to several (e.g., 3).

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 halogen atoms, a $C_{1-6}$ alkoxy group, a nitro group etc.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 halogen atoms, a $C_{1-6}$ alkyl group, a $C_{1-5}$ alkoxy group, a nitro group etc.

Examples of the carbonyl-protecting group include cyclic acetal (e.g., 1,3-dioxane), non-cyclic acetal (e.g., di-$C_{1-5}$ alkyl acetal) and the like.

Removal of the above-mentioned protecting group can be performed according to a known method, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be used.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel.

In the enantiomer separation conditions by HPLC or SFC (Supercritical Fluid Chromatography) of racemate compounds, an optical isomer corresponding to one having a longer retention time is indicated as retention time long, and an optical isomer corresponding to one having a shorter retention time is indicated as retention time short.

$^1$H NMR (proton nuclear magnetic resonance spectrum) was measured by Fourier-transform NMR. For the analysis, ACD/SpecManager (trade name) and the like were used. Very mild peaks showing protons of hydroxyl group, amino group, hydrochloride and the like are not described.

MS (mass spectrum) was measured by LC/MS (liquid chromatography mass spectrometer). As the ionization method, ESI (ElectroSpray Ionization) method or APCI (Atmospheric Pressure Chemical Ionization) method was used as API (Atmospheric Pressure Ionization), and the measurement was performed in a positive mode (API+) or negative mode (API−). The data indicates measured values (found). Generally, a molecular ion peak is observed, but an ion peak added with a solvent such as acetonitrile ($CH_3CN$) and the like or sodium ion (Na+) is sometimes observed. When a compound having a tert-butoxycarbonyl group (-Boc) is used, a peak free of a tert-butoxycarbonyl group or tert-butyl group (-tert-Bu) may be observed as a fragment ion. In addition, when a compound having a hydroxyl group (—OH) is used, a peak free of $H_2O$ may be observed as a fragment ion. In the case of a salt, generally, a molecular ion peak of a free form or a fragment ion peak is observed.

In the following Examples, the following abbreviations are used.

mp: melting point, $CDCl_3$: deuterated chloroform, DMSO-$d_6$: deuterated dimethyl sulfoxide, TFA: trifluoroacetic acid, DMSO: dimethyl sulfoxide, DMF: N,N-dimethylfomamide, THF: tetrahydrofuran.

Example 1

4-(trans-2-aminocyclopropyl)-N-phenylbenzamide hydrochloride

A) ethyl 4-(trans-2-(tert-butoxycarbonyl)cyclopropyl)benzoate

To a suspension of sodium hydride (60% in oil) (374 mg) in DMSO (50 mL) was added trimethylsulfoxonium iodide (2.06 g), and the mixture was stirred at room temperature for 1 hr. To the reaction mixture was added ethyl 4-((1E)-3-tert-butoxy-3-oxoprop-1-en-1-yl)benzoate (2.15 g) described in a document (J. Org. Chem. 2011, 76, 5061-5073.), and the mixture was stirred under a nitrogen atmosphere at 100-110° C. for 2 days. Water (40 mL) was added to the reaction mixture, and the mixture was extracted 3 times with ethyl acetate (80 mL each time). The extracts were combined, washed twice with saturated brine (60 mL each time), dried over anhydrous sodium sulfate, and concentrated under reduced pressure. The residue was purified by silica gel column chromatography (petroleum ether/ethyl acetate) to give the title compound (1.42 g).

$^1$H NMR (400 MHz, $CDCl_3$) δ 1.36 (3H, t, J=6.8 Hz), 1.46 (9H, s), 1.55-1.62 (2H, m), 1.81-1.94 (1H, m), 2.42-2.51 (1H, m), 4.35 (2H, q, J=7.2 Hz), 7.12 (2H, d, J=8.0 Hz), 7.93 (2H, d, J=8.4 Hz).

B) trans-2-(4-(ethoxycarbonyl)phenyl)cyclopropanecarboxylic acid

A solution of ethyl 4-(trans-2-(tert-butoxycarbonyl)cyclopropyl)benzoate (300 mg) in dichloromethane (5 mL) was cooled to 0° C., TFA (3.07 g) was added, and the mixture was stirred at room temperature for 3 hr. Water (30 mL) was added to the reaction mixture, and the mixture was extracted 3 times with ethyl acetate (40 mL each time). The extracts were combined, washed with saturated brine (40 mL), dried over anhydrous sodium sulfate, and concentrated under reduced pressure. The obtained residue was combined with a residue separately prepared by a similar operation from ethyl 4-(trans-2-(tert-butoxycarbonyl)cyclopropyl)benzoate (1.10 g), and the mixture was purified by silica gel column chromatography (petroleum ether/ethyl acetate) to give the title compound (987 mg).

$^1$H NMR (400 MHz, DMSO-$d_6$) δ 1.29 (3H, t, J=7.2 Hz), 1.33-1.42 (1H, m), 1.42-1.51 (1H, m), 1.83-1.93 (1H, m), 2.41-2.49 (1H, m), 4.27 (2H, q, J=7.2 Hz), 7.29 (2H, d, J=8.8 Hz), 7.83 (2H, d, J=8.4 Hz), 12.38 (1H, brs).

C) ethyl 4-(trans-2-((tert-butoxycarbonyl)amino)cyclopropyl)benzoate

To a solution of trans-2-(4-(ethoxycarbonyl)phenyl)cyclopropanecarboxylic acid (1.30 g) in anhydrous tert-butyl alcohol (20 mL) were added diphenylphosphoryl azide (2.29 g) and triethylamine (842 mg) at room temperature, and the mixture was stirred at 80-90° C. for 3 hr. The obtained reaction mixture was combined with a reaction mixture separately prepared by a similar method from trans-2-(4-(ethoxycarbonyl)phenyl)cyclopropanecarboxylic acid (1.30 g). Water (60 mL) was added and the mixture was extracted 3 times with ethyl acetate (60, 80, 80 mL). The extracts were combined, washed successively with saturated aqueous sodium hydrogen carbonate solution (80 mL) and saturated brine (80 mL), dried over anhydrous sodium sulfate, and concentrated under reduced pressure. The residue was purified by silica gel column chromatography (petroleum ether/ethyl acetate), and washed with a mixed solvent of petroleum ether (40 mL) and ethyl acetate (2 mL) to give the title compound (1.37 g).

MS (API+): [M−Boc+H]$^+$ 205.8.

D) 4-(trans-2-((tert-butoxycarbonyl)amino)cyclopropyl)benzoic acid

Ethyl 4-(trans-2-((tert-butoxycarbonyl)amino)cyclopropyl)benzoate (500 mg) was dissolved in ethanol (10 mL), a 4 mol/L aqueous sodium hydroxide solution (3.0 mL) was added at room temperature, and the mixture was stirred at room temperature for 3 hr. To the reaction mixture were added water (30 mL) and ethyl acetate (30 mL), and the mixture was stirred well. The organic layer was extracted with water (30 mL). The aqueous layers were combined, adjusted to pH 3-4 with 1 mol/L hydrochloric acid, and extracted 3 times with ethyl acetate (40 mL each time). The extracts were combined, washed with saturated brine (40 mL), dried over anhydrous sodium sulfate, and concentrated under reduced pressure to give the title compound (440 mg).

$^1$H NMR (400 MHz, DMSO-d$_6$) δ 1.14-1.24 (2H, m), 1.38 (9H, s), 1.93-2.01 (1H, m), 2.60-2.78 (1H, m), 7.19 (2H, d, J=8.4 Hz), 7.33 (1H, brs), 7.82 (2H, d, J=8.4 Hz), 12.79 (1H, brs).

E) tert-butyl (trans-2-(4-(phenylcarbamoyl)phenyl)cyclopropyl)carbamate 4-(trans-2-((tert-Butoxycarbonyl)amino)cyclopropyl)benzoic acid (300 mg), N-ethyl-N'-(3-dimethylaminopropyl)carbodiimide hydrochloride (250 mg) and 1-hydroxybenzotriazole (176 mg) were dissolved in anhydrous DMF (5 mL), aniline (121 mg) and triethylamine (218 mg) were added, and the mixture was stirred at room temperature for 4 hr. Water (30 mL) was added to the reaction mixture, and the mixture was extracted 3 times with ethyl acetate (30, 50, 50 mL). The extracts were combined, washed 3 times with saturated brine (40 mL each time), dried over anhydrous sodium sulfate, and concentrated under reduced pressure. The residue was purified by silica gel column chromatography (petroleum ether/ethyl acetate) and washed with a mixed solvent of petroleum ether (40 mL) and ethyl acetate (2 mL) to give the title compound (233 mg).

MS (API+): [M+H]$^+$ 353.1.

F) 4-(trans-2-aminocyclopropyl)-N-phenylbenzamide hydrochloride tert-Butyl (trans-2-(4-(phenylcarbamoyl)phenyl)cyclopropyl)carbamate (100 mg) was suspended in 10% hydrogen chloride/methanol solution (10.0 mL), and the suspension was stirred at room temperature for 7 hr. The reaction mixture was concentrated under reduced pressure to give the title compound (83 mg).

$^1$H NMR (300 MHz, Methanol-d$_4$) δ 1.14-1.93 (2H, m), 2.49 ($^1$H, brs), 2.95 (1H, brs), 6.80-8.26 (9H, m).

Example 2

4-(trans-2-aminocyclopropyl)-N-benzylbenzamide hydrochloride

A) tert-butyl (trans-2-(4-(benzylcarbamoyl)phenyl)cyclopropyl)carbamate

To a solution of 4-(trans-2-((tert-butoxycarbonyl) amino)cyclopropyl)benzoic acid (52.2 mg) and benzylamine (24.7 μL) in DMF (0.94 mL) were added 1-hydroxybenzotriazole (38.2 mg) and N-ethyl-N'-(3-dimethylaminopropyl)carbodiimide hydrochloride (54.1 mg). The mixture was stirred at room temperature overnight, poured into a saturated aqueous ammonium chloride solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give the title compound (66.1 mg).

MS (API+): [M+H]$^+$ 367.3.

B) 4-(trans-2-aminocyclopropyl)-N-benzylbenzamide hydrochloride tert-Butyl (trans-2-(4-(benzylcarbamoyl)phenyl)cyclopropyl)carbamate (66.1 mg) was dissolved in a 4 mol/L hydrogen chloride/ethyl acetate solution (1 mL), the mixture was stirred at room temperature for 2 hr, and the solvent was evaporated under reduced pressure. The residue was recrystallized from methanol/diisopropy ether to give the title compound (44.2 mg).

$^1$H NMR (300 MHz, DMSO-d$_6$) δ 1.20-1.32 (1H, m), 1.33-1.45 (1H, m), 2.23-2.38 (1H, m), 2.79-2.92 (1H, m), 4.47 (2H, d, =5.8 Hz), 7.20-7.38 (7H, m), 7.83 (2H, d, J=8.3 Hz), 8.13 (3H, brs), 9.00 (1H, t, J=5.8 Hz).

Example 3

4-(trans-2-aminocyclopropyl)-N-methyl-N-phenylbenzamide hydrochloride

A) tert-butyl (trans-2-(4-(methyl(phenyl)carbamoyl)phenyl)cyclopropyl)carbamate To a solution of 4-(trans-2-((tert-butoxycarbonyl)amino)cyclopropyl)benzoic acid (49.5 mg) and N-methylaniline (23.2 μL) in DMF (0.89 mL) were added 1-hydroxybenzotriazole (36.2 mg) and N-ethyl-N'-(3-dimethylaminopropyl)carbodiimide hydrochloride (51.3 mg). The mixture was stirred at 60° C. overnight, and poured into 0.5 mol/L hydrochloric acid, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give the title compound (65.5 mg).

MS (API+): [M+H]$^-$ 367.3.

B) 4-(trans-2-aminocyclopropyl)-N-methyl-N-phenylbenzamide hydrochloride tert-Butyl (trans-2-(4-(methyl(phenyl)carbamoyl)phenyl)cyclopropyl)carbamate (65.5 mg) was dissolved in a 4 mol/L hydrogen chloride/ethyl acetate solution (1 mL), the mixture was stirred at room temperature overnight, and the solvent was evaporated under reduced pressure. The residue was dissolved in methanol, and basified with sodium hydrogen carbonate, and excess sodium hydrogen carbonate was filtered off. The filtrate was concentrated under reduced pressure, and the residue was purified by silica gel column chromatography (NH, hexane/ethyl acetate). A 4 mol/L hydrogen chloride/ethyl acetate solution was added, and the precipitated crystals were collected by filtration to give the title compound (24.9 mg).

¹H NMR (300 MHz, DMSO-d$_6$) δ 1.10-1.22 (1H, m), 1.26-1.39 (1H, m), 2.12-2.25 (1H, m), 2.84-3.01 (1H, m), 3.35 (3H, s), 6.99 (2H, d, J=7.7 Hz), 7.12-7.20 (5H, m), 7.22-7.30 (2H, m), 8.26 (3H, brs).

Example 4

4-(trans-2-aminocyclopropyl)-N-(3-(trifluoromethyl) phenyl)benzamide hydrochloride To a solution of 4-(trans-2-((tert-butoxycarbonyl)amino) cyclopropyl)benzoic acid (48.0 mg) and 3-aminobenzotrifluoride (25.8 μL) in DMF (0.87 mL) were added 1-hydroxybenzotriazole (35.1 mg) and N-ethyl-N'-(3-dimethylaminopropyl)carbodiimide hydrochloride (49.8 mg). The mixture was stirred at room temperature overnight, and poured into saturated aqueous ammonium chloride solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give a mixture (105.6 mg) containing tert-butyl (trans-2-(4-((3-(trifluoromethyl)phenyl)carbamoyl)-phenyl)cyclopropyl)carbamate. A part (66.1 mg) of the obtained mixture was dissolved in 4 mol/L hydrogen chloride/ethyl acetate solution (1 mL), and the mixture was stirred at room temperature overnight. The solvent was evaporated under reduced pressure. The residue was dissolved in methanol, and basified with sodium hydrogen carbonate, and excess sodium hydrogen carbonate was filtered off. The filtrate was concentrated under reduced pressure, and the residue was purified by silica gel column chromatography (NH, hexane/ethyl acetate). A 4 mol/L hydrogen chloride/ethyl acetate solution was added and the solvent was evaporated under reduced pressure. The residue was recrystallized from methanol/diisopropy ether to give the title compound (14.2 mg).

¹H NMR (300 MHz, DMSO-d$_6$) δ 1.24-1.36 (1H, m), 1.39-1.50 (1H, m), 2.32-2.44 (1H, m), 2.88-2.94 (1H, m), 7.33 (2H, d, J=8.4 Hz), 7.45 (1H, d, J=7.7 Hz), 7.60 (1H, dd, J=8.3, 7.7 Hz), 7.94 (2H, d, J=8.3 Hz), 8.06 (1H, d, J=8.3 Hz), 8.28 (1H, brs), 8.26 (3H, s), 10.52 (1H, s).

Example 5

4-(trans-2-aminocyclopropyl)-N-(1H-pyrazol-4-yl) benzamide dihydrochloride

A) tert-butyl (trans-2-(4-(1H-pyrazol-4-ylcarbamoyl)phenyl)cyclopropyl)carbamate To a solution of 4-(trans-2-((tert-butoxycarbonyl)amino) cyclopropyl)benzoic acid (50.7 mg) and 1H-pyrazol-4-amine (18.2 mg) in DMF (0.91 mL) were added 1-hydroxybenzotriazole (37.1 mg) and N-ethyl-N'-(3-dimethylaminopropyl)carbodiimide hydrochloride (52.6 mg). The mixture was stirred at room temperature overnight, and poured into saturated aqueous ammonium chloride solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by silica gel column chromatography (hexane/ethyl acetate) to give the title compound (56.3 mg).

MS (API+): [M+H]$^+$ 343.3.

B) 4-(trans-2-aminocyclopropyl)-N-(1H-pyrazol-4-yl)benzamide dihydrochloride tert-Butyl (trans-2-(4-(1H-pyrazol-4-ylcarbamoyl)phenyl)cyclopropyl)carbamate (56.3 mg) was dissolved in a 4 mol/L hydrogen chloride/ethyl acetate solution (1 mL), the mixture was stirred at room temperature overnight, and the solvent was evaporated under reduced pressure. The residue was recrystallized from methanol/diisopropy ether to give the title compound (32.3 mg).

¹H NMR (300 MHz, DMSO-d$_6$) δ 1.25-1.35 (1H, m), 1.42-1.52 (1H, m), 2.37-2.46 (1H, m), 2.85-2.96 (1H, m), 7.30 (2H, d, J=8.3 Hz), 7.86 (2H, s), 7.91 (2H, d, J=8.3 Hz), 8.52 (3H, d, J=3.5 Hz), 10.43 (1H, s).

Anal. Calcd for $C_{13}H_{16}Cl_2N_4O \cdot 0.2H_2O$: C, 48.98; H, 5.19; N, 17.57.

Found: C, 48.84; H, 5.30; N, 17.59.

Example 6

4-(trans-2-aminocyclopropyl)-N-cyclohexylbenzamide hydrochloride

A) tert-butyl (trans-2-(4-(cyclohexylcarbamoyl)phenyl)cyclopropyl)carbamate

To a solution of 4-(trans-2-((tert-butoxycarbonyl)amino) cyclopropyl)benzoic acid (38.8 mg) and cyclohexylamine (19.2 μL) in DMF (0.70 mL) were added 1-hydroxybenzotriazole (28.4 mg) and N-ethyl-N'-(3-dimethylaminopropyl) carbodiimide hydrochloride (40.2 mg). The mixture was stirred at room temperature for 3 hr, and poured into 0.5 mol/L hydrochloric acid, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give the title compound (48.9 mg).

MS (API+): [M+H]$^+$ 359.3.

B) 4-(trans-2-aminocyclopropyl)-N-cyclohexylbenzamide hydrochloride tert-Butyl (trans-2-(4-(cyclohexylcarbamoyl)phenyl)cyclopropyl)carbamate (48.9 mg) was dissolved in a 4 mol/L hydrogen chloride/cyclopentyl methyl ether solution (1 mL), the mixture was stirred at room temperature for 2 hr, and the solvent was evaporated under reduced pressure. The residue was recrystallized from methanol/diisopropy ether to give the title compound (30.3 mg).

¹H NMR (300 MHz, DMSO-d$_6$) δ 1.03-1.19 (1H, m), 1.20-1.40 (6H, m), 1.57-1.65 (1H, m), 1.67-1.84 (4H, m), 2.23-2.31 (1H, m), 2.77-2.90 (1H, m), 3.67-3.80 (1H, m), 7.20 (2H, d, J=8.3 Hz), 7.77 (2H, d, J=8.3 Hz), 7.94 (3H, brs), 8.13 (1H, d, J=7.9 Hz).

Example 7

(4-(trans-2-aminocyclopropyl)phenyl)(piperidin-1-yl)methanone hydrochloride

A) tert-butyl (trans-2-(4-(piperidin-1-ylcarbonyl) phenyl)cyclopropyl)carbamate

To a solution of 4-(trans-2-((tert-butoxycarbonyl)amino) cyclopropyl)benzoic acid (50.7 mg) and piperidine (21.7 μL)

in DMF (0.91 mL) were added 1-hydroxybenzotriazole (37.1 mg) and N-ethyl-N'-(3-dimethylaminopropyl)carbodiimide hydrochloride (52.6 mg). The mixture was stirred at room temperature for 3 hr, and poured into 0.5 mol/L hydrochloric acid, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give the title compound (46.9 mg).

MS (API+): [M+H]$^+$ 345.2.

B) (4-(trans-2-aminocyclopropyl)phenyl) (piperidin-1-yl)methanone hydrochloride tert-Butyl (trans-2-(4-(piperidin-1-ylcarbonyl)phenyl)cyclopropyl)carbamate (46.9 mg) was dissolved in a 4 mol/L hydrogen chloride/cyclopentyl methyl ether solution (1 mL), the mixture was stirred at room temperature for 2 hr, and the solvent was evaporated under reduced pressure to give the title compound (36.5 mg).

$^1$H NMR (300 MHz, DMSO-d$_6$) δ 1.35-1.67 (8H, m), 2.24-2.38 (1H, m), 2.78-2.91 (1H, m), 3.11-3.44 (2H, m), 3.47-3.68 (2H, m), 7.21 (2H, d, J=8.3 Hz), 7.29 (2H, d, J=8.3 Hz), 8.25 (3H, brs).

Example 8

4-(trans-2-((cyclopropylmethyl)amino)cyclopropyl)-N-phenylbenzamide hydrochloride 4-(trans-2-Aminocyclopropyl)-N-phenylbenzamide hydrochloride (61.9 mg) and sodium hydrogen carbonate (36.0 mg) were dissolved in THF (0.54 mL)/methanol (0.54 mL), and cyclopropanecarbaldehyde (20.8 μL) was added. The mixture was stirred at 60° C. for 2 hr, and sodium borohydride (16.2 mg) was added under ice-cooling. The mixture was stirred at room temperature for 1 hr, and poured into saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (NH, hexane/ethyl acetate), a 4 mol/L hydrogen chloride/cyclopentyl methyl ether solution (0.54 mL) was added, and the solvent was evaporated under reduced pressure. The residue was recrystallized from methanol/diisopropy ether to give the title compound (24.0 mg).

$^1$H NMR (300 MHz, DMSO-d$_6$) δ 0.28-0.41 (2H, m), 0.51-0.63 (2H, m), 0.97-1.12 (1H, m), 1.28-1.45 (1H, m), 1.46-1.67 (1H, m), 2.52-2.62 (1H, m), 2.87-3.09 (3H, m), 7.02-7.14 (1H, m), 7.27-7.40 (4H, m), 7.77 (2H, d, J=8.2 Hz), 7.91 (2H, d, J=8.2 Hz), 9.14 (2H, brs), 10.19 (1H, s).

Example 9

4-(trans-2-aminocyclopropyl)-N-benzyl-N-methyl-benzamide hydrochloride

A) tert-butyl (trans-2-(4-(benzyl(methyl)carbamoyl)phenyl)cyclopropyl)carbamate

To a mixture of 4-(trans-2-((tert-butoxycarbonyl) amino)cyclopropyl)benzoic acid (144 mg), N-methylbenzylamine (94 mg) and triethylamine (210 mg), O-(7-azabenzotriazol-1-yl)-N,N,N',N'-tetramethyluronium hexafluorophosphate (395 mg) was added under ice-cooling, and the mixture was stirred at room temperature for 6 hr. To the reaction mixture was added a saturated aqueous sodium hydrogen carbonate solution under ice-cooling, and the mixture was extracted with ethyl acetate. The extracts were combined, is washed with a saturated aqueous sodium hydrogen carbonate solution and saturated brine, dried over anhydrous sodium sulfate, and concentrated under reduced pressure. The residue was purified by silica gel column chromatography (hexane/ethyl acetate) to give the title compound (193 mg).

MS (API+): [M+H]$^+$ 381.2.

B) 4-(trans-2-aminocyclopropyl)-N-benzyl-N-methylbenzamide hydrochloride

Under ice-cooling, tert-butyl (trans-2-(4-(benzyl(methyl)carbamoyl)phenyl)cyclopropyl)carbamate (190 mg) was suspended in 4 mol/L hydrogen chloride/cyclopentyl methyl ether solution (4 mL), and the suspension was stirred at room temperature overnight. The reaction mixture was concentrated under reduced pressure. To the residue was added ethyl acetate and the mixture was concentrated under reduced pressure to give the title compound (157 mg).

$^1$H NMR (300 MHz, DMSO-d$_6$) δ 1.17-1.43 (2H, m), 2.22-2.31 (1H, m), 2.77-2.96 (3H, m), 4.37-4.78 (2H, m), 7.10-7.45 (7H, m), 7.82-8.26 (2H, m).

Example 10

N-benzyl-4-(trans-2-((cyclopropylmethyl)amino)cyclopropyl)-N-methylbenzamide hydrochloride 4-(trans-2-Aminocyclopropyl)-N-benzyl-N-methylbenzamide hydrochloride (157 mg) and sodium hydrogen carbonate (45.8 mg) were dissolved in THF (1.5 mL)/methanol (1.5 mL), and cyclopropanecarbaldehyde (53.7 mg) was added. The mixture was stirred at 60° C. for 1 hr under a nitrogen atmosphere, and sodium borohydride (46.9 mg) was added under ice-cooling. The mixture was stirred for 1 hr under ice-cooling, saturated aqueous sodium hydrogen carbonate solution was added under ice-cooling, and the mixture was extracted with diethyl ether. The extract was washed with saturated brine, and dried over anhydrous sodium sulfate. Ethyl acetate (5 mL) was added, and the mixture was concentrated under reduced pressure until the total amount of the solution became about 2 mL. The residue was purified by silica gel column chromatography (NH, hexane/ethyl acetate), a 4 mol/L hydrogen chloride/cyclopentyl methyl ether solution (1.24 mL) was added, and the solvent was evaporated under reduced pressure to give the title compound (114.3 mg).

$^1$H NMR (300 MHz, CD$_3$OD) δ 0.34-0.53 (2H, m), 0.62-0.79 (2H, m), 1.04-1.24 (1H, m), 1.38-1.51 (1H, m), 1.52-1.69 (1H, m), 2.49-2.66 (1H, m), 2.78-3.14 (6H, m), 4.47-4.78 (2H, m), 6.62 (1H, s), 7.11-7.52 (9H, m).

Example 11

3-(trans-2-aminocyclopropyl)-N-phenylbenzamide hydrochloride

A) methyl 3-(trans-2-(tert-butoxycarbonyl)cyclopropyl)benzoate

To a suspension of sodium hydride (60% in oil) (1.05 g) in DMSO (100 mL) was added trimethylsulfoxonium iodide (4.90 g), and the mixture was stirred at room temperature for 1 hr. To the reaction mixture was added methyl 3-((1E)-3-tert-butoxy-3-oxoprop-1-en-1-yl)benzoate (4.77 g) described in a document (Org. Biomol. Chem. 2009, 7, 2110-2119.), and the mixture was stirred under a nitrogen atmosphere at 100° C. overnight. Water (200 mL) was added to the reaction mixture, and the mixture was extracted twice with ethyl acetate (200 mL each time). The extracts were combined, washed with saturated brine (20.0 mL), dried over anhydrous sodium sulfate, and concentrated under reduced pressure. The obtained residue was combined with the residue separately prepared by a similar operation from methyl 3-((1E)-3-tert-butoxy-3-oxoprop-1-en-1-yl)benzoate (4.46 g), and purified by silica gel column chromatography (hexane/ethyl acetate) to give the title compound (4.21 g).

$^1$H NMR (300 MHz, CDCl$_3$) δ 1.25-1.30 (1H, m), 1.47 (9H, s), 1.53-1.60 (1H, m), 1.87 (1H, ddd, J=8.4, 5.4, 4.4 Hz), 2.49 (1H, ddd, J=9.1, 6.4, 4.2 Hz), 3.91 (3H, s), 7.27-7.38 (2H, m), 7.73-7.76 (1H, m), 7.84-7.89 (1H, m).

B) trans-2-(3-(methoxycarbonyl)phenyl)cyclopropanecarboxylic acid

Methyl 3-(trans-2-(tert-butoxycarbonyl)cyclopropyl)benzoate (4.21 g) was cooled to 0° C., TFA (11.7 mL) was added, and the mixture was stirred at room temperature overnight. Water (100 mL) was added to the reaction mixture, and the mixture was extracted twice with ethyl acetate (100 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (2.89 g).

$^1$H NMR (300 MHz, CDCl$_3$) δ 1.47 (1H, ddd, J=8.1, 6.6, 4.9 Hz), 1.67-1.75 (1H, m), 1.91-2.00 (1H, m), 2.66 (1H, ddd, J=9.3, 6.6, 4.2 Hz), 3.92 (3H, s), 7.31-7.41 (2H, m), 7.77 (1H, s), 7.90 (1H, dt, J=7.0, 1.6 Hz), 10.57 (1H, brs).

C) methyl 3-(trans-2-((tert-butoxycarbonyl)amino)cyclopropyl)benzoate

To a solution of trans-2-(3-(methoxycarbonyl)phenyl)cyclopropanecarboxylic acid (2.85 g) in anhydrous toluene (65.0 mL) were added diphenylphosphoryl azide (4.18 mL) and triethylamine (2.71 mL), and the mixture was stirred at room temperature for 1 hr. To the reaction mixture was added anhydrous tert-butyl alcohol (12.1 mL), and the mixture was stirred under a nitrogen atmosphere at 80° C. overnight. To the reaction mixture was added saturated aqueous ammonium chloride solution (100 mL) and the mixture was extracted twice with ethyl acetate (100 mL each time). The extracts were combined, washed successively with water (100 mL) and saturated brine (10.0 mL), dried over anhydrous sodium sulfate, and concentrated under reduced pressure. The residue was purified by silica gel column chromatography (hexane/ethyl acetate) to give the title compound (1.23 g).

MS (API+): [M−Boc+H]$^+$ 192.2.

D) 3-(trans-2-((tert-butoxycarbonyl)amino)cyclopropyl)benzoic acid

Methyl 3-(trans-2-((tert-butoxycarbonyl) amino) cyclopropyl)benzoate (1.23 g) was dissolved in methanol (20.0 mL), a 8 mol/L aqueous sodium hydroxide solution (2.64 mL) was added, and the mixture was stirred at room temperature for 3 hr. To the reaction mixture were added water (50.0 mL) and ethyl acetate (50.0 mL), and the organic layer was extracted with water (50.0 mL). The aqueous layers were combined, adjusted to pH 3-4 with 1 mol/L hydrochloric acid, and the mixture was extracted twice with ethyl acetate (50.0 mL each time). The extracts were combined, washed with saturated brine (10.0 mL), dried over anhydrous sodium sulfate, and concentrated under reduced pressure to give the title compound (1.10 g).

$^1$H NMR (300 MHz, DMSO-d$_6$) δ 1.07-1.21 (2H, m), 1.38 (9H, s), 1.94-2.03 (1H, m), 2.55-2.65 (1H, m), 7.27 (1H, brs), 7.30-7.35 (1H, m), 7.35-7.41 (1H, m), 7.67 (1H, s), 7.73 (1H, dt, J=7.2, 1.5 Hz), 12.83 (1H, brs).

E) tert-butyl (trans-2-(3-(phenylcarbamoyl)phenyl)cyclopropyl)carbamate 3-(trans-2-((tert-Butoxycarbonyl)amino)cyclopropyl)benzoic acid (500 mg), O-(7-azabenzotriazol-1-yl)-N,N,N',N'-tetramethyluronium hexafluorophosphate (823 mg) and aniline (204 mg) were dissolved in anhydrous DMF (10.0 mL), triethylamine (0.754 mL) was added, and the mixture was stirred at room temperature overnight. Water (50.0 mL) was added to the reaction mixture, and the mixture was extracted twice with ethyl acetate (50.0 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (515 mg).

MS (API+): [M+H]$^+$ 353.2.

F) 3-(trans-2-aminocyclopropyl)-N-phenylbenzamide hydrochloride tert-Butyl (trans-2-(3-(phenylcarbamoyl)phenyl)cyclopropyl)carbamate (468 mg) was dissolved in methanol (15.0 mL)/THF (5.00 mL), and the mixture was cooled to 0° C. A 4 mol/L hydrogen chloride/ethyl acetate solution (4.98 mL) was added, and the mixture was stirred at room temperature overnight. The reaction mixture was concentrated under reduced pressure, and the residue was recrystallized from methanol/diisopropy ether to give the title compound (381 mg).

$^1$H NMR (300 MHz, DMSO-d$_6$) δ 1.30-1.38 (1H, m), 1.45 (1H, dt, 30=9.9, 5.1 Hz), 2.39-2.48 (1H, m), 2.85-2.95 (1H, m), 7.08-7.14 (1H, m), 7.32-7.42 (3H, m), 7.43-7.49 (1H, m), 7.70-7.85 (4H, m), 8.47 (3H, brs), 10.24 (1H, brs).

Example 12

3-(trans-2-aminocyclopropyl)-N-benzylbenzamide hydrochloride

A) tert-butyl (trans-2-(3-(benzylcarbamoyl)phenyl)cyclopropyl)carbamate 3-(trans-2-((tert-Butoxycarbonyl)amino)cyclopropyl)benzoic acid (500 mg), O-(7-azabenzotriazol-1-yl)-N,N,N',N'-tetramethyluronium hexafluorophosphate (823 mg) and benzylamine (237 mg) were dissolved in anhydrous DMF (10.0 mL), triethylamine (0.754 mL) was added, and the mixture was stirred at room temperature overnight. To the reaction mixture was added water (50.0 mL), and the mixture was extracted twice with ethyl acetate (50.0 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (501 mg).

MS (API+): [M+H]$^+$ 367.3.

B) 3-(trans-2-aminocyclopropyl)-N-benzylbenzamide hydrochloride tert-Butyl (trans-2-(3-(benzylcarbamoyl)phenyl)cyclopropyl)carbamate (482 mg) was dissolved in methanol (10.0 mL), and the mixture was cooled to 0° C. A 4 mol/L hydrogen chloride/ethyl acetate solution (4.93 mL) was added, and the mixture was stirred at room temperature overnight. The reaction mixture was concentrated under reduced pressure, and the residue was recrystallized from methanol/ethyl acetate to give the title compound (413 mg).

$^1$H NMR (300 MHz, DMSO-$d_6$) δ 1.24-1.32 (1H, m), 1.39-1.48 (1H, m), 2.40 (1H, ddd, J=9.9, 6.3, 3.8 Hz), 2.88 (1H, dt. J=7.8, 4.1 Hz), 4.48 (2H, d, J=6.1 Hz), 7.20-7.29 (1H, m), 7.29-7.43 (6H, m), 7.66 (1H, s), 7.75 (1H, dt, J=7.5, 1.6 Hz), 8.49 (3H, brs), 9.07 (1H, t, J=6.1 Hz).

Example 13

3-(trans-2-((cyclopropylmethyl)amino)cyclopropyl)-N-phenylbenzamide hydrochloride A) tert-butyl (cyclopropylmethyl)(trans-2-(3-(phenylcarbamoyl)phenyl)cyclopropyl)carbamate 3-(trans-2-Aminocyclopropyl)-N-phenylbenzamide hydrochloride (200 mg) and sodium hydrogen carbonate (116 mg) were dissolved in THF (2.00 mL)/methanol (2.00 mL), and cyclopropanecarbaldehyde (58.3 mg) was added. The mixture was stirred at 60° C. for 2 hr, and sodium borohydride (52.4 mg) was added under ice-cooling. The mixture was stirred at room temperature for 2 hr, di-tert-butyl dicarbonate (0.241 mL) was added to the reaction mixture, and the mixture was stirred at room temperature overnight under a nitrogen atmosphere. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (223 mg).

$^1$H NMR (300 MHz, CDCl$_3$)δb 0.10-0.20 (1H, m), 0.22- (1H, m), 0.39-0.55 (2H, m), 0.95-1.10 (1H, m), 1.22-1.36 (2H, m), 1.44 (9H, s), 2.19 (1H, ddd, J=9.7, 6.6, 3.4 Hz), 2.90 (1H, ddd, J=7.5, 4.4, 3.6 Hz), 3.02 (1H, dd, J=14.4, 7.2 Hz), 3.31 (1H, dd, J=14.4, 6.8 Hz), 7.13-7.20 (1H, m), 7.31-7.43 (4H, m), 7.60-7.68 (4H, m), 7.81 (1H, brs).

B) 3-(trans-2-((cyclopropylmethyl)amino)cyclopropyl)-N-phenylbenzamide hydrochloride tert-Butyl (cyclopropylmethyl)(trans-2-(3-(phenylcarbamoyl)phenyl)cyclopropyl)carbamate (223 mg) was dissolved in THF (1.00 mL), and the mixture was cooled to 0° C. A 4 mol/L hydrogen chloride/ethyl acetate solution (2.74 mL) was added, and the mixture was stirred at room temperature overnight. The reaction mixture was concentrated under reduced pressure, and the residue was recrystallized from methanol/diisopropy ether to give the title compound (150 mg).

$^1$H NMR (300 MHz, DMSO-$d_6$) δ 0.32-0.41 (2H, m), 0.53-0.63 (2H, m), 0.98-1.14 (1H, m), 1.35-1.46 (1H, m), 1.50-1.64 (1H, m), 2.56 (1H, dd, J=9.5, 5.3 Hz), 2.98 (2H, d, J=7.6 Hz), 3.03-3.09 (1H, m), 7.06-7.16 (1H, m), 7.31-7.50 (4H, m), 7.70-7.85 (4H, m), 9.13 (2H, brs), 10.23 (1H, brs).

Example 14

N-benzyl-3-(trans-2-((cyclopropylmethyl)amino) cyclopropyl)benzamide hydrochloride A) tert-butyl (cyclopropylmethyl)(trans-2-(3-(benzylcarbamoyl)phenyl)cyclopropyl)carbamate 3-(trans-2-Aminocyclopropyl)-N-benzylbenzamide hydrochloride (200 mg) and sodium hydrogen carbonate (111 mg) were dissolved in THF (2.00 mL)/methanol (2.00 mL), and cyclopropanecarbaldehyde (55.6 mg) was added. The mixture was stirred at 60° C. for 2 hr, and sodium borohydride (50.0 mg) was added under ice-cooling. The mixture was stirred at room temperature for 2 hr, to the reaction mixture was added di-tert-butyl dicarbonate (0.230 mL), and the mixture was stirred under a nitrogen atmosphere at room temperature overnight. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (105 mg).

$^1$H NMR (300 MHz, CDCl$_3$) δ 0.10-0.19 (1H, m), 0.20-0.29 (1H, m), 0.37-0.53 (2H, m), 0.95-1.07 (1H, m), 1.19-1.32 (2H, m), 1.42 (9H, s), 2.15 (1H, ddd, J=9.6, 6.3, 3.4 Hz), 2.87 (1H, ddd, J=7.5, 4.6, 3.4 Hz), 3.01 (1H, dd, J=14.4, 7.2 Hz), 3.28 (1H, dd, J=14.4, 6.8 Hz), 4.66 (2H, d, J=5.7 Hz), 6.38 (1H, brs), 7.26-7.40 (7H, m), 7.54 (1H, dt, J=6.9, 1.8 Hz), 7.58 (1H, s).

B)N-benzyl-3-(trans-2-((cyclopropylmethyl)amino) cyclopropyl)benzamide hydrochloride tert-Butyl (cyclopropylmethyl)(trans-2-(3-(benzylcarbamoyl)phenyl)cyclopropyl)carbamate (105 mg) was dissolved in THF (1.00 mL), and the mixture was cooled to 0° C. A 4 mol/L hydrogen chloride/ethyl acetate solution (1.25 mL) was added, and the mixture was stirred at room temperature overnight. The reaction mixture was concentrated under reduced pressure, and the residue was recrystallized from methanol/ethyl acetate to give the title compound (54.9 mg).

$^1$H NMR (300 MHz, DMSO-$d_6$) δ 0.32-0.39 (2H, m), 0.54-0.62 (2H, m), 0.99-1.11 (1H, m), 1.31-1.41 (1H, m), 1.48-1.56 (1H, m), 2.53-2.56 (1H, m), 2.92-3.06 (3H, m), 4.48 (2H, d, J=6.1 Hz), 7.20-7.27 (1H, m), 7.28-7.45 (6H, m), 7.67 (1H, s), 7.75 (1H, dt, J=7.2, 1.5 Hz), 9.03 (1H, t, J=5.1 Hz), 9.09 (2H, brs).

Example 15

4-(trans-2-((cyclopropylmethyl)amino)cyclopropyl)-N-((5-methylpyrazin-2-yl)methyl)benzamide bis (trifluoroacetate)

A) tert-butyl (trans-2-(4-bromophenyl)cyclopropyl) (cyclopropylmethyl)carbamate tert-Butyl (trans-2-(4-bromophenyl)cyclopropyl)carbamate (950 mg) described in the document (Bioorg. Med.

Chem. 2011, 19, 3709-3716.) was dissolved in anhydrous DMF (15.0 mL), the mixture was cooled to 0° C., and sodium hydride (60% in oil) (243 mg) was added. The mixture was stirred at 0° C. for 10 min, a solution of (bromomethyl)cyclopropane (0.443 mL) in anhydrous DMF (1.00 mL) was added at 0° C., and the mixture was stirred at room temperature for 2.5 hr. Water was added to the reaction mixture under ice-cooling, and the mixture was extracted with ethyl acetate. The extracts were combined, washed with saturated brine, dried over anhydrous sodium sulfate, and concentrated under reduced pressure. The residue was purified by silica gel column chromatography (hexane/ethyl acetate) to give the title compound (970 mg).

$^1$H NMR (300 MHz, CDCl$_3$) δ 0.09-0.31 (2H, m), 0.36-0.54 (2H, m), 0.92-1.09 (1H, m), 1.13-1.21 (1H, m), 1.23-1.31 (1H, m), 1.39 (9H, s), 2.00-2.12 (1H, m), 2.75-2.84 (1H, m), 3.02 (1H, dd, J=14.4, 6.8 Hz), 3.26 (1H, dd, J=14.4, 6.8 Hz), 6.96-7.06 (2H, m), 7.33-7.44 (2H, m).

B) methyl 4-(trans-2-((tert-butoxycarbonyl)(cyclopropylmethyl)amino)cyclopropyl)benzoate tert-Butyl (trans-2-(4-bromophenyl)cyclopropyl)(cyclopropylmethyl)carbamate (1.06 g) and dichloro(1,1'-bis(diphenylphosphino)ferrocene)palladium (212 mg) were dissolved in methanol (30.0 mL), and triethylamine (0.444 mL) was added. The mixture was stirred under carbon monoxide atmosphere (3 atm) at 90° C. for 2 days, the insoluble material was collected by filtration, and the filtrate was concentrated under reduced pressure. The residue was purified by silica gel column chromatography (hexane/ethyl acetate) to give the title compound (875 mg).

$^1$H NMR (300 MHz, CDCl$_3$) δ 0.08-0.18 (1H, m), 0.19-0.29 (1H, m), 0.37-0.54 (2H, m), 0.93-1.07 (1H, m), 1.29-1.39 (2H, m), 1.41 (9H, s), 2.08-2.19 (1H, m), 2.83-2.93 (1H, m), 3.05 (1H, dd, J=14.2, 7.0 Hz), 3.26 (1H, dd, J=14.2, 7.0 Hz), 3.90 (3H, s), 7.10-7.19 (2H, m), 7.90-7.98 (2H, m).

C) 4-(trans-2-((tert-butoxycarbonyl)(cyclopropylmethyl)amino)cyclopropyl)benzoic acid Methyl 4-(trans-2-((tert-butoxycarbonyl)(cyclopropylmethyl)amino)cyclopropyl)benzoate (870 mg) was dissolved in methanol (15.0 mL), a 8 mol/L aqueous sodium hydroxide solution (2.52 mL) was added at room temperature, and the mixture was stirred at room temperature overnight. The reaction mixture was concentrated under reduced pressure. To the reaction mixture were added water and diethyl ether, and the mixture was stirred well. The organic layer was extracted with water. The aqueous layers were combined, adjusted to pH 3-4 with 6 mol/L hydrochloric acid, and the mixture was extracted with ethyl acetate. The extracts were combined, washed with saturated brine, and dried over anhydrous sodium sulfate to give the title compound (631 mg).

$^1$H NMR (300 MHz, DMSO-d$_6$) δ 0.04-0.14 (1H, m), 0.17-0.28 (1H, m), 0.32-0.52 (2H, m), 0.91-1.01 (1H, m), 1.20-1.39 (11H, m), 2.09-2.22 (1H, m), 2.78-2.85 (1H, m), 2.97 (1H, dd, J=14.2, 7.0 Hz), 3.21 (1H, dd, J=14.2, 7.0 Hz), 7.24 (2H, d, J=8.3 Hz), 7.83 (2H, d, J=8.3 Hz), 12.77 (1H, brs).

D) 4-(trans-2-((cyclopropylmethyl)amino)cyclopropyl)-N-((5-methylpyrazin-2-yl)methyl)benzamide bis(trifluoroacetate)

To a solution of 4-(trans-2-((tert-butoxycarbonyl)(cyclopropylmethyl)amino)cyclopropyl)benzoic acid (26.5 mg), 2-(aminomethyl)-5-methylpyrazine (19.7 mg) and N,N-diisopropylethylamine (0.0557 mL) in DMF (1.50 mL) was added O-(7-azabenzotriazol-1-yl)-N,N,N',N'-tetramethyluronium hexafluorophosphate (60.8 mg), and the mixture was stirred at room temperature overnight. To the reaction solution were added water and ethyl acetate, the organic layer was extracted, and the solvent was evaporated by an air blowing apparatus. To the residue was added TFA (0.50 mL), and the mixture was stirred for 1 hr, and TFA was evaporated by an air blowing apparatus. The residue was purified by HPLC (C18, mobile phase: acetonitrile/water (with 0.1% TFA)), and the solvent was evaporated by an air blowing apparatus to give the title compound (46.9 mg).

By a method similar to that in Example 15, the compounds of Examples 16 to 30 were produced.

Example 31

N-benzyl-4-(trans-2-((4-tert-butylbenzyl)amino)cyclopropyl)benzamide trifluoroacetate A solution of 4-(trans-2-aminocyclopropyl)-N-benzylbenzamide (21.0 mg) and 4-tert-butylbenzaldehyde (25.9 mg) in DMF (1.00 mL) was stirred at room temperature overnight, a solution of sodium borohydride (12.0 mg) in methanol (1.00 mL) was added dropwise, and the mixture was stirred for 1 hr. To the reaction solution were added a saturated aqueous sodium hydrogen carbonate solution and ethyl acetate, and the organic layer was extracted, and the solvent was evaporated by an air blowing apparatus. The residue was purified by HPLC (C18, mobile phase: acetonitrile/water (with 0.1% TFA)), and the solvent was evaporated by an air blowing apparatus to give the title compound (17.8 mg).

By a method similar to that in Example 31, the compounds of Examples 32 to 49 were produced.

Example 50

4-(trans-2-aminocyclopropyl)-N-(4-(pyrimidin-2-yl)phenyl)benzamide dihydrochloride

A) tert-butyl (trans-2-(4-((4-(pyrimidin-2-yl)phenyl)carbamoyl)phenyl)cyclopropyl)carbamate 4-(trans-2-((tert-Butoxycarbonyl)amino)cyclopropyl)benzoic acid (400 mg), 4-(pyrimidin-2-yl)aniline (305 mg) and O-(7-azabenzotriazol-1-yl)-N,N,N',N'-tetramethyluronium hexafluorophosphate (658 mg) were dissolved in anhydrous DMF (10.0 mL), triethylamine (0.603 mL) was added, and the mixture was stirred at room temperature overnight. To the reaction mixture was added water (50.0 mL), and the mixture was extracted twice with ethyl acetate (50.0 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (482 mg).

MS (API+): [M+H]$^+$ 431.2.

B) 4-(trans-2-aminocyclopropyl)-N-(4-(pyrimidin-2-yl)phenyl)benzamide dihydrochloride tert-Butyl (trans-2-(4-((4-(pyrimidin-2-yl)phenyl)carbamoyl)phenyl)cyclopropyl)carbamate (472 mg) was dissolved in THF (15.0 mL)/methanol (15.0 mL), and the mixture was cooled to 0° C. A 4 mol/L hydrogen chloride/ ethyl acetate solution (4.11 mL) was added, and the mixture was stirred at room temperature overnight. The reaction mixture was concentrated under reduced pressure, and the residue was recrystallized from methanol/ethyl acetate to give the title compound (442 mg).

$^1$H NMR (300 MHz, DMSO-d$_6$) δ 1.28-1.37 (1H, m), 1.45-1.53 (1H, m), 2.40-2.46 (1H, m), 2.89-2.97 (1H, m), 7.34 (2H, d, J=8.3 Hz), 7.41 (1H, t, J=4.9 Hz), 7.92-7.99 (4H, m), 8.36-8.42 (2H, m), 8.51 (3H, brs), 8.88 (2H, d, J=4.9 Hz), 10.45 (1H, s).

Example 51

4-(trans-2-aminocyclopropyl)-N-(1-methyl-1H-pyrazol-4-yl)benzamide dihydrochloride A) tert-butyl (trans-2-(4-((1-methyl-1H-pyrazol-4-yl)carbamoyl)phenyl)cyclopropyl)carbamate 4-(trans-2-((tert-Butoxycarbonyl)amino)cyclopropyl) benzoic acid (400 mg), 1-methyl-1H-pyrazol-4-amine (147 mg) and O-(7-azabenzotriazol-1-yl)-N,N,N',N'-tetramethyluronium hexafluorophosphate (658 mg) were dissolved in anhydrous DMF (10.0 mL), triethylamine (0.603 mL) was added, and the mixture was stirred at room temperature overnight. To the reaction mixture was added water (50.0 mL), and the mixture was extracted twice with ethyl acetate (50.0 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (259 mg).

MS (API+): [M+H]$^+$ 357.2.

B) 4-(trans-2-aminocyclopropyl)-N-(1-methyl-1H-pyrazol-4-yl)benzamide dihydrochloride tert-Butyl (trans-2-(4-((1-methyl-1H-pyrazol-4-yl)carbamoyl)phenyl)cyclopropyl)carbamate (256 mg) was dissolved in THF (3.00 mL)/methanol (9.00 mL), and the mixture was cooled to 0° C. A 4 mol/L hydrogen chloride/ethyl acetate solution (2.69 mL) was added, and the mixture was stirred at room temperature overnight. The reaction mixture was concentrated under reduced pressure, and the residue was recrystallized from methanol/ethyl acetate to give the title compound (232 mg).

$^1$H NMR (300 MHz, DMSO-d$_6$) δ 1.25-1.34 (1H, m), 1.43-1.54 (1H, m), 2.38-2.47 (1H, m), 2.85-2.95 (1H, m), 3.82 (3H, s), 7.29 (2H, d, J=8.3 Hz), 7.59 (1H, s), 7.90 (2H, d, J=8.3 Hz), 8.02 (1H, s), 8.59 (3H, brs), 10.43 (1H, s).

Example 52

4-(trans-2-((cyclopropylmthyl)amino)cyclopropyl)-N-(4-(pyrimidin-2-yl)phenyl)benzamide dihydrochloride A) tert-butyl (cyclopropylmethyl)(trans-2-(4-((4-(pyrimidin-2-yl)phenyl)carbamoyl)phenyl)cyclopropyl)carbamate 4-(trans-2-Aminocyclopropyl)-N-(4-(pyrimidin-2-yl) phenyl)benzamide dihydrochloride (400 mg) and sodium hydrogen carbonate (167 mg) were dissolved in THF (4.00 mL)/methanol (4.00 mL), and cyclopropanecarbaldehyde (83.0 mg) was added. The mixture was stirred at 60° C. for 2 hr, and sodium borohydride (75.0 mg) was added under ice-cooling. The mixture was stirred at room temperature for 2 hr, to the reaction mixture was added di-tert-butyl dicarbonate (0.345 mL), and the mixture was stirred under a nitrogen atmosphere at room temperature overnight. To the reaction mixture was added water (40.0 mL), and the mixture was extracted twice with ethyl acetate (40.0 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (244 mg).

MS (API+): [M+H]$^+$ 485.2.

B) 4-(trans-2-((cyclopropylmethyl)amino)cyclopropyl)-N-(4-(pyrimidin-2-yl)phenyl)benzamide dihydrochloride tert-Butyl (cyclopropylmethyl)(trans-2-(4-((4-(pyrimidin-2-yl)phenyl)carbamoyl)phenyl)cyclopropyl)carbamate (244 mg) was dissolved in THF (5.00 mL)/methanol (5.00 mL), and the mixture was cooled to 0° C. A 4 mol/L hydrogen chloride/ethyl acetate solution (1.89 mL) was added, and the mixture was stirred at room temperature overnight. The reaction mixture was concentrated under reduced pressure, and the residue was recrystallized from methanol/diisopropy ether to give the title compound (203 mg).

$^1$H NMR (300 MHz, DMSO-d$_6$) δ 0.34-0.41 (2H, m), 0.55-0.63 (2H, m), 1.02-1.11 (1H, m), 1.36-1.45 (1H, m), 1.57-1.66 (1H, m), 2.55-2.62 (1H, m), 2.94-3.02 (2H, m), 3.04-3.10 (1H, m), 7.36 (2H, d, J=8.3 Hz), 7.41 (1H, t, J=4.7 Hz), 7.93-7.99 (4H, m), 8.36-8.42 (2H, m), 8.88 (2H, d, J=4.9 Hz), 9.24 (2H, brs), 10.43 (1H, s).

Example 53

4-(trans-2-((cyclopropylmethyl)amino)cyclopropyl)-N-(1-methyl-1H-pyrazol-4-yl)benzamide dihydrochloride A) tert-butyl (cyclopropylmethyl) (trans-2-(4-((1-methyl-1H-pyrazol-4-yl) carbamoyl)phenyl)cyclopropyl) carbamate 4-(trans-2-Aminocyclopropyl)-N-(1-methyl-1H-pyrazol-4-yl)benzamide dihydrochloride (200 mg) and sodium hydrogen carbonate (153 mg) were dissolved in THF (2.00 mL)/methanol (2.00 mL), and cyclopropanecarbaldehyde (51.1 mg) was added. The mixture was stirred at 60° C. for 2 hr, and sodium borohydride (46.0 mg) was added under ice-cooling. The mixture was stirred at room temperature for 2 hr, di-tert-butyl dicarbonate (0.212 mL) was added to the reaction mixture, and the mixture was stirred under a nitrogen atmosphere at room temperature overnight. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (148 mg).

$^1$H NMR (300 MHz, CDCl$_3$) δ 0.11-0.20 (1H, m), 0.20-0.29 (1H, m), 0.38-0.54 (2H, m), 0.96-1.08 (1H, m), 1.29-1.40 (2H, m), 1.43 (9H, s), 2.11-2.19 (1H, m), 2.85-2.93 (1H, m), 3.06 (1H, dd, J=14.2, 7.0 Hz), 3.27 (1H, dd, J=14.0, 7.2 Hz), 3.90 (3H, s), 7.21 (2H, d, J=8.3 Hz), 7.48 (1H, s), 7.71 (1H, s), 7.75 (2H, d, J=8.3 Hz), 8.05 (1H, s).

B) 4-(trans-2-((cyclopropylmethyl)amino)cyclopropyl)-N-(1-methyl-1H-pyrazol-4-yl)benzamide dihydrochloride tert-Butyl (cyclopropylmethyl)(trans-2-(4-((1-methyl-1H-pyrazol-4-yl)carbamoyl)phenyl)cyclopropyl)carbamate (148 mg) was dissolved in THF (5.00 mL)/methanol (5.00 mL), and the mixture was cooled to 0° C. A 4 mol/L hydrogen chloride/ethyl acetate solution (1.36 mL) was added, and the mixture was stirred at room temperature overnight. The reaction mixture was concentrated under reduced pressure, and the residue was recrystallized from methanol/diisopropy ether to give the title compound (114 mg).
$^1$H NMR (300 MHz, DMSO-$d_6$) δ 0.33-0.40 (2H, m), 0.54-0.61 (2H, m), 1.02-1.13 (1H, m), 1.33-1.41 (1H, m), 1.57-1.67 (1H, m), 2.56-2.63 (1H, m), 2.92-3.00 (2H, m), 3.01-3.07 (1H, m), 3.82 (3H, s), 7.31 (2H, d, J=8.3 Hz), 7.58 (1H, s), 7.90 (2H, d, J=8.3 Hz), 8.01 (1H, s), 9.38 (2H, brs), 10.41 (1H, s).

Example 54

3-(trans-2-aminocyclopropyl)-N-(4-(pyrimidin-2-yl)phenyl)benzamide dihydrochloride A) tert-butyl (trans-2-(3-((4-(pyrimidin-2-yl)phenyl)carbamoyl)phenyl)cyclopropyl)carbamate 3-(2-((tert-Butoxycarbonyl)amino)cyclopropyl)benzoic acid (250 mg), O-(7-azabenzotriazol-1-yl)-N,N,N',N'-tetramethyluronium hexafluorophosphate (411 mg) and 4-(pyrimidin-2-yl)aniline (191 mg) were dissolved in anhydrous DMF (10.0 mL), triethylamine (0.377 mL) was added, and the mixture was stirred at room temperature overnight. To the reaction mixture was added water (25.0 mL), and the mixture was extracted twice with ethyl acetate (25.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (234 mg).
MS (API+): [M+H]$^+$ 431.2.

B) 3-(trans-2-aminocyclopropyl)-N-(4-(pyrimidin-2-yl)phenyl)benzamide dihydrochloride tert-Butyl (trans-2-(3-((4-(pyrimidin-2-yl)phenyl)carbamoyl)phenyl)cyclopropyl)carbamate (222 mg) was dissolved in THF (5.00 mL)/methanol (5.00 mL), and the mixture was cooled to 0° C. A 4 mol/L hydrogen chloride/ethyl acetate solution (1.93 mL) was added, and the mixture was stirred at room temperature overnight. The reaction mixture was concentrated under reduced pressure, and the residue was recrystallized from methanol/ethyl acetate to give the title compound (189 mg).
$^1$H NMR (300 MHz, DMSO-$d_6$) δ 1.31-1.40 (1H, m), 1.41-1.50 (1H, m), 2.39-2.45 (1H, m), 2.91-3.01 (1H, m), 7.39-7.42 (1H, m), 7.43 (1H, s), 7.45-7.51 (1H, m), 7.75 (1H, s), 7.81-7.86 (1H, m), 7.93-7.99 (2H, m), 8.37-8.43 (2H, m), 8.46 (3H, brs), 8.89 (2H, d, J=4.5 Hz), 10.49 (1H, s).

Example 55

3-(trans-2-aminocyclopropyl)-N-(1-methyl-1H-pyrazol-4-yl)benzamide dihydrochloride A) tert-butyl (trans-2-(3-((1-methyl-1H-pyrazol-4-yl)carbamoyl)phenyl)cyclopropyl)carbamate 3-(2-((tert-Butoxycarbonyl)amino)cyclopropyl)benzoic acid (250 mg), O-(7-azabenzotriazol-1-yl)-N,N,N',N'-tetramethyluronium hexafluorophosphate (411 mg) and 1-methyl-1H-pyrazol-4-amine (92.0 mg) were dissolved in anhydrous DMF (10.0 mL), triethylamine (0.377 mL) was added, and the mixture was stirred at room temperature overnight. To the reaction mixture was added water (25.0 mL), and the mixture was extracted twice with ethyl acetate (25.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (214 mg).
MS (API+): [M+H]$^+$ 357.2.

B) 3-(trans-2-aminocyclopropyl)-N-(1-methyl-1H-pyrazol-4-yl)benzamide dihydrochloride tert-Butyl (trans-2-(3-((1-methyl-1H-pyrazol-4-yl)carbamoyl)phenyl)cyclopropyl)carbamate (205 mg) was dissolved in THF (5.00 mL)/methanol (5.00 mL), and the mixture was cooled to 0° C. A 4 mol/L hydrogen chloride/ethyl acetate solution (2.16 mL) was added, and the mixture was stirred at room temperature overnight. The reaction mixture was concentrated under reduced pressure, and the residue was recrystallized from methanol/ethyl acetate to give the title compound (167 mg).
$^1$H NMR (300 MHz, DMSO-$d_6$) δ 1.27-1.36 (1H, m), 1.41-1.50 (1H, m), 2.38-2.47 (1H, m), 2.88-2.98 (1H, m), 3.82 (3H, s), 7.34-7.40 (1H, m), 7.40-7.47 (1H, m), 7.59 (1H, s), 7.73 (1H, s), 7.79 (1H, d, J=7.6 Hz), 8.02 (1H, s), 8.52 (3H, brs), 10.48 (1H, brs).

Example 56

3-(trans-2-aminocyclopropyl)-N-cyclopentylbenzamide hydrochloride

A) tert-butyl (trans-2-(3-(cyclopentylcarbamoyl)phenyl)cyclopropyl)carbamate 3-(trans-2-((tert-Butoxycarbonyl)amino)cyclopropyl)benzoic acid (250 mg), O-(7-azabenzotriazol-1-yl)-N,N,N',N'-tetramethyluronium hexafluorophosphate (411 mg) and cyclopentanamine (81.0 mg) were dissolved in anhydrous DMF (10.0 mL), triethylamine (0.377 mL) was added, and the mixture was stirred at room temperature overnight. To the reaction mixture was added water (25.0 mL), and the mixture was extracted twice with ethyl acetate (25.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (286 mg).
MS (API+): [M+H]$^+$ 345.2.

B) 3-(trans-2-aminocyclopropyl)-N-cyclopentylbenzamide hydrochloride tert-Butyl (trans-2-(3-(cyclopentylcarbamoyl)phenyl)cyclopropyl)carbamate (280 mg) was dissolved in THF (5.00 mL)/methanol (5.00 mL), and the mixture was cooled to 0° C. A 4 mol/L hydrogen chloride/ethyl acetate solution (3.05 mL) was added, and the mixture was stirred at room temperature overnight. The reaction mixture was concentrated under reduced pressure, and the residue was recrystallized from methanol/ethyl acetate to give the title compound (207 mg).

$^1$H NMR (300 MHz, DMSO-d$_6$) δ 1.23-1.32 (1H, m), 1.38-1.47 (1H, m), 1.49-1.60 (4H, m), 1.64-1.75 (2H, m), 1.83-1.94 (2H, m), 2.35-2.44 (1H, m), 2.84-2.91 (1H, m), 4.17-4.29 (1H, m), 7.28-7.33 (1H, m), 7.34-7.40 (1H, m), 7.59 (1H, s), 7.68 (1H, dt, J=7.4, 1.4 Hz), 8.28 (1H, d, J=7.2 Hz), 8.49 (3H, brs).

Example 57

(3-(trans-2-aminocyclopropyl)phenyl)(pyrrolidin-1-yl)methanone hydrochloride

A) tert-butyl (trans-2-(3-(pyrrolidine-1-carbonyl)phenyl)cyclopropyl)carbamate 3-(trans-2-((tert-Butoxycarbonyl)amino)cyclopropyl)benzoic acid (250 mg), O-(7-azabenzotriazol-1-yl)-N,N,N',N'-tetramethyluronium hexafluorophosphate (411 mg) and pyrrolidine (67.5 mg) were dissolved in anhydrous DMF (10.0 mL), triethylamine (0.377 mL) was added, and the mixture was stirred at room temperature overnight. To the reaction mixture was added water (25.0 mL), and the mixture was extracted twice with ethyl acetate (25.0 mL), each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (190 mg).

MS (API+): [M+H]-' 331.3.

B) (3-(trans-2-aminocyclopropyl)phenyl)(pyrrolidin-1-yl)methanone hydrochloride tert-Butyl (trans-2-(3-(pyrrolidine-1-carbonyl)phenyl)cyclopropyl)carbamate (190 mg) was dissolved in THF (5.00 mL)/methanol (5.00 mL), and the mixture was cooled to 0° C. A 4 mol/L hydrogen chloride/ethyl acetate solution (2.16 mL) was added, and the mixture was stirred at room temperature overnight. The reaction mixture was concentrated under reduced pressure, and the residue was recrystallized from methanol/ethyl acetate to give the title compound (150 mg).

$^1$H NMR (300 MHz, DMSO-d$_6$) δ 1.22-1.31 (1H, m), 1.33-1.42 (1H, m), 1.74-1.92 (4H, m), 2.31-2.39 (1H, m), 2.82-2.90 (1H, m), 3.33 (2H, t, J=6.2 Hz), 3.45 (2H, t, J=6.6 Hz), 7.22-7.26 (1H, m), 7.28 (1H, s), 7.31-7.39 (2H, m), 8.31 (3H, brs).

Example 58

3-(trans-2-((cyclopropylmethyl)amino)cyclopropyl)-N-(4-(pyrimidin-2-yl)phenyl)benzamide dihydrochloride A) tert-butyl (cyclopropylmethyl)(trans-2-(3-((4-(pyrimidin-2-yl)phenyl)carbamoyl)phenyl)cyclopropyl)carbamate 3-(trans-2-Aminocyclopropyl)-N-(4-(pyrimidin-2-yl)phenyl)benzamide dihydrochloride (173 mg) and sodium hydrogen carbonate (108 mg) were dissolved in THF (5.00 mL)/methanol (5.00 mL), and cyclopropanecarbaldehyde (36.2 mg) was added. The mixture was stirred at 60° C. for 2 hr, and is sodium borohydride (32.5 mg) was added under ice-cooling. The mixture was stirred at room temperature for 2 hr, to the reaction mixture was added di-tert-butyl dicarbonate (0.150 mL), and the mixture was stirred at room temperature overnight under a nitrogen atmosphere. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (172 mg).

$^1$H NMR (300 MHz, CDCl$_3$) δ 0.12-0.21 (1H, m), 0.23-0.31 (1H, m), 0.39-0.55 (2H, m), 0.81-0.94 (1H, m), 0.97-1.09 (1H, m), 1.31-1.37 (1H, m), 1.44 (9H, s), 2.16-2.25 (1H, m), 2.87-2.94 (1H, m), 3.02 (1H, dd, J=14.0, 7.2 Hz), 3.32 (1H, dd, J=14.2, 6.6 Hz), 7.17 (1H, t, J=4.7 Hz), 7.33-7.38 (1H, m), 7.38-7.44 (1H, m), 7.67 (1H, dd, J=7.6, 1.5 Hz), 7.70 (1H, brs), 7.78-7.85 (2H, m), 7.97 (1H, brs), 8.45-8.52 (2H, m), 8.80 (2H, d, J 4.9 Hz).

B) 3-(trans-2-((cyclopropylmethyl)amino)cyclopropyl)-N-(4-(pyrimidin-2-yl)phenyl)benzamide dihydrochloride tert-Butyl (cyclopropylmethyl)(trans-2-(3-((4-(pyrimidin-2-yl)phenyl)carbamoyl)phenyl)cyclopropyl)carbamate (223 mg) was dissolved in THF (1.00 mL), and the mixture was cooled to 0° C. A 4 mol/L hydrogen chloride/ethyl acetate solution (2.74 mL) was added, and the mixture was stirred at room temperature overnight. The reaction mixture was concentrated under reduced pressure, and the residue was recrystallized from methanol/diisopropy ether to give the title compound (150 mg).

$^1$H NMR (300 MHz, DMSO-d$_6$) δ 0.34-0.42 (2H, m), 0.54-0.62 (2H, m), 1.03-1.15 (1H, m), 1.37-1.47 (1H, m), 1.57-1.67 (1H, m), 2.60-2.68 (1H, m), 2.94-3.02 (2H, m), 3.05-3.12 (1H, m), 7.41 (1H, t, J=4.9 Hz), 7.44 (1H, t, J=1.5 Hz), 7.46-7.51 (1H, m), 7.79 (1H, s), 7.84 (1H, dt, J=7.2, 1.5 Hz), 7.97 (2H, d, J=9.1 Hz), 8.37-8.43 (2H, m), 8.89 (2H, d, J=4.5 Hz), 9.39 (2H, brs), 10.51 (1H, s).

Example 59

3-(trans-2-((cyclopropylmethyl)amino)cyclopropyl)-N-(1-methyl-1H-pyrazol-4-yl)benzamide dihydrochloride A) tert-butyl (cyclopropylmethyl)(trans-2-(3-((1-methyl-1H-pyrazol-4-yl)carbamoyl)phenyl)cyclopropyl)carbamate 3-(2-Aminocyclopropyl)-N-(1-methyl-1H-pyrazol-4-yl)benzamide dihydrochloride (152 mg) and sodium hydrogen carbonate (117 mg) were dissolved in THF (5.00 mL)/methanol (5.00 mL), and cyclopropanecarbaldehyde (38.9 mg) was added. The mixture was stirred at 60° C. for 2 hr, and sodium borohydride (35.0 mg) was added under ice-cooling. The mixture was stirred at room temperature for 2 hr, di-tert-butyl dicarbonate (0.161 mL) was added to the reaction mixture, and the mixture was stirred at room temperature overnight under a nitrogen atmosphere. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (100 mg).

$^1$H NMR (300 MHz, CDCl$_3$) δ 0.11-0.20 (1H, m), 0.22-(1H, m), 0.40-0.55 (2H, m), 0.82-0.93 (1H, m), 0.97-1.08 (1H, m), 1.28-1.35 (1H, m), 1.44 (9H, s), 2.12-2.24 (1H, m), 2.86-2.93 (1H, m), 3.01 (1H, dd, J=14.6, 7.0 Hz), 3.31 (1H, dd, J=14.2, 6.2 Hz), 3.91 (3H, s), 7.30-7.35 (1H, m), 7.35-7.41 (1H, m), 7.50 (1H, s), 7.59-7.65 (2H, m), 7.81 (1H, brs), 8.06 (1H, s).

B) 3-(trans-2-((cyclopropylmethyl)amino)cyclopropyl)-N-(1-methyl-1H-pyrazol-4-yl)benzamide dihydrochloride tert-Butyl (cyclopropylmethyl)(trans-2-(3-((1-methyl-1H-pyrazol-4-yl)carbamoyl)phenyl)cyclopropyl)carbamate (100 mg) was dissolved in THF (5.00 mL)/methanol (5.00 mL), and the mixture was cooled to 0° C. A 4 mol/L hydrogen chloride/ethyl acetate solution (0.914 mL) was added, and the mixture was stirred at room temperature overnight. The reaction mixture was concentrated under reduced pressure, and the residue was recrystallized from methanol/ethyl acetate to give the title compound (79.0 mg).

$^1$H NMR (300 MHz, DMSO-d$_6$) δ 0.32-0.40 (2H, m), 0.54-0.62 (2H, m), 1.00-1.14 (1H, m), 1.35-1.44 (1H, m), 1.53-1.63 (1H, m), 2.56-2.63 (1H, m), 2.93-3.02 (2H, m), 3.03-3.11 (1H, m), 3.83 (3H, s), 7.36-7.41 (1H, m), 7.42-7.48 (1H, m), 7.59 (1H, s), 7.75 (1H, s), 7.78-7.82 (1H, m), 8.02 (1H, s), 9.25 (2H, d, J 15.5 Hz), 10.45 (1H, s).

Example 60

N-cyclopentyl-3-(trans-2-((cyclopropylmethyl)amino)cyclopropyl)benzamide hydrochloride A) tert-butyl (trans-2-(3-(cyclopentylcarbamoyl)phenyl)-cyclopropyl)(cyclopropylmethyl)carbamate 3-(trans-2-Aminocyclopropyl)-N-cyclopentylbenzamide hydrochloride (190 mg) and sodium hydrogen carbonate (170 mg) were dissolved in THF (5.00 mL)/methanol (5.00 mL), and cyclopropanecarbaldehyde (56.8 mg) was added. The mixture was stirred at 60° C. for 2 hr, and sodium borohydride (51.1 mg) was added under ice-cooling. The mixture was stirred at room temperature for 2 hr, di-tert-butyl dicarbonate (0.235 mL) was added to the reaction mixture, and the mixture was stirred at room temperature overnight under a nitrogen atmosphere. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (153 mg).

$^1$H NMR (300 MHz, CDCl$_3$) δ 0.11-0.20 (1H, m), 0.20-(1H, m), 0.37-0.54 (2H, m), 0.96-1.08 (1H, m), 1.21-1.32 (2H, m), 1.43 (9H, s), 1.46-1.55 (2H, m), 1.60-1.80 (4H, m), 2.06-2.19 (3H, m), 2.85-2.91 (1H, m), 3.03 (1H, dd, J=14.4, 7.2 Hz), 3.28 (1H, dd, J=14.2, 7.0 Hz), 4.34-4.47 (1H, m), 6.01 (1H, d, J=6.8 Hz), 7.24-7.35 (2H, m), 7.48 (1H, dt, J=7.2, 1.5 Hz), 7.54 (1H, s).

B)N-cyclopentyl-3-(trans-2-((cyclopropylmethyl)amino)cyclopropyl)benzamide hydrochloride tert-Butyl (trans-2-(3-(cyclopentylcarbamoyl)phenyl)-cyclopropyl)(cyclopropylmethyl)carbamate (153 mg) was dissolved in THF (5.00 mL)/methanol (5.00 mL), and the mixture was cooled to 0° C. A 4 mol/L hydrogen chloride/ethyl acetate solution (1.44 mL) was added, and the mixture was stirred at room temperature overnight. The reaction mixture was concentrated under reduced pressure, and the residue was recrystallized from methanol/ethyl acetate to give the title compound (91.0 mg).

$^1$H NMR (300 MHz, DMSO-d$_6$) δ 0.32-0.40 (2H, m), 0.54-0.62 (2H, m), 0.98-1.11 (1H, m), 1.31-1.40 (1H, m), 1.49-1.59 (6H, m), 1.64-1.76 (2H, m), 1.82-1.94 (2H, m), 2.92-3.05 (3H, m), 4.15-4.27 (1H, m), 7.29-7.34 (1H, m), 7.33-7.40 (1H, m), 7.61 (1H, s), 7.69 (1H, dt, J=7.6, 1.5 Hz), 8.26 (1H, d, J=7.2 Hz), 9.17 (2H, brs).

Example 61

(3-(trans-2-((cyclopropylmethyl)amino)cyclopropyl)phenyl)(pyrrolidin-1-yl)methanone hydrochloride A) tert-butyl (cyclopropylmethyl)(trans-2-(3-(pyrrolidine-1-carbonyl)phenyl)cyclopropyl)carbamate (3-(trans-2-Aminocyclopropyl)phenyl) (pyrrolidin-1-yl) methanone hydrochloride (150 mg) and sodium hydrogen carbonate (142 mg) were dissolved in THF (5.00 mL)/methanol (5.00 mL), and cyclopropanecarbaldehyde (47.4 mg) was added. The mixture was stirred at 60° C. for 2 hr, and sodium borohydride (42.7 mg) was added under ice-cooling. The mixture was stirred at room temperature for 2 hr, and di-tert-butyl dicarbonate (0.196 ml) was added to the reaction mixture, and the mixture was stirred at room temperature overnight under a nitrogen atmosphere. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (121 mg).

MS (API+): [M+H]$^+$ 385.3.

B) (3-(trans-2-((cyclopropylmethyl)amino)cyclopropyl)phenyl) (pyrrolidin-1-yl)methanone hydrochloride tert-Butyl (cyclopropylmethyl)(trans-2-(3-(pyrrolidine-1-carbonyl)phenyl)cyclopropyl)carbamate (121 mg) was dissolved in THF (5.00 mL)/methanol (5.00 mL), and the mixture was cooled to 0° C. A 4 mol/L hydrogen chloride/ethyl acetate solution (1.18 mL) was added, and the mixture was stirred at room temperature overnight. The reaction mixture was concentrated under reduced pressure, and the residue was recrystallized from methanol/ethyl acetate to give the title compound (102 mg).

$^1$H NMR (300 MHz, DMSO-d$_6$) δ 0.33-0.39 (2H, m), 0.52-0.61 (2H, m), 1.01-1.14 (1H, m), 1.29-1.37 (1H, m), 1.49-1.60 (1H, m), 1.72-1.92 (4H, m), 2.53-2.59 (1H, m), 2.90-3.03 (3H, m), 3.34 (2H, t, J=6.4 Hz), 3.42-3.48 (2H, m), 7.24-7.30 (2H, m), 7.32-7.39 (2H, m), 9.33 (2H, brs).

Example 62

4-(trans-2-((1,1-dioxidotetrahydro-2H-thiopyran-4-yl)amino)cyclopropyl)-N-(3-(trifluoromethyl)phenyl)benzamide hydrochloride

A) methyl 4-(trans-2-(tert-butoxycarbonyl)cyclopropyl)benzoate

To a suspension of sodium hydride (60% in oil) (2.03 g) in DMSO (200 mL) was added trimethylsulfoxonium iodide (9.48 g), and the mixture was stirred at room temperature for 1 hr. To the reaction mixture was added methyl 4-((1E)-3-tert-butoxy-3-oxoprop-1-en-1-yl)benzoate (4.77 g) described in a document (Org. Biomol. Chem. 2009, 7, 2110-2119.), and the mixture was stirred at 100° C. overnight under a nitrogen atmosphere. Water (200 mL) was added to the reaction mixture, and the mixture was extracted twice with ethyl acetate (200 mL each time). The extracts were combined, washed with saturated brine (20.0 mL), dried over anhydrous sodium sulfate, and concentrated under reduced pressure. The residue was purified by silica gel column chromatography (hexane/ethyl acetate) to give the title compound (6.60 g).

$^1$H NMR (300 MHz, CDCl$_3$) δ 1.25-1.31 (1H, m), 1.47 (9H, s), 1.57-1.63 (1H, m), 1.89 (1H, ddd, J=8.5, 5.5, 4.2 Hz), 2.47 (1H, ddd, J=9.1, 6.1, 4.2 Hz), 3.90 (3H, s), 7.10-7.16 (2H, m), 7.91-7.97 (2H, m).

B) trans-2-(4-(methoxycarbonyl)phenyl)cyclopropanecarboxylic acid

Methyl 4-(trans-2-(tert-butoxycarbonyl)cyclopropyl)benzoate (4.54 g) was cooled to 0° C., TFA (12.7 mL) was added, and the mixture was stirred at room temperature overnight. Water (100 mL) was added to the reaction mixture, and the mixture was extracted twice with ethyl acetate (100 mL each time). The extracts were combined, washed with saturated brine (10.0 mL), dried over anhydrous sodium sulfate, and concentrated under reduced pressure. The residue was purified by silica gel column chromatography (hexane/ethyl acetate) to give the title compound (2.89 g).

$^1$H NMR (300 MHz, CDCl$_3$) δ 1.45 (1H, ddd, J=8.3, 6.6, 4.7 Hz), 1.69-1.77 (1H, m), 1.97 (1H, ddd, J=8.3, 5.3, 4.2 Hz), 2.58-2.68 (1H, m), 3.91 (3H, s), 7.13-7.19 (2H, m), 7.93-7.99 (2H, m).

C) methyl 4-(trans-2-((tert-butoxycarbonyl)amino)cyclopropyl)benzoate

To a solution of trans-2-(4-(methoxycarbonyl)phenyl)cyclopropanecarboxylic acid (2.95 g) in anhydrous toluene (65.0 mL) were added diphenylphosphoryl azide (4.33 mL) and triethylamine (2.80 mL), and the mixture was stirred at room temperature for 1 hr. To the reaction mixture was added anhydrous tert-butyl alcohol (12.6 mL), and the mixture was stirred at 80° C. overnight under a nitrogen atmosphere. To the reaction mixture was added saturated aqueous ammonium chloride solution (100 mL) and the mixture was extracted twice with ethyl acetate (100 mL each time). The extracts were combined, washed successively with water (100 mL) and saturated brine (10.0 mL), dried over anhydrous sodium sulfate, and concentrated under reduced pressure. The residue was purified by silica gel column chromatography (hexane/ethyl acetate) to give the title compound (2.01 g).

$^1$H NMR (300 MHz, CDCl$_3$) δ 1.20-1.26 (2H, m), 1.44 (9H, s), 2.08 (1H, td, J=7.9, 3.2 Hz), 2.78 (1H, brs), 3.89 (3H, s), 4.83 (1H, brs), 7.16 (2H, d, J=8.3 Hz), 7.90-7.96 (2H, m).

D) methyl 4-(trans-2-aminocyclopropyl)benzoate hydrochloride

Methyl 4-(trans-2-((tert-butoxycarbonyl)amino)cyclopropyl)benzoate (828 mg) was dissolved in THF (10.0 mL)/methanol (10.0 mL), and the mixture was cooled to 0° C. A 4 mol/L hydrogen chloride/ethyl acetate solution (10.7 mL) was added, and the mixture was stirred at room temperature overnight. The reaction mixture was concentrated under reduced pressure, and the residue was recrystallized from methanol/diisopropy ether to give the title compound (599 mg).

$^1$H NMR (300 MHz, DMSO-d$_6$) δ 1.26-1.36 (1H, m), 1.42-1.51 (1H, m), 2.36-2.45 (1H, m), 2.88-2.95 (1H, m), 3.84 (3H, s), 7.31 (2H, d, J=8.3 Hz), 7.81-7.94 (2H, m), 8.42 (3H, brs).

E) methyl 4-(trans-2-((1,1-dioxidotetrahydro-2H-thiopyran-4-yl)amino)cyclopropyl)benzoate Methyl 4-(trans-2-aminocyclopropyl)benzoate hydrochloride (300 mg) and dihydro-2H-thiopyran-4(3H)-one 1,1-dioxide (234 mg) was dissolved in methanol (36.0 mL)/acetic acid (3.60 mL), borane-2-methylpyridine complex (211 mg) was added, and the mixture was stirred at room temperature overnight under a nitrogen atmosphere. To the reaction mixture was added aqueous sodium hydrogen carbonate solution (20.0 mL), and the mixture was extracted twice with ethyl acetate (20.0 mL each time). The extracts were combined, washed with saturated brine (5.00 mL), and dried over anhydrous sodium sulfate to give the title compound (114 mg).

MS (API+): [M+H]$^+$ 324.1.

F) methyl 4-(trans-2-((tert-butoxycarbonyl)(1,1-dioxidotetrahydro-2H-thiopyran-4-yl)amino)cyclopropyl)benzoate Methyl 4-(trans-2-((1,1-dioxidotetrahydro-2H-thiopyran-4-yl)amino)cyclopropyl)benzoate (114 mg) was dissolved in THF (5.00 mL), and the mixture was cooled to 0° C. Di-tert-butyl dicarbonate (0.328 mL) and then triethylamine (0.099 mL) were added, and the mixture was stirred under a nitrogen atmosphere at room temperature for 3 days. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (70.6 mg).

$^1$H NMR (300 MHz, CDCl$_3$) δ 1.32-1.39 (1H, m), 1.41 (9H, s), 1.45-1.51 (1H, m), 2.07-2.23 (3H, m), 2.40-2.77 (3H, m), 3.02-3.14 (4H, m), 3.90 (3H, s), 3.93-4.07 (1H, m), 7.15 (2H, d, J=8.3 Hz), 7.93-7.99 (2H, m).

G) 4-(trans-2-((tert-butoxycarbonyl)(1,1-dioxidotetrahydro-2H-thiopyran-4-yl)amino)cyclopropyl)benzoic acid Methyl 4-(trans-2-((tert-butoxycarbonyl)(1,1-dioxidotetrahydro-2H-thiopyran-4-yl)amino)cyclopropyl)benzoate (90.4 mg) was dissolved in methanol (5.00 mL), 1 mol/L aqueous sodium hydroxide solution (1.07 mL) was added at room temperature, and the mixture was stirred at room temperature overnight. The reaction mixture was cooled to 0° C., 1 mol/L hydrochloric acid (1.12 mL) was added, water (20.0 mL) was further added, and the mixture was extracted twice with ethyl acetate (20.0 mL each time). The extracts were combined, washed with saturated brine (5.00 mL), and dried over anhydrous sodium sulfate to give the title compound (64.7 mg).

$^1$H NMR (300 MHz, CDCl$_3$) δ 1.34-1.53 (11H, m), 2.07-2.26 (3H, m), 2.41-2.77 (3H, m), 3.02-3.16 (4H, m), 3.93-4.07 (1H, m), 7.18 (2H, d, J=8.3 Hz), 8.02 (2H, d, J=8.3 Hz).

H) tert-butyl (1,1-dioxidotetrahydro-2H-thiopyran-4-yl) (trans-2-(4-((3-(trifluoromethyl)phenyl)carbamoyl)phenyl)cyclopropyl)-carbamate 4-(trans-2-((tert-Butoxycarbonyl)(1,1-dioxidotetrahydro-2H-thiopyran-4-yl)amino)cyclopropyl)benzoic acid (67.8 mg), 3-(trifluoromethyl)aniline (32.0 mg) and O-(7-azabenzotriazol-1-yl)-N,N,N',N'-tetramethyluronium hexafluorophosphate (76.0 mg) were dissolved in anhydrous DMF (2.00 mL), triethylamine (0.069 mL) was added, and the mixture was stirred at room temperature overnight. To the reaction mixture was added water (20.0 mL), and the mixture was extracted twice with ethyl acetate (20.0 mL each time). The extracts were combined, washed with saturated brine (5.00 mL), dried over anhydrous sodium sulfate, and concentrated under reduced pressure. The residue was purified by silica gel column chromatography (hexane/ethyl acetate) to give the title compound (22.2 mg).

MS (API+): [M+H]$^+$ 553.2.

I) 4-(trans-2-((1,1-dioxidotetrahydro-2H-thiopyran-4-yl)amino)cyclopropyl)-N-(3-(trifluoromethyl)phenyl)benzamide hydrochloride tert-Butyl (1,1-dioxidotetrahydro-2H-thiopyran-4-yl) (trans-2-(4-((3-(trifluoromethyl)phenyl)carbamoyl)phenyl) cyclopropyl)carbamate (22.2 mg) was dissolved in THF (2.00 mL), and the mixture was cooled to 0° C. A 4 mol/L hydrogen chloride/ethyl acetate solution (0.151 mL) was added, and the mixture was stirred at room temperature overnight. The reaction mixture was concentrated under reduced pressure, and the residue was recrystallized from methanol/diisopropy ether to give the title compound (17.4 mg).

$^1$H NMR (300 MHz, DMSO-d$_6$) δ 1.44 (1H, q, J=7.6 Hz), 1.63-1.73 (1H, m), 2.06-2.26 (2H, m), 2.39-2.60 (2H, m), 2.61-2.71 (1H, m), 3.08-3.19 (1H, m), 3.22-3.33 (5H, m), 7.38 (2H, d, J=8.3 Hz), 7.44 (1H, d, J=7.6 Hz), 7.60 (1H, t, J=8.0 Hz), 7.96 (2H, d, J=8.3 Hz), 8.07 (1H, d, J=8.3 Hz), 8.27 (1H, s), 9.84 (2H, brs), 10.53 (1H, s).

Example 63

3-(trans-2-aminocyclopropyl)-N-(1-(cyclopropylmethyl)-1H-pyrazol-4-yl)benzamide dihydrochloride

A) methyl 3-(trans-2-(tert-butoxycarbonyl)cyclopropyl)benzoate

To a suspension of sodium hydride (60% in oil) (13.9 g) in DMSO (1800 mL) was added trimethylsulfoxonium iodide (76.5 g), and the mixture was stirred at room temperature for 1 hr under a nitrogen atmosphere. To the reaction mixture was added methyl 3-((1E)-3-tert-butoxy-3-oxoprop-1-en-1-yl)benzoate (76.0 g) described in a document (Org. Biomol. Chem. 2009, 7, 2110-2119.), and the mixture was stirred under a nitrogen atmosphere at room temperature for 18 hr. To the reaction mixture was added saturated aqueous ammonium chloride solution (500 mL), and the mixture was extracted three times with ethyl acetate (500 mL each time). The extracts were combined, washed with water and saturated brine, dried over anhydrous sodium sulfate, and concentrated under reduced pressure. The obtained residue was purified by silica gel column chromatography (petroleum ether/ethyl acetate) to give the title compound (50.0 g).

$^1$H NMR (400 MHz, CDCl$_3$) δ1.25-1.27 (1H, m), 1.48 (9H, s), 1.56-1.59 (1H, m), 1.71-1.86 (1H, m), 2.47-2.50 (1H, m), 3.90 (3H, s), 7.28-7.36 (2H, m), 7.74 (1H, s), 7.84-7.87 (1H, m).

B) trans-2-(3-(methoxycarbonyl)phenyl)cyclopropanecarboxylic acid

Methyl 3-(trans-2-(tert-butoxycarbonyl)cyclopropyl)benzoate (2.48 g) was cooled to 0° C., TFA (6.91 mL) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (1.76 g).

MS (API-): [M-H]$^-$ 219.1.

C) methyl 3-(trans-2-((tert-butoxycarbonyl)amino) cyclopropyl)benzoate

To a solution of trans-2-(3-(methoxycarbonyl)phenyl)cyclopropanecarboxylic acid (2.44 g) in anhydrous tert-butyl alcohol (20.8 mL) were added triethylamine (1.85 mL) and diphenylphosphoryl azide (2.86 mL), and the mixture was stirred at room temperature for 1 hr and at 80° C. for 16 hr under a nitrogen atmosphere. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (2.48 g).

$^1$H NMR (300 MHz, CDCl$_3$) δ1.18-1.27 (2H, m), 1.45 (9H, s), 2.09 (1H, ddd, J=9.5, 6.4, 3.0 Hz), 2.75 (1H, brs), 3.90 (3H, s), 4.84 (1H, brs), 7.32-7.40 (2H, m), 7.76 (1H, s), 7.82-7.87 (1H, m).

D) 3-(trans-2-((tert-Butoxycarbonyl)amino)cyclopropyl)benzoic acid

Methyl 3-(trans-2-((tert-Butoxycarbonyl)amino)cyclopropyl)benzoate (14.0 g) was dissolved in methanol (30.0 mL), 8 mol/L aqueous sodium hydroxide solution (30.0 mL) was added, and the mixture was stirred at room temperature for 18 hr. The reaction mixture was washed with ethyl acetate, the aqueous layer was neutralized with 1 mol/L hydrochloric acid under ice-cooling, and the mixture was extracted with ethyl acetate. The extract was washed successively with water and saturated brine, dried over anhydrous sodium sulfate, and concentrated under reduced pressure to give the title compound (13.0 g).

$^1$H NMR (400 MHz, DMSO-d$_6$) δ1.09-1.15 (2H, m), 1.36 (9H, s), 1.94-1.99 (1H, m), 2.55-2.65 (1H, m), 7.25 (1H, brs), 7.29-7.38 (2H, m), 7.65 (1H, s), 7.71 (1H, d, J=7.6 Hz), 12.87 (1H, brs).

E) tert-butyl (trans-2-(3-((1-(cyclopropylmethyl)-1H-pyrazol-4-yl)carbamoyl)phenyl)cyclopropyl) carbamate 3-(trans-2-((tert-Butoxycarbonyl)amino)cyclopropyl) benzoic acid (1.00 g), O-(7-azabenzotriazol-1-yl)-N,N,N',N'-tetramethyluronium hexafluorophosphate (1.51 g) and 1-(cyclopropylmethyl)-1H-pyrazol-4-amine hydrochloride (689 mg) were dissolved in anhydrous DMF (30.0 mL), triethylamine (2.01 mL) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (1.38 g).

MS (API+): [M+H]$^+$ 397.3.

F) 3-(trans-2-aminocyclopropyl)-N-(1-(cyclopropylmethyl)-1H-pyrazol-4-yl)benzamide dihydrochloride tert-Butyl (trans-2-(3-((1-(cyclopropylmethyl)-1H-pyrazol-4-yl)carbamoyl)phenyl)cyclopropyl)carbamate (485 mg) was dissolved in methanol (15.0 mL)/THF (15.0 mL), and the mixture was cooled to 0° C. A 4 mol/L hydrogen chloride/ethyl acetate solution (4.58 mL) was added, and the mixture was stirred at room temperature for 18 hr. The reaction mixture was concentrated under reduced pressure, and the residue was crystallized from methanol/diisopropy ether to give the title compound (450 mg).

$^1$H NMR (300 MHz, DMSO-d$_6$) δ 0.31-0.39 (2H, m), 0.48-0.57 (2H, m), 1.16-1.27 (1H, m), 1.27-1.36 (1H, m), 1.41-1.51 (1H, m), 2.39-2.46 (1H, m), 2.92 (1H, brs), 3.96 (2H, d, J=7.2 Hz), 7.35-7.40 (1H, m), 7.41-7.47 (1H, m), 7.61 (1H, s), 7.73 (1H, s), 7.79 (1H, d, J=7.6 Hz), 8.10 (1H, s), 8.52 (3H, brs), 10.48 (1H, d, J=3.0 Hz).

Example 64

3-(trans-2-aminocyclopropyl)-N-(5-methyl-1,3,4-thiadiazol-2-yl)benzamide dihydrochloride A) tert-butyl (trans-2-(3-((5-methyl-1,3,4-thiadiazol-2-yl)carbamoyl)phenyl)cyclopropyl)carbamate 3-(trans-2-((tert-Butoxycarbonyl)amino)cyclopropyl) benzoic acid (4.00 g), 5-methyl-1,3,4-thiadiazol-2-amine (1.92 g) and triethylamine (8.04 mL) were dissolved in anhydrous DMF (40.0 mL), and the mixture was cooled to 0° C. O-(7-Azabenzotriazol-1-yl)-N,N,N',N'-tetramethyluronium hexafluorophosphate (6.58 g) was added, and the mixture was stirred at room temperature for 30 min, at 50° C. for 1 hr, and at room temperature overnight. The reaction mixture was poured into water, and the mixture was extracted with ethyl acetate. The extract was washed successively with water and saturated brine, dried over anhydrous magnesium sulfate, and concentrated under reduced pressure. The residue was washed with diisopropy ether to give the title compound (5.08 g).

MS (API+): [M+H]$^+$ 375.1.

B) 3-(trans-2-aminocyclopropyl)-N-(5-methyl-1,3,4-thiadiazol-2-yl)benzamide dihydrochloride tert-Butyl (trans-2-(3-((5-methyl-1,3,4-thiadiazol-2-yl) carbamoyl)phenyl)cyclopropyl) carbamate (768 mg) was dissolved in methanol (5.00 mL), a 4 mol/L hydrogen chloride/ethyl acetate solution (15.4 mL) was added, and the mixture was stirred at room temperature overnight. The reaction mixture was concentrated under reduced pressure, and the residue was washed with ethyl acetate to give the title compound (712 mg).

$^1$H NMR (300 MHz, DMSO-d$_6$) δ1.29-1.52 (2H, m), 2.38-2.46 (1H, m), 2.65 (3H, s), 2.87-3.02 (1H, m), 7.42-7.56 (2H, m), 7.80-7.85 (1H, m), 7.88-7.96 (1H, m), 8.39-8.57 (3H, m), 12.61-12.99 (1H, m).

Example 65

3-(trans-2-aminocyclopropyl)-N-(1-tert-butyl-1H-pyrazol-4-yl)benzamide dihydrochloride A) tert-butyl (trans-2-(3-((1-(tert-butyl)-1H-pyrazol-4-yl)carbamoyl)phenyl)cyclopropyl)carbamate 3-(trans-2-((tert-Butoxycarbonyl)amino)cyclopropyl) benzoic acid (670 mg), 1-(tert-butyl)-1H-pyrazol-4-amine (460 mg) and triethylamine (1.35 mL) were dissolved in anhydrous DMF (15.0 mL), and the mixture was cooled to 0° C. O-(7-Azabenzotriazol-1-yl)-N,N,N',N'-tetramethyluronium hexafluorophosphate (1.84 g) was added, and the mixture was stirred at room temperature for 2 days. Water was added to the reaction mixture, and the mixture was extracted with ethyl acetate. The extracts were combined, washed with saturated aqueous sodium hydrogen carbonate solution and saturated brine, and dried over anhydrous sodium sulfate. The solution was purified by short silica gel column chromatography (ethyl acetate), purified by NH silica gel column chromatography (ethyl acetate) and concentrated under reduced pressure. The obtained residue was washed with diisopropy ether under insonation to give the title compound (776 mg).

MS (API+): [M+H]$^+$ 399.4.

B) 3-(trans-2-aminocyclopropyl)-N-(1-tert-butyl-1H-pyrazol-4-yl)benzamide dihydrochloride tert-Butyl (trans-2-(3-((1-(tert-butyl)-1H-pyrazol-4-yl) carbamoyl)phenyl)cyclopropyl)carbamate (775 mg) was dissolved in methanol (40.0 mL), a 2 mol/L hydrogen chloride/methanol solution (14.6 mL) was added, and the mixture was stirred at room temperature for 20 hr. The reaction mixture was concentrated under reduced pressure, and the residue was crystallized from tetrahydrofuran/diethyl ether to give the title compound (703 mg).

$^1$H NMR (300 MHz, DMSO-d$_6$) δ1.27-1.36 (1H, m), 1.41-1.48 (1E, m), 1.52 (9H, s), 2.37-2.45 (1H, m), 2.87-2.97 (1H, m), 7.34-7.48 (2H, m), 7.64 (1H, s), 7.69-7.73 (1H, m), 7.76-7.82 (1H, m), 8.09 (1H, s), 8.45 (3H, brs), 10.43 (1H, s).

Example 66

3-(trans-2-aminocyclopropyl)-N-(4,4-difluorocyclohexyl)benzamide hydrochloride

A) tert-butyl (trans-2-(3-((4,4-difluorocyclohexyl) carbamoyl)phenyl)cyclopropyl)carbamate 3-(trans-2-((tert-Butoxycarbonyl)amino)cyclopropyl) benzoic acid (300 mg), O-(7-azabenzotriazol-1-yl)-N,N,N', N'-tetramethyluronium hexafluorophosphate (494 mg) and 4,4-difluorocyclohexanamine (154 mg) were dissolved in anhydrous DMF (10.0 mL), triethylamine (0.452 mL) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (357 mg).

MS (API+): [M−(tert-Bu)+E]+ 339.2.

B) 3-(trans-2-aminocyclopropyl)-N-(4,4-difluorocyclohexyl)benzamide hydrochloride tert-Butyl (trans-2-(3-((4,4-difluorocyclohexyl)carbamoyl)phenyl)cyclopropyl)carbamate (352 mg) was dissolved in methanol (25.0 mL)/THF (10.0 mL), and the mixture was cooled to 0° C. A 4 mol/L hydrogen chloride/ethyl acetate solution (3.35 mL) was added, and the mixture was stirred at room temperature for 18 hr. The reaction mixture was concentrated under reduced pressure, and the residue was crystallized from methanol/diisopropy ether to give the title compound (289 mg).

$^1$H NMR (300 MHz, DMSO-$d_6$) δ1.28 (1H, q, J=6.6 Hz), 1.35-1.45 (1H, m), 1.56-1.72 (2H, m), 1.88 (3H, dd, J=14.0, 3.0 Hz), 1.99-2.11 (3H, m), 2.33-2.42 (1H, m), 2.83-2.93 (1H, m), 3.92-4.06 (1H, m), 7.29-7.34 (1H, m), 7.35-7.41 (1H, m), 7.60 (1H, s), 7.69 (1H, dt, J=7.4, 1.4 Hz), 8.26 (1H, d, J=8.0 Hz), 8.36 (3H, brs).

Example 67

3-(trans-2-aminocyclopropyl)-N-(tetrahydro-2H-pyran-4-yl)benzamide hydrochloride A) tert-butyl (trans-2-(3-((tetrahydro-2H-pyran-4-yl)carbamoyl)phenyl)cyclopropyl)carbamate 3-(trans-2-((tert-Butoxycarbonyl)amino)cyclopropyl) benzoic acid (250 mg), O-(7-azabenzotriazol-1-yl)-N,N,N', N'-tetramethyluronium hexafluorophosphate (411 mg) and tetrahydro-2H-pyran-4-amine (115 mg) were dissolved in anhydrous DMF (10.0 mL), triethylamine (0.377 mL) was added, and the mixture was stirred at room temperature for 18 hr. Water was added to the reaction mixture, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (294 mg).

MS (API+): [M+H]+ 361.3.

B) 3-(trans-2-aminocyclopropyl)-N-(tetrahydro-2H-pyran-4-yl)benzamide hydrochloride tert-Butyl (trans-2-(3-((tetrahydro-2H-pyran-4-yl)carbamoyl)phenyl)cyclopropyl)carbamate (905 mg) was dissolved in methanol (30.0 mL), and the mixture was cooled to 0° C. A 4 mol/L hydrogen chloride/ethyl acetate solution (9.42 mL) was added, and the mixture was stirred at room temperature for 18 hr. The reaction mixture was concentrated under reduced pressure, and the residue was crystallized from methanol/diethyl ether to give the title compound (759 mg).

$^1$H NMR (300 MHz, DMSO-$d_6$) δ1.27 (1H, q, J=6.7 Hz), 1.39-1.49 (1H, m), 1.59 (2H, qd, J=11.9, 4.4 Hz), 1.70-1.80 (2H, m), 2.37-2.46 (1H, m), 2.88 (1H, dq, J=8.0, 4.0 Hz), 3.38 (2H, td, J=11.6, 1.7 Hz), 3.88 (2H, dd, J=11.9, 2.5 Hz), 3.94-4.07 (1H, m), 7.29-7.34 (1H, m), 7.34-7.41 (1H, m), 7.62 (1H, s), 7.69 (1H, dt, J=7.5, 1.4 Hz), 8.32 (1H, d, J=3.0 Hz), 8.57 (3H, brs).

Example 68

3-(trans-2-aminocyclopropyl)-N-methyl-N-phenyl-benzamide hydrochloride

Example 69

3-(trans-2-aminocyclopropyl)-N-(3-(pyrimidin-2-yl)phenyl)benzamide dihydrochloride Example 70

3-(trans-2-aminocyclopropyl)-N-(4-(2-oxopyrrolidin-1-yl) phenyl) benzamide hydrochloride Example 71

3-(trans-2-aminocyclopropyl)-N-(1-(4-fluorophenyl)-1H-pyrazol-4-yl)benzamide dihydrochloride Example 72

3-(trans-2-aminocyclopropyl)-N-(4-fluorophenyl) benzamide hydrochloride

Example 73

3-(trans-2-aminocyclopropyl)-N-(1,1-dioxidotetrahydro-2H-thiopyran-4-yl)benzamide hydrochloride By a method similar to that in Example 67, the compounds of Examples 68 to 73 were produced.

Example 74

3-(trans-2-aminocyclopropyl)-N-(1-ethyl-1H-pyrazol-4-yl)benzamide dihydrochloride A) tert-butyl (trans-2-(3-((1-ethyl-1H-pyrazol-4-yl)carbamoyl)phenyl)cyclopropyl)carbamate 3-(trans-2-((tert-Butoxycarbonyl)amino)cyclopropyl) benzoic acid (400 mg), 1-ethyl-1H-pyrazol-4-amine (0.226 mL) and triethylamine (0.302 mL) were dissolved in anhydrous DMF (10.0 mL), O-(7-azabenzotriazol-1-yl)-N,N,N', N'-tetramethyluronium hexafluorophosphate (658 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (489 mg).

MS (API+): [M+H]+ 371.2.

B) 3-(trans-2-aminocyclopropyl)-N-(1-ethyl-1H-pyrazol-4-yl)benzamide dihydrochloride tert-Butyl (trans-2-(3-((1-ethyl-1H-pyrazol-4-yl)carbamoyl)phenyl)cyclopropyl)carbamate (480 mg) was dissolved in methanol (15.0 mL)/THF (15.0 mL), and the mixture was cooled to 0° C. A 4 mol/L hydrogen chloride/ethyl acetate solution (4.85 mL) was added, and the mixture was stirred at room temperature for 18 hr. The reaction mixture was concentrated under reduced pressure, and the residue was crystallized from methanol/diisopropy ether to give the title compound (428 mg).

$^1$H NMR (300 MHz, DMSO-d$_6$) δ1.27-1.39 (4H, m), 1.49 (1H, ddd, J=10.0, 5.9, 4.5 Hz), 2.44-2.48 (1H, m), 2.94 (1H, dq, J=8.0, 4.1 Hz), 4.12 (2H, q, J=7.2 Hz), 7.34-7.40 (1H, m), 7.40-7.46 (1H, m), 7.65 (1H, s), 7.76 (1H, s), 7.80 (1H, dt, J=7.6, 1.5 Hz), 8.07 (1H, s), 8.69 (3H, brs), 10.57 (1H, s).

Example 75

5-(trans-2-aminocyclopropyl)-N-cyclopentyl-2-fluorobenzamide hydrochloride

A) methyl 5-((1E)-3-tert-butoxy-3-oxoprop-1-en-1-yl)-2-fluorobenzoate

To a solution of anhydrous lithium chloride (1.16 g) in acetonitrile (80.0 mL) were added methyl 2-fluoro-5-formylbenzoate (4.00 g) and tert-butyl diethylphosphonoacetate (5.81 mL) under ice-cooling, and the mixture was stirred at 0° C. for 5 min under a nitrogen atmosphere. To the reaction mixture was added 1,8-diazabicyclo[5.4.0]undec-7-ene (3.69 mL), and the mixture was stirred under a nitrogen atmosphere at room temperature for 6 hr. Water was added to the reaction mixture, and the mixture was extracted twice with ethyl acetate (150 mL each time). The extracts were combined, washed with water (100 mL) and saturated brine (100 mL), dried over anhydrous sodium sulfate, and concentrated under reduced pressure. The obtained residue was purified by silica gel column chromatography (hexane/ethyl acetate) to give the title compound (4.50 g).

$^1$H NMR (400 MHz, CDCl$_3$) δ1.48 (9H, s), 3.87 (3H, s), 6.56 (1H, d, J=16.0 Hz), 7.39 (1H, dd, J=10.6, 8.8 Hz), 7.60 (1H, d, J=16.0 Hz), 8.03-8.07 (1H, m), 8.14 (1H, dd, J=7.0, 2.2 Hz).

B) methyl 5-(trans-2-(tert-butoxycarbonyl)cyclopropyl)-2-fluorobenzoate

To a suspension of sodium hydride (50% in oil) (960 mg) in DMSO (150 mL) was added a solution of trimethylsulfoxonium iodide (4.42 g) in DMSO (2.00 mL), and the mixture was stirred at room temperature for 1 hr under a nitrogen atmosphere. A solution of methyl 5-((1E)-3-tert-butoxy-3-oxoprop-1-en-1-yl)-2-fluorobenzoate (4.50 g) in DMSO (50.0 mL) was added to the reaction mixture, and the mixture was stirred at room temperature for 18 hr under a nitrogen atmosphere. To the reaction mixture was added saturated aqueous ammonium chloride solution (100 mL), and the mixture was extracted twice with ethyl acetate (150 mL each time). The extracts were combined, washed with water (100 mL) and saturated brine (100 mL), dried over anhydrous sodium sulfate, and concentrated under reduced pressure. The obtained residue was purified by silica gel column chromatography (hexane/ethyl acetate) to give the title compound (3.50 g).

$^1$H-NMR (400 MHz, DMSO-d$_6$) δ1.30-1.33 (1H, m), 1.40 (9H, s), 1.45-1.48 (1H, m), 1.83-1.87 (1H, m), 2.44-2.47 (1H, m), 3.84 (3H, s), 7.25 (1H, dd, J=10.7, 8.8 Hz), 7.43-7.47 (1H, m), 7.65 (1H, dd, J=6.8, 2.4 Hz).

C) trans-2-(4-fluoro-3-(methoxycarbonyl)phenyl)cyclopropanecarboxylic acid

Methyl 5-(trans-2-(tert-butoxycarbonyl)cyclopropyl)-2-fluorobenzoate (3.80 g) was cooled to 0° C., TFA (10.0 mL) was added, and the mixture was stirred at 0° C. for 18 hr. The reaction mixture was concentrated, water (50.0 mL) was added, and the mixture was extracted with ethyl acetate (200 mL). The extract was washed with water (50.0 mL) and saturated brine (100 mL), dried over anhydrous sodium sulfate, and concentrated under reduced pressure. The residue was washed with pentane, the solid was suspended in toluene, and the mixture was concentrated to give the title compound (3.00 g).

$^1$H-NMR (400 MHz, DMSO-d$_6$) δ1.37-1.39 (1H, m), 1.40-1.45 (1H, m), 1.80-1.84 (1H, m), 3.60-3.66 (1H, brs), 3.87 (3H, s), 7.25 (1H, dd, J=10.6, 8.8 Hz), 7.41-7.48 (1H, m), 7.64-7.66 (1H, m), 12.41 (1H, brs).

D) methyl 5-(trans-2-((tert-butoxycarbonyl)amino)cyclopropyl)-2-fluorobenzoate

To a solution of trans-2-(4-fluoro-3-(methoxycarbonyl)phenyl)cyclopropanecarboxylic acid (1.00 g) in anhydrous Cert-butyl alcohol (8.00 mL) were added triethylamine (0.70 mL) and diphenylphosphoryl azide (1.10 mL), and the mixture was stirred at room temperature for 1 hr and at 80° C. for 16 hr. Water (100 mL) was added to the reaction mixture, and the mixture was extracted twice with ethyl acetate (100 mL each time). The extracts were combined, washed successively with water (50.0 mL) and saturated brine (100 mL), dried over anhydrous sodium sulfate, and concentrated under reduced pressure. The residue was purified by silica gel column chromatography (hexane/ethyl acetate) to give the title compound (600 mg).

MS (API+): [M+H]$^+$ 310.2.

E) 5-(trans-2-((tert-butoxycarbonyl)amino)cyclopropyl)-2-fluorobenzoic acid

Methyl 5-(trans-2-((tert-butoxycarbonyl)amino)cyclopropyl)-2-fluorobenzoate (1.80 g) was dissolved in methanol (9.00 mL), 8 mol/L aqueous sodium hydroxide solution (4.50 mL) was added, and the mixture was stirred at room temperature for 1 hr. The reaction mixture was neutralized with 1 mol/L hydrochloric acid under ice-cooling, and the resulting precipitate was collected by filtration, and washed with water to give the title compound (1.60 g).

MS (API−): [M−H]$^−$ 294.2.

F) tert-butyl (trans-2-(3-(cyclopentylcarbamoyl)-4-fluorophenyl)cyclopropyl)carbamate 5-(trans-2-((tert-Butoxycarbonyl)amino)cyclopropyl)-2-fluorobenzoic acid (200 mg), cyclopentanamine (0.081 mL) and triethylamine (0.142 mL) were dissolved in anhydrous DMF (10.0 mL), O-(7-azabenzotriazol-1-yl)-N,N,N',N'-tetramethyluronium hexafluorophosphate (309 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (149 mg).

MS (API+): [M+H]$^+$ 363.2.

G) 5-(trans-2-aminocyclopropyl)-N-cyclopentyl-2-fluorobenzamide hydrochloride tert-Butyl (trans-2-(3-(cyclopentylcarbamoyl)-4-fluorophenyl)cyclopropyl)carbamate (140 mg) was dissolved in methanol (5.00 mL)/THF (5.00 mL), and the mixture was cooled to 0° C. A 4 mol/L hydrogen chloride/ethyl acetate solution (1.45 mL) was added, and the mixture was stirred at room temperature for 18 hr. The reaction mixture was concentrated under reduced pressure, and the residue was crystallized from methanol/ethyl acetate to give the title compound (90.0 mg).

$^1$H NMR (300 MHz, DMSO-d$_6$) 151.19-1.28 (1H, m), 1.30-1.41 (1H, m), 1.43-1.59 (4H, m), 1.60-1.72 (2H, m), 1.82-1.93 (2H, m), 2.34 (1H, ddd, J=9.8, 6.1, 3.8 Hz), 2.78-2.85 (1H, m), 4.12-4.25 (1H, m), 7.15-7.22 (1H, m), 7.25-7.35 (2H, m), 8.23 (1H, d, J=7.2 Hz), 8.28 (3H, brs).

Example 76

5-(trans-2-aminocyclopropyl)-N-cyclopentyl-2-methoxybenzamide hydrochloride

A) methyl 5-((1E)-3-tert-butoxy-3-oxoprop-1-en-1-yl)-2-methoxybenzoate

To a solution of anhydrous lithium chloride (500 mg) in acetonitrile (50.0 mL) were added methyl 5-formyl-2-methoxybenzoate (2.00 g) and tert-butyl diethylphosphonoacetate (2.50 mL) under ice-cooling, and the mixture was stirred at 0° C. for 5 min under a nitrogen atmosphere. To the reaction mixture was added 1,8-diazabicyclo[5.4.0]undec-7-ene (1.60 mL), and the mixture was stirred under a nitrogen atmosphere at room temperature for 16 hr. Water was added to the reaction mixture, and the mixture was extracted twice with ethyl acetate (75.0 mL each time). The extracts were combined, washed with water (70.0 mL) and saturated brine (100 mL), dried over anhydrous sodium sulfate, and concentrated under reduced pressure. The obtained residue was purified by silica gel column chromatography (hexane/ethyl acetate) to give the title compound (2.80 g).

$^1$H-NMR (400 MHz, DMSO-d$_6$) δ1.52 (9H, s), 3.89 (3H, s), 3.92 (3H, s), 6.28 (1H, d, J=15.9 Hz), 6.96 (1H, d, J=8.7 Hz), 7.51 (1H, d, J=15.9 Hz), 7.59 (1H, dd, J=8.6, 2.2 Hz), 7.96 (1H, d, J=2.2 Hz).

B) methyl 5-(trans-2-(tert-butoxycarbonyl)cyclopropyl)-2-methoxybenzoate

To a suspension of sodium hydride (50% in oil) (552 mg) in DMSO (70.0 mL) was added a solution of trimethylsulfoxonium iodide (2.50 g) in DMSO (2.00 mL), and the mixture was stirred at room temperature for 1 hr under a nitrogen atmosphere. A solution of methyl 5-((1E)-3-tert-butoxy-3-oxoprop-1-en-1-yl)-2-methoxybenzoate (2.80 g) in DMSO (30.0 mL) was added to the reaction mixture, and the mixture was stirred at room temperature for 20 hr under a nitrogen atmosphere. To the reaction mixture was added saturated aqueous ammonium chloride solution (100 mL), and the mixture was extracted twice with ethyl acetate (150 mL each time). The extracts were combined, washed with water (100 mL) and saturated brine (100 mL), dried over anhydrous sodium sulfate, and concentrated under reduced pressure. The obtained residue was purified by silica gel column chromatography (hexane/ethyl acetate) to give the title compound (1.70 g).

MS (API+): [M+H]$^+$ 307.0.

C) trans-2-(4-methoxy-3-(methoxycarbonyl)phenyl)cyclopropanecarboxylic acid

Methyl 5-(trans-2-(tert-butoxycarbonyl)cyclopropyl)-2-methoxybenzoate (1.70 g) was cooled to 0° C., TFA (4.20 mL) was added, and the mixture was stirred at room temperature for 18 hr. Water (50.0 mL) was added to the reaction mixture, and the mixture was extracted with ethyl acetate (200 mL). The extract was washed with water (50.0 mL) and saturated brine (100 mL), dried over anhydrous sodium sulfate, and concentrated under reduced pressure. The residue was purified by silica gel column chromatography (hexane/ethyl acetate) to give the title compound (1.20 g).

$^1$H-NMR (400 MHz, DMSO-d$_6$) δ1.35-1.39 (1H, m), 1.61-1.65 (1H, m), 1.82-1.87 (1H, m), 2.55-2.59 (1H, m), 3.88 (6H, s), 6.89 (1H, d, J=8.6 Hz), 7.21 (1H, d, J=2.2 Hz), 7.53 (1H, d, J=2.2 Hz).

D) methyl 5-(trans-2-((tert-butoxycarbonyl)amino)cyclopropyl)-2-methoxybenzoate To a solution of trans-2-(4-methoxy-3-(methoxycarbonyl)phenyl)cyclopropanecarboxylic acid (5.00 g) in anhydrous tert-butyl alcohol (40.0 mL) were added triethylamine (3.40 mL) and diphenylphosphoryl azide (5.18 mL), and the mixture was stirred at room temperature for 1 hr and at 80° C. for 16 hr under a nitrogen atmosphere. Water (100 mL) was added to the reaction mixture, and the mixture was extracted twice with ethyl acetate (100 mL each time). The extracts were combined, washed successively with water (50.0 mL) and saturated brine (100 mL), dried over anhydrous sodium sulfate, and concentrated under reduced pressure. The residue was purified by silica gel column chromatography (hexane/ethyl acetate) to give the title compound (3.50 g).

MS (API+): [M+H]$^+$ 321.8.

E) 5-(trans-2-((tert-butoxycarbonyl)amino)cyclopropyl)-2-methoxybenzoic acid Methyl 5-(trans-2-((tert-butoxycarbonyl)amino)cyclopropyl)-2-methoxybenzoate (2.20 g) was dissolved in methanol (20.0 mL), 8 mol/L aqueous sodium hydroxide solution (6.00 mL) was added, and the mixture was stirred at room temperature for 18 hr. The reaction mixture was neutralized with 1 mol/L hydrochloric acid under ice-cooling, and the resulting precipitate was collected by filtration, and washed with water to give the title compound (1.20 g).

MS (API+): [M+H]$^+$ 308.2.

F) tert-butyl (trans-2-(3-(cyclopentylcarbamoyl)-4-methoxyphenyl)cyclopropyl)carbamate 5-(trans-2-((tert-Butoxycarbonyl)amino)cyclopropyl)-2-methoxybenzoic acid (200 mg), cyclopentanamine (0.078 mL) and triethylamine (0.136 mL) were dissolved in anhydrous DMF (10.0 mL), O-(7-azabenzotriazol-1-yl)-N,N,N',N'-tetramethyluronium hexafluorophosphate (297 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (hexane/ethyl acetate) to give the title compound (203 mg).
MS (API+): [M+H]$^+$ 375.3.

G) 5-(trans-2-aminocyclopropyl)-N-cyclopentyl-2-methoxybenzamide hydrochloride tert-Butyl (trans-2-(3-(cyclopentylcarbamoyl)-4-methoxyphenyl)cyclopropyl)carbamate (193 mg) was dissolved in methanol (10.0 mL)/THF (10.0 mL), and the mixture was cooled to 0° C. A 4 mol/L hydrogen chloride/ethyl acetate solution (1.94 mL) was added, and the mixture was stirred at room temperature for 18 hr. The reaction mixture was concentrated under reduced pressure, and the residue was crystallized from methanol/diisopropy ether to give the title compound (165 mg).
$^1$H NMR (300 MHz, DMSO-d$_6$) δ1.12-1.21 (1H, m), 1.29-1.37 (1H, m), 1.42-1.74 (6H, m), 1.81-1.94 (2H, m), 2.26-2.37 (1H, m), 2.68-2.78 (1H, m), 3.84 (3H, s), 4.19 (1H, sxt, J=6.7 Hz), 7.04 (1H, d, J=8.7 Hz), 7.23 (1H, dd, J=8.5, 2.5 Hz), 7.48 (1H, d, J=2.3 Hz), 7.99 (1H, d, J=7.2 Hz), 8.35 (3H, brs).

Example 77

3-(trans-2-((cyclopropylmethyl)amino)cyclopropyl)-N-(1-(cyclopropylmethyl)-1H-pyrazol-4-yl)benzamide dihydrochloride A) tert-butyl (cyclopropylmethyl)(trans-2-(3-((1-(cyclopropylmethyl)-1H-pyrazol-4-yl)carbamoyl)phenyl)cyclopropyl)carbamate 3-(trans-2-Aminocyclopropyl)-N-(1-(cyclopropylmethyl)-1H-pyrazol-4-yl)benzamide dihydrochloride (400 mg) and sodium hydrogen carbonate (273 mg) was dissolved in THF (20.0 mL)/methanol (20.0 mL), and cyclopropanecarbaldehyde (91.0 mg) was added. The mixture was stirred at 60° C. for 3 hr, and sodium borohydride (82 mg) was added under ice-cooling. The mixture was stirred at room temperature for 2 hr, di-tert-butyl dicarbonate (0.377 mL) was added to the reaction mixture, and the mixture was stirred at room temperature for 16 hr. Water was added to the reaction mixture, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (263 mg).
MS (API+): [M+H]$^+$ 451.3.

B) 3-(trans-2-((cyclopropylmethyl)amino)cyclopropyl)-N-(1-(cyclopropylmethyl)-1H-pyrazol-4-yl)benzamide dihydrochloride tert-Butyl (cyclopropylmethyl) (trans-2-(3-((1-(cyclopropylmethyl)-1H-pyrazol-4-yl)carbamoyl)phenyl)cyclopropyl)carbamate (263 mg) was dissolved in THF (5.00 mL)/methanol (5.00 mL), and the mixture was cooled to 0° C. A 4 mol/L hydrogen chloride/ethyl acetate solution (2.19 mL) was added, and the mixture was stirred at room temperature for 18 hr. The reaction mixture was concentrated under reduced pressure, and the residue was crystallized from methanol/diisopropy ether to give the title compound (185 mg).
$^1$H NMR (300 MHz, DMSO-d$_6$) δ0.32-0.40 (4H, m), 0.48-0.62 (4H, m), 1.02-1.12 (1H, m), 1.15-1.28 (1H, m), 1.39 (1H, q, J=6.7 Hz), 1.53-1.63 (1H, m), 2.58 (1H, brs), 2.92-3.03 (2H, m), 3.03-3.12 (1H, m), 3.96 (2H, d, J=7.2 Hz), 7.36-7.41 (1H, m), 7.42-7.48 (1H, m), 7.61 (1H, s), 7.75 (1H, s), 7.78-7.83 (1H, m), 8.10 (1H, s), 9.27 (2H, brs), 10.45 (1H, d, J=2.3 Hz).

Example 78

N-(1-tert-butyl-1H-pyrazol-4-yl)-3-(trans-2-((cyclopropylmethyl)amino)cyclopropyl)benzamide dihydrochloride 3-(trans-2-Aminocyclopropyl)-N-(1-tert-butyl-1H-pyrazol-4-yl)benzamide dihydrochloride (50.0 mg) and sodium hydrogen carbonate (42.2 mg) were added to TEF (2.00 mL)/methanol (2.00 mL), and the mixture was stirred at room temperature for 30 min, and cyclopropanecarbaldehyde (0.015 mL) was added under ice-cooling. The mixture was stirred at 60° C. for 3 hr and then at room temperature overnight. Under ice-cooling, sodium borohydride (12.7 mg) was added, and the mixture was stirred at room temperature overnight. Under ice-cooling, to the reaction mixture was added saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by NH silica gel column chromatography (hexane/ethyl acetate), and the obtained fraction was cooled to 0° C. A 4 mol/L hydrogen chloride/ethyl acetate solution (2.00 mL) was added, and the mixture was stirred under ice-cooling for 30 min. The reaction mixture was concentrated under reduced pressure to give the title compound (43.3 mg).
$^1$H NMR (300 MHz, DMSO-d$_6$) δ0.33-0.42 (2H, m), 0.54-0.62 (2H, m), 1.06-1.14 (1H, m), 1.36-1.42 (1H, m), 1.52 (9H, s), 1.55-1.63 (1H, m), 2.56-2.64 (1H, m), 2.93-3.11 (3H, m), 7.35-7.49 (2H, m), 7.64 (1H, s), 7.72-7.83 (2H, m), 8.09 (1E, s), 9.15-9.45 (2H, m), 10.43 (1H, s).

Example 79

3-(trans-2-((cyclopropylmethyl)amino)cyclopropyl)-N-(2-methyl-1,3-thiazol-5-yl)benzamide dihydrochloride A) tert-butyl (trans-2-(3-((2-methylthiazol-5-yl)carbamoyl)phenyl)cyclopropyl)carbamate 3-(trans-2-((tert-Butoxycarbonyl)amino)cyclopropyl) benzoic acid (600 mg), 2-methylthiazol-5-amine hydrochloride (342 mg) and triethylamine (0.905 mL) were dissolved in anhydrous DMF (10.8 mL), O-(7-azabenzotriazol-1-yl)-

N,N,N',N'-tetramethyluronium hexafluorophosphate (987 mg) was added, and the mixture was stirred at room temperature overnight, and at 60° C. overnight. Water was added to the reaction mixture, and the mixture was extracted with ethyl acetate. The extracts were combined, washed with saturated brine, dried over anhydrous magnesium sulfate, and concentrated under reduced pressure. The residue was purified by silica gel column chromatography (hexane/ethyl acetate) to give the title compound (717 mg).

MS (API+): [M+H]$^+$ 374.2.

B) 3-(trans-2-aminocyclopropyl)-N-(2-methylthiazol-5-yl)benzamide dihydrochloride To tert-butyl (trans-2-(3-((2-methylthiazol-5-yl)carbamoyl)phenyl)cyclopropyl)carbamate (717 mg) was added a 4 mol/L hydrogen chloride/ethyl acetate solution (10.0 mL), and the mixture was stirred at room temperature overnight. The resulting precipitate was collected by filtration to give the title compound (650 mg).

MS (API+): [M−HCl+H]$^+$ 274.1.

C) 3-(trans-2-((cyclopropylmethyl)amino)cyclopropyl)-N-(2-methyl-1,3-thiazol-5-yl)benzamide dihydrochloride 3-(trans-2-Aminocyclopropyl)-N-(2-methylthiazol-5-yl)benzamide dihydrochloride (100 mg) and sodium hydrogen carbonate (72.8 mg) were dissolved in THF (2.00 mL)/methanol (2.00 mL), and cyclopropanecarbaldehyde (0.065 mL) was added under ice-cooling. The mixture was stirred at room temperature overnight, sodium borohydride (21.9 mg) was added under ice-cooling, and the mixture was stirred at room temperature for 1 hr. To the reaction mixture was added saturated aqueous sodium hydrogen carbonate solution, and the mixture was extracted with ethyl acetate. The extracts were combined, washed with saturated brine, dried over anhydrous magnesium sulfate, and concentrated under reduced pressure. The residue was purified by NH silica gel column chromatography (hexane/ethyl acetate), a 4 mol/L hydrogen chloride/ethyl acetate solution was added, and the reaction mixture was concentrated under reduced pressure. The obtained residue was recrystallized from methanol/ethyl acetate to give the title compound (57.0 mg).

$^1$H NMR (300 MHz, DMSO-d$_6$) δ0.31-0.42 (2H, m), 0.51-0.62 (2H, m), 1.01-1.17 (1H, m), 1.37-1.48 (1H, m), 1.55-1.67 (1H, m), 2.55-2.67 (4H, m), 2.91-3.03 (2H, m), 3.05-3.16 (1H, m), 7.42-7.53 (2H, m), 7.67 (1H, s), 7.82-7.92 (2H, m), 9.24-9.50 (2H, m), 11.92 (1H, s).

Example 80

3-(trans-2-((cyclopropylmethyl)amino)cyclopropyl)-N-methyl-N-phenylbenzamide hydrochloride Example 81

3-(trans-2-((cyclopropylmethyl)amino)cyclopropyl)-N-(3-(pyrimidin-2-yl)phenyl)benzamide dihydrochloride Example 82

3-(trans-2-((cyclopropylmethyl)amino)cyclopropyl)-N-(4-(2-oxopyrrolidin-1-yl)phenyl)benzamide hydrochloride Example 83

N-cyclopentyl-3-(trans-2-((tetrahydro-2H-pyran-4-ylmethyl)amino)cyclopropyl)benzamide hydrochloride Example 84

N-(4,4-difluorocyclohexyl)-3-(trans-2-((tetrahydro-2H-pyran-4-ylmethyl)amino)cyclopropyl)benzamide hydrochloride Example 85

3-(trans-2-((2,2-dimethylpropyl)amino)cyclopropyl)-N-(1,1-dioxidotetrahydro-2H-thiopyran-4-yl)benzamide hydrochloride By a method similar to that in Example 77, the compounds of Examples 80 to 85 were produced.

Example 86

N-(1-ethyl-1H-pyrazol-4-yl)-3-(trans-2-((tetrahydro-2H-pyran-4-ylmethyl)amino)cyclopropyl)benzamide dihydrochloride A) tert-butyl (tetrahydro-2H-pyran-4-ylmethyl) (trans-2-(3-((1-ethyl-1H-pyrazol-4-yl)carbamoyl)phenyl)cyclopropyl)carbamate 3-(trans-2-Aminocyclopropyl)-N-(1-ethyl-1H-pyrazol-4-yl)benzamide dihydrochloride (100 mg) and sodium hydrogen carbonate (82.0 mg) were dissolved in THF (5.00 mL)/methanol (5.00 mL), and tetrahydro-2H-pyran-4-carbaldehyde (0.034 mL) was added. The mixture was stirred at 60° C. for 3 hr, and sodium borohydride (24.7 mg) was added under ice-cooling. The mixture was stirred at room temperature for 2 hr, di-tert-butyl dicarbonate (0.114 mL) was added to the reaction mixture, and the mixture was stirred at room temperature for 16 hr. Water was added to the reaction mixture, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (52.2 mg).

MS (API−): [M−H]$^-$ 467.3.

B) N-(1-ethyl-1H-pyrazol-4-yl)-3-(trans-2-((tetrahydro-2H-pyran-4-ylmethyl)amino)cyclopropyl)benzamide dihydrochloride tert-Butyl (tetrahydro-2H-pyran-4-ylmethyl)(trans-2-(3-((1-ethyl-1H-pyrazol-4-yl)carbamoyl)phenyl)cyclopropyl)

carbamate (52.2 mg) was dissolved in methanol (5.00 mL), and the mixture was cooled to 0° C. A 4 mol/L hydrogen chloride/ethyl acetate solution (0.418 mL) was added, and the mixture was stirred at room temperature for 18 hr, and at 60° C. for 3 hr. The reaction mixture was concentrated under reduced pressure, and the residue was crystallized from ethanol/heptane to give the title compound (41.0 mg).

$^1$H NMR (300 MHz, DMSO-$d_6$) δ1.19-1.30 (2H, m), 1.35-1.42 (2H, m), 1.51-1.62 (1H, m), 1.68 (2H, d, J=12.2 Hz), 1.97 (1H, brs), 2.61 (1H, brs), 2.96-3.03 (2H, m), 3.04-3.11 (1H, m), 3.22-3.32 (4H, m), 3.83-3.89 (3H, m), 4.15 (1H, d, J=3.2 Hz), 7.35-7.42 (1H, m), 7.45 (1H, t, J=7.5 Hz), 7.60 (1H, s), 7.75 (1H, brs), 7.80 (1H, d, J=8.6 Hz), 8.05 (1H, s), 9.20 (2H, brs), 9.90 (1H, s), 10.45 (1H, brs).

Example 87

N-(1-(cyclopropylmethyl)-1H-pyrazol-4-yl)-3-(trans-2-((tetrahydro-2H-pyran-4-ylmethyl)amino)cyclopropyl)benzamide dihydrochloride Example 88

N-(1-tert-butyl-1H-pyrazol-4-yl)-3-(trans-2-((2,2-dimethylpropyl)amino)cyclopropyl)benzamide dihydrochloride Example 89

N-(1-tert-butyl-1H-pyrazol-4-yl)-3-(trans-2-((tetrahydro-2H-pyran-4-ylmethyl)amino)cyclopropyl)benzamide dihydrochloride Example 90

N-(2-methyl-1,3-thiazol-5-yl)-3-(trans-2-((tetrahydro-2H-pyran-4-ylmethyl)amino)cyclopropyl)benzamide dihydrochloride Example 91

5-(trans-2-((cyclopropylmethyl)amino)cyclopropyl)-2-fluoro-N-(1-methyl-1H-pyrazol-4-yl)benzamide dihydrochloride By a method similar to that in Example 78, the compounds of Examples 87 to 91 were produced.

Example 92

N-(3-methyl-1,2-oxazol-5-yl)-3-(trans-2-((tetrahydro-2H-pyran-4-ylmethyl)amino)cyclopropyl)benzamide hydrochloride A) tert-butyl (trans-2-(3-((3-methylisoxazol-5-yl)carbamoyl)phenyl)cyclopropyl)carbamate 3-(trans-2-((tert-butoxycarbonyl)amino)cyclopropyl)benzoic acid (80.0 mg) and one drop of DMF were dissolved in THF (1.00 mL), and the mixture was cooled to 0° C. Oxalyl chloride (0.038 mL) was added and the mixture was stirred at 0° C. for 30 min, and concentrated under reduced pressure. The obtained residue was dissolved in THF (1.00 mL), the solution was added to a solution of 3-methylisoxazol-5-amine (56.6 mg) in THF (1.00 mL), and the mixture was stirred at room temperature overnight. To the reaction mixture was added saturated aqueous sodium hydrogen carbonate solution, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate) to give the title compound (17.0 mg).

MS (API-): [M-H]$^-$ 356.2.

B) N-(3-methyl-1,2-oxazol-5-yl)-3-(trans-2-((tetrahydro-2H-pyran-4-ylmethyl)amino)cyclopropyl)benzamide hydrochloride tert-Butyl (trans-2-(3-((3-methylisoxazol-5-yl)carbamoyl)phenyl)cyclopropyl)carbamate (17.0 mg) was dissolved in ethyl acetate (1.00 mL), a 4 mol/L hydrogen chloride/ethyl acetate solution (3.00 mL) was added, and the mixture was stirred at room temperature for 5 hr, and concentrated under reduced pressure to give 3-(trans-2-aminocyclopropyl)-N-(3-methylisoxazol-5-yl)benzamide dihydrochloride (11.0 mg).

The obtained 3-(trans-2-aminocyclopropyl)-N-(3-methylisoxazol-5-yl)benzamide hydrochloride (11.0 mg) and sodium hydrogen carbonate (9.44 mg) were dissolved in THF (1.00 mL)/methanol (1.00 mL), and tetrahydro-2H-pyran-4-carbaldehyde (0.00585 mL) was added. Under a nitrogen atmosphere, the mixture was stirred at 60° C. for 3 hr, and sodium borohydride (2.83 mg) was added under ice-cooling. The mixture was stirred at room temperature for 2 hr, di-tert-butyl dicarbonate (0.013 mL) was added, and the mixture was stirred under a nitrogen atmosphere at room temperature for 16 hr. Water was added to the reaction mixture, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate), and concentrated under reduced pressure. To the obtained residue was added a 4 mol/L hydrogen chloride/ethyl acetate solution (3.00 mL), and the mixture was stirred at room temperature for 3 hr, and concentrated under reduced pressure. The obtained residue was crystallized from ethanol/diisopropy ether to give the title compound (4.00 mg).

$^1$H NMR (300 MHz, CD$_3$OD) δ1.25-1.79 (7H, m), 1.92-2.14 (1H, m), 2.28 (3H, s), 2.54-2.70 (1H, m), 3.05-3.17 (3H, m), 3.38-3.50 (2H, m), 3.85-4.06 (2H, m), 6.38 (1H, s), 7.41-7.57 (2H, m), 7.75-7.90 (2H, m).

Example 93

N-(3-methyl-1,2-thiazol-5-yl)-3-(trans-2-((tetrahydro-2H-pyran-4-ylmethyl)amino)cyclopropyl)benzamide dihydrochloride By a method similar to that in Example 92, the compound of Example 93 was produced.

Example 94

5-(trans-2-((cyclopropylmethyl)amino)cyclopropyl)-2-methoxy-N-(1-methyl-1H-pyrazol-4-yl)benzamide dihydrochloride By a method similar to that in Example 79, the compound of Example 94 was produced.

Example 95

3-(trans-2-((cyclopropylmethyl)amino)cyclopropyl)-N-(5-methyl-1,3,4-thiadiazol-2-yl)benzamide dihydrochloride

A) methyl 3-(trans-2-Aminocyclopropyl)benzoate hydrochloride

Methyl 3-(trans-2-((tert-Butoxycarbonyl)amino)cyclopropyl)benzoate (2.00 g) was dissolved in methanol (40.0 mL), and the mixture was cooled to 0° C. A 4 mol/L hydrogen chloride/ethyl acetate solution (25.7 mL) was added, and the mixture was stirred at room temperature for 1B hr. The reaction mixture was concentrated under reduced pressure, and the residue was crystallized from methanol/diisopropy ether to give the title compound (1.63 g).

MS (API+): [M−HCl+H]$^+$ 192.2.

B) methyl 3-(trans-2-((tert-butoxycarbonyl)(cyclopropylmethyl)amino)cyclopropyl)benzoate Methyl 3-(trans-2-aminocyclopropyl)benzoate hydrochloride (1.10 g) and sodium hydrogen carbonate (808 mg) were dissolved in THF (15.0 mL)/methanol (15.0 mL), and cyclopropanecarbaldehyde (0.435 mL) was added. The mixture was stirred at 60° C. for 2 hr, and sodium borohydride (364 mg) was added under ice-cooling. The mixture was stirred at room temperature for 2 hr, di-tert-butyl dicarbonate (1.68 mL) was added under a nitrogen atmosphere, and the mixture was stirred at room temperature for 2 hr. Water was added to the reaction mixture, and the mixture was extracted with ethyl acetate. The extracts were combined, washed with water and saturated brine, dried over anhydrous magnesium sulfate, and concentrated under reduced pressure. The residue was purified by silica gel column chromatography (hexane/ethyl acetate) to give the title compound (1.57 g).

MS (API+): [M−Boc+H]$^+$ 246.2.

C) 3-(trans-2-((tert-butoxycarbonyl)(cyclopropylmethyl)amino)cyclopropyl)benzoic acid Methyl 3-(trans-2-((tert-Butoxycarbonyl)(cyclopropylmethyl)amino)cyclopropyl)benzoate (1.57 g) was dissolved in methanol (20.0 mL), a 8 mol/L aqueous sodium hydroxide solution (2.84 mL) was added, and the mixture was stirred at room temperature for 16 hr. To the reaction mixture was added 1 mol/L hydrochloric acid (22.0 mL) under ice-cooling, and the mixture was extracted with ethyl acetate. The extracts were combined, washed with water and saturated brine, dried over anhydrous magnesium sulfate, and concentrated under reduced pressure to give the title compound (1.27 g).

MS (API−): [M−H]$^-$ 330.2.

D) tert-butyl (cyclopropylmethyl)(trans-2-(3-((5-methyl-1,3,4-thiadiazol-2-yl)carbamoyl)phenyl)cyclopropyl)carbamate 3-(trans-2-((tert-Butoxycarbonyl) (cyclopropylmethyl)amino)cyclopropyl)benzoic acid (400 mg), 5-methyl-1,3,4-thiadiazol-2-amine (167 mg) and triethylamine (0.505 mL) were dissolved in anhydrous DMF (15.0 mL), and the mixture was cooled to 0° C. O-(7-Azabenzotriazol-1-yl)-N,N,N',N'-tetramethyluronium hexafluorophosphate (551 mg) was added, and the mixture was stirred at room temperature overnight. The reaction mixture was poured into saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (390 mg).

MS (API+): [M+H]$^+$ 429.3.

E) 3-(trans-2-((cyclopropylmethyl)amino)cyclopropyl)-N-(5-methyl-1,3,4-thiadiazol-2-yl)benzamide dihydrochloride tert-Butyl (cyclopropylmethyl) (trans-2-(3-((5-methyl-1,3,4-thiadiazol-2-yl)carbamoyl)phenyl)cyclopropyl)carbamate (48.0 mg) was dissolved in methanol (2.00 mL), a 2 mol/L hydrogen chloride/methanol solution (0.84 mL) was added, and the mixture was stirred at room temperature for 3 days. The reaction mixture was concentrated under reduced pressure, and the residue was crystallized from methanol-tetrahydrofuran mixture/diisopropy ether to give the title compound (27.4 mg).

$^1$H NMR (300 MHz, DMSO-d$_6$) δ0.33-0.40 (2H, m), 0.54-0.63 (2H, m), 1.04-1.13 (1H, m), 1.41-1.50 (1H, m), 1.54-1.64 (1H, m), 2.56-2.62 (1H, m), 2.65 (3H, s), 2.93-3.12 (3H, m), 7.45-7.57 (2H, m), 7.82-7.96 (2H, m), 8.98-9.43 (2H, m), 12.81 (1H, s).

(1H of HCl was not observed)

Example 96

3-(trans-2-((cyclopropylmethyl)amino)cyclopropyl)-N-(5-methyl-1,3,4-thiadiazol-2-yl)benzamide hydrochloride 3-(trans-2-Aminocyclopropyl)-N-(5-methyl-1,3,4-thiadiazol-2-yl)benzamide dihydrochloride (4.67 g) and sodium hydrogen carbonate (4.52 g) were dissolved in THF (67.2 mL)/methanol (67.2 mL), and cyclopropanecarbaldehyde (1.21 mL) was added under ice-cooling. The mixture was stirred at 50° C. for 1 hr, and cyclopropanecarbaldehyde (1.21 mL) was added at room temperature. The mixture was stirred at 50° C. for 2 hr, sodium borohydride (611 mg) was added under ice-cooling, and the mixture was stirred at room temperature for 2 hr. To the reaction mixture was added saturated aqueous sodium hydrogen carbonate solution, and the mixture was extracted with ethyl acetate. The extracts were combined, washed with water and saturated brine, dried over anhydrous magnesium sulfate, and concentrated under reduced pressure. The residue was purified by NH silica gel column chromatography (hexane/ethyl acetate), and concentrated under reduced pressure. The obtained residue was purified by silica gel column chromatography (hexane/ethyl acetate), a 4 mol/L hydrogen chloride/ethyl acetate solution was added, and the mixture was concentrated under reduced pressure. The obtained residue was recrystallized from ethanol/heptane to give the title compound (3.15 g).

$^1$H NMR (300 MHz, DMSO-d$_6$) δ0.33-0.41 (2H, m), 0.53-0.63 (2H, m), 1.00-1.16 (1H, m), 1.39-1.50 (1H, m), 1.55-1.66 (1H, m), 2.55-2.69 (4H, m), 2.90-3.14 (3H, m), 7.50 (2H, d, J=7.2 Hz), 7.86 (1H, s), 7.89-7.96 (1H, m), 9.13-9.52 (2H, m), 12.84 (1H, br. s).

Example 97

3-(trans-2-((cyclopropylmethyl)amino)cyclopropyl)-N-(5-methyl-1,3,4-thiadiazol-2-yl)benzamide hydrochloride (Optical Isomer, Retention Time Short)

A) 3-(trans-2-((cyclopropylmethyl)amino)cyclopropyl)-N-(5-methyl-1,3,4-thiadiazol-2-yl)benzamide 3-(trans-2-((Cyclopropylmethyl)amino)cyclopropyl)-N-(5-methyl-1,3,4-thiadiazol-2-yl)benzamide hydrochloride (120 mg) was dissolved in methanol (4.00 mL)/water (2.00 mL), sodium hydrogen carbonate (138 mg) was added under ice-cooling, and the mixture was stirred at room temperature for 10 min. The reaction mixture was poured into a saturated aqueous sodium hydrogen carbonate solution (5.00 mL), and the mixture was extracted with ethyl acetate (40.0 mL). The organic layer was washed successively with water (10.0 mL) and saturated brine (5.00 mL), and dried over anhydrous sodium sulfate. The aqueous layer was extracted with ethyl acetate (20.0 mL), and the extract was washed with saturated brine (5.00 mL), and dried over anhydrous sodium sulfate. The extracts were combined, and concentrated under reduced pressure to give the title compound (110 mg).
MS (API+): [M+H]$^+$ 329.1.

B) tert-butyl (cyclopropylmethyl)(trans-2-(3-((5-methyl-1,3,4-thiadiazol-2-yl)carbamoyl)phenyl)cyclopropyl)carbamate 3-(trans-2-((Cyclopropylmethyl)amino)cyclopropyl)-N-(5-methyl-1,3,4-thiadiazol-2-yl)benzamide (105 mg) and di-tert-butyl dicarbonate (0.111 mL) were dissolved in THF (2.00 mL)/methanol (2.00 mL), sodium hydrogen carbonate (40.3 mg) was added under ice-cooling, and the mixture was stirred at room temperature for 2 days. The reaction mixture was poured into water, and the mixture was extracted with ethyl acetate. The extracts were combined, washed with water and saturated brine, dried over anhydrous sodium sulfate, and concentrated under reduced pressure. The residue was purified by silica gel column chromatography (hexane/ethyl acetate) to give the title compound (121 mg).
MS (API+): [M+H]$^+$ 429.3.

C) tert-butyl (cyclopropylmethyl)(trans-2-(3-((5-methyl-1,3,4-thiadiazol-2-yl)carbamoyl)phenyl)cyclopropyl)carbamate (Optical Isomer, Retention Time Short)

A racemate (119 mg) of tert-butyl (cyclopropylmethyl)(trans-2-(3-((5-methyl-1,3,4-thiadiazol-2-yl)carbamoyl)phenyl)cyclopropyl)carbamate was fractionated by SFC (column: CHIRALPAK ADH (trade name), 4.6 mmID×150 mmL, manufactured by Daicel Corporation, mobile phase: carbon dioxide/methanol=80/20) to give the title compound with a shorter retention time (53.0 mg).
MS (API+): [M+H]$^+$ 429.3.

D) 3-(trans-2-((cyclopropylmethyl)amino)cyclopropyl)-N-(5-methyl-1,3,4-thiadiazol-2-yl)benzamide hydrochloride (optical isomer, retention time short)

tert-Butyl (cyclopropylmethyl)(trans-2-(3-((5-methyl-1,3,4-thiadiazol-2-yl)carbamoyl)phenyl)cyclopropyl)carbamate (optical isomer, retention time short) (51.0 mg) was dissolved in methanol (3.00 mL)/ethyl acetate (1.00 mL), a 2 mol/L hydrogen chloride/methanol solution (0.893 mL) was added, and the mixture was stirred at room temperature overnight and at 60° C. for 40 min. The reaction mixture was concentrated under reduced pressure, and the residue was recrystallized from ethanol/heptane to give the title compound (34.3 mg).
$^1$H NMR (300 MHz, DMSO-d$_6$) δ0.31-0.40 (2H, m), 0.53-0.62 (2H, m), 0.98-1.14 (1H, m), 1.40-1.49 (1H, m), 1.54-1.64 (1H, m), 2.55-2.62 (1H, m), 2.65 (3H, s), 2.93-3.00 (2H, m), 3.02-3.09 (1H, m), 7.44-7.58 (2H, m), 7.85 (1H, s), 7.89-7.97 (1H, m), 9.26 (2H, brs), 12.81 (1H, brs).

Example 98

3-(trans-2-((cyclopropylmethyl)amino)cyclopropyl)-N-(5-methyl-1,3,4-thiadiazol-2-yl)benzamide hydrochloride (Optical Isomer, Retention Time Long)

3-(trans-2-Aminocyclopropyl)-N-(5-methyl-1,3,4-thiadiazol-2-yl)benzamide dihydrochloride [optical isomer, a compound derived from methyl 3-(trans-2-((tert-butoxycarbonyl)amino)cyclopropyl)benzoate (optical isomer, retention time long)] (250 mg) and sodium hydrogen carbonate (242 mg) were dissolved in THF (3.80 mL)/methanol (3.80 mL), and cyclopropanecarbaldehyde (0.065 mL) was added under ice-cooling. The mixture was stirred at 50° C. for 1 hr, and cyclopropanecarbaldehyde (0.065 mL) was added at room temperature. The mixture was stirred at 50° C. for 1 hr, sodium borohydride (32.7 mg) was added under ice-cooling, and the mixture was stirred at room temperature for 1 hr. To the reaction mixture was added saturated aqueous sodium hydrogen carbonate solution under ice-cooling, and the mixture was extracted with ethyl acetate/THF mixture. The extracts were combined, washed with water and saturated brine, dried over anhydrous magnesium sulfate, and concentrated under reduced pressure. The residue was purified by silica gel column chromatography (ethyl acetate/methanol), to the obtained fraction was added a 2 mol/L hydrogen chloride/methanol solution (3.00 mL), and the mixture was concentrated under reduced pressure. The residue was crystallized from ethanol/methanol/heptane to give the title compound (151 mg).
$^1$H NMR (300 MHz, DMSO-d$_6$) δ0.31-0.39 (2H, m), 0.53-0.62 (2H, m), 1.00-1.13 (1H, m), 1.39-1.49 (1H, m), 1.52-1.64 (1H, m), 2.53-2.62 (1H, m), 2.65 (3H, s), 2.93-3.00 (2H, m), 3.01-3.09 (1H, m), 7.42-7.57 (2H, m), 7.83-7.88 (1H, m), 7.93 (1H, dt, J=7.2, 1.5 Hz), 9.23 (1H, brs), 12.84 (1H, brs).
mp 202-204° C.
Anal. Calcd for C$_{17}$H$_{20}$N$_4$OS—HCl: C, 55.96; H, 5.80; N, 15.35.
Found: C, 55.90; H, 5.81; N, 15.25.
HPLC retention time 16.815 min (column: CHIROBIOTIC V2 (trade name), 4.6 mmID×250 mmL, manufactured by Sigma-Aldrich Co. LLC, mobile phase: methanol/triethylammonium acetate=1000/1, flow rate: 1.0 mL/min, temperature: 30° C., detection: UV 254 nm, concentration: 0.5 mg/mL, injection volume: 0.010 mL)

Example 99

3-(trans-2-((cyclopropylmethyl)amino)cyclopropyl)-N-(3,3-difluorocyclobutyl)benzamide hydrochloride

A) tert-butyl (cyclopropylmethyl) (trans-2-(3-((3,3-difluorocyclobutyl)carbamoyl)phenyl)cyclopropyl)carbamate 3-(trans-2-((tert-Butoxycarbonyl)(cyclopropylmethyl)amino)cyclopropyl)benzoic acid (400 mg), 3,3-difluorocyclobutanamine hydrochloride (173 mg) and triethylamine (0.336 mL) were dissolved in anhydrous DMF (5.00 mL), O-(7-azabenzotriazol-1-yl)-N,N,N',N'-tetramethyluronium hexafluorophosphate (505 mg) was added, and the mixture was stirred at room temperature for 4 hr. To the reaction mixture was added saturated aqueous sodium hydrogen carbonate solution, and the mixture was extracted with ethyl acetate. The extract was washed successively with water and saturated brine, dried over anhydrous magnesium sulfate, and concentrated under reduced pressure. The obtained residue was purified by silica gel column chromatography (hexane/ethyl acetate), and concentrated under reduced pressure to give the title compound (495 mg).

MS (API-): [M-H]⁻419.2.

B) 3-(trans-2-((cyclopropylmethyl)amino)cyclopropyl)-N-(3,3-difluorocyclobutyl)benzamide hydrochloride tert-Butyl (cyclopropylmethyl)(trans-2-(3-((3,3-difluorocyclobutyl)carbamoyl)phenyl)cyclopropyl)carbamate (490 mg) was dissolved in ethyl acetate (5.00 mL), a 4 mol/L hydrogen chloride/ethyl acetate solution (7.00 mL) was added, and the mixture was stirred at room temperature for 5 hr. The reaction mixture was concentrated under reduced pressure, and the residue was recrystallized from ethanol/water/heptane to give the title compound (230 mg).

$^1$H NMR (300 MHz, DMSO-$d_6$) δ0.28-0.44 (2H, m), 0.50-0.64 (2H, m), 0.94-1.19 (1H, m), 1.28-1.40 (1H, m), 1.50-1.69 (1H, m), 2.53-3.09 (8H, m), 4.15-4.39 (1H, m), 7.29-7.47 (2H, m), 7.61-7.77 (2H, m), 8.90 (1H, d, J=6.4 Hz), 9.39 (2H, brs).

Example 100

3-(trans-2-((cyclopropylmethyl)amino)cyclopropyl)-N-(tetrahydro-2H-pyran-4-yl)benzamide hydrochloride A) tert-butyl (cyclopropylmethyl)(trans-2-(3-((tetrahydro-2H-pyran-4-yl) carbamoyl)phenyl)cyclopropyl) carbamate 3-(trans-2-((tert-Butoxycarbonyl)(cyclopropylmethyl)amino)cyclopropyl)benzoic acid (100 mg), tetrahydro-2H-pyran-4-amine (37.4 mg) and triethylamine (0.126 mL) were dissolved in anhydrous DMF (5.00 mL), O-(7-azabenzotriazol-1-yl)-N,N,N',N'-tetramethyluronium hexafluorophosphate (138 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The obtained residue was purified by silica gel column chromatography (hexane/ethyl acetate), and concentrated under reduced pressure to give the title compound (111 mg).

MS (API-): [M-H]⁻ 413.1.

B) 3-(trans-2-((cyclopropylmethyl)amino)cyclopropyl)-N-(tetrahydro-2H-pyran-4-yl)benzamide hydrochloride tert-Butyl (cyclopropylmethyl)(trans-2-(3-((tetrahydro-2H-pyran-4-yl)carbamoyl)phenyl)cyclopropyl)carbamate (111 mg) was dissolved in THF (5.00 mL)/methanol (5.00 mL), a 4 mol/L hydrogen chloride/ethyl acetate solution (1.00 mL) was added at 0° C., and the mixture was stirred at room temperature for 18 hr, and at 60° C. for 3 hr. The reaction mixture was concentrated under reduced pressure, and the residue was crystallized from methanol/diisopropy ether to give the title compound (60.2 mg).

$^1$H NMR (300 MHz, DMSO-$d_6$) δ0.33-0.39 (2H, m), 0.53-0.62 (2H, m), 1.00-1.11 (1H, m), 1.30-1.40 (1H, m), 1.58 (3H, qd, J=11.9, 4.4 Hz), 1.71-1.79 (2H, m), 2.53-2.58 (1H, m), 2.93-3.03 (3H, m), 3.34-3.43 (2H, m), 3.88 (2H, dd, J=11.4, 2.3 Hz), 3.94-4.07 (1H, m), 7.30-7.35 (1H, m), 7.36-7.42 (1H, m), 7.62 (1H, s), 7.67-7.72 (1H, m), 8.29 (1H, d, J=7.6 Hz), 9.17 (2H, brs).

Example 101

3-(trans-2-((cyclopropylmethyl)amino)cyclopropyl)-N-(1-ethyl-1H-pyrazol-4-yl)benzamide dihydrochloride A) tert-butyl (cyclopropylmethyl)(trans-2-(3-((1-ethyl-1H-pyrazol-4-yl)carbamoyl)phenyl)cyclopropyl)carbamate 3-(trans-2-((tert-Butoxycarbonyl)(cyclopropylmethyl)amino)cyclopropyl)benzoic acid (80.0 mg), 1-ethyl-1H-pyrazol-4-amine (34.9 mg) and O-(7-azabenzotriazol-1-yl)-N,N,N',N'-tetramethyluronium hexafluorophosphate (101 mg) were dissolved in DMF (1.00 mL), triethylamine (0.067 mL) was added, and the mixture was stirred at room temperature overnight. Water was added to the reaction mixture, and the mixture was extracted with ethyl acetate. The extract was washed with saturated brine, dried over anhydrous sodium sulfate, and concentrated under reduced pressure. The obtained residue was purified by silica gel column chromatography (hexane/ethyl acetate), and concentrated under reduced pressure to give the title compound (85.0 mg).

$^1$H NMR (300 MHz, CDCl$_3$) δ0.08-0.33 (2H, m), 0.37-0.59 (2H, m), 0.90-1.11 (1H, m), 1.20-1.34 (2H, m), 1.44 (9H, s), 1.51 (3H, t, J=7.4 Hz), 2.13-2.25 (1H, m), 2.83-2.93 (1H, m), 3.00 (1H, dd, J=14.4, 7.2 Hz), 3.31 (1H, dd, J=14.4, 6.8 Hz), 4.18 (2H, q, J=7.2 Hz), 7.29-7.43 (2H, m), 7.51 (1H, s), 7.59-7.70 (2H, m), 7.90 (1H, brs), 8.11 (1H, s).

B) 3-(trans-2-((cyclopropylmethyl)amino)cyclopropyl)-N-(1-ethyl-1H-pyrazol-4-yl)benzamide dihydrochloride tert-Butyl (cyclopropylmethyl)(trans-2-(3-((1-ethyl-1H-pyrazol-4-yl)carbamoyl)phenyl)cyclopropyl)carbamate (85.0 mg) was dissolved in ethyl acetate (2.00 mL), a 4 mol/L hydrogen chloride/ethyl acetate solution (2.00 mL) was added, and the mixture was stirred at room temperature for 5 hr. The reaction mixture was concentrated under reduced pressure, and the residue was recrystallized from ethanol/diisopropy ether to give the title compound (79.0 mg).

$^1$H NMR (300 MHz, DMSO-$d_6$) δ0.30-0.44 (2H, m), 0.49-0.67 (2H, m), 0.95-1.21 (1H, m), 1.28-1.45 (4H, m), 1.53-1.73 (1H, m), 2.58-2.69 (1H, m), 2.88-3.16 (3H, m), 4.12 (2H, q, J=7.2 Hz), 6.23 (1H, brs), 7.22-7.52 (2H, m), 7.63 (1H, d, J=0.8 Hz), 7.72-7.86 (2H, m), 8.06 (1H, s), 9.51 (2H, brs), 10.51 (1H, s).

Example 102

3-(trans-2-((cyclopropylmethyl)amino)cyclopropyl)-N-(4,4-difluorocyclohexyl)benzamide hydrochloride A) tert-butyl (cyclopropylmethyl) (trans-2-(3-((4,4-difluorocyclohexyl)carbamoyl)phenyl)cyclopropyl)carbamate 3-(trans-2-((tert-Butoxycarbonyl)(cyclopropylmethyl)amino)cyclopropyl)benzoic acid (106 mg), 4,4-difluorocyclohexanamine (51.8 mg) and O-(7-azabenzotriazol-1-yl)-N,N,N',N'-tetramethyluronium hexafluorophosphate (146 mg) were dissolved in anhydrous ONE (5.00 mL), triethylamine (0.133 mL) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The obtained residue was purified by silica gel column chromatography (hexane/ethyl acetate), and concentrated under reduced pressure to give the title compound (99.7 mg).

MS (API+): [M−(tert-Bu)+H]+ 393.2.

B) 3-(trans-2-((cyclopropylmethyl)amino)cyclopropyl)-N-(4,4-difluorocyclohexyl)benzamide hydrochloride tert-Butyl (cyclopropylmethyl)(trans-2-(3-((4,4-difluorocyclohexyl)carbamoyl)phenyl)cyclopropyl)carbamate (99.7 mg) was dissolved in THF (2.50 mL)/methanol (2.50 mL), a 4 mol/L hydrogen chloride/ethyl acetate solution (0.834 mL) was added at 0° C., and the mixture was stirred at room temperature for 18 hr, and at 60° C. for 3 hr. The reaction mixture was concentrated under reduced pressure, and the residue was crystallized from methanol/diisopropy ether to give the title compound (65.9 mg).

$^1$H NMR (300 MHz, DMSO-$d_6$) δ0.33-0.40 (2H, m), 0.52-0.61 (2H, m), 1.03-1.16 (1H, m), 1.34 (1H, q, J=6.4 Hz), 1.56-1.74 (3H, m), 1.81-2.12 (6H, m), 2.57-2.66 (1H, m), 2.95 (2H, d, J=7.2 Hz), 2.97-3.03 (1H, m), 3.92-4.06 (1H, m), 7.31-7.35 (1H, m), 7.35-7.42 (1H, m), 7.63 (1H, s), 7.70 (1H, d, J=7.6 Hz), 8.31 (1H, d, J=7.6 Hz), 9.49 (2H, brs).

Example 103

3-(trans-2-((cyclopropylmethyl)amino)cyclopropyl)-N-(5-methyl-1,2-oxazol-3-yl)benzamide hydrochloride 3-(trans-2-((tert-Butoxycarbonyl)amino)cyclopropyl)benzoic acid (500 mg) and one drop of DMF were dissolved in THF (5 mL), and the mixture was cooled to 0° C. Oxalyl chloride (0.196 mL) was added, and the mixture was stirred at 0° C. for 1 hr and concentrated under reduced pressure. The obtained residue was dissolved in THF (3.00 mL), the solution was added to a solution of 5-methylisoxazol-3-amine (265 mg) and N,N-dimethyl-4-aminopyridine (110 mg) in pyridine (5.00 mL) at 60° C., and the mixture was stirred at 60° C. for 2 hr. To the reaction mixture was added saturated aqueous sodium hydrogen carbonate solution, and the mixture was extracted with ethyl acetate. The extract was washed with water and saturated brine, dried over anhydrous magnesium sulfate, and concentrated under reduced pressure. The obtained residue was dissolved in methanol (5.00 mL), a 2 mol/L hydrogen chloride/methanol solution (10.0 mL) was added, and the mixture was stirred at room temperature for 5 hr. The reaction mixture was concentrated under reduced pressure, the obtained residue and sodium hydrogen carbonate (756 mg) were dissolved in THF (5.00 mL)/methanol (5.00 mL), and cyclopropanecarbaldehyde (0.420 mL) was added. The mixture was stirred at 60° C. for 12 hr, sodium borohydride (204 mg) was added under ice-cooling, and the mixture was stirred at room temperature for 2 hr. Water was poured into the reaction mixture, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate), and a 4 mol/L hydrogen chloride/ethyl acetate solution (5.00 mL) was added to the obtained fraction. The solution was concentrated under reduced pressure, and the residue was recrystallized from ethanol/water/heptane to give the title compound (190 mg).

$^1$H NMR (300 MHz, DMSO-$d_6$) δ0.29-0.43 (2H, m), 0.50-0.65 (2H, m), 0.96-1.19 (1H, m), 1.36-1.47 (1H, m), 1.51-1.67 (1H, m), 2.42 (3H, d, J=0.8 Hz), 2.58 (1H, ddd, J=9.8, 6.2, 3.2 Hz), 2.96 (2H, d, J=7.6 Hz), 3.03 (1H, dt, J=7.8, 4.1 Hz), 6.76 (1H, d, J=0.8 Hz), 7.36-7.54 (2H, m), 7.72-7.79 (1H, m), 7.79-7.92 (1H, m), 9.29 (2H, brs), 11.27 (1H, s).

Example 104

3-(trans-2-((cyclopropylmethyl)amino)cyclopropyl)-N-(5-methyl-1,2-oxazol-3-yl)benzamide hydrochloride (Optical Isomer, Retention Time Short)

By a method similar to that in Example 105, the compound of Example 104 was produced.

Example 105

3-(trans-2-((cyclopropylmethyl)amino)cyclopropyl)-N-(5-methyl-1,2-oxazol-3-yl)benzamide hydrochloride (Optical Isomer, Retention Time Long)

3-(trans-2-((tert-Butoxycarbonyl)amino)cyclopropyl)benzoic acid [optical isomer, a compound derived from methyl 3-(trans-2-((tert-butoxycarbonyl)amino)cyclopropyl)benzoate (optical isomer, retention time long)] (300 mg) and one drop of DMF were dissolved in THF (5.00 mL), and the mixture was cooled to 0° C. Oxalyl chloride (0.117 mL) was added, and the mixture was stirred at 0° C. for 1 hr, and concentrated under reduced pressure. The obtained residue was dissolved in THF (3.00 mL), the solution was added to a solution of 5-methylisoxazol-3-amine (159 mg) and N,N-dimethyl-4-aminopyridine (66.1 mg) in pyridine (5.00 mL) at 60° C., and the mixture was stirred at 60° C. for 2 hr. To the reaction mixture was added saturated aqueous sodium hydrogen carbonate solution, and the mixture was extracted with ethyl acetate. The extract was washed successively with water and saturated brine, dried over anhydrous magnesium sulfate, and concentrated under reduced pressure. The residue was purified by silica gel column chromatography (hexane/ethyl acetate), and concentrated under reduced pressure. The obtained residue was dissolved in THF (2.00 mL), the solution was added to a 4 mol/L hydrogen chloride/ethyl acetate solution (10.0 mL), and the mixture was stirred at room temperature for 3 hr. The reaction mixture was concentrated under reduced pressure, the obtained residue and sodium hydrogen carbonate (223 mg) were dissolved in THF (2.50 mL)/methanol (2.50 mL), and cyclopropanecarbaldehyde (0.124 mL) was added. The mixture was stirred at 60° C. for 3 hr, sodium borohydride (60.2 mg) was added under ice-cooling, and the mixture was stirred at room temperature for 2 hr. The reaction mixture was poured into water, and the mixture was extracted with ethyl acetate. The extract was washed successively with water and saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution (5.00 mL) was added to the obtained fraction. The solution was concentrated under reduced pressure, and the residue was recrystallized from ethanol/water/heptane to give the title compound (83.0 mg).

$^1$H NMR (300 MHz, DMSO-d$_6$) δ0.29-0.45 (2H, m), 0.51-0.67 (2H, m), 0.93-1.20 (1H, m), 1.33-1.49 (1H, m), 1.52-1.69 (1H, m), 2.42 (3H, d, J=0.8 Hz), 2.54-2.65 (1H, m), 2.96 (2H, d, J=7.6 Hz), 3.01-3.06 (1H, m), 6.76 (1H, d, J=1.1 Hz), 7.40-7.51 (2H, m), 7.73-7.88 (2H, m), 9.35 (2H, brs), 11.27 (1H, s).

mp 185-190° C.

Anal. Calcd for C$_{18}$H$_{21}$N$_3$O$_2$·HCl: C, 62.15; H, 6.37; N, 12.08; Cl, 10.19. Found: C, 62.05; H, 6.28; N, 11.96; Cl, 10.21.

HPLC retention time 13.091 min (column: CHIROBIOTIC V2 (trade name), 4.6 mmID×250 mmL, manufactured by Sigma-Aldrich Co. LLC, mobile phase: methanol/triethylamine/acetic acid=1000/1/1, flow rate: 1.0 mL/min, temperature: 30° C., detection: UV 220 nm, concentration: 0.5 mg/mL, injection volume: 0.010 mL)

Example 106

3-(trans-2-((cyclopropylmethyl)amino)cyclopropyl)-N-(3-methyl-1,2-oxazol-5-yl)benzamide hydrochloride 3-(trans-2-((tert-Butoxycarbonyl)amino)cyclopropyl)benzoic acid (500 mg) and one drop of DMF were dissolved in THF (1.00 mL), and the mixture was cooled to 0° C. Oxalyl chloride (0.196 mL) was added, and the mixture was stirred at 0° C. for 1 hr, and concentrated under reduced pressure. The obtained residue was dissolved in THF (2.00 mL), the solution was added to a solution of 3-methylisoxazol-5-amine (265 mg) in pyridine (5.00 mL) at 60° C., and the mixture was stirred at 60° C. for 2 hr. Under ice-cooling, to the reaction mixture was added saturated aqueous sodium hydrogen carbonate solution, and the mixture was extracted with ethyl acetate. The extract was washed with water and saturated brine, dried over anhydrous magnesium sulfate, and concentrated under reduced pressure. The obtained residue was dissolved in methanol (5.00 mL), a 2 mol/L hydrogen chloride/methanol solution (10.0 mL) was added, and the mixture was stirred at room temperature for 5 hr. The reaction mixture was concentrated under reduced pressure, the obtained residue and sodium hydrogen carbonate (756 mg) were dissolved in THF (15.0 mL)/methanol (15.0 mL), and cyclopropanecarbaldehyde (0.407 mL) was added. The mixture was stirred at 60° C. for 6 hr, sodium borohydride (204 mg) was added under ice-cooling, and the mixture was stirred at room temperature for 2 hr. The reaction mixture was poured into water, and the mixture was extracted with ethyl acetate. The extract was washed with water and saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution (5.00 mL) was added to the obtained fraction. The solution was concentrated under reduced pressure, and the solid was washed with ethyl acetate and recrystallized from ethanol/water/heptane to give the title compound (100 mg).

$^1$H NMR (300 MHz, DMSO-d$_6$) δ0.30-0.42 (2H, m), 0.52-0.62 (2H, m), 1.01-1.15 (1H, m), 1.32-1.47 (1H, m), 1.55-1.67 (1H, m), 2.22 (3H, s), 2.61 (1H, ddd, J=10.0, 6.4, 3.6 Hz), 2.96 (2H, d, J=7.2 Hz), 3.04 (1H, dt, J=7.5, 4.0 Hz), 6.32 (1H, s), 7.42-7.54 (2H, m), 7.78 (1H, s), 7.81-7.90 (1H, m), 9.39 (2H, brs), 11.89 (1H, s).

Example 107

3-(trans-2-((cyclopropylmethyl)amino)cyclopropyl)-N-(1,3-dimethyl-1H-pyrazol-5-yl)benzamide dihydrochloride 3-(trans-2-((tert-Butoxycarbonyl)(cyclopropylmethyl)amino)cyclopropyl)benzoic acid (50.0 mg) and one drop of DMF were dissolved in THF (1.00 mL). Oxalyl chloride (0.015 mL) was added, and the mixture was stirred at room temperature for 30 min, and concentrated under reduced pressure. The obtained residue was dissolved in THF (1.00 mL), a solution of 1,3-dimethyl-1H-pyrazol-5-amine (18.5 mg), triethylamine (0.063 mL) and N,N-dimethyl-4-aminopyridine (3.69 mg) in THF (1.00 mL) was added, and the mixture was stirred at room temperature overnight. Under ice-cooling, to the reaction mixture was added saturated aqueous sodium hydrogen carbonate solution, and the mixture was extracted with ethyl acetate. The extract was washed with water and saturated brine, dried over anhydrous magnesium sulfate, and concentrated under reduced pressure. The obtained residue was purified by silica gel column chromatography (hexane/ethyl acetate) and concentrated under reduced pressure. The obtained residue was dissolved in ethyl acetate (1.00 mL), a 4 mol/L hydrogen chloride/ethyl acetate solution (3.00 mL) was added, and the mixture was stirred at room temperature for 3 hr. The reaction mixture was concentrated under reduced pressure to give the title compound (15.0 mg).

$^1$H NMR (300 MHz, DMSO-d$_6$) δ0.30-0.42 (2H, m), 0.50-0.66 (2H, m), 0.95-1.15 (1H, m), 1.29-1.47 (1H, m), 1.47-1.66 (1H, m), 2.13 (3H, s), 2.54-2.70 (1H, m), 2.88-3.13 (3H, m), 3.60 (3H, s), 6.01 (1H, s), 7.39-7.51 (2H, m), 7.71-7.86 (2H, m), 9.27 (2H, brs), 10.28 (1H, s).

Example 108

3-(trans-2-((cyclopropylmethyl)amino)cyclopropyl)-N-(1-(2,2,2-trifluoroethyl)piperidin-4-yl)benzamide dihydrochloride A) tert-butyl (cyclopropylmethyl)(trans-2-(3-((1-(2,2,2-trifluoroethyl)piperidin-4-yl)carbamoyl)phenyl)cyclopropyl)carbamate 3-(trans-2-((tert-Butoxycarbonyl)(cyclopropylmethyl)amino)cyclopropyl)benzoic acid (60.0 mg), 1-(2,2,2-trifluoroethyl)piperidin-4-amine dihydrochloride (55.4 mg) and triethylamine (0.076 mL) were dissolved in anhydrous DMF (5.00 mL), O-(7-azabenzotriazol-1-yl)-N,N,N',N'-tetramethyluronium hexafluorophosphate (83.0 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The obtained residue was purified by silica gel column chromatography (hexane/ethyl acetate), and concentrated under reduced pressure to give the title compound (44.4 mg).

MS (API+): [M+H]$^+$ 496.3.

B) 3-(trans-2-((cyclopropylmethyl)amino)cyclopropyl)-N-(1-(2,2,2-trifluoroethyl)piperidin-4-yl)benzamide dihydrochloride tert-Butyl (cyclopropylmethyl)(trans-2-(3-((1-(2,2,2-trifluoroethyl)piperidin-4-yl)carbamoyl)phenyl)cyclopropyl)carbamate (56.6 mg) was dissolved in THF (5.00 mL)/methanol (5.00 mL), and the mixture was cooled to 0° C. A 4 mol/L hydrogen chloride/ethyl acetate solution (0.428 mL) was added, and the mixture was stirred at room temperature overnight. The reaction mixture was concentrated under reduced pressure, and the residue was recrystallized from methanol/ethyl acetate to give the title compound (65.2 mg).

$^1$H NMR (300 MHz, DMSO-d$_6$) δ0.32-0.41 (2H, m), 0.52-0.61 (2H, m), 1.08 (1H, t, J=5.9 Hz), 1.35 (1H, q, J=6.6 Hz), 1.52-1.63 (1H, m), 1.69-1.96 (4H, m), 2.54-2.62 (2H, m), 2.87-3.07 (4H, m), 3.10-3.26 (1H, m), 7.31-7.42 (2H, m), 7.65 (1H, s), 7.70 (1H, d, J=7.2 Hz), 8.37 (1H, brs), 9.37 (2H, brs).

Example 109

3-(trans-2-((cyclopropylmethyl)amino)cyclopropyl)-4-fluoro-N-(5-methyl-1,3,4-thiadiazol-2-yl)benzamide dihydrochloride A) tert-butyl (trans-2-(5-bromo-2-fluorophenyl)cyclopropyl)carbamate To a solution of trans-2-(5-bromo-2-fluorophenyl)cyclopropanecarboxylic acid (2.10 g) in anhydrous tert-butyl alcohol (20.0 mL) were added triethylamine (1.35 mL) and diphenylphosphoryl azide (2.10 mL), and the mixture was stirred at room temperature for 1 hr and at 80° C. for 16 hr under a nitrogen atmosphere. Water (100 mL) was added to the reaction mixture, and the mixture was extracted twice with ethyl acetate (100 mL each time). The extracts were combined, washed successively with water (50.0 mL) and saturated brine (100 mL), dried over anhydrous sodium sulfate, and concentrated under reduced pressure. The residue was purified by silica gel column chromatography (hexane/ethyl acetate) to give the title compound (1.70 g).

$^1$H NMR (400 MHz, DMSO-d$_6$) δ1.68-1.20 (2H, m), 1.37 (9H, s), 1.94-1.98 (1H, m), 2.99 (1H, brs), 7.10-7.50 (4H, m)

B) methyl 3-(trans-2-((tert-butoxycarbonyl)amino)cyclopropyl)-4-fluorobenzoate tert-Butyl (trans-2-(5-bromo-2-fluorophenyl)cyclopropyl)carbamate (2.40 g) was dissolved in methanol (70.0 mL), and N,N-diisopropylethylamine (0.444 mL) and dichloro(1,1'-bis(diphenylphosphino)ferrocene)palladium dichloromethane complex (600 mg) were added. The mixture was stirred at 75° C. for 3 hr under carbon monoxide atmosphere (60 psi), the insoluble material was collected by filtration, and the filtrate was concentrated under reduced pressure. The residue was purified by silica gel column chromatography (hexane/ethyl acetate) to give the title compound (750 mg).

MS (API+): [M+H]$^+$ 310.2.

C) methyl 3-(trans-2-aminocyclopropyl)-4-fluorobenzoate hydrochloride

Methyl 3-(trans-2-((tert-Butoxycarbonyl)amino)cyclopropyl)-4-fluorobenzoate (650 mg) was dissolved in methanol (10.0 mL), and the mixture was cooled to 0° C. A 2 mol/L hydrogen chloride/methanol solution (15.8 mL) was added, and the mixture was stirred at room temperature for 18 hr. The reaction mixture was concentrated under reduced pressure, and the obtained residue was washed under insonation with an ethyl acetate-diisopropy ether mixture to give the title compound (431 mg).

MS (API+): [M−HCl+H]$^+$ 210.2.

D) methyl 3-(trans-2-((tert-butoxycarbonyl)(cyclopropylmethyl)amino)cyclopropyl)-4-fluorobenzoate Methyl 3-(trans-2-aminocyclopropyl)-4-fluorobenzoate hydrochloride (430 mg) and sodium hydrogen carbonate (294 mg) were added to THF (5.00 mL)/methanol (7.00 mL), the mixture was stirred at room temperature for 20 min, and cyclopropanecarbaldehyde (0.158 mL) was added. The mixture was stirred at 60° C. for 3 hr, and sodium borohydride (132 mg) was added under ice-cooling. The mixture was stirred at room temperature for 1 hr, to the reaction mixture was added di-tert-butyl dicarbonate (0.610 mL), and the mixture was stirred at room temperature overnight. The reaction mixture was poured into water, and the mixture was extracted with ethyl acetate. The extracts were combined, washed with water and saturated brine, dried over anhydrous magnesium sulfate, and concentrated under reduced pressure. The residue was purified by silica gel column chromatography (hexane/ethyl acetate) to give the title compound (576 mg).

$^1$H NMR (300 MHz, CDCl$_3$) δ0.12-(2H, m), 0.39-0.54 (2H, m), 0.96-1.10 (1H, m), 1.29-1.39 (2H, m), 1.42 (9H, s), 2.25-2.34 (1H, m), 2.91-2.98 (1H, m), 3.09 (1H, dd, J=14.2, 6.6 Hz), 3.28 (1H, dd, J=14.2, 6.6 Hz), 3.90 (3H, s), 7.03-7.11 (1H, m), 7.63 (1H, dd, J=7.4, 2.1 Hz), 7.82-7.89 (1H, m).

E) 3-(trans-2-((tert-butoxycarbonyl)(cyclopropylmethyl)amino)cyclopropyl)-4-fluorobenzoic acid Methyl 3-(trans-2-((tert-butoxycarbonyl)(cyclopropylmethyl)amino)cyclopropyl)-4-fluorobenzoate (575 mg) was dissolved in methanol (6.00 mL)/THF (4.00 mL), a 2 mol/L aqueous sodium hydroxide solution (3.96 mL) was added, and the mixture was stirred at room temperature overnight. The reaction mixture was diluted with water and washed with hexane. The aqueous layer was acidified with 6 mol/L hydrochloric acid, and extracted with ethyl acetate. The extracts were combined, washed with saturated brine, dried over anhydrous sodium sulfate, and concentrated under reduced pressure to give the title compound (541 mg).

MS (API+): [M−(tert-Bu)+H]$^+$ 294.2.

F) tert-butyl (cyclopropylmethyl) (trans-2-(2-fluoro-5-((5-methyl-1,3,4-thiadiazol-2-yl)carbamoyl)phenyl)cyclopropyl)carbamate 3-(trans-2-((tert-Butoxycarbonyl)(cyclopropylmethyl)amino)cyclopropyl)-4-fluorobenzoic acid (80.0 mg), 5-methyl-1,3,4-thiadiazol-2-amine (31.6 mg) and triethylamine (0.096 mL) were dissolved in anhydrous DMF (4.00 mL), and the mixture was cooled to 0° C. O-(7-Azabenzotriazol-1-yl)-N,N,N',N'-tetramethyluronium hexafluorophosphate (104 mg) was added, and the mixture was stirred at room temperature overnight. The reaction mixture was poured into saturated aqueous sodium hydrogen carbonate solution, and the mixture was extracted with ethyl acetate. The extracts were combined, washed successively with water and saturated brine, dried over anhydrous sodium sulfate, and concentrated under reduced pressure. The obtained residue was purified by silica gel column chromatography (hexane/ethyl acetate), and concentrated under reduced pressure to give the title compound (80.9 mg).

MS (API+): [M+H]$^+$ 447.3.

G) 3-(trans-2-((cyclopropylmethyl)amino)cyclopropyl)-4-fluoro-N-(5-methyl-1,3,4-thiadiazol-2-yl)benzamide dihydrochloride tert-Butyl (cyclopropylmethyl)(trans-2-(2-fluoro-5-((5-methyl-1,3,4-thiadiazol-2-yl)carbamoyl)phenyl)cyclopropyl)carbamate (80.0 mg) was dissolved in a methanol (3.00 mL)-ethyl acetate (2.00 mL) mixture, a 2 mol/L hydrogen chloride/methanol solution (1.34 mL) was added, and the mixture was stirred at room temperature for 18 hr. The reaction mixture was concentrated under reduced pressure, and the residue was recrystallized from methanol/tetrahydrofuran-ethyl acetate mixture to give the title compound (55.9 mg).

$^1$H NMR (300 MHz, DMSO-d$_6$) δ0.33-0.42 (2H, m), 0.53-0.64 (2H, m), 1.02-1.16 (1H, m), 1.48-1.57 (1H, m), 1.61-1.71 (1H, m), 2.65 (3H, s), 2.68-2.76 (1H, m), 2.93-3.04 (2H, m), 3.11-3.23 (1H, m), 7.33-7.46 (1H, m), 7.85 (1H, dd, J=7.2, 2.3 Hz), 7.95-8.07 (1H, m), 9.21-9.57 (2H, m), 12.84 (1H, brs).

Example 110

5-(trans-2-((cyclopropylmethyl)amino)cyclopropyl)-2-fluoro-N-(5-methyl-1,3,4-thiadiazol-2-yl)benzamide dihydrochloride A) methyl 5-(trans-2-aminocyclopropyl)-2-fluorobenzoate hydrochloride Methyl 5-(trans-2-((tert-butoxycarbonyl)amino)cyclopropyl)-2-fluorobenzoate (860 mg) was dissolved in methanol (25.0 mL), and the mixture was cooled to 0° C. A 2 mol/L hydrogen chloride/methanol solution (20.8 mL) was added, and the mixture was stirred at room temperature for 18 hr. The reaction mixture was concentrated under reduced pressure, and the obtained residue was washed under insonation with an ethyl acetate-diisopropy ether mixture to give the title compound (602 mg).

$^1$H NMR (300 MHz, DMSO-d$_6$) δ1.22-1.30 (1H, m), 1.36-1.45 (1H, m), 2.42 (1H, ddd, J=10.0, 6.4, 3.6 Hz), 2.79-2.86 (1H, m), 3.86 (3H, s), 7.25-7.34 (1H, m), 7.43-7.51 (1H, m), 7.66-7.72 (1H, m), 8.44 (3H, brs).

B) methyl 5-(trans-2-((tert-butoxycarbonyl)(cyclopropylmethyl)amino)cyclopropyl)-2-fluorobenzoate Methyl 5-(trans-2-aminocyclopropyl)-2-fluorobenzoate hydrochloride (430 mg) and sodium hydrogen carbonate (294 mg) were added to THF (5.00 mL)/methanol (7.00 mL), the mixture was stirred at room temperature for 20 min, and cyclopropanecarbaldehyde (0.158 mL) was added. The mixture was stirred at 60° C. for 3 hr, and sodium borohydride (132 mg) was added under ice-cooling. The mixture was stirred at room temperature for 1 hr, to the reaction mixture was added di-tert-butyl dicarbonate (0.610 mL), and the mixture was stirred at room temperature overnight. The reaction mixture was poured into water, and the mixture was extracted with ethyl acetate. The extracts were combined, washed with water and saturated brine, dried over anhydrous magnesium sulfate, and concentrated under reduced pressure. The residue was purified by silica gel column chromatography (hexane/ethyl acetate) to give the title compound (563 mg).

$^1$H NMR (300 MHz, CDCl$_3$) δ0.10-0.29 (2H, m), 0.38-0.54 (2H, m), 0.94-1.08 (1H, m), 1.14-1.23 (1H, m), 1.25-1.30 (1H, m), 1.43 (9H, s), 2.08-2.16 (1H, m), 2.78-2.84 (1H, m), 2.98 (1H, dd, J=14.4, 6.8 Hz), 3.30 (1H, dd, J=14.4, 6.8 Hz), 3.93 (3H, s), 7.00-7.09 (1H, m), 7.30-7.38 (1H, m), 7.64-7.69 (1H, m).

C) 5-(trans-2-((tert-butoxycarbonyl)(cyclopropylmethyl)amino)cyclopropyl)-2-fluorobenzoic acid Methyl 5-(trans-2-((tert-butoxycarbonyl)(cyclopropylmethyl)amino)cyclopropyl)-2-fluorobenzoate (563 mg) was dissolved in methanol (6.00 mL)/THF (4.00 mL), a 2 mol/L aqueous sodium hydroxide solution (3.87 mL) was added, and the mixture was stirred at room temperature overnight. The reaction mixture was diluted with water and washed with hexane. The aqueous layer was acidified with 6 mol/L hydrochloric acid, and extracted with ethyl acetate. The extracts were combined, washed with saturated brine, dried over anhydrous sodium sulfate, and concentrated under reduced pressure to give the title compound (550 mg).

MS (API+): [M−(tert-Bu)+H]$^+$ 294.3.

D) tert-butyl (cyclopropylmethyl)(trans-2-(4-fluoro-3-((5-methyl-1,3,4-thiadiazol-2-yl)carbamoyl)phenyl)cyclopropyl)carbamate 5-(trans-2-((tert-Butoxycarbonyl)(cyclopropylmethyl)amino)cyclopropyl)-2-fluorobenzoic acid (80.0 mg), 5-methyl-1,3,4-thiadiazol-2-amine (31.6 mg) and triethylamine (0.096 mL) were dissolved in anhydrous DMF (4.00 mL), and the mixture was cooled to 0° C. O -(7-Azabenzotriazol-1-yl)-N,N,N',N'-tetramethyluronium hexafluorophosphate (104 mg) was added, and the mixture was stirred at room temperature overnight. The reaction mixture was poured into saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (98.0 mg).

MS (API+): [M+H]$^+$ 447.3.

E) 5-(trans-2-((cyclopropylmethyl)amino)cyclopropyl)-2-fluoro-N-(5-methyl-1,3,4-thiadiazol-2-yl)benzamide dihydrochloride tert-Butyl (cyclopropylmethyl) (trans-2-(4-fluoro-3-((5-methyl-1,3,4-thiadiazol-2-yl)carbamoyl)phenyl)cyclopropyl)carbamate (98.0 mg) was dissolved in a mixture of methanol (3.00 mL)/ethyl acetate (2.00 mL), a 2 mol/L hydrogen chloride/methanol solution (1.65 mL) was added, and the mixture was stirred at room temperature for 18 hr. The reaction mixture was concentrated under reduced pressure, and the residue was recrystallized from methanol/tetrahydrofuran-ethyl acetate mixture to give the title compound (71.0 mg).

$^1$H NMR (300 MHz, DMSO-$d_6$) δ0.32-0.41 (2H, m), 0.53-0.62 (2H, m), 0.98-1.13 (1H, m), 1.34-1.43 (1H, m), 1.52-1.62 (1H, m), 2.54-2.61 (1H, m), 2.66 (3H, s), 2.88-3.09 (3H, m), 7.26-7.37 (1H, m), 7.44-7.60 (2H, m), 9.15-9.45 (2H, m), 12.87 (1H, brs).

Example 111

5-(trans-2-((cyclopropylmethyl)amino)cyclopropyl)-2-fluoro-N-(tetrahydro-2H-pyran-4-yl)benzamide hydrochloride A) tert-butyl (cyclopropylmethyl) (trans-2-(4-fluoro-3-((tetrahydro-2H-pyran-4-yl)carbamoyl)phenyl)cyclopropyl)carbamate 5-(trans-2-((tert-Butoxycarbonyl)(cyclopropylmethyl)amino)cyclopropyl)-2-fluorobenzoic acid (84.3 mg), tetrahydro-2H-pyran-4-amine (29.9 mg) and O-(7-azabenzotriazol-1-yl)-N,N,N',N'-tetramethyluronium hexafluorophosphate (110 mg) were dissolved in anhydrous DMF (5.00 mL), triethylamine (0.101 mL) was added, and the mixture was stirred at room temperature for 18 hr. Water was added to the reaction mixture, and the mixture was extracted with ethyl acetate. The extracts were combined, washed successively with water and saturated brine, dried over anhydrous sodium sulfate, and concentrated under reduced pressure. The obtained residue was purified by silica gel column chromatography (hexane/ethyl acetate), and concentrated under reduced pressure to give the title compound (93.9 mg).

MS (API+): [M−(tert-Bu)+H]$^+$ 377.2.

B) 5-(trans-2-((cyclopropylmethyl)amino)cyclopropyl)-2-fluoro-N-(tetrahydro-2H-pyran-4-yl)benzamide hydrochloride tert-Butyl (cyclopropylmethyl)(trans-2-(4-fluoro-3-((tetrahydro-2H-pyran-4-yl)carbamoyl)phenyl)cyclopropyl)carbamate (93.9 mg) was dissolved in THF (5.00 mL)/methanol (5.00 mL), and the mixture was cooled to 0° C. A 4 mol/L hydrogen chloride/ethyl acetate solution (0.814 mL) was added, and the mixture was stirred at room temperature for 18 hr and at 60° C. for 3 hr. The reaction mixture was concentrated under reduced pressure, and the residue was crystallized from methanol/diisopropy ether to give the title compound (47.6 mg).

$^1$H NMR (300 MHz, DMSO-$d_6$) δ0.36 (2H, d, J=4.2 Hz), 0.52-0.61 (2H, m), 1.07 (1H, brs), 1.25-1.34 (1H, m), 1.44-1.60 (3H, m), 1.76 (2H, d, J=12.1 Hz), 2.55 (1H, brs), 2.94 (3H, d, J=7.2 Hz), 3.37-3.43 (2H, m), 3.85 (2H, d, J=11.0 Hz), 3.92-4.03 (1H, m), 7.16-7.25 (1H, m), 7.28-7.38 (2H, m), 8.28 (1H, d, J=7.2 Hz), 9.34 (2H, brs).

Example 112

N-(5-methyl-1,3,4-thiadiazol-2-yl)-3-(trans-2-((tetrahydro-2H-pyran-4-ylmethyl)amino)cyclopropyl)benzamide dihydrochloride A) methyl 3-(trans-2-((tert-butoxycarbonyl)((tetrahydro-2H-pyran-4-yl)methyl)amino)cyclopropyl)benzoate Methyl 3-(trans-2-aminocyclopropyl)benzoate hydrochloride (246 mg) and sodium hydrogen carbonate (182 mg) were added to THF (3.00 mL)/methanol (5.00 mL), and tetrahydro-2H-pyran-4-carbaldehyde (0.135 mL) was added. The mixture was stirred at 60° C. for 2 hr, and sodium borohydride (82.0 mg) was added under ice-cooling. The mixture was stirred at room temperature for 1 hr, to the reaction mixture was added di-tert-butyl dicarbonate (0.376 mL), and the mixture was stirred at room temperature overnight. The reaction mixture was poured into water, and the mixture was extracted with ethyl acetate. The extracts were combined, washed with saturated brine, dried over anhydrous sodium sulfate, and concentrated under reduced pressure. The residue was purified by silica gel column chromatography (hexane/ethyl acetate) to give the title compound (150 mg).

MS (API+): [M−Boc+H]$^+$ 290.3.

B) 3-(trans-2-((tert-butoxycarbonyl) ((tetrahydra-2H-pyran-4-yl)methyl)amino)cyclopropyl)benzoic acid Methyl 3-(trans-2-((tert-butoxycarbonyl) ((tetrahydro-2H-pyran-4-yl)methyl) amino)cyclopropyl)benzoate (149 mg) was dissolved in THF (2.00 mL)/methanol (2.00 mL), a 2 mol/L aqueous sodium hydroxide solution (0.956 mL) was added, and the mixture was stirred at room temperature overnight. The reaction mixture was diluted with water and washed with hexane. The aqueous layer was acidified with 6 mol/L hydrochloric acid, and the mixture was extracted with ethyl acetate. The extracts were combined, washed with saturated brine, dried over anhydrous sodium sulfate, and concentrated under reduced pressure to give the title compound (140 mg).

MS (API+): [M−Boc+H]$^+$ 276.3.

C) N-(5-methyl-1,3,4-thiadiazol-2-yl)-3-(trans-2-((tetrahydro-2H-pyran-4-ylmethyl)amino)cyclopropyl)benzamide dihydrochloride 3-(trans-2-((tert-Butoxycarbonyl)((tetrahydro-2H-pyran-4-yl)methyl)amino)cyclopropyl)benzoic acid (140 mg), 5-methyl-1,3,4-thiadiazol-2-amine (51.5 mg) and triethylamine (0.156 mL) were dissolved in anhydrous DMF (8.00 mL), and the mixture was cooled to 0° C. O-(7-Azabenzotriazol-1-yl)-N,N,N',N'-tetramethyluronium hexafluorophosphate (170 mg) was added, and the mixture was stirred at room temperature overnight. The reaction mixture was poured into saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate) and concentrated under reduced pressure. The obtained residue was dissolved in methanol (16.0 mL), a 2 mol/L hydrogen chloride/methanol solution (4.00 mL) was added under ice-cooling, and the mixture was stirred at room temperature overnight. The reaction mixture was concentrated under reduced pressure, and the residue was crystallized from a mixture of methanol-tetrahydrofuran/ethyl acetate to give the title compound (92.3 mg).

$^1$H NMR (300 MHz, DMSO-$d_6$) δ1.21-1.35 (2H, m), 1.38-1.51 (1H, m), 1.54-1.75 (3H, m), 1.87-1.97 (1H, m), 2.54-2.69 (4H, m), 2.94-3.14 (3H, m), 3.23-3.33 (2H, m), 3.83-3.85 (1H, m), 3.87-3.90 (1H, m), 7.45-7.58 (2H, m), 7.83-7.88 (1H, m), 7.90-7.99 (1H, m), 9.02-9.28 (2H, m), 12.83 (1H, brs).

Example 113

(3-(trans-2-((cyclopropylmethyl)amino)cyclopropyl) phenyl) (1,3-dihydro-2H-isoindol-2-yl)methanone trifluoroacetate To a solution of 3-(trans-2-((tert-butoxycarbonyl)(cyclopropylmethyl)amino)cyclopropyl)benzoic acid (19.9 mg) and 1,3-dihydro-2H-isoindole (14.3 mg) in DMF (0.50 mL) was added a solution of O-(7-azabenzotriazol-1-yl)-N,N,N',N'-tetramethyluronium hexafluorophosphate (45.6 mg) in DMF (0.50 mL). N,N-Diisopropylethylamine (0.0262 mL) was added to the mixture, and the mixture was stirred at room temperature for 3 hr. To the reaction solution were added water and ethyl acetate, the organic layer was extracted, and the solvent was evaporated by an air blowing apparatus. A 2 mol/L hydrogen chloride/methanol solution (0.50 mL) was added to the residue, the mixture was shaken for 1.5 hr, and the solvent was evaporated by an air blowing apparatus. The residue was purified by HPLC (column: YMC Triart C18, mobile phase: acetonitrile/water (with 0.1% TFA)), and the solvent was evaporated by an air blowing apparatus to give the title compound (21.8 mg).

Example 114

N-tert-butyl-3-(trans-2-((cyclopropylmethyl)amino) cyclopropyl)benzamide trifluoroacetate

Example 115

3-(trans-2-((cyclopropylmethyl)amino)cyclopropyl)-N-(3,3-difluorocyclobutyl) benzamide trifluoroacetate

Example 116

3-(trans-2-((cyclopropylmethyl)amino)cyclopropyl)-N-((3,3-difluorocyclobutyl) methyl) benzamide trifluoroacetate

Example 117

3-(trans-2-((cyclopropylmethyl)amino)cyclopropyl)-N-(2-oxoazepan-3-yl) benzamide trifluoroacetate

Example 118

N-(1-benzylpyrrolidin-3-yl)-3-(trans-2-((cyclopropylmethyl)amino)cyclopropyl)benzamide bis(trifluoroacetate)

Example 119

N-(1-benzylpiperidin-4-yl)-3-(trans-2-((cyclopropylmethyl)amino)cyclopropyl)benzamide bis (trifluoroacetate)

Example 120

3-(trans-2-((cyclopropylmethyl)amino)cyclopropyl)-N-(2-phenylethyl) benzamide trifluoroacetate By a method similar to that in Example 113, the compounds of Examples 114 to 120 were produced.

Example 121

3-(trans-2-((cyclopropylmethyl)amino)cyclopropyl)-N-(2-fluorophenyl) benzamide trifluoroacetate To a solution of 3-(trans-2-((tert-butoxycarbonyl)(cyclopropylmethyl)amino)cyclopropyl)benzoic acid (19.9 mg) and 2-fluoroaniline (13.3 mg) in DMF (0.50 mL) was added a solution of O-(7-azabenzotriazol-1-yl)-N,N,N',N'-tetramethyluronium hexafluorophosphate (45.6 mg) in DMF (0.50 mL). N,N-Diisopropylethylamine (0.0262 mL) was added to the mixture, and the mixture was stirred at 60° C. for 3 hr. To the reaction solution were added water and ethyl acetate, the organic layer was extracted, and the solvent was evaporated by an air blowing apparatus. A 2 mol/L hydrogen chloride/methanol solution (0.50 mL) was added to the residue, the mixture was shaken for 1.5 hr, and the solvent was evaporated by an air blowing apparatus. The residue was purified by HPLC (column: YMC Triart C18, mobile phase: acetonitrile/water (with 0.1% TFA)), and the solvent was evaporated by an air blowing apparatus to give the title compound (18 mg).

Example 122

3-(trans-2-((cyclopropylmethyl)amino)cyclopropyl)-N-(3-fluorophenyl) benzamide trifluoroacetate

Example 123

3-(trans-2-((cyclopropylmethyl)amino)cyclopropyl)-N-(4-(trifluoromethoxy)phenyl)benzamide trifluoroacetate

Example 124

3-(trans-2-((cyclopropylmethyl)amino)cyclopropyl)-N-(4-(methylsulfonyl)phenyl)benzamide trifluoroacetate

Example 125

3-(trans-2-((cyclopropylmethyl)amino)cyclopropyl)-N-(4-(morpholin-4-yl)phenyl)benzamide bis(trifluoroacetate)

Example 126

3-(trans-2-((cyclopropylmethyl)amino)cyclopropyl)-N-(4-((1,1-dioxidothiomorpholin-4-yl)methyl)phenyl)benzamide bis (trifluoroacetate)

Example 127

3-(trans-2-((cyclopropylmethyl)amino)cyclopropyl)-N-(4-(2,3-dihydroimidazo[2,1-b][1,3]thiazol-6-yl) phenyl)benzamide bis(trifluoroacetate)

Example 128

3-(trans-2-((cyclopropylmethyl)amino)cyclopropyl)-N-(4-(4,6-dimethoxypyrimidin-2-yl)phenyl)benzamide trifluoroacetate

Example 129

N-(4-benzylphenyl)-3-(trans-2-((cyclopropylmethyl)amino)cyclopropyl)benzamide trifluoroacetate

Example 130

N-(biphenyl-3-yl)-3-(trans-2-((cyclopropylmethyl)amino)cyclopropyl)benzamide trifluoroacetate

Example 131

3-(trans-2-((cyclopropylmethyl)amino)cyclopropyl)-N-(3-(2-methyl-1,3-thiazol-4-yl)phenyl)benzamide trifluoroacetate

Example 132

3-(trans-2-((cyclopropylmethyl)amino)cyclopropyl)-N-(3-((4,6-dimethylpyrimidin-2-yl)sulfanyl)phenyl)benzamide trifluoroacetate

Example 133

3-(trans-2-((cyclopropylmethyl)amino)cyclopropyl)-N-(3-(6,7,8,9-tetrahydro-5H-[1,2,4]triazolo[4,3-a]azepin-3-yl)phenyl)benzamide trifluoroacetate

Example 134

3-(trans-2-((cyclopropylmethyl)amino)cyclopropyl)-N-(6-(morpholin-4-yl)pyridin-3-yl)benzamide tris(trifluoroacetate)

Example 135

3-(trans-2-((cyclopropylmethyl)amino)cyclopropyl)-N-(6-phenoxy-1,3-benzothiazol-2-yl)benzamide trifluoroacetate

Example 136

3-(trans-2-((cyclopropylmethyl)amino)cyclopropyl)-N-(1-methyl-3-(2-thienyl)-1H-pyrazol-5-yl)benzamide bis(trifluoroacetate)

Example 137

3-(trans-2-((cyclopropylmethyl)amino)cyclopropyl)-N-(6-(4-fluorophenoxyl)pyridin-3-yl)benzamide bis(trifluoroacetate)

Example 138

3-(trans-2-((cyclopropylmethyl)amino)cyclopropyl)-N-(1,3-thiazol-2-yl)benzamide trifluoroacetate

Example 139

3-(trans-2-((cyclopropylmethyl)amino)cyclopropyl)-N-(5-methyl-1,3,4-thiadiazol-2-yl)benzamide trifluoroacetate

Example 140

3-(trans-2-((cyclopropylmethyl)amino)cyclopropyl)-N-(3-ethyl-1,2,4-thiadiazol-5-yl)benzamide trifluoroacetate

Example 141

N-(3-tert-butyl-1-methyl-1H-pyrazol-5-yl)-3-(trans-2-((cyclopropylmethyl)amino)cyclopropyl)benzamide bis(trifluoroacetate)

Example 142

3-(trans-2-((cyclopropylmethyl)amino)cyclopropyl)-N-(3,5-dimethyl-1,2-oxazol-4-yl)benzamide trifluoroacetate

Example 143

3-(trans-2-((cyclopropylmethyl)amino)cyclopropyl)-N-(quinoxalin-6-yl)benzamide bis(trifluoroacetate)

Example 144

N-(1,3-benzothiazol-6-yl)-3-(trans-2-((cyclopropylmethyl)amino)cyclopropyl)benzamide trifluoroacetate

Example 145

N-(1H-benzimidazol-5-yl)-3-(trans-2-((cyclopropylmethyl)amino)cyclopropyl)benzamide bis(trifluoroacetate)

Example 146

3-(trans-2-((cyclopropylmethyl)amino)cyclopropyl)-N-(1H-indazol-5-yl)benzamide trifluoroacetate

Example 147

3-(trans-2-((cyclopropylmethyl)amino)cyclopropyl)-N-(2-oxo-2,3-dihydro-1,3-benzothiazol-6-yl)benzamide trifluoroacetate

Example 148

3-(trans-2-((cyclopropylmethyl)amino)cyclopropyl)-N-(7,8,9,10-tetrahydro-6H-azepino[1,2-a]benzimidazol-3-yl)benzamide bis(trifluoroacetate)

Example 149

3-(trans-2-((cyclopropylmethyl)amino)cyclopropyl)-N-(4-ethyl-3-oxo-3,4-dihydro-2H-1,4-benzoxazin-7-yl)benzamide trifluoroacetate

Example 150

3-(trans-2-((cyclopropylmethyl)amino)cyclopropyl)-N-(4-hydroxy-5,6,7,8-tetrahydroquinazolin-2-yl)benzamide trifluoroacetate By a method similar to that in Example 121, the compounds of Examples 122 to 150 were produced.

Example 151

3-(trans-2-((cyclopropylmethyl)amino)cyclopropyl)-N-(1-(2,2,2-trifluoroethyl)-1H-pyrazol-4-yl)benzamide hydrochloride

Example 152

3-(trans-2-((cyclopropylmethyl)amino)cyclopropyl)-N-(3-methyl-1,2-thiazol-5-yl)benzamide hydrochloride By a method similar to that in Example 99, the compounds of Example 151 and Example 152 were produced.

Example 153

3-(trans-2-((2,2-dimethylpropyl)amino)cyclopropyl)-N-(tetrahydro-2H-pyran-4-yl)benzamide hydrochloride

Example 154

N-(3,3-difluorocyclobutyl)-3-(trans-2-((2,2-dimethylpropyl)amino)cyclopropyl)benzamide hydrochloride

Example 155

3-(trans-2-((2,2-dimethylpropyl)amino)cyclopropyl)-N-(1-methyl-1H-pyrazol-4-yl)benzamide dihydrochloride

Example 156

3-(trans-2-((2,2-dimethylpropyl)amino)cyclopropyl)-N-(1,5-dimethyl-1H-pyrazol-4-yl)benzamide dihydrochloride

Example 157

3-(trans-2-((2,2-dimethylpropyl)amino)cyclopropyl)-N-(1,3-dimethyl-1H-pyrazol-4-yl)benzamide dihydrochloride

Example 158

3-(trans-2-((2,2-dimethylpropyl)amino)cyclopropyl)-N-(5-methyl-1,3,4-thiadiazol-2-yl)benzamide dihydrochloride By a method similar to that in Example 95, the compounds of Examples 153 to 158 were produced.

Example 159

5-(trans-2-((cyclopropylmethyl)amino)cyclopropyl)-2-methoxy-N-(5-methyl-1,3,4-thiadiazol-2-yl)benzamide dihydrochloride

Example 160

5-(trans-2-((cyclopropylmethyl)amino)cyclopropyl)-2-methoxy-N-(tetrahydro-2H-pyran-4-yl)benzamide hydrochloride By a method similar to that in Example 110, the compounds of Examples 159 and 160 were produced.

Example 161

3-(trans-2-((cyclopropylmethyl)amino)cyclopropyl)-4-methyl-N-(5-methyl-1,3,4-thiadiazol-2-yl)benzamide dihydrochloride A) methyl 3-((1E)-3-tert-butoxy-3-oxoprop-1-en-1-yl)-4-methylbenzoate To a solution of anhydrous lithium chloride (1.16 g) in acetonitrile (80.0 mL) were added methyl 3-formyl-4-methylbenzoate (4.00 g) and tert-butyl diethylphosphonoacetate (5.40 mL) under ice-cooling, and the mixture was stirred at 0° C. for 5 min under a nitrogen atmosphere. To the reaction mixture was added 1,8-diazabicyclo[5.4.0]undec-7-ene (3.48 mL), and the mixture was stirred under a nitrogen atmosphere at room temperature for 16 hr. Water was added to the reaction mixture, and the mixture was extracted twice with ethyl acetate (100 mL each time). The extracts were combined, washed with water (100 mL) and saturated brine (100 mL), dried over anhydrous sodium sulfate, and concentrated under reduced pressure. The obtained residue was purified by silica gel column chromatography (hexane/ethyl acetate) to give the title compound (4.00 g).

$^1$H NMR (400 MHz, CDCl$_3$) δ1.49 (9H, s), 2.45 (3H, s), 3.82 (3H, s), 6.43 (1H, d, J=15.8 Hz), 7.42 (1H, d, J=7.9 Hz), 7.78 (1H, d, J=15.9 Hz), 7.86 (1H, d, J=8.1 Hz), 8.15 (1H, s).

B) methyl 3-(trans-2-(tert-butoxycarbonyl)cyclopropyl)-4-methylbenzoate

To a suspension of sodium hydride (50% in oil) (834 mg) in DMSO (100 mL) was added a solution of trimethylsulfoxonium iodide (3.80 g) in DMSO (2.00 mL), and the mixture was stirred at room temperature for 1 hr under a nitrogen atmosphere. A solution of methyl 3-((1E)-3-tert-butoxy-3-oxoprop-1-en-1-yl)-4-methylbenzoate (4.00 g) in DMSO (30.0 mL) was added to the reaction mixture, and the mixture was stirred at room temperature for 20 hr under a nitrogen atmosphere. To the reaction mixture was added saturated aqueous ammonium chloride solution (100 mL), and the mixture was extracted three times with ethyl acetate (100 mL each time). The extracts were combined, washed with water (100 mL) and saturated brine (100 mL), dried over anhydrous sodium sulfate, and concentrated under reduced pressure. The obtained residue was purified by silica gel column chromatography (hexane/ethyl acetate) to give the title compound (3.00 g).

¹H-NMR (400 MHz, CDCl₃) δ1.31-1.32 (1H, m), 1.47 (9H, s), 1.55-1.56 (1H, m), 1.70-1.72 (1H, m), 2.42-2.46 (4H, m), 3.89 (3H, s), 7.21 (1H, d, J=7.8 Hz), 7.63 (1H, s), 7.78 (1H, d, J=7.8 Hz).

C) trans-2-(5-(methoxycarbonyl)-2-methylphenyl) cyclopropanecarboxylic acid

Methyl 3-(trans-2-(tert-butoxycarbonyl)cyclopropyl)-4-methylbenzoate (2.00 g) was cooled to 0° C., TFA (5.30 mL) was added, and the mixture was stirred at room temperature for 18 hr. Water (50.0 mL) was added to the reaction mixture, and the mixture was extracted twice with ethyl acetate (100 mL each time). The extract was washed with water (50.0 mL) and saturated brine (100 mL), dried over anhydrous sodium sulfate, and concentrated under reduced pressure. The residue was purified by silica gel column chromatography (hexane/ethyl acetate) to give the title compound (1.30 g).
¹H-NMR (400 MHz, CDCl₃) δ1.36-1.38 (1H, m), 1.40-1.45 (1H, m), 1.65-1.70 (1H, m), 2.40 (4H, m), 3.83 (3H, s), 7.34 (1H, d, J=7.8 Hz), 7.58 (1H, s), 7.74 (1H, d, J=7.8 Hz), 12.39 (1H, brs).

D) methyl 3-(trans-2-((tert-butoxycarbonyl)amino) cyclopropyl)-4-methylbenzoate

To a solution of trans-2-(5-(methoxycarbonyl)-2-methylphenyl)cyclopropanecarboxylic acid (2.00 g) in anhydrous tert-butyl alcohol (17.0 mL) were added triethylamine (1.40 mL) and diphenylphosphoryl azide (2.20 mL), and the mixture was stirred at room temperature for 1 hr and at 80° C. for 16 hr under a nitrogen atmosphere. Water (100 mL) was added to the reaction mixture, and the mixture was extracted 3 times with ethyl acetate (100 mL each time). The extracts were combined, washed successively with water (50.0 mL) and saturated brine (100 mL), dried over anhydrous sodium sulfate, and concentrated under reduced pressure. The residue was purified by silica gel column chromatography (hexane/ethyl acetate) to give the title compound (1.00 g).
MS (API+): [M+H]⁺ 306.0.

E) methyl 3-(trans-2-aminocyclopropyl)-4-methylbenzoate hydrochloride

Methyl 3-(trans-2-((tert-butoxycarbonyl)amino)cyclopropyl)-4-methylbenzoate (1.07 g) was dissolved in methanol (15.0 mL), and the mixture was cooled to 0° C. A 2 mol/L hydrogen chloride/methanol solution (26.4 mL) was added, and the mixture was stirred at room temperature for 18 hr. The reaction mixture was concentrated under reduced pressure, and the obtained residue was washed under insonation with an ethyl acetate-diisopropy ether mixture to give the title compound (749 mg).
¹H NMR (300 MHz, DMSO-d₆) δ1.17-1.25 (1H, m), 1.34-1.42 (1H, m), 2.36-2.44 (1H, m), 2.46 (3H, s), 2.79-2.86 (1H, m), 3.83 (3H, s), 7.35 (1H, d, J=8.0 Hz), 7.60 (1H, d, J=1.5 Hz), 7.75 (1H, dd, J=8.0, 1.5 Hz), 8.42 (3H, brs).

F) methyl 3-(trans-2-((tert-butoxycarbonyl)(cyclopropylmethyl)amino)cyclopropyl)-4-methylbenzoate Methyl 3-(trans-2-aminocyclopropyl)-4-methylbenzoate hydrochloride (430 mg) and sodium hydrogen carbonate (299 mg) were added to THF (5.00 mL)/methanol (7.00 mL), the mixture was stirred at room temperature for 20 min, and cyclopropanecarbaldehyde (0.161 mL) was added. The mixture was stirred at 60° C. for 3 hr, and sodium borohydride (135 mg) was added under ice-cooling. The mixture was stirred at room temperature for 1 hr, to the reaction mixture was added di-tert-butyl dicarbonate (0.620 mL), and the mixture was stirred at room temperature overnight. The reaction mixture was poured into water, and the mixture was extracted with ethyl acetate. The extracts were combined, washed with saturated brine, dried over anhydrous magnesium sulfate, and concentrated under reduced pressure. The residue was purified by silica gel column chromatography (hexane/ethyl acetate) to give the title compound (582 mg).
¹H NMR (300 MHz, CDCl₃) δ0.15-0.31 (2H, m), 0.42-0.56 (2H, m), 0.99-1.11 (2H, m), 1.27-1.35 (1H, m), 1.43 (9H, s), 2.08-2.17 (1H, m), 2.47 (3H, s), 2.97-3.12 (2H, m), 3.34 (1H, dd, J=14.0, 6.8 Hz), 3.89 (3H, s), 7.21 (1H, d, J=8.0 Hz), 7.70 (1H, s), 7.73-7.79 (1H, m).

G) 3-(trans-2-((tert-butoxycarbonyl)(cyclopropylmethyl)amino)cyclopropyl)-4-methylbenzoic acid Methyl 3-(trans-2-((tert-butoxycarbonyl)(cyclopropylmethyl)amino)cyclopropyl)-4-methylbenzoate (581 mg) was dissolved in methanol (6.00 mL)/THF (4.00 mL), a 2 mol/L aqueous sodium hydroxide solution (4.04 mL) was added, and the mixture was stirred at room temperature overnight. The reaction mixture was diluted with water and washed with hexane, the aqueous layer was acidified with 6 mol/L hydrochloric acid, and the mixture was extracted with ethyl acetate. The extracts were combined, washed with saturated brine, dried over anhydrous sodium sulfate, and concentrated under reduced pressure to give the title compound (560 mg).
MS (API+): [M−(tert-Bu)+H]⁺ 290.3.

H) tert-butyl (cyclopropylmethyl)(trans-2-(2-methyl-5-((5-methyl-1,3,4-thiadiazol-2-yl)carbamoyl)phenyl)cyclopropyl)carbamate 3-(trans-2-((tert-Butoxycarbonyl) (cyclopropylmethyl) amino)cyclopropyl)-4-methylbenzoic acid (75.0 mg), 5-methyl-1,3,4-thiadiazol-2-amine (30.0 mg) and triethylamine (0.091 mL) were dissolved in anhydrous DMF (4.00 mL), and the mixture was cooled to 0° C. 0-(7-Azabenzotriazol-1-yl)-N,N,N',N'-tetramethyluronium hexafluorophosphate (99.0 mg) was added, and the mixture was stirred at room temperature overnight. The reaction mixture was poured into saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (50.2 mg).
MS (API+): [M+H]⁺ 443.4.

I) 3-(trans-2-((cyclopropylmethyl)amino)cyclopropyl)-4-methyl-N-(5-methyl-1,3,4-thiadiazol-2-yl) benzamide dihydrochloride tert-Butyl (cyclopropylmethyl)(trans-2-(2-methyl-5-((5-methyl-1,3,4-thiadiazol-2-yl)carbamoyl)phenyl)cyclopropyl)carbamate (50.0 mg) was dissolved in methanol (3.00 mL), a 2 mol/L hydrogen chloride/methanol solution (0.847 mL) was added, and the mixture was stirred at room temperature for 18 hr. The reaction mixture was concentrated under reduced pressure, and the residue was crystallized from a methanol/tetrahydrofuran/ethyl acetate mixture to give the title compound (42.9 mg).

$^1$H NMR (300 MHz, DMSO-$d_6$) δ0.35-0.44 (2H, m), 0.56-0.64 (2H, m), 1.03-1.18 (1H, m), 1.34-1.45 (1H, m), 1.50-1.63 (1H, m), 2.56-2.68 (4H, m), 2.94-3.04 (2H, m), 3.06-3.17 (1H, m), 7.39 (1H, d, J=8.3 Hz), 7.71 (1H, d, J=1.7 Hz), 7.87 (1H, dd, J=8.3, 1.7 Hz), 9.13-9.32 (2H, m), 12.75 (1H, brs).

(peak of 3H of tolyl was not observed with DMSO)

Example 162

3-(trans-2-((cyclopropylmethyl)amino)cyclopropyl)-4-methoxy-N-(5-methyl-1,3,4-thiadiazol-2-yl)benzamide dihydrochloride Example 163

3-(trans-2-((cyclopropylmethyl)amino)cyclopropyl)-5-methoxy-N-(5-methyl-1,3,4-thiadiazol-2-yl)benzamide dihydrochloride By a method similar to that in Example 161, the compounds of Examples 162 and 163 were produced.

Example 164

N-(5-methyl-1,3,4-thiadiazol-2-yl)-3-(trans-2-(tetrahydro-2H-pyran-4-ylamino)cyclopropyl)benzamide dihydrochloride 3-(trans-2-Aminocyclopropyl)-N-(5-methyl-1,3,4-thiadiazol-2-yl)benzamide dihydrochloride (50.0 mg), dihydro-2H-pyran-4(3H)-one (0.016 mL) and N,N-diisopropylethylamine (0.025 mL) were dissolved in methanol (4.00 mL)/acetic acid (0.40 mL), borane-2-methylpyridine complex (23.1 mg) was added, and the mixture was stirred at room temperature overnight under a nitrogen atmosphere. To the reaction mixture was added dihydro-2H-pyran-4(3H)-one (0.13 mL), and the mixture was stirred under a nitrogen atmosphere at 60° C. for 20 min. To the reaction mixture was added saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by NH silica gel column chromatography (ethyl acetate/methanol), to the obtained fraction was added a 2 mol/L hydrogen chloride/methanol solution (2.00 mL) under ice-cooling, and the mixture was stirred at 0° C. for 20 min. The reaction mixture was concentrated under reduced pressure, and the obtained residue was washed under insonation with diethyl ether to give the title compound (20.2 mg).

$^1$H NMR (300 MHz, DMSO-$d_6$) δ1.41-1.52 (1H, m), 1.58-1.78 (3H, m), 1.92-2.05 (2H, m), 2.60-2.69 (4H, m), 3.01-3.13 (1H, m), 3.25-3.37 (2H, m), 3.41-3.53 (1H, m), 3.85-3.98 (2H, m), 7.43-7.58 (2H, m), 7.82-7.88 (1H, m), 7.89-7.98 (1H, m), 9.45-9.83 (2H, m), 12.84 (1H, brs).

Example 165

N-(5-methyl-1,3,4-thiadiazol-2-yl)-3-(trans-2-(tetrahydro-2H-pyran-4-ylamino)cyclopropyl)benzamide fumarate 3-(trans-2-Aminocyclopropyl)-N-(5-methyl-1,3,4-thiadiazol-2-yl)benzamide dihydrochloride (173 mg) and borane-2-methylpyridine complex (92.0 mg) was dissolved in methanol (4.00 mL)/acetic acid (0.40 mL), to the reaction mixture was added dihydro-2H-pyran-4(3H)-one (0.160 mL), and the mixture was stirred at room temperature overnight under a nitrogen atmosphere. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by NH silica gel column chromatography (ethyl acetate/methanol) and concentrated under reduced pressure. The obtained residue was dissolved in methanol (2.00 mL)/ethyl acetate (2.00 mL), and a solution of fumaric acid (44.7 mg) in methanol (1.00 mL) was added. The mixture was concentrated under reduced pressure, and the residue was recrystallized from ethanol/water/heptane to give the title compound (145 mg).

$^1$H NMR (300 MHz, DMSO-$d_6$) δ1.03-1.19 (2H, m), 1.22-1.41 (2H, m), 1.70-1.82 (2H, m), 1.88-1.97 (1H, m), 2.39-2.47 (1H, m), 2.64 (3H, s), 2.75-2.88 (1H, m), 3.28 (2H, d, J=1.9 Hz), 3.76-3.88 (2H, m), 6.60 (2H, s), 7.35-7.45 (2H, m), 7.71 (1H, s), 7.80-7.87 (1H, m).

Example 166

3-(trans-2-((4,4-difluorocyclohexyl)amino)cyclopropyl)-N-(5-methyl-1,3,4-thiadiazol-2-yl)benzamide dihydrochloride 3-(trans-2-Aminocyclopropyl)-N-(5-methyl-1,3,4-thiadiazol-2-yl)benzamide dihydrochloride (50.0 mg) and borane-2-methylpyridine complex (23.1 mg) were dissolved in methanol (4.00 mL)/acetic acid (0.40 TEL), 4,4-difluorocyclohexanone (0.089 mL) was added, and the mixture was stirred at room temperature for 2 days. Under ice-cooling, to the reaction mixture was added saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by NH silica gel column chromatography (ethyl acetate/methanol). To the obtained fraction was added a 2 mol/L hydrogen chloride/methanol solution (2.00 mL) under ice-cooling, and the mixture was stirred at 0° C. for 30 min. The reaction mixture was concentrated under reduced pressure, and the obtained residue was crystallized from tetrahydrofuran/diethyl ether to give the title compound (31.1 mg).

$^1$H NMR (300 MHz, DMSO-$d_6$) δ1.45-1.53 (1H, m), 1.56-1.65 (1H, m), 1.66-1.75 (2H, m), 1.81-2.02 (2H, m), 2.06-2.21 (4H, m), 2.55-2.63 (1H, m), 2.65 (3H, s), 3.05-3.16 (1H, m), 3.39-3.46 (1H, m), 7.45-7.59 (2H, m), 7.83-7.87 (1H, m), 7.90-7.97 (1H, m), 9.35-9.58 (2H, m), 12.81 (1H, brs).

Example 167

3-(trans-2-((4,4-difluorocyclohexyl)amino)cyclopropyl)-N-(5-methyl-1,3,4-thiadiazol-2-yl)benzamide hydrochloride 3-(trans-2-Aminocyclopropyl)-N-(5-methyl-1,3,4-thiadiazol-2-yl)benzamide dihydrochloride (150 mg) and borane-2-methylpyridine complex (69.3 mg) were dissolved in methanol (4.00 mL)/acetic acid (0.40 mL), 4,4-difluorocyclohexanone (0.267 mL) was added, and the mixture was stirred at room temperature overnight under a nitrogen atmosphere. To the reaction mixture was added saturated aqueous sodium hydrogen carbonate solution, and the mixture was extracted with ethyl acetate. The extracts were combined, washed with saturated brine, dried over anhydrous magnesium sulfate, and concentrated under reduced pressure. The residue was purified by NH silica gel column chromatography (ethyl acetate/methanol), and a 4 mol/L hydrogen chloride/ethyl acetate solution was added to the obtained fraction. The solvent was evaporated under reduced pressure, and the residue was recrystallized from ethanol/diisopropy ether/hexane to give the title compound (123 mg).

$^1$H NMR (300 MHz, DMSO-$d_6$) δ1.43-1.54 (1H, m), 1.56-2.24 (9H, m), 2.55-2.69 (4H, m), 3.04-3.17 (1H, m), 3.33-3.49 (1H, m), 7.46-7.59 (2H, m), 7.85 (1H, s), 7.90-7.97 (1H, m), 9.35-9.61 (2H, m), 12.74-12.88 (1H, m).

Example 168

N-cyclopentyl-3-(trans-2-(tetrahydro-2H-pyran-4-ylamino)cyclopropyl)benzamide hydrochloride A) tert-butyl (trans-2-(3-(cyclopentylcarbamoyl)phenyl)cyclopropyl)carbamate 3-(trans-2-((tert-Butoxycarbonyl)amino)cyclopropyl)benzoic acid (400 mg), O-(7-azabenzotriazol-1-yl)-N,N,N',N'-tetramethyluronium hexafluorophosphate (658 mg) and cyclopentanamine (0.173 mL) were dissolved in anhydrous DMF (20.0 mL), triethylamine (0.603 mL) was added, and the mixture was stirred at room temperature for 18 hr. Water was added to the reaction mixture, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (483 mg).

MS (API+): [M+H]$^+$ 345.2.

B) 3-(trans-2-aminocyclopropyl)-N-cyclopentylbenzamide hydrochloride tert-Butyl (trans-2-(3-(cyclopentylcarbamoyl)phenyl)cyclopropyl)carbamate (426 mg) were dissolved in THF (15.0 mL)/methanol (15.0 mL), and the mixture was cooled to 0° C. A 4 mol/L hydrogen chloride/ethyl acetate solution (4.64 mL) was added, and the mixture was stirred at room temperature for 18 hr. The reaction mixture was concentrated under reduced pressure, and the residue was crystallized from methanol/diisopropy ether to give the title compound (414 mg).

MS (API+): [M–HCl+H]$^+$ 245.2.

C) N-cyclopentyl-3-(trans-2-(tetrahydro-2H-pyran-4-ylamino)cyclopropyl)benzamide hydrochloride 3-(trans-2-Aminocyclopropyl)-N-cyclopentylbenzamide hydrochloride (200 mg) and borane-2-methylpyridine complex (114 mg) were dissolved in methanol (20.0 mL)/acetic acid (2.00 mL), dihydro-2H-pyran-4(3H)-one (0.207 mL) was added, and the mixture was stirred at room temperature for 18 hr. To the reaction mixture was added saturated aqueous sodium hydrogen carbonate solution under ice-cooling, and the mixture was extracted with ethyl acetate. The extract was washed with water and saturated brine, dried over anhydrous sodium sulfate, and concentrated under reduced pressure. The residue was purified by NH silica gel column chromatography (ethyl acetate/hexane) and concentrated under reduced pressure. The obtained residue was dissolved in methanol (10.0 mL), and a 4 mol/L hydrogen chloride/ethyl acetate solution (0.356 mL) was added. After stirring at room temperature for 1 hr, the solvent was evaporated under reduced pressure, and the residue was recrystallized from ethanol/heptane to give the title compound (104 mg).

$^1$H NMR (300 MHz, DMSO-$d_6$)δ1.34-1.44 (1H, m), 1.46-1.79 (10H, m), 1.83-2.01 (4H, m), 2.53-2.56 (1H, m), 3.03 (1H, dd, J=9.1, 4.2 Hz), 3.34-3.39 (1H, m), 3.41-3.55 (1H, m), 3.87-3.97 (2H, m), 4.16-4.29 (1H, m), 7.31-7.35 (1H, m), 7.35-7.42 (1H, m), 7.60 (1H, s), 7.69 (1H, dt, J=7.2, 1.3 Hz), 8.24 (1H, d, J 7.2 Hz), 9.12 (2H, brs).

Example 169

3-(trans-2-(cyclobutylamino)cyclopropyl)-N-(1-methyl-1H-pyrazol-4-yl)benzamide dihydrochloride A) tert-butyl (trans-2-(3-((1-methyl-1H-pyrazol-4-yl)carbamoyl)phenyl)cyclopropyl)carbamate 3-(2-((tert-Butoxycarbonyl)amino)cyclopropyl)benzoic acid (250 mg), 1-methyl-1H-pyrazol-4-amine (96.0 mg) and triethylamine (0.377 mL) were dissolved in anhydrous DMF (4.00 mL), O-(7-azabenzotriazol-1-yl)-N,N,N',N'-tetramethyluronium hexafluorophosphate (377 mg) was added, and the mixture was stirred at 60° C. overnight. The reaction mixture was poured into water, and the mixture was extracted with ethyl acetate. The extracts were combined, washed with water and saturated brine, dried over anhydrous magnesium sulfate, and concentrated under reduced pressure to give the title compound (285 mg).

MS (API+): [M+H]$^+$ 357.3.

B) 3-(trans-2-aminocyclopropyl)-N-(1-methyl-1H-pyrazol-4-yl)benzamide dihydrochloride tert-Butyl (trans-2-(3-((1-methyl-1H-pyrazol-4-yl)carbamoyl)phenyl)cyclopropyl)carbamate (676 mg) was dissolved in THF (20.0 mL)/methanol (20.0 mL), and the mixture was cooled to 0° C. A 4 mol/L hydrogen chloride/ethyl acetate solution (7.11 mL) was added, and the mixture was stirred at room temperature for 18 hr. The reaction mixture was concentrated under reduced pressure, and the residue was crystallized from methanol/ethyl acetate to give the title compound (655 mg).

MS (API+): [M–HCl+H]$^+$ 257.2.

C) 3-(trans-2-(cyclobutylamino)cyclopropyl)-N-(1-methyl-1H-pyrazol-4-yl)benzamide dihydrochloride 3-(trans-2-Aminocyclopropyl)-N-(1-methyl-1H-pyrazol-4-yl)benzamide dihydrochloride (100 mg) and borane-2-methylpyridine complex (48.7 mg) were dissolved in methanol (2.00 mL)/acetic acid (0.20 mL), cyclobutanone (63.9 mg) was added, and the mixture was stirred at room temperature overnight under a nitrogen atmosphere. Furthermore, cyclobutanone (63.9 mg) was added, and the mixture was stirred at room temperature for 2 hr under a nitrogen atmosphere. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by silica gel column chromatography (ethyl acetate/methanol), and a 4 mol/L hydrogen chloride/ethyl acetate solution (1.14 mL) was added to the obtained fraction. The solvent was evaporated under reduced pressure, and the residue was recrystallized from methanol/diisopropy ether to give the title compound (36.0 mg).

$^1$H NMR (300 MHz, DMSO-d$_6$) δ1.30-1.43 (1H, m), 1.47-1.60 (1H, m), 1.72-1.91 (2H, m), 2.12-2.33 (4H, m), 2.42-2.60 (2H, m), 2.88-3.01 (1H, m), 3.82 (3H, s), 7.35-7.48 (2H, m), 7.58 (1H, d, J=0.8 Hz), 7.70-7.74 (1H, m), 7.77-7.82 (1H, m), 8.02 (1H, s), 9.53 (2H, br. s), 10.43 (1H, s).

Example 170

3-(trans-2-(dicyclobutylamino)cyclopropyl)-N-(1-methyl-1H-pyrazol-4-yl)benzamide dihydrochloride By a method similar to that in Example 169, the compound of Example 170 was produced.

Example 171

N-(1-methyl-1H-pyrazol-4-yl)-3-(trans-2-((1-(2,2,2-trifluoroethyl)piperidin-4-yl)amino)cyclopropyl) benzamide trihydrochloride 3-(trans-2-Aminocyclopropyl)-N-(1-methyl-1H-pyrazol-4-yl)benzamide dihydrochloride (100 mg) and borane-2-methylpyridine complex (48.7 mg) were dissolved in methanol (2.00 mL)/acetic acid (0.20 mL), 1-(2,2,2-trifluoroethyl)piperidin-4-one (245 mg) was added, and the mixture was stirred under a nitrogen atmosphere at room temperature for 18 hr. Under ice-cooling, to the reaction mixture was added saturated aqueous sodium hydrogen carbonate solution, and the mixture was extracted with ethyl acetate. The extracts were combined, washed with saturated brine (10.0 mL), dried over anhydrous sodium sulfate, and concentrated under reduced pressure. The residue was purified by silica gel column chromatography (hexane/ethyl acetate), and a 4 mol/L hydrogen chloride/ethyl acetate solution (1.14 mL) was added to the obtained fraction. The solvent was evaporated under reduced pressure, and the residue was recrystallized from methanol/diisopropy ether to give the title compound (80.0 mg).

$^1$H NMR (300 MHz, DMSO-d$_6$) δ1.34-1.47 (1H, m), 1.56-1.89 (3H, m), 2.01-2.16 (2H, m), 2.52-2.71 (3H, m), 3.01-3.18 (3H, m), 3.20-3.52 (3H, m), 3.82 (3H, s), 7.37-7.49 (2H, m), 7.60 (1H, s), 7.74-7.83 (2H, m), 8.03 (1H, s), 9.56-9.80 (2H, m), 10.46-10.53 (1H, m).

Example 172

3-(trans-2-(cyclopentylamino)cyclopropyl)-N-(1-methyl-1H-pyrazol-4-yl)benzamide dihydrochloride 3-(trans-2-Aminocyclopropyl)-N-(1-methyl-1H-pyrazol-4-yl)benzamide dihydrochloride (50.0 mg) and borane-2-methylpyridine complex (24.4 mg) were dissolved in methanol (2.00 mL)/acetic acid (0.20 mL), cyclopentanone (0.040 mL) was added, and the mixture was stirred at room temperature overnight under a nitrogen atmosphere. Furthermore, cyclopentanone (0.134 mL) was added, and the mixture was stirred at room temperature for 3 hr under a nitrogen atmosphere. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by NH silica gel column chromatography (hexane/ethyl acetate), and a 4 mol/L hydrogen chloride/ethyl acetate solution was added to the obtained fraction. The solvent was evaporated under reduced pressure, and the residue was recrystallized from methanol/diisopropy ether to give the title compound (35.0 mg).

$^1$H NMR (300 MHz, DMSO-d$_6$) δ1.31-1.47 (1H, m), 1.47-1.80 (7H, m), 1.90-2.05 (2H, m), 2.53-2.62 (1H, m), 2.98-3.13 (1H, m), 3.53-3.75 (1H, m), 3.82 (3H, s), 7.36-7.49 (2H, m), 7.56-7.60 (1H, m), 7.71-7.76 (1H, m), 7.77-7.83 (1H, m), 7.98-8.06 (1H, m), 9.01-9.34 (2H, m), 10.34-10.46 (1H, m).

Example 173

3-(trans-2-(cyclobutylamino)cyclopropyl)-N-(5-methyl-1,3,4-thiadiazol-2-yl)benzamide dihydrochloride 3-(trans-2-Aminocyclopropyl)-N-(5-methyl-1,3,4-thiadiazol-2-yl)benzamide dihydrochloride (50.0 mg) and borane-2-methylpyridine complex (23.1 mg) were dissolved in methanol (4.0 mL)/acetic acid (0.4 mL), cyclobutanone (0.043 mL) was added under ice-cooling, and the mixture was stirred at room temperature for 18 hr. Furthermore, cyclobutanone (0.022 mL) was added under ice-cooling, and the mixture was stirred at room temperature for 3 days. To the reaction mixture was added borane-2-methylpyridine complex (11.6 mg) under ice-cooling, and the mixture was stirred at room temperature overnight. Under ice-cooling, to the reaction mixture was added saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by silica gel column chromatography (ethyl acetate/methanol), to the obtained fraction was added a 2 mol/L hydrogen chloride/methanol solution (2.00 mL) under ice-cooling, and the mixture was stirred at 0° C. for 30 min. The reaction mixture was concentrated under reduced pressure, and the residue was crystallized from a mixture of methanol-tetrahydrofuran/ethyl acetate to give the title compound (21.8 mg).

$^1$H NMR (300 MHz, DMSO-d$_6$) δ1.37-1.48 (1H, m), 1.49-1.59 (1H, m), 1.71-1.92 (2H, m), 2.12-2.33 (4H, m), 2.54-2.59 (1H, m), 2.65 (3H, s), 2.89-3.02 (1H, m), 3.80-3.94 (1H, m), 7.42-7.57 (2H, m), 7.78-7.86 (1H, m), 7.89-7.96 (1H, m), 9.37-9.64 (2H, m), 12.82 (1H, brs).

Example 174

3-(trans-2-(cyclobutylamino)cyclopropyl)-N-(5-methyl-1,3,4-thiadiazol-2-yl)benzamide hydrochloride 3-(trans-2-Aminocyclopropyl)-N-(5-methyl-1,3,4-thiadiazol-2-yl)benzamide dihydrochloride (216 mg) and borane-2-methylpyridine complex (100 mg) were dissolved in methanol (12.0 mL)/acetic acid (1.2 mL), cyclobutanone (0.139 mL) was added under ice-cooling, and the mixture was stirred at room temperature for 18 hr. Furthermore, borane-2-methylpyridine complex (49.9 mg) was added under ice-cooling, and the mixture was stirred at room temperature for 9 hr. To the reaction mixture was added cyclobutanone (0.070 mL) under ice-cooling, and the mixture was stirred at room temperature overnight. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by silica gel column chromatography (ethyl acetate/methanol), to the obtained fraction was added a 2 mol/L hydrogen chloride/methanol solution (4.00 mL), and the mixture was stirred at room temperature for 20 min. The reaction mixture was concentrated under reduced pressure, and the residue was crystallized from ethanol/heptane to give the title compound (58.7 mg).

$^1$H NMR (300 MHz, DMSO-$d_6$) δ1.37-1.48 (1H, m), 1.51-1.60 (1H, m), 1.71-1.91 (2H, m), 2.15-2.29 (4H, m), 2.53-2.61 (1H, m), 2.65 (3H, s), 2.88-3.00 (1H, m), 3.80-3.92 (1H, m), 7.44-7.56 (2H, m), 7.81-7.86 (1H, m), 7.89-7.95 (1H, m), 9.46-9.73 (2H, m), 12.82 (1H, brs).

Example 175

3-(trans-2-((1-cyclopropylpiperidin-4-yl)amino)cyclopropyl)-N-(5-methyl-1,3,4-thiadiazol-2-yl)benzamide trihydrochloride 3-(trans-2-Aminocyclopropyl)-N-(5-methyl-1,3,4-thiadiazol-2-yl)benzamide dihydrochloride (33.0 mg) and borane-2-methylpyridine complex (15.3 mg) were dissolved in methanol (2.00 mL)/acetic acid (0.20 mL), 1-cyclopropylpiperidin-4-one (0.046 mL) was added under ice-cooling, and the mixture was stirred at room temperature for 18 hr. Under ice-cooling, to the reaction mixture was added saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by NH silica gel column chromatography (ethyl acetate/methanol), to the obtained fraction was added a 4 mol/L hydrogen chloride/ethyl acetate solution (2.00 mL) under ice-cooling, and the mixture was stirred at 0° C. for 30 min. The reaction mixture was concentrated under reduced pressure, and the obtained residue was crystallized from tetrahydrofuran/diethyl ether to give the title compound (21.2 mg).

$^1$H NMR (300 MHz, DMSO-$d_6$) δ0.73-0.84 (2H, m), 1.00-1.11 (2H, m), 1.42-1.54 (1H, m), 1.57-1.68 (1H, m), 1.92-2.12 (2H, m), 2.20-2.35 (3H, m), 2.65 (3H, s), 3.04-3.28 (3H, m), 3.39-3.65 (4H, m), 7.43-7.58 (2H, m), 7.79-7.88 (1H, m), 7.89-8.00 (1H, m), 9.66-10.32 (3H, m), 12.83 (1H, brs).

Example 176

3-(trans-2-((1-cyclopropylpiperidin-4-yl)amino)cyclopropyl)-N-(5-methyl-1,3,4-thiadiazol-2-yl)benzamide fumarate 3-(trans-2-Aminocyclopropyl)-N-(5-methyl-1,3,4-thiadiazol-2-yl)benzamide dihydrochloride (130 mg) and borane-2-methylpyridine complex (60.1 mg) were dissolved in methanol (8.00 mL)/acetic acid (0.80 mL), 1-cyclopropylpiperidin-4-one (0.136 mL) was added under ice-cooling, and the mixture was stirred at room temperature for 18 hr. Under ice-cooling, to the reaction mixture was added saturated aqueous sodium hydrogen carbonate solution, and the mixture was extracted with tetrahydrofuran. The extracts were combined, dried over anhydrous sodium sulfate, and concentrated under reduced pressure. The residue was purified by NH silica gel column chromatography (ethyl acetate/methanol), and concentrated under reduced pressure. The obtained residue was dissolved in methanol (4.00 mL)/ethyl acetate (2.00 mL), a solution of fumaric acid (24.0 mg) in methanol (2.00 mL) was added, and the mixture was stirred at room temperature for 40 min. The reaction mixture was concentrated under reduced pressure, and the residue was crystallized from ethanol/heptane to give the title compound (76.1 mg).

$^1$H NMR (300 MHz, DMSO-$d_6$) δ0.22-0.28 (2H, m), 0.34-0.41 (2H, m), 1.03-1.16 (2H, m), 1.17-1.33 (2H, m), 1.51-1.60 (1H, m), 1.70-1.82 (2H, m), 1.86-1.95 (1H, m), 2.09-2.21 (2H, m), 2.37-2.42 (1H, m), 2.54-2.62 (1H, m), 2.64 (3H, s), 2.81-2.92 (2H, m), 6.58 (2H, s), 7.34-7.45 (2H, m), 7.67-7.73 (1H, m), 7.79-7.87 (1H, m).

Example 177

N-(4,4-difluorocyclohexyl)-3-(trans-2-(tetrahydro-2H-pyran-4-ylamino)cyclopropyl)benzamide hydrochloride 3-(trans-2-Aminocyclopropyl)-N-(4,4-difluorocyclohexyl)benzamide hydrochloride (100 mg) and borane-2-methylpyridine complex (48.5 mg) were dissolved in methanol (10.0 mL)/acetic acid (1.00 mL), dihydro-2H-pyran-4(3H)-one (0.088 mL) was added, and the mixture was stirred under a nitrogen atmosphere at room temperature for 18 hr. To the reaction mixture was added saturated aqueous sodium hydrogen carbonate solution under ice-cooling, and the mixture was extracted with ethyl acetate. The extract was washed with water and saturated brine, dried over anhydrous sodium sulfate, and concentrated under reduced pressure. The residue was purified by NH silica gel column chromatography (hexane/ethyl acetate), and concentrated under reduced pressure. The obtained residue was dissolved in methanol (5.00 mL), and a 4 mol/L hydrogen chloride/ethyl acetate solution (0.378 mL) was added. The solvent was evaporated under reduced pressure, and the residue was recrystallized from methanol/diisopropy ether to give the title compound (51.7 mg).

$^1$H NMR (300 MHz, DMSO-$d_6$) δ1.36 (1H, q, J=6.4 Hz), 1.58-1.77 (5H, m), 1.81-2.13 (9H, m), 2.64 (1H, ddd, J=9.7, 6.1, 3.6 Hz), 3.01 (1H, d, J=3.0 Hz), 3.31 (2H, t, J=11.4 Hz), 3.91 (2H, dd, J=11.4, 3.4 Hz), 3.96-4.06 (1H, m), 7.32-7.43 (2H, m), 7.64 (1H, s), 7.70 (1H, d, J=7.2 Hz), 8.33 (1H, d, J 7.6 Hz), 9.75 (2H, brs).

Example 178

3-(trans-2-((4,4-difluorocyclohexyl)amino)cyclopropyl)-N-(tetrahydro-2H-pyran-4-yl)benzamide hydrochloride 3-(trans-2-Aminocyclopropyl)-N-(tetrahydro-2H-pyran-4-yl)benzamide hydrochloride (103 mg) and borane-2-methylpyridine complex (55.7 mg) were dissolved in methanol (2.00 mL)/acetic acid (0.20 mL), 4,4-difluorocyclohexanone (69.8 mg) was added, and the mixture was stirred at room temperature overnight under a nitrogen atmosphere. To the reaction mixture was added saturated aqueous sodium hydrogen carbonate solution, and the mixture was extracted with ethyl acetate. The extracts were combined, washed with saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution was added to the obtained fraction. The solvent was evaporated under reduced pressure, and the residue was recrystallized from ethanol/heptane to give the title compound (80.0 mg).

$^1$H NMR (300 MHz, DMSO-$d_6$) δ1.33-1.45 (1H, m), 1.48-2.25 (13H, m), 2.53-2.62 (1H, m), 2.96-3.12 (1H, m), 3.34-3.47 (3H, m), 3.81-4.08 (3H, m), 7.31-7.44 (2H, m), 7.58-7.66 (1H, m), 7.67-7.75 (1H, m), 8.22-8.34 (1H, m), 9.21-9.53 (2H, m).

Example 179

3-(trans-2-(cyclobutylamino)cyclopropyl)-N-(tetrahydro-2H-pyran-4-yl)benzamide hydrochloride 3-(trans-2-Aminocyclopropyl)-N-(tetrahydro-2H-pyran-4-yl)benzamide hydrochloride (300 mg) and borane-2-methylpyridine complex (162 mg) were dissolved in methanol (4.00 mL)/acetic acid (0.40 mL), cyclobutanone (0.083 mL) was added, and the mixture was stirred under a nitrogen atmosphere at room temperature for 18 hr. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by silica gel column chromatography (ethyl acetate/methanol), and concentrated under reduced pressure. A 4 mol/L hydrogen chloride/ethyl acetate solution was added, the solvent was evaporated under reduced pressure, and the residue was recrystallized from ethanol/diisopropy ether to give the title compound (142 mg).

$^1$H NMR (300 MHz, DMSO-$d_6$) δ1.28-1.39 (1H, m), 1.44-1.67 (3H, m), 1.69-1.90 (4H, m), 2.11-2.31 (4H, m), 2.42-2.49 (1H, m), 2.84-2.95 (1H, m), 3.33-3.44 (2H, m), 3.77-4.09 (4H, m), 7.29-7.44 (2H, m), 7.60 (1H, s), 7.66-7.74 (1H, m), 8.23-8.34 (1H, m), 9.22-9.60 (2H, m).

Example 180

3-(trans-2-aminocyclopropyl)-N-(1,3-dimethyl-1H-pyrazol-5-yl)benzamide dihydrochloride 3-(trans-2-((tert-Butoxycarbonyl)amino)cyclopropyl) benzoic acid (300 mg), 1,3-dimethyl-1H-pyrazol-5-amine (132 mg) and triethylamine (0.302 mL) were dissolved in DMF (3.00 mL), O-(7-azabenzotriazol-1-yl)-N,N,N',N'-tetramethyluronium hexafluorophosphate (452 mg) was added, and the mixture was stirred at room temperature overnight. To the reaction mixture was added saturated aqueous sodium hydrogen carbonate solution, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate) and concentrated under reduced pressure. To the obtained residue was added a 4 mol/L hydrogen chloride/ethyl acetate solution (10.0 mL), and the mixture was stirred at room temperature for 3 hr. The reaction mixture was concentrated under reduced pressure to give the title compound (373 mg).

$^1$H NMR (300 MHz, DMSO-$d_6$) δ1.24-1.37 (1H, m), 1.41-1.52 (1H, m), 2.15 (3H, s), 2.38-2.48 (1H, m), 2.82-3.02 (1H, m), 3.63 (3H, s), 6.05 (1H, s), 7.39-7.53 (2H, m), 7.68-7.88 (2H, m), 8.58 (3H, brs), 10.39 (1H, s).

Example 181

3-(trans-2-(cyclobutylamino)cyclopropyl)-N-(1,3-dimethyl-1H-pyrazol-5-yl)benzamide dihydrochloride 3-(2-Aminocyclopropyl)-N-(1,3-dimethyl-1H-pyrazol-5-yl)benzamide dihydrochloride (215 mg) and borane-2-methylpyridine complex (100 mg) were dissolved in methanol (2.00 mL)/acetic acid (0.10 mL), cyclobutanone (0.187 mL) was added, and the mixture was stirred at room temperature overnight. To the reaction mixture was added saturated aqueous sodium hydrogen carbonate solution, and the mixture was extracted with ethyl acetate. The extract was washed with water and saturated brine, dried over anhydrous sodium sulfate, and concentrated under reduced pressure. The residue was purified by silica gel column chromatography (ethyl acetate/methanol), and concentrated under reduced pressure. To the obtained residue was added a 4 mol/L hydrogen chloride/ethyl acetate solution (5.00 mL), the solvent was evaporated under reduced pressure, and the solid was washed with ethyl acetate to give the title compound (16.0 mg).

$^1$H NMR (300 MHz, DMSO-$d_6$) δ1.28-1.44 (1H, m), 1.48-1.64 (1H, m), 1.68-1.90 (2H, m), 2.14 (3H, s), 2.16-2.38 (4H, m), 2.54-2.66 (1H, m), 2.86-3.04 (1H, m), 3.61 (3H, s), 3.73-3.95 (1H, m), 6.02 (1H, s), 7.39-7.51 (2H, m), 7.71-7.86 (2H, m), 9.68 (2H, brs), 10.32 (1H, s).

Example 182

5-(trans-2-aminocyclopropyl)-2-fluoro-N-(5-methyl-1,3,4-thiadiazol-2-yl)benzamide dihydrochloride A) tert-butyl (trans-2-(4-fluoro-3-((5-methyl-1,3,4-thiadiazol-2-yl)carbamoyl)phenyl)cyclopropyl)carbamate 5-(trans-2-((tert-Butoxycarbonyl)amino)cyclopropyl)-2-fluorobenzoic acid (300 mg), 5-methyl-1,3,4-thiadiazol-2-amine (140 mg) and triethylamine (0.425 mL) were dissolved in anhydrous DMF (15.0 mL), and the mixture was cooled to 0° C. 0-(7-Azabenzotriazol-1-yl)-N,N,N',N'-tetramethyluronium hexafluorophosphate (464 mg) was added, and the mixture was stirred at room temperature overnight. Water was added to the reaction mixture, and the mixture was extracted with ethyl acetate. The extracts were combined, washed successively with saturated aqueous sodium hydrogen carbonate solution, water and saturated brine, and dried over anhydrous sodium sulfate. The solution was concentrated under reduced pressure, and the residue was purified by NH silica gel column chromatography (hexane/ethyl acetate) and concentrated under reduced pressure to give the title compound (279 mg).

MS (API+): [M+H]$^+$ 393.3.

B) 5-(trans-2-aminocyclopropyl)-2-fluoro-N-(5-methyl-1,3,4-thiadiazol-2-yl)benzamide dihydrochloride tert-Butyl (trans-2-(4-fluoro-3-((5-methyl-1,3,4-thiadiazol-2-yl)carbamoyl)phenyl)cyclopropyl)carbamate (244 mg) was dissolved in methanol (20.0 mL), a 2 mol/L hydrogen chloride/methanol solution (4.66 mL) was added, and the mixture was stirred at room temperature overnight and at 60° C. for 30 min. The reaction mixture was concentrated under reduced pressure to give the title compound (227 mg).

$^1$H NMR (300 MHz, DMSO-d$_6$) δ1.27-1.35 (1H, m), 1.38-1.47 (1H, m), 2.35-2.45 (1H, m), 2.66 (3H, s), 2.83-2.96 (1H, m), 7.31 (1H, dd, J=10.2, 8.3 Hz), 7.43-7.57 (2H, m), 8.48 (3H, brs), 12.86 (1H, brs).

Example 183

5-(trans-2-(cyclobutylamino)cyclopropyl)-2-fluoro-N-(5-methyl-1,3,4-thiadiazol-2-yl)benzamide dihydrochloride 5-(trans-2-Aminocyclopropyl)-2-fluoro-N-(5-methyl-1,3,4-thiadiazol-2-yl)benzamide dihydrochloride (125 mg) and borane-2-methylpyridine complex (54.9 mg) were dissolved in methanol (8.00 mL)/acetic acid (0.80 mL), cyclobutanone (0.077 mL) was added under ice-cooling, and the mixture was stirred at room temperature for 18 hr. Furthermore, borane-2-methylpyridine complex (27.5 mg) was added under ice-cooling, and the mixture was stirred at room temperature overnight. To the reaction mixture was added cyclobutanone (0.038 mL) under ice-cooling, and the mixture was stirred at room temperature overnight. To the reaction mixture was added saturated aqueous sodium hydrogen carbonate solution under ice-cooling, and the mixture was extracted with ethyl acetate. The extracts were combined, washed with water and saturated brine, dried over anhydrous sodium sulfate, and concentrated under reduced pressure. The residue was purified by silica gel column chromatography (ethyl acetate/methanol), to the obtained fraction was added a 2 mol/L hydrogen chloride/methanol solution (2.00 mL) under ice-cooling, and the mixture was stirred at 0° C. for 30 min. The solvent was evaporated under reduced pressure, and the residue was crystallized from a mixture of methanol-tetrahydrofuran/a mixture of ethyl acetate-diisopropy ether to give the title compound (23.5 mg).

$^1$H NMR (300 MHz, DMSO-d$_6$) δ1.30-1.40 (1H, m), 1.45-1.57 (1H, m), 1.71-1.90 (2H, in), 2.14-2.32 (4H, m), 2.53-2.59 (1H, m), 2.66 (3H, s), 2.84-2.97 (1H, m), 3.75-3.90 (1H, m), 7.21-7.39 (1H, m), 7.43-7.59 (2H, m), 9.41-9.65 (2H, m), 12.85 (1H, brs).

Example 184

4-methyl-N-(5-methyl-1,3,4-thiadiazol-2-yl)-3-(trans-2-(tetrahydro-2H-pyran-4-ylamino)cyclopropyl)benzamide dihydrochloride A) 3-(trans-2-((tert-Butoxycarbonyl)amino)cyclopropyl)-4-methylbenzoic acid Methyl 3-(trans-2-((tert-butoxycarbonyl)amino)cyclopropyl)-4-methylbenzoate (1.50 g) was dissolved in methanol (20.0 mL), a 8 mol/L aqueous sodium hydroxide solution (4.00 mL) was added, and the mixture was stirred at room temperature for 18 hr. The reaction mixture was neutralized with 1 mol/L hydrochloric acid under ice-cooling, and the resulting precipitate was collected by filtration, and washed with water to give the title compound (900 mg).

MS (API+): [M+H]$^+$ 290.3.

B) tert-butyl (trans-2-(2-methyl-5-((5-methyl-1,3,4-thiadiazol-2-yl)carbamoyl)phenyl)cyclopropyl)carbamate 3-(trans-2-((tert-Butoxycarbonyl)amino)cyclopropyl)-4-methylbenzoic acid (200 mg), 5-methyl-1,3,4-thiadiazol-2-amine (95.0 mg) and triethylamine (0.287 mL) were dissolved in anhydrous DMF (7.00 mL), and the mixture was cooled to 0° C. 0-(7-Azabenzotriazol-1-yl)-N,N,N',N'-tetramethyluronium hexafluorophosphate (313 mg) was added, and the mixture was stirred at room temperature overnight. Under ice-cooling, to the reaction mixture was added saturated aqueous sodium hydrogen carbonate solution, and the mixture was extracted with ethyl acetate. The extracts were combined, washed with water and saturated brine, and dried over anhydrous sodium sulfate. The solution was concentrated under reduced pressure, and the residue was crystallized from ethyl acetate/diisopropy ether to give the title compound (156 mg).

MS (API+): [M+H]$^+$ 389.3.

C) 3-(trans-2-aminocyclopropyl)-4-methyl-N-(5-methyl-1,3,4-thiadiazol-2-yl)benzamide dihydrochloride tert-Butyl (trans-2-(2-methyl-5-((5-methyl-1,3,4-thiadiazol-2-yl)carbamoyl)phenyl)cyclopropyl)carbamate (156 mg) was dissolved in methanol (6.00 mL)/THF (6.00 mL), a 2 mol/L hydrogen chloride/methanol solution (3.01 mL) was added, and the mixture was stirred at room temperature for 18 hr. The reaction mixture was concentrated under reduced pressure to give the title compound (145 mg).

MS (API+): [M+H]$^+$ 289.2.

D) 4-methyl-N-(5-methyl-1,3,4-thiadiazol-2-yl)-3-(trans-2-(tetrahydro-2H-pyran-4-ylamino)cyclopropyl)benzamide dihydrochloride 3-(trans-2-Aminocyclopropyl)-4-methyl-N-(5-methyl-1,3,4-thiadiazol-2-yl)benzamide dihydrochloride (144 mg) and borane-2-methylpyridine complex (63.9 mg) were dissolved in methanol (8.00 mL)/acetic acid (0.80 mL), dihydro-2H-pyran-4(3H)-one (0.110 mL) was added, and the mixture was stirred at room temperature for 2 days. Under ice-cooling, to the reaction mixture was added saturated aqueous sodium hydrogen carbonate solution, and the mixture was extracted with ethyl acetate. The extracts were combined, washed with saturated brine, dried over anhydrous sodium sulfate, and concentrated under reduced pressure. The residue was purified by NH silica gel column chromatography (ethyl acetate/methanol), and concentrated under reduced pressure. The obtained residue was dissolved in methanol (3.00 mL)/ethyl acetate (1.00 mL), a 2 mol/L hydrogen chloride/methanol solution (1.00 mL) was added, and the mixture was stirred at room temperature for 30 min. The reaction mixture was concentrated under reduced pressure, and the obtained residue was crystallized from methanol/THF/ethyl acetate to give the title compound (13.3 mg).

$^1$H NMR (300 MHz, DMSO-d$_6$) δ1.36-1.48 (1H, m), 1.53-1.79 (3H, m), 1.97-2.07 (2H, m), 2.60-2.68 (4H, m), 3.10-3.20 (1H, m), 3.27-3.40 (2H, m), 3.42-3.57 (1H, m), 3.94-3.98 (2H, m), 7.39 (1H, d, J=7.8 Hz), 7.68 (1H, d, J=1.7 Hz), 7.86 (1H, dd, J=7.8, 1.7 Hz), 9.41 (2H, brs), 12.74 (1H, brs).

Example 185

4-methyl-N-(5-methyl-1,3,4-thiadiazol-2-yl)-3-(trans-2-(tetrahydro-2H-pyran-4-ylamino)cyclopropyl)benzamide hydrochloride 3-(trans-2-Aminocyclopropyl)-4-methyl-N-(5-methyl-1,3,4-thiadiazol-2-yl)benzamide dihydrochloride (360 mg) and borane-2-methylpyridine complex (160 mg) were dissolved in methanol (25.0 mL)/acetic acid (2.50 mL), dihydro-2H-pyran-4(3H)-one (0.276 mL) was added, and the mixture was stirred at room temperature for 2 days under a nitrogen atmosphere. Under ice-cooling, to the reaction mixture was added saturated aqueous sodium hydrogen carbonate solution, and the mixture was extracted with an ethyl acetate/THF mixture. The extracts were combined, washed with saturated brine, dried over anhydrous sodium sulfate, and concentrated under reduced pressure. The residue was recrystallized from ethyl acetate to give 4-methyl-N-(5-methyl-1,3,4-thiadiazol-2-yl)-3-(trans-2-(tetrahydro-2H-pyran-4-ylamino)cyclopropyl)benzamide (210 mg). The obtained 4-methyl-N-(5-methyl-1,3,4-thiadiazol-2-yl)-3-(trans-2-(tetrahydro-2H-pyran-4-ylamino)cyclopropyl)benzamide (210 mg) was dissolved in methanol (20.0 mL)/THF (10.0 mL), a 2 mol/L hydrogen chloride/methanol solution (4.00 mL) was added, and the mixture was stirred at room temperature for 30 min. The solvent was evaporated under reduced pressure, and the residue was recrystallized from ethanol/ethyl acetate to give the title compound (214 mg).

$^1$H NMR (300 MHz, DMSO-$d_6$) δ1.37-1.48 (1H, m), 1.56-1.79 (3H, IT), 1.95-2.09 (2H, m), 2.61-2.74 (4H, m), 3.08-3.20 (1H, m), 3.29-3.39 (2H, m), 3.44-3.54 (1H, m), 3.90-3.96 (2H, m), 7.39 (1H, d, J=8.3 Hz), 7.68 (1H, d, J=1.5 Hz), 7.86 (1H, dd, J=8.3, 1.7 Hz), 9.58 (2H, brs), 12.75 (1H, brs).

Example 186

5-(trans-2-((4,4-difluorocyclohexyl)amino)cyclopropyl)-2-fluoro-N-(1-methyl-1H-pyrazol-4-yl)benzamide hydrochloride A) tert-butyl (trans-2-(4-fluoro-3-((1-methyl-1H-pyrazol-4-yl)carbamoyl)phenyl)cyclopropyl)carbamate 5-(2-((tert-Butoxycarbonyl)amino)cyclopropyl)-2-fluorobenzoic acid (300 mg), 1-methyl-1H-pyrazol-4-amine (109 mg) and triethylamine (0.425 mL) were dissolved in anhydrous DMF (5.00 mL), O-(7-azabenzotriazol-1-yl)-N,N,N',N'-tetramethyluronium hexafluorophosphate (464 mg) was added, and the mixture was stirred at room temperature overnight under a nitrogen atmosphere. Water was added to the reaction mixture, and the mixture was extracted with ethyl acetate. The extracts were combined, washed with saturated brine, and dried over anhydrous magnesium sulfate. The solution was concentrated under reduced pressure to give the title compound (350 mg).

MS (API+): [M+H]$^+$ 375.2.

B) 5-(trans-2-aminocyclopropyl)-2-fluoro-N-(1-methyl-1H-pyrazol-4-yl)benzamide dihydrochloride tert-Butyl (trans-2-(4-fluoro-3-((1-methyl-1H-pyrazol-4-yl)carbamoyl)phenyl)cyclopropyl)carbamate (350 mg) was dissolved in ethyl acetate (5.00 mL), a 4 mol/L hydrogen chloride/ethyl acetate solution (10.0 mL) was added, and the mixture was stirred at room temperature overnight. The reaction mixture was concentrated under reduced pressure to give the title compound (200 mg).

MS (API+): [M+H]$^+$ 275.2.

C) 5-(trans-2-((4,4-difluorocyclohexyl)amino)cyclopropyl)-2-fluoro-N-(1-methyl-1H-pyrazol-4-yl)benzamide dihydrochloride 5-(trans-2-Aminocyclopropyl)-2-fluoro-N-(1-methyl-1H-pyrazol-4-yl)benzamide dihydrochloride (60.0 mg) and borane-2-methylpyridine complex (27.7 mg) were dissolved in methanol (2.00 mL)/acetic acid (0.20 mL), 4,4-difluorocyclohexanone (34.8 mg) was added, and the mixture was stirred at room temperature overnight under a nitrogen atmosphere. To the reaction mixture was added saturated aqueous sodium hydrogen carbonate solution, and the mixture was extracted with ethyl acetate. The extracts were combined, washed with saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution was added to the obtained fraction. The solvent was evaporated under reduced pressure, and the residue was recrystallized from ethanol/heptane to give the title compound (56.0 mg).

$^1$H NMR (300 MHz, DMSO-$d_6$) δ1.29-1.43 (1H, m), 1.51-2.24 (9H, m), 2.54-2.66 (1H, m), 2.97-3.13 (1H, m), 3.30-3.50 (1H, m), 3.82 (3H, s), 7.23-7.32, (1H, m), 7.36-7.48 (2H, m), 7.52 (1H, d, J=0.8 Hz), 7.98 (1H, s), 9.43-9.65 (2H, m), 10.43 (1H, s).

Example 187

N-(1-(cyclopropylmethyl)-1H-pyrazol-4-yl)-3-(trans-2-((1-cyclopropylpiperidin-4-yl)amino)cyclopropyl)benzamide dihydrochloride By a method similar to that in Example 164, the compound of Example 187 was produced.

Example 188

N-(1-(cyclopropylmethyl)-1H-pyrazol-4-yl)-3-(trans-2-((1-cyclopropylpiperidin-4-yl)amino)cyclopropyl)benzamide trihydrochloride [optical isomer, compound derived from N-(1-(cyclopropylmethyl)-1H-pyrazol-4-yl)-3-(trans-2-((1-cyclopropylpiperidin-4-yl)amino)cyclopropyl)benzamide (optical isomer, retention time short)]

N-(1-(Cyclopropylmethyl)-1H-pyrazol-4-yl)-3-(trans-2-((1-cyclopropylpiperidin-4-yl)amino)cyclopropyl)benzamide dihydrochloride (75.0 mg) was dissolved in ethyl acetate, a saturated aqueous sodium hydrogen carbonate solution was added, and the mixture was extracted with ethyl acetate. The extract was washed with water and saturated brine, dried over anhydrous magnesium sulfate, and concentrated under reduced pressure. The obtained racemate (56.8 mg) of N-(1-(cyclopropylmethyl)-1H-pyrazol-4-yl)-3-(trans-2-((1-cyclopropylpiperidin-4-yl)amino)cyclopropyl)benzamide was fractionated by SEC (column: CHIRALPAK AYH (trade name), 4.6 mmID×150 mmL, manufactured by Daicel Corporation, mobile phase: carbon dioxide/ethanol/diethylamine=600/300/3), to the obtained fraction having a shorter retention time was added a 4 mol/L hydrogen chloride/ethyl acetate solution, and the mixture was concentrated under reduced pressure. A saturated aqueous sodium hydrogen carbonate solution was added to the residue, and the mixture was extracted with ethyl acetate. The extract was washed with saturated brine, and dried over anhydrous magnesium sulfate. To the solution was added a 4 mol/L hydrogen chloride/ethyl acetate solution, and the mixture was concentrated under reduced pressure. The residue was recrystallized from ethanol/heptane to give the title compound (10.0 mg).

$^1$H NMR (300 MHz, DMSO-$d_6$) δ0.31-0.41 (2H, m), 0.48-0.58 (2H, m), 0.71-0.90 (2H, m), 1.01-1.12 (2H, m), 1.14-1.31 (1H, m), 1.33-1.49 (1H, m), 1.54-1.70 (1H, m), 1.93-2.15 (2H, m), 2.22-2.37 (3H, m), 3.02-3.71 (7H, m), 3.96 (2H, d, J=6.8 Hz), 7.36-7.51 (2H, m), 7.62 (1H, s), 7.74-7.84 (2H, m), 8.10 (1H, s), 9.74-10.07 (2H, m), 10.19-10.38 (1H, m), 10.44-10.53 (1H, m).

Example 189

N-(1-(cyclopropylmethyl)-1H-pyrazol-4-yl)-3-(trans-2-((1-cyclopropylpiperidin-4-yl)amino)cyclopropyl)benzamide trihydrochloride [optical isomer, compound derived from N-(I (cyclopropylmethyl)-1H-pyrazol-4-yl)-3-(trans-2-((1-cyclopropylpiperidin-4-yl)amino)cyclopropyl)benzamide (optical isomer, retention time long)]

N-(1-(Cyclopropylmethyl)-1H-pyrazol-4-yl)-3-(trans-2-((1-cyclopropylpiperidin-4-yl)amino)cyclopropyl)benzamide dihydrochloride (75.0 mg) was dissolved in ethyl acetate, a saturated aqueous sodium hydrogen carbonate solution was added, and the mixture was extracted with ethyl acetate. The extract was washed with water and saturated brine, dried over anhydrous magnesium sulfate, and concentrated under reduced pressure. The obtained racemate (56.8 mg) of N-(1-(cyclopropylmethyl)-1H-pyrazol-4-yl)-3-(trans-2-((1-cyclopropylpiperidin-4-yl)amino)cyclopropyl)benzamide was fractionated by SFC (column: CHIRALPAK AYH (trade name), 4.6mmID×150 mmL, manufactured by Daicel Corporation, mobile phase: carbon dioxide/ethanol/diethylamine=600/300/3). To the obtained fraction having a longer retention time was added a 4 mol/L hydrogen chloride/ethyl acetate solution, and the mixture was concentrated under reduced pressure. A saturated aqueous sodium hydrogen carbonate solution was added to the residue, and the mixture was extracted with ethyl acetate. The extract was washed with saturated brine, and dried over anhydrous magnesium sulfate. To the solution was added a 4 mol/L hydrogen chloride/ethyl acetate solution, and the mixture was concentrated under reduced pressure. The residue was recrystallized from ethanol/heptane to give the title compound (20.0 mg).

$^1$H NMR (300 MHz, DMSO-$d_6$) δ0.30-0.40 (2H, m), 0.49-0.57 (2H, m), 0.73-0.84 (2H, m), 1.00-1.11 (2H, m), 1.15-1.28 (1H, m), 1.36-1.48 (1H, m), 1.54-1.67 (1H, m), 1.92-2.14 (2H, m), 2.20-2.43 (3H, m), 3.06-3.60 (7H, m), 3.92-4.00 (2H, m), 7.36-7.51 (2H, m), 7.60-7.63 (1H, m), 7.72-7.84 (2H, m), 8.08-8.11 (1H, m), 9.65-9.90 (2H, m), 10.00-10.18 (1H, m), 10.41-10.48 (1H, m).

Example 190

N-(1-(cyclopropylmethyl)-1H-pyrazol-4-yl)-3-(trans-2-(tetrahydro-2H-pyran-4-ylamino)cyclopropyl)benzamide dihydrochloride By a method similar to that in Example 164, the compound of Example 190 was produced.

Example 191

N-(1-(cyclopropylmethyl)-1H-pyrazol-4-yl)-3-(trans-2-(tetrahydro-2H-pyran-4-ylamino)cyclopropyl)benzamide dihydrochloride [optical isomer, compound derived from N-(1-(cyclopropylmethyl)-1H-pyrazol-4-yl)-3-(trans-2-(tetrahydro-2H-pyran-4-ylamino)cyclopropyl)benzamide (optical isomer, retention time short)]

N-(1-(Cyclopropylmethyl)-1H-pyrazol-4-yl)-3-(trans-2-(tetrahydro-2H-pyran-4-ylamino)cyclopropyl)benzamide dihydrochloride (65.0 mg) was dissolved in ethyl acetate, a saturated aqueous sodium hydrogen carbonate solution was added, and the mixture was extracted with ethyl acetate. The extract was washed with water and saturated brine, dried over anhydrous magnesium sulfate, and concentrated under reduced pressure. The obtained racemate (47.9 mg) of N-(1-(cyclopropylmethyl)-1H-pyrazol-4-yl)-3-(trans-2-((1-cyclopropylpiperidin-4-yl)amino)cyclopropyl)benzamide was fractionated by HPLC (column: CHIRALCEL OD (trade name), 4.6 mmID×250 mmL, manufactured by Daicel Corporation, mobile phase: hexane/isopropanol=50/50), to the obtained fraction having a shorter retention time was added a 4 mol/L hydrogen chloride/ethyl acetate solution, and the mixture was concentrated under reduced pressure. The residue was recrystallized from ethanol/heptane to give the title compound (16.0 mg).

$^1$H NMR (300 MHz, DMSO-$d_6$) δ0.32-0.39 (2H, m), 0.49-0.57 (2H, m), 1.12-1.29 (1H, m), 1.36-1.48 (1H, m), 1.50-1.74 (3H, m), 1.91-2.04 (2H, m), 2.52-2.62 (1H, m), 3.03-3.16 (1H, m), 3.24-3.58 (3H, m), 3.88-3.99 (4H, m), 7.36-7.51 (2H, m), 7.58-7.62 (1H, m), 7.71-7.76 (1H, m), 7.77-7.84 (1H, m), 8.06-8.11 (1H, m), 9.16-9.45 (2H, m), 10.37-10.47 (1H, m).

Example 192

N-(1-(cyclopropylmethyl)-1H-pyrazol-4-yl)-3-(trans-2-(tetrahydro-2H-pyran-4-ylamino)cyclopropyl)benzamide dihydrochloride [optical isomer, compound derived from N-(1-(cyclopropylmethyl)-1H-pyrazol-4-yl)-3-(trans-2-(tetrahydro-2H-pyran-4-ylamino)cyclopropyl)benzamide (optical isomer, retention time long)]

N-(1-(Cyclopropylmethyl)-1H-pyrazol-4-yl)-3-(trans-2-(tetrahydro-2H-pyran-4-ylamino)cyclopropyl)benzamide dihydrochloride (65.0 mg) was dissolved in ethyl acetate, a saturated aqueous sodium hydrogen carbonate solution was added, and the mixture was extracted with ethyl acetate. The extract was washed with water and saturated brine, dried over anhydrous magnesium sulfate, and concentrated under reduced pressure. The obtained racemate (47.9 mg) of N-(1-(cyclopropylmethyl)-1H-pyrazol-4-yl)-3-(trans-2-((1-cyclopropylpiperidin-4-yl)amino)cyclopropyl)benzamide was fractionated by HPLC (column: CHIRALCEL OD (trade name), 4.6 mmID×250 mmL, manufactured by Daicel Corporation, mobile phase: hexane/isopropanol=50/50). To the obtained fraction having a longer retention time was added a 4 mol/L hydrogen chloride/ethyl acetate solution, and the mixture was concentrated under reduced pressure. The residue was recrystallized from ethanol/heptane to give the title compound (16.0 mg).

$^1$H NMR (300 MHz, DMSO-$d_6$) δ0.31-0.40 (2H, m), 0.47-0.58 (2H, m), 1.12-1.30 (1H, m), 1.34-1.48 (1H, m), 1.52-1.77 (3H, m), 1.91-2.04 (2H, m), 2.54-2.66 (1H, m), 3.01-3.16 (1H, m), 3.23-3.58 (3H, m), 3.87-4.00 (4H, m), 7.37-7.49 (2H, m), 7.59-7.62 (1H, m), 7.72-7.77 (1H, m), 7.77-7.84 (1H, m), 8.09 (1H, s), 9.31-9.55 (2H, m), 10.41-10.47 (1H, m).

Example 193

3-(trans-2-((1,1-dioxidotetrahydro-2H-thiopyran-4-yl)amino)cyclopropyl)-N-(4-(pyrimidin-2-yl)phenyl)benzamide dihydrochloride

Example 194

N-(1-tert-butyl-1H-pyrazol-4-yl)-3-(trans-2-(tetrahydro-2H-pyran-4-ylamino)cyclopropyl)benzamide dihydrochloride

Example 195

N-(1-tert-butyl-1H-pyrazol-4-yl)-3-(trans-2-((1-cyclopropylpiperidin-4-yl)amino)cyclopropyl)benzamide dihydrochloride

Example 196

N-(1-(4-fluorophenyl)-1H-pyrazol-4-yl)-3-(trans-2-(tetrahydro-2H-pyran-4-ylamino)cyclopropyl)benzamide dihydrochloride

Example 197

3-(trans-2-((1,1-dioxidotetrahydro-2H-thiopyran-4-yl)amino)cyclopropyl)-N-(1-(4-fluorophenyl)-1H-pyrazol-4-yl)benzamide dihydrochloride

Example 198

N-cyclopentyl-3-(trans-2-((1,1-dioxidotetrahydro-2H-thiopyran-4-yl)amino)cyclopropyl)benzamide hydrochloride By a method similar to that in Example 164, the compounds of Examples 193 to 198 were produced.

Example 199

N-cyclopentyl-3-(trans-2-((1-cyclopropylpiperidin-4-yl)amino)cyclopropyl)benzamide dihydrochloride 3-(trans-2-Aminocyclopropyl)-N-cyclopentylbenzamide hydrochloride (50.0 mg) and borane-2-methylpyridine complex (28.6 mg) were dissolved in methanol (5.00 mL)/acetic acid (0.50 mL), 1-cyclopropylpiperidin-4-one (0.066 mL) was added, and the mixture was stirred at room temperature for 18 hr. To the reaction mixture was added a saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (hexane/ethyl acetate), and concentrated under reduced pressure. The obtained residue was dissolved in methanol (5.00 mL), and the mixture was cooled to 0° C. A 4 mol/L hydrogen chloride/ethyl acetate solution (0.223 mL) was added under ice-cooling, and the mixture was stirred at room temperature for 18 hr. The solvent was evaporated under reduced pressure, and the residue was crystallized from methanol/diisopropyl ether to give the title compound (27.6 mg).

$^1$H NMR (300 MHz, DMSO-$d_6$) δ0.73-0.82 (2H, m), 1.09 (2H, brs), 1.37 (1H, q, J=6.4 Hz), 1.45-1.77 (7H, m), 1.83-1.94 (2H, m), 1.97-2.13 (2H, m), 2.23-2.35 (2H, m), 2.56-2.66 (1H, m), 2.72 (1H, d, J=1.9 Hz), 3.03-3.27 (3H, m), 3.40-3.73 (3H, m), 4.15-4.29 (1H, m), 7.30-7.35 (1H, m), 7.35-7.41 (1H, m), 7.62 (1H, s), 7.67-7.73 (1H, m), 8.29 (1H, d, J=7.2 Hz), 9.91 (2H, brs), 10.41 (1H, brs).

Example 200

N-cyclopentyl-3-(trans-2-((1-methylpiperidin-4-yl)amino)cyclopropyl)benzamide dihydrochloride

Example 201

3-(trans-2-(cyclobutylamino)cyclopropyl)-N-(1-(cyclopropylmethyl)-1H-pyrazol-4-yl)benzamide dihydrochloride

Example 202

N-(1-(cyclopropylmethyl)-1H-pyrazol-4-yl)-3-(trans-2-((1-methylpiperidin-4-yl)amino)cyclopropyl)benzamide trihydrochloride

Example 203

N-(1-(cyclopropylmethyl)-1H-pyrazol-4-yl)-3-(trans-2-((1-(2,2,2-trifluoroethyl)piperidin-4-yl)amino) cyclopropyl) benzamide trihydrochloride

Example 204

N-(1-(cyclopropylmethyl)-1H-pyrazol-4-yl)-3-(trans-2-((4,4-difluorocyclohexyl)amino)cyclopropyl)benzamide dihydrochloride

Example 205

3-(trans-2-((4,4-difluorocyclohexyl)amino)cyclopropyl)-N-(1-methyl-1H-pyrazol-4-yl)benzamide dihydrochloride

Example 206

3-(trans-2-((1-acetylpiperidin-4-yl)amino)cyclopropyl)-N-(4-fluorophenyl) benzamide hydrochloride

Example 207

N-(4-fluorophenyl)-3-(trans-2-(tetrahydro-2H-pyran-4-ylamino)cyclopropyl)benzamide hydrochloride By a method similar to that in Example 164, the compounds of Examples 200 to 207 were produced.

Example 208

3-(trans-2-((1-cyclopropylpiperidin-4-yl)amino)cyclopropyl)-N-(4,4-difluorocyclohexyl)benzamide dihydrochloride 3-(trans-2-Aminocyclopropyl)-N-(4,4-difluorocyclohexyl)benzamide hydrochloride (50.0 mg) and borane-2-methylpyridine complex (24.3 mg) were dissolved in methanol (5.00 mL)/acetic acid (0.50 mL), 1-cyclopropylpiperidin-4-one (0.056 mL) was added, and the mixture was stirred at room temperature for 18 hr. To the reaction mixture was added a saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (hexane/ethyl acetate), and concentrated under reduced pressure. The obtained residue was dissolved in methanol (5.00 mL), a 4 mol/L hydrogen chloride/ethyl acetate solution (0.189 mL) was added under ice-cooling, and the mixture was stirred under ice-cooling for 18 hr. The solvent was evaporated under reduced pressure, and the residue was crystallized from methanol/ethyl acetate to give the title compound (31.3 mg).

$^1$H NMR (300 MHz, DMSO-$d_6$) δ0.74-0.87 (2H, m), 1.10 (2H, brs), 1.36 (1H, q, J=6.7 Hz), 1.58-1.74 (3H, m), 1.82-2.14 (9H, m), 2.31 (2H, d, J=13.3 Hz), 2.59-2.79 (2H, m), 3.02-3.29 (2H, m), 3.49-3.75 (3H, m), 3.91-4.06 (1H, m), 7.32-7.43 (2H, m), 7.64 (1H, s), 7.71 (1H, d, J=7.2 Hz), 8.35 (1H, d, J=7.6 Hz), 10.00 (2H, brs), 10.51 (1H, brs).

Example 209

3-(trans-2-((4,4-difluorocyclohexyl)amino)cyclopropyl)-N-(1-ethyl-1H-pyrazol-4-yl)benzamide dihydrochloride Example 210

3-(trans-2-(cyclobutylamino)cyclopropyl)-N-(2-methyl-1,3-thiazol-5-yl)benzamide dihydrochloride Example 211

3-(trans-2-((4,4-difluorocyclohexyl)amino)cyclopropyl)-N-(2-methyl-1,3-thiazol-5-yl)benzamide dihydrochloride By a method similar to that in Example 164, the compounds of Examples 209 to 211 were produced.

Example 212

N-(2-methyl-1,3-thiazol-5-yl)-3-(trans-2-(tetrahydro-2H-pyran-4-ylamino)cyclopropyl)benzamide dihydrochloride 3-(trans-2-Aminocyclopropyl)-N-(2-methylthiazol-5-yl)benzamide dihydrochloride (100 mg) and borane-2-methylpyridine complex (46.3 mg) were dissolved in methanol (2.00 mL)/acetic acid (0.20 mL), dihydro-2H-pyran-4(3H)-one (43.4 mg) was added, and the mixture was stirred at room temperature overnight under a nitrogen atmosphere. To the reaction mixture was added saturated aqueous sodium hydrogen carbonate solution, and the mixture was extracted with ethyl acetate. The extracts were combined, washed successively with water and saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution was added to the obtained fraction. The solvent was evaporated under reduced pressure, and the residue was crystallized from methanol/ethyl acetate to give the title compound (25.0 mg).

$^1$H NMR (300 MHz, DMSO-$d_6$) δ1.38-1.50 (1H, m), 1.54-1.80 (3H, m), 1.93-2.05 (2H, m), 2.59 (4H, s), 3.07-3.20 (1H, m), 3.25-3.38 (2H, m), 3.39-3.57 (1H, m), 3.84-3.98 (2H, m), 7.48 (2H, s), 7.63 (1H, s), 7.85 (2H, s), 9.34-9.61 (2H, m), 11.78-11.89 (1H, m).

Example 213

N-cyclopentyl-2-fluoro-5-(trans-2-(tetrahydro-2H-pyran-4-ylamino)cyclopropyl)benzamide hydrochloride 5-(trans-2-Aminocyclopropyl)-N-cyclopentyl-2-fluorobenzamide hydrochloride (72.2 mg) and borane-2-methylpyridine complex (38.8 mg) were dissolved in methanol (7.00 mL)/acetic acid (0.70 mL), dihydro-2H-pyran-4(3H)-one (0.070 mL) was added, and the mixture was stirred at room temperature for 18 hr. To the reaction mixture was added saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (hexane/ethyl acetate), and concentrated under reduced pressure. The obtained residue was dissolved in methanol (5.00 mL), a 4 mol/L hydrogen chloride/ethyl acetate solution (0.302 mL) was added under ice-cooling, and the mixture was stirred at room temperature for 18 hr. The solvent was evaporated under reduced pressure, and the residue was crystallized from methanol/diisopropy ether to give the title compound (30.7 mg).

$^1$H NMR (300 MHz, DMSO-$d_6$) δ1.30 (1H, d, J=5.3 Hz), 1.41-1.76 (9H, m), 1.80-2.04 (4H, m), 2.57 (1H, brs), 2.99 (1H, brs), 3.17 (1H, d, J=1.9 Hz), 3.31 (2H, t, J=11.5 Hz), 3.91 (2H, d, J=9.5 Hz), 4.18 (1H, d, J=6.1 Hz), 7.15-7.24 (1H, m), 7.31 (2H, d, J=5.3 Hz), 8.24 (1H, d, J=6.1 Hz), 9.60 (2H, brs).

Example 214

N-cyclopentyl-2-methoxy-5-(trans-2-(tetrahydro-2H-pyran-4-ylamino)cyclopropyl)benzamide hydrochloride 5-(2-Aminocyclopropyl)-N-cyclopentyl-2-methoxybenzamide hydrochloride (125 mg) and borane-2-methylpyridine complex (64.4 mg) were dissolved in methanol (12.4 mL)/acetic acid (1.24 mL), dihydro-2H-pyran-4(3H)-one (0.116 mL) was added, and the mixture was stirred at room temperature for 18 hr. To the reaction mixture was added saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (hexane/ethyl acetate), and concentrated under reduced pressure. The obtained residue was dissolved in methanol (5.00 mL), a 4 mol/L hydrogen chloride/ethyl acetate solution (0.501 mL) was added under ice-cooling, and the mixture was stirred under ice-cooling for 18 hr. The solvent was evaporated under reduced pressure to give the title compound (38.0 mg).

$^1$H NMR (300 MHz, DMSO-$d_6$) δ1.21-1.30 (1H, m), 1.41-1.74 (9H, m), 1.80-2.02 (4H, m), 2.86-2.98 (1H, m), 3.25-3.55 (4H, m), 3.85 (3H, s), 3.92 (2H, dd, J=12.1, 3.4 Hz), 4.14-4.25 (1H, m), 7.06 (1H, d, J=8.7 Hz), 7.26 (1H, dd, J=8.5, 2.1 Hz), 7.47 (1H, d, J=2.3 Hz), 7.99 (1H, d, J=7.6 Hz), 9.27 (2H, brs).

Example 215

3-(trans-2-((4,4-difluorocyclohexyl)amino)cyclopropyl)-N-(1,3-dimethyl-1H-pyrazol-5-yl)benzamide dihydrochloride 3-(2-Aminocyclopropyl)-N-(1,3-dimethyl-1H-pyrazol-5-yl)benzamide dihydrochloride (76.0 mg) and borane-2-methylpyridine complex (35.5 mg) were dissolved in methanol (2.00 mL)/acetic acid (0.20 mL), 4,4-difluorocyclohexanone (89.0 mg) was added, and the mixture was stirred under a nitrogen atmosphere at room temperature for 18 hr. To the reaction mixture was added saturated aqueous sodium hydrogen carbonate solution under ice-cooling, and the mixture was extracted with ethyl acetate. The extracts were combined, washed successively with water and saturated brine, dried over anhydrous magnesium sulfate, and concentrated under reduced pressure. The residue was purified by NH silica gel column chromatography (hexane/ethyl acetate), and concentrated under reduced pressure. The obtained residue was fractionated by HPLC (C18, mobile phase: water/acetonitrile (with 0.1% TFA). To the obtained fraction was added a saturated aqueous sodium hydrogen carbonate solution, and the mixture was extracted with ethyl acetate, and dried over anhydrous magnesium sulfate, and a 4 mol/L hydrogen chloride/ethyl acetate solution was added. The solvent was evaporated under reduced pressure to give the title compound (40.0 mg).

$^1$H NMR (300 MHz, CD$_3$OD) δ1.49-2.09 (6H, m), 2.11-2.35 (4H, m), 2.44 (3H, s), 2.59-2.75 (1H, m), 3.12-3.24 (1H, m), 3.44-3.63 (1H, m), 3.95 (3H, s), 6.65 (1H, s), 7.45-7.62 (2H, m), 7.81-7.99 (2H, m).

Example 216

3-(trans-2-((4,4-difluorocyclohexyl)amino)cyclopropyl)-N-(3-methyl-1,2-oxazol-5-yl)benzamide hydrochloride

Example 217

N-(1-(4-fluorobenzyl)-1H-pyrazol-4-yl)-3-(trans-2-(tetrahydro-2H-pyran-4-ylamino)cyclopropyl)benzamide dihydrochloride

Example 218

3-(trans-2-((1-acetylpiperidin-4-yl)amino)cyclopropyl)-N-(1-(4-fluorobenzyl)-1H-pyrazol-4-yl)benzamide dihydrochloride

Example 219

3-(trans-2-((1-acetylpiperidin-4-yl)amino)cyclopropyl)-N-(2-(4-fluorophenyl)-1,3-thiazol-5-yl)benzamide dihydrochloride

Example 220

N-(3-methyl-1,2-thiazol-5-yl)-3-(trans-2-(tetrahydro-2H-pyran-4-ylamino)cyclopropyl)benzamide hydrochloride

Example 221

2-methoxy-N-(5-methyl-1,3,4-thiadiazol-2-yl)-5-(trans-2-(tetrahydro-2H-pyran-4-ylamino)cyclopropyl)benzamide

Example 222

5-(trans-2-((4,4-difluorocyclohexyl)amino)cyclopropyl)-2-methoxy-N-(5-methyl-1,3,4-thiadiazol-2-yl)benzamide dihydrochloride By a method similar to that in Example 184, the compounds of Examples 216 to 222 were produced.

Example 223

5-(trans-2-((4,4-difluorocyclohexyl)amino)cyclopropyl)-2-fluoro-N-(5-methyl-1,3,4-thiadiazol-2-yl)benzamide dihydrochloride 5-(trans-2-Aminocyclopropyl)-2-fluoro-N-(5-methyl-1,3,4-thiadiazol-2-yl)benzamide dihydrochloride (125 mg) and borane-2-methylpyridine complex (54.9 mg) were dissolved in methanol (8.00 mL)/acetic acid (0.80 mL), 4,4-difluorocyclohexanone (138 mg) was added under ice-cooling, and the mixture was stirred at room temperature for 6 hr. Under ice-cooling, a saturated aqueous sodium hydrogen carbonate solution was added, and the mixture was extracted with ethyl acetate. The extracts were combined, washed with saturated brine, dried over anhydrous sodium sulfate, and concentrated under reduced pressure. The residue was purified by NH silica gel column chromatography (ethyl acetate/methanol). To the obtained fraction was added a 2 mol/L hydrogen chloride/methanol solution (2.00 mL) under ice-cooling, and the mixture was stirred under ice-cooling for 30 min. The solvent was evaporated under reduced pressure, and the residue was crystallized from methanol mixture of ethyl acetate-diisopropy ether to give the title compound (48.6 mg).

$^1$H NMR (300 MHz, DMSO-d$_6$) δ1.37-1.46 (1H, m), 1.52-1.61 (1H, m), 1.62-1.78 (2H, m), 1.81-2.03 (2H, m), 2.06-2.21 (4H, m), 2.53-2.63 (1H, m), 2.66 (3H, s), 3.02-3.14 (1H, m), 3.29-3.48 (1H, m), 7.26-7.38 (1H, m), 7.48-7.57 (2H, m), 9.36-9.56 (2H, m), 12.86 (1H, brs).

Example 224

4-fluoro-N-(5-methyl-1,3,4-thiadiazol-2-yl)-3-(trans-2-(tetrahydro-2H-pyran-4-ylamino)cyclopropyl)benzamide fumarate Example 225

5-(trans-2-(cyclobutylamino)cyclopropyl)-2-fluoro-N-(1-methyl-1H-pyrazol-4-yl)benzamide dihydrochloride Example 226

5-(trans-2-(cyclobutylamino)cyclopropyl)-2-methoxy-N-(1-methyl-1H-pyrazol-4-yl)benzamide dihydrochloride Example 227

5-(trans-2-((4,4-difluorocyclohexyl)amino)cyclopropyl)-2-methoxy-N-(1-methyl-1H-pyrazol-4-yl)benzamide dihydrochloride Example 228

3-(trans-2-(cyclobutylamino)cyclopropyl)-4-fluoro-N-(1-methyl-1H-pyrazol-4-yl)benzamide hydrochloride By a method similar to that in Example 184, the compounds of Examples 224 to 228 were produced.

Example 229

3-(trans-2-((cyclopropylmethyl)amino)cyclopropyl)-4-fluoro-N-(tetrahydro-2H-pyran-4-yl)benzamide hydrochloride A) tert-butyl (cyclopropylmethyl) (2-(2-fluoro-5-((tetrahydro-2H-pyran-4-yl) carbamoyl)phenyl)cyclopropyl) carbamate 3-(trans-2-((tert-Butoxycarbonyl)(cyclopropylmethyl)amino)cyclopropyl)-4-fluorobenzoic acid (90.0 mg), tetrahydro-2H-pyran-4-amine (0.032 mL) and triethylamine (0.108 mL) were dissolved in anhydrous DMF (4.00 mL), and the mixture was cooled to 0° C. O-(7-Azabenzotriazol-1-yl)-N,N,N',N'-tetramethyluronium hexafluorophosphate (118 mg) was added, and the mixture was stirred at room temperature overnight. To the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (111 mg).

MS (API+): [M−(tert-Bu)+H]$^+$ 377.2.

B) 3-(trans-2-((cyclopropylmethyl)amino)cyclopropyl)-4-fluoro-N-(tetrahydro-2H-pyran-4-yl)benzamide hydrochloride tert-Butyl (cyclopropylmethyl) (2-(2-fluoro-5-((tetrahydro-2H-pyran-4-yl)carbamoyl)phenyl)cyclopropyl)carbamate (110 mg) was dissolved in methanol (3.00 mL)/ethyl acetate (2.00 mL), a 2 mol/L hydrogen chloride/methanol solution (1.91 mL) was added, and the mixture was stirred at room temperature for 18 hr and at 60° C. for 30 min. The reaction mixture was concentrated under reduced pressure, and the residue was recrystallized from ethanol/heptane to give the title compound (75.7 mg).

$^1$H NMR (300 MHz, DMSO-d$_6$) δ0.33-0.39 (2H, m), 0.53-0.62 (2H, m), 0.98-1.15 (1H, m), 1.39-1.47 (1H, m), 1.49-1.64 (3H, m), 1.69-1.79 (2H, m), 2.59-2.68 (1H, m), 2.98 (2H, d, J=7.6 Hz), 3.09-3.16 (1H, m), 3.34-3.43 (2H, m), 3.81-4.07 (3H, m), 7.22-7.35 (1H, m), 7.57 (1H, dd, J=7.4, 2.1 Hz), 7.68-7.88 (1H, m), 8.23-8.38 (1H, m), 9.20 (2H, brs).

Example 230

3-(trans-2-((cyclopropylmethyl)amino)cyclopropyl)-4-methyl-N-(tetrahydro-2H-pyran-4-yl)benzamide hydrochloride A) tert-butyl (cyclopropylmethyl)(2-(2-methyl-5-((tetrahydro-2H-pyran-4-yl)carbamoyl)phenyl)cyclopropyl)carbamate 3-(trans-2-((tert-Butoxycarbonyl)(cyclopropylmethyl)amino)cyclopropyl)-4-methylbenzoic acid (90.0 mg), tetrahydro-2H-pyran-4-amine (0.032 mL) and triethylamine (0.109 mL) were dissolved in anhydrous DMF (4.00 mL), and the mixture was cooled to 0° C. O-(7-Azabenzotriazol-1-yl)-N,N,N',N'-tetramethyluronium hexafluorophosphate (119 mg) was added, and the mixture was stirred at room temperature overnight. To the reaction mixture was added saturated aqueous sodium hydrogen carbonate solution (50.0 mL), and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (114 mg).

MS (API+): [M−(tert-Bu)+H]$^+$ 373.3.

B) 3-(trans-2-((cyclopropylmethyl)amino)cyclopropyl)-4-methyl-N-(tetrahydro-2H-pyran-4-yl)benzamide hydrochloride tert-Butyl (cyclopropylmethyl)(2-(2-methyl-5-((tetrahydro-2H-pyran-4-yl)carbamoyl)phenyl)cyclopropyl)carbamate (112 mg) was dissolved in methanol (3.00 mL)/ethyl acetate (2.00 mL), a 2 mol/L hydrogen chloride/methanol solution (1.96 mL) was added, and the mixture was stirred at room temperature for 18 hr and at 60° C. for 30 min. The reaction mixture was concentrated under reduced pressure, and the residue was recrystallized from ethanol/heptane to give the title compound (82.7 mg).

¹H NMR (300 MHz, DMSO-d₆) δ0.34-0.42 (2H, m), 0.55-0.64 (2H, m), 1.03-1.15 (1H, m), 1.23-1.31 (1H, m), 1.45-1.64 (3H, m), 1.68-1.78 (2H, m), 2.43 (3H, s), 2.53-2.59 (1H, m), 2.94-3.09 (3H, m), 3.33-3.43 (2H, m), 3.81-4.06 (3H, m), 7.27 (1H, d, J=8.0 Hz), 7.44 (1H, d, J=1.5 Hz), 7.61-7.68 (1H, m), 8.20 (1H, d, J=7.6 Hz), 9.09 (2H, brs).

Example 231

N-(5-methyl-1,2-oxazol-3-yl)-3-(trans-2-((tetrahydro-2H-pyran-4-ylmethyl)amino)cyclopropyl)benzamide A) tert-butyl (trans-2-(3-((5-methylisoxazol-3-yl)carbamoyl)phenyl)cyclopropyl)carbamate 3-(trans-2-((tert-Butoxycarbonyl)amino)cyclopropyl)benzoic acid (500 mg) and two drops of DMF were dissolved in THF (5.00 mL), and the mixture was cooled to 0° C. Oxalyl chloride (0.196 mL) was added, and the mixture was stirred at 0° C. for 1 hr and concentrated under reduced pressure. The obtained residue was dissolved in THF (3.00 mL), the solution was added to a solution of 5-methylisoxazol-3-amine (265 mg) and N,N-dimethyl-4-aminopyridine (110 mg) in pyridine (5.00 mL) at 60° C., and the mixture was stirred at 60° C. for 2 hr. To the reaction mixture was added a saturated aqueous sodium hydrogen carbonate solution, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate), and concentrated under reduced pressure to give the title compound (436 mg).
MS (API+): [M+H]⁺ 358.0.

B) 3-(trans-2-aminocyclopropyl)-N-(5-methylisoxazol-3-yl)benzamide dihydrochloride To tert-butyl (trans-2-(3-((5-methylisoxazol-3-yl)carbamoyl)phenyl)cyclopropyl)carbamate (436 mg) was added a 4 mol/L hydrogen chloride/ethyl acetate solution (10.0 mL), and the mixture was stirred at room temperature for 5 hr. The reaction mixture was concentrated under reduced pressure to give the title compound (325 mg).
MS (API+): [M−2HCl+H]⁺ 257.8.

C) N-(5-methyl-1,2-oxazol-3-yl)-3-(trans-2-((tetrahydro-2H-pyran-4-ylmethyl)amino)cyclopropyl)benzamide 3-(trans-2-Aminocyclopropyl)-N-(5-methylisoxazol-3-yl)benzamide dihydrochloride (153 mg) and sodium hydrogen carbonate (131 mg) were dissolved in THF (1.00 mL)/methanol (1.00 mL), and tetrahydro-2H-pyran-4-carbaldehyde (0.081 mL) was added. The mixture was stirred at 60° C. for 3 hr, sodium borohydride (39.4 mg) was added under ice-cooling, and the mixture was stirred at room temperature for 5 hr. Water was poured into the reaction mixture, and the mixture was extracted with ethyl acetate. The extract was washed with water and saturated brine, dried over anhydrous magnesium sulfate, and concentrated under reduced pressure. The residue was purified by NH silica gel column chromatography (hexane/ethyl acetate), concentrated under reduced pressure, and the residue was recrystallized from ethanol/heptane to give the title compound (50.0 mg).

¹H NMR (300 MHz, DMSO-d₆) δ0.89-1.27 (4H, m), 1.50-1.71 (3H, m), 1.82-1.88 (1H, m), 2.24-2.35 (1H, m), 2.41 (3H, d, J=0.8 Hz), 2.40-2.50 (2H, m), 3.17-3.29 (2H, m), 3.67-3.91 (2H, m), 6.75 (1H, d, J=0.8 Hz), 7.27-7.42 (2H, m), 7.56-7.65 (1H, m), 7.69-7.80 (1H, m), 11.23 (1H, s).

Example 232

3-(trans-2-(cyclobutylamino)cyclopropyl)-N-(5-methyl-1,2-oxazol-3-yl)benzamide hydrochloride 3-(trans-2-Aminocyclopropyl)-N-(5-methylisoxazol-3-yl)benzamide dihydrochloride (175 mg) and borane-2-methylpyridine complex (96.0 mg) were dissolved in methanol (2.00 mL)/acetic acid (0.10 mL), cyclobutanone (125 mg) was added, and the mixture was stirred at room temperature for 4 hr. Furthermore, cyclobutanone (125 mg) and borane-2-methylpyridine complex (96.0 mg) were added, and the mixture was stirred at room temperature for 4 hr. To the reaction mixture was added a saturated aqueous sodium hydrogen carbonate solution under ice-cooling, and the mixture was extracted with ethyl acetate. The extract was washed with water and saturated brine, dried over anhydrous magnesium sulfate, and concentrated under reduced pressure. The residue was purified by silica gel column chromatography (methanol/ethyl acetate), and concentrated under reduced pressure. To the obtained residue was added a 4 mol/L hydrogen chloride/ethyl acetate solution (1.99 mL), and the solvent was evaporated under reduced pressure to give the title compound (20.0 mg).

¹H NMR (300 MHz, DMSO-d₆) δ1.33-1.60 (2H, m), 1.65-1.90 (2H, m), 2.00-2.35 (4H, m), 2.42 (3H, d, J=0.8 Hz), 2.53-2.63 (1H, m), 2.83-3.04 (1H, m), 3.65-4.06 (1H, m), 6.76 (1H, d, J=1.1 Hz), 7.40-7.52 (2H, m), 7.69-7.77 (1H, m), 7.84 (1H, d, J=10.6 Hz), 9.55 (2H, brs), 11.26 (1H, s).

Example 233

3-(trans-2-(dicyclobutylamino)cyclopropyl)-N-(5-methyl-1,2-oxazol-3-yl)benzamide hydrochloride
By a method similar to that in Example 232, the compound of Example 233 was produced.

Example 234

N-(3,3-difluorocyclobutyl)-3-(trans-2-((4,4-difluorocyclohexyl)amino)cyclopropyl)benzamide hydrochloride A) 3-(trans-2-aminocyclopropyl)-N-(3,3-difluorocyclobutyl)benzamide hydrochloride 3-(trans-2-((tert-Butoxycarbonyl)amino)cyclopropyl)benzoic acid (200 mg), 3,3-difluorocyclobutanamine hydrochloride (104 mg) and triethylamine (0.302 mL) were dissolved in anhydrous DMF (2.00 mL), O-(7-azabenzotriazol-1-yl)-N,N,N',N'-tetramethyluronium hexafluorophosphate (302 mg) was added, and the mixture was stirred at room temperature overnight. To the reaction mixture was added a saturated aqueous sodium hydrogen carbonate solution (50.0 mL), and the mixture was extracted twice with ethyl acetate (50.0 mL each time). The extracts were combined, washed with water (50.0 mL) and saturated brine (10.0 mL), dried over anhydrous magnesium sulfate, and concentrated under reduced pressure. The obtained residue was cooled to 0° C., a 4 mol/L hydrogen chloride/ethyl acetate solution (10.0 mL) was added, and the mixture was stirred at room temperature for 4 hr. The reaction mixture was concentrated under reduced pressure to give the title compound (218 mg).

MS (API+): [M−HCl+H]$^+$ 266.9.

B) N-(3,3-difluorocyclobutyl)-3-(trans-2-((4,4-difluorocyclohexyl)amino)cyclopropyl)benzamide hydrochloride 3-(trans-2-Aminocyclopropyl)-N-(3,3-difluorocyclobutyl)benzamide hydrochloride (218 mg) and borane-2-methylpyridine complex (116 mg) were dissolved in methanol (2.00 mL)/acetic acid (0.20 mL), 4,4-difluorocyclohexanone (193 mg) was added, and the mixture was stirred under a nitrogen atmosphere at room temperature for 4 hr. To the reaction mixture was added aqueous sodium hydrogen carbonate solution (50.0 mL), and the mixture was extracted with ethyl acetate. The extracts were combined, washed with water and saturated brine, dried over anhydrous magnesium sulfate, and concentrated under reduced pressure. The residue was purified by NH silica gel column chromatography (hexane/ethyl acetate), and concentrated under reduced pressure. A 4 mol/L hydrogen chloride/ethyl acetate solution (5.00 mL) was added to the obtained residue, the solvent was evaporated under reduced pressure, and the residue was recrystallized from ethanol/heptane to give the title compound (170 mg).

$^1$H NMR (300 MHz, DMSO-d) δ1.26-2.25 (10H, m), 2.55-3.14 (6H, m), 3.21-3.51 (1H, m), 4.07-4.41 (1H, m), 7.31-7.54 (2H, m), 7.59-7.79 (2H, m), 8.88 (1H, d, J=6.4 Hz), 9.57 (2H, brs).

Example 235

N-(3-methyl-1,2-oxazol-5-yl)-3-(trans-2-(tetrahydro-2H-pyran-4-ylamino)cyclopropyl)benzamide hydrochloride 3-(trans-2-((tert-Butoxycarbonyl)amino)cyclopropyl) benzoic acid (500 mg) and one drop of DMF were dissolved in THF (5.00 mL), and the mixture was cooled to 0° C. Oxalyl chloride (0.196 mL) was added, and the mixture was stirred at 0° C. for 1 hr, and concentrated under reduced pressure. The obtained residue was dissolved in THF (2.00 mL), the solution was added to a solution of 3-methylisoxazol-5-amine (265 mg) in pyridine (5.00 mL) at 60° C., and the mixture was stirred at 60° C. overnight. Under ice-cooling, to the reaction mixture was added a saturated aqueous sodium hydrogen carbonate solution, and the mixture was extracted with ethyl acetate. The extract was washed with water and saturated brine, dried over anhydrous magnesium sulfate, and concentrated under reduced pressure. The residue was purified by NH silica gel column chromatography (hexane/ethyl acetate), and concentrated under reduced pressure. To the obtained residue was added a 4 mol/L hydrogen chloride/ethyl acetate solution (5.00 mL), and the mixture was stirred at room temperature for 3 hr. The solvent was evaporated under reduced pressure, the obtained residue and borane-2-methylpyridine complex (298 mg) were dissolved in methanol (5.00 mL)/acetic acid (0.50 mL), dihydro-2H-pyran-4(3H)-one (0.538 mL) was added, and the mixture was stirred at room temperature overnight. To the reaction mixture was added a saturated aqueous sodium hydrogen carbonate solution under ice-cooling, and the mixture was extracted with ethyl acetate. The extract was washed with water and saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution (4.00 mL) was added. The solvent was evaporated under reduced pressure, and the residue was recrystallized from ethanol/heptane to give the title compound (200 mg).

$^1$H NMR (300 MHz, DMSO-d$_6$) δ1.34-1.77 (4H, m), 1.87-2.08 (2H, m), 2.22 (3H, s), 2.60-2.65 (1H, m), 2.99-3.14 (1H, m), 3.23-3.58 (3H, m), 3.78-3.98 (2H, m), 6.32 (1H, s), 7.35-7.56 (2H, m), 7.68-8.05 (2H, m), 9.52 (2H, brs), 11.89 (1H, s).

Example 236

3-(trans-2-((cyclopropylmethyl)amino)cyclopropyl)-4-methyl-N-(1-methyl-1H-pyrazol-4-yl)benzamide dihydrochloride

A) tert-butyl (cyclopropylmethyl) (2-(2-methyl-5-((1-methyl-1H-pyrazol-4-yl)carbamoyl)phenyl)cyclopropyl)carbamate 3-(trans-2-((tert-Butoxycarbonyl) (cyclopropylmethyl) amino)cyclopropyl)-4-methylbenzoic acid (90.0 mg), 1-methyl-1H-pyrazol-4-amine. dihydrochloride (57.6 mg) and triethylamine (0.145 mL) were dissolved in anhydrous DMF (4.00 mL), and the mixture was cooled to 0° C. O-(7-Azabenzotriazol-1-yl)-N,N,N',N'-tetramethyluronium hexafluorophosphate (119 mg) was added, and the mixture was stirred at room temperature overnight. To the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ ethyl acetate), and concentrated under reduced pressure to give the title compound (111 mg).

MS (API+): [M+H]$^+$ 369.3.

B) 3-(trans-2-((cyclopropylmethyl)amino)cyclopropyl)-4-methyl-N-(1-methyl-1H-pyrazol-4-yl)benzamide dihydrochloride tert-Butyl (cyclopropylmethyl)(2-(2-methyl-5-((1-methyl-1H-pyrazol-4-yl)carbamoyl)phenyl)cyclopropyl) carbamate (111 mg) was dissolved in methanol (5.00 mL), a 2 mol/L hydrogen chloride/methanol solution (1.96 mL) was added, and the mixture was stirred at room temperature overnight and at 60° C. for 30 min. The reaction mixture was concentrated under reduced pressure, and the residue was crystallized from ethanol/heptane to give the title compound (89.8 mg).

$^1$H NMR (300 MHz, DMSO-d$_6$) δ0.36-0.43 (2H, m), 0.56-0.64 (2H, m), 1.02-1.15 (1H, m), 1.26-1.36 (1H, m), 1.52-1.60 (1H, m), 2.46 (3H, s), 2.57-2.66 (1H, m), 2.95-3.05 (2H, m), 3.08-3.18 (1H, m), 3.82 (3H, s), 7.33 (1H, d, J=8.0 Hz), 7.54-7.64 (2H, m), 7.74 (1H, dd, J=8.0, 1.5 Hz), 8.00 (1H, s), 9.17-9.42 (2H, m), 10.38 (1H, s).

Example 237

3-(trans-2-((cyclopropylmethyl)amino)cyclopropyl)-4-fluoro-N-(1-methyl-1H-pyrazol-4-yl)benzamide dihydrochloride

A) tert-butyl (cyclopropylmethyl) (2-(2-fluoro-5-((1-methyl-1H-pyrazol-4-yl)carbamoyl)phenyl)cyclopropyl)carbamate 3-(trans-2-((tert-Butoxycarbonyl)(cyclopropylmethyl)amino)cyclopropyl)-4-fluorobenzoic acid (90.0 mg), 1-methyl-1H-pyrazol-4-amine dihydrochloride (56.9 mg) and triethylamine (0.144 mL) were dissolved in anhydrous DMF (4.00 mL), and the mixture was cooled to 0° C. O-(7-Azabenzotriazol-1-yl)-N,N,N',N'-tetramethyluronium hexafluorophosphate (118 mg) was added, and the mixture was stirred at room temperature overnight. To the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (87.2 mg).
MS (API+): [M+H]$^+$ 373.3.

B) 3-(trans-2-((cyclopropylmethyl)amino)cyclopropyl)-4-fluoro-N-(1-methyl-1H-pyrazol-4-yl)benzamide dihydrochloride tert-Butyl (cyclopropylmethyl) (2-(2-fluoro-5-((1-methyl-1H-pyrazol-41)carbamoyl)phenyl)cyclopropyl)carbamate (110 mg) was dissolved in methanol (5.00 mL), 2 mol/L hydrogen chloride/methanol solution (1.93 mL) was added, and the mixture was stirred at room temperature overnight and at 60° C. for 30 min. The reaction mixture was concentrated under reduced pressure, and the residue was recrystallized from methanol/diisopropy ether to give the title compound (87.2 mg).
$^1$H NMR (300 MHz, DMSO-d$_6$) δ0.32-0.42 (2H, m), 0.52-0.65 (2H, m), 0.99-1.17 (1H, m), 1.41-1.52 (1H, m), 1.58-1.68 (1H, m), 2.64-2.73 (1H, m), 2.93-3.03 (2H, m), 3.17-3.28 (1H, m), 3.82 (3H, s), 7.30-7.39 (1H, m), 7.59 (1H, s), 7.73 (1H, dd, J=7.4, 2.1 Hz), 7.83-7.91 (1H, m), 8.01 (1H, s), 9.20-9.48 (2H, m), 10.49 (1H, s).

Example 238

3-(trans-2-(cyclobutylamino)cyclopropyl)-4-methyl-N-(1-methyl-1H-pyrazol-4-yl)benzamide hydrochloride

A) tert-butyl (trans-2-(2-methyl-5-((1-methyl-1H-pyrazol-4-yl)carbamoyl)phenyl)cyclopropyl)carbamate 3-(trans-2-((tert-Butoxycarbonyl)amino)cyclopropyl)-4-methylbenzoic acid (400 mg), 1-methyl-1H-pyrazol-4-amine dihydrochloride (257 mg) and triethylamine (0.957 mL) were dissolved in DMF (10.0 mL), O-(7-azabenzotriazol-1-yl)-N,N,N',N'-tetramethyluronium hexafluorophosphate (626 mg) was added under ice-cooling, and the mixture was stirred at room temperature overnight. To the reaction mixture was added a saturated aqueous sodium hydrogen carbonate solution, and the mixture was extracted with ethyl acetate. The extracts were combined, washed with water and saturated brine, dried over anhydrous magnesium sulfate, and concentrated under reduced pressure to give the title compound (500 mg).
MS (API+): [M+H]$^+$ 371.2.

B) 3-(trans-2-aminocyclopropyl)-4-methyl-N-(1-methyl-1H-pyrazol-4-yl)benzamide dihydrochloride To tert-butyl (trans-2-(2-methyl-5-((1-methyl-1H-pyrazol-4-yl)carbamoyl)phenyl)cyclopropyl)carbamate (500 mg) was added a 4 mol/L hydrogen chloride/ethyl acetate solution (5.00 mL), and the mixture was stirred at room temperature for 18 hr. The resulting precipitate was collected by filtration to give the title compound (460 mg).
MS (API+): [M−2HCl+H]$^+$ 271.3.

C) 3-(trans-2-(cyclobutylamino)cyclopropyl)-4-methyl-N-(1-methyl-1H-pyrazol-4-yl)benzamide hydrochloride 3-(trans-2-Aminocyclopropyl)-4-methyl-N-(1-methyl-1H-pyrazol-4-yl)benzamide dihydrochloride (200 mg) and borane-2-methylpyridine complex (93.0 mg) were dissolved in methanol (4.00 mL)/acetic acid (0.40 mL), cyclobutanone (0.065 mL) was added, and the mixture was stirred at room temperature overnight under a nitrogen atmosphere. Furthermore, cyclobutanone (0.044 mL) and borane-2-methylpyridine complex (93.0 mg) were added, and the mixture was stirred under a nitrogen atmosphere at room temperature for 3 hr. Under ice-cooling, to the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by silica gel column chromatography (ethyl acetate/methanol), and a 4 mol/L hydrogen chloride/ethyl acetate solution (2.19 mL) was added. The solvent was concentrated under reduced pressure, and the residue was recrystallized from ethanol/heptane to give the title compound (159 mg).
$^1$H NMR (300 MHz, DMSO-d$_6$) δ1.22-1.35 (1H, m), 1.47-1.58 (1H, m), 1.73-1.93 (2H, m), 2.15-2.34 (4H, m), 2.45 (3H, s), 2.52-2.61 (1H, m), 2.93-3.06 (1H, m), 3.82 (3H, s), 3.84-3.97 (1H, m), 7.32 (1H, d, J=8.0 Hz), 7.56 (1H, d, J=1.5 Hz), 7.58-7.60 (1H, m), 7.70-7.76 (1H, m), 8.00 (1H, s), 9.47-9.72 (2H, m), 10.37 (1H, s).

Example 239

3-(trans-2-(cyclopentylamino)cyclopropyl)-4-methyl-N-(1-methyl-1H-pyrazol-4-yl)benzamide hydrochloride 3-(trans-2-Aminocyclopropyl)-4-methyl-N-(1-methyl-1H-pyrazol-4-yl)benzamide dihydrochloride (150 mg) and borane-2-methylpyridine complex (70.1 mg) were dissolved in methanol (4.00 mL)/acetic acid (0.40 mL), cyclopentanone (0.116 mL) was added, and the mixture was stirred under a nitrogen atmosphere at room temperature for 4 hr. Furthermore, cyclopentanone (0.116 mL) and borane-2-methylpyridine complex (70.1 mg) were added, and the mixture was stirred at room temperature overnight under a nitrogen atmosphere. Under ice-cooling, to the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The residue was purified by NH silica gel column chromatography (hexane/ethyl acetate), and a 4 mol/L hydrogen chloride/ethyl acetate solution (1.64 mL) was added. The solvent was concentrated under reduced pressure, and the residue was recrystallized from ethanol/heptane to give the title compound (80.0 mg).

$^1$H NMR (300 MHz, DMSO-d$_6$) δ1.29-1.38 (1H, m), 1.48-1.81 (7H, m), 1.93-2.11 (2H, m), 2.46 (3H, s), 2.53-2.66 (1H, m), 3.06-3.17 (1H, m), 3.66-3.74 (1H, m), 3.82 (3H, s), 7.31-7.37 (1H, m), 7.54-7.59 (2H, m), 7.70-7.76 (1H, m), 7.98-8.01 (1H, m), 8.99-9.25 (2H, m), 10.29-10.35 (1H, m).

Example 240

3-(trans-2-((cyclopropylmethyl)amino)cyclopropyl)-N-(3,3-difluorocyclobutyl)-4-fluorobenzamide hydrochloride A) tert-butyl (cyclopropylmethyl)(trans-2-(5-((3,3-difluorocyclobutyl)carbamoyl)-2-fluorophenyl)cyclopropyl)carbamate 3-(trans-2-((tert-Butoxycarbonyl) (cyclopropylmethyl)amino)cyclopropyl)-4-fluorobenzoic acid (90.0 mg), 3,3-difluorocyclobutanamine hydrochloride (48.1 mg) and triethylamine (0.144 mL) were dissolved in anhydrous DMF (4.00 mL), and the mixture was cooled to 0° C. O-(7-Azabenzotriazol-1-yl)-N,N,N',N'-tetramethyluronium hexafluorophosphate (118 mg) was added, and the mixture was stirred at room temperature for 1 hr. To the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (110 mg).

MS (API+): [M−(tert-Bu)+H]$^+$ 383.3.

B) 3-(trans-2-((cyclopropylmethyl)amino)cyclopropyl)-N-(3,3-difluorocyclobutyl)-4-fluorobenzamide hydrochloride tert-Butyl (cyclopropylmethyl) (trans-2-(5-((3,3-difluorocyclobutyl)carbamoyl)-2-fluorophenyl)cyclopropyl)carbamate (110 mg) was dissolved in methanol (5.00 mL), a 2 mol/L hydrogen chloride/methanol solution (1.89 mL) was added, and the mixture was stirred at room temperature overnight. The reaction mixture was concentrated under reduced pressure, and the residue was crystallized from ethanol/heptane to give the title compound (73.3 mg).

$^1$H NMR (300 MHz, DMSO-d$_6$) δ0.31-0.41 (2H, m), 0.52-0.63 (2H, m), 0.97-1.15 (1H, m), 1.36-1.48 (1H, m), 1.52-1.64 (1H, m), 2.58-2.85 (3H, m), 2.87-3.03 (4H, m), 3.10-3.20 (1H, m), 4.15-4.33 (1H, m), 7.25-7.41 (1H, m), 7.53-7.66 (1H, m), 7.71-7.85 (1H, m), 8.88 (1H, d, J=6.4 Hz), 9.17 (2H, brs).

Example 241

5-(trans-2-((cyclopropylmethyl)amino)cyclopropyl)-N-(3,3-difluorocyclobutyl)-2-fluorobenzamide hydrochloride A) tert-butyl (cyclopropylmethyl)(trans-2-(3-((3,3-difluorocyclobutyl)carbamoyl)-4-fluorophenyl)cyclopropyl)carbamate 5-(trans-2-((tert-Butoxycarbonyl)(cyclopropylmethyl)amino)cyclopropyl)-2-fluorobenzoic acid (90.0 mg), 3,3-difluorocyclobutanamine hydrochloride (48.1 mg) and triethylamine (0.144 mL) were dissolved in anhydrous DMF (4.00 mL), and the mixture was cooled to 0° C. O-(7-Azabenzotriazol-1-yl)-N,N,N',N'-tetramethyluronium hexafluorophosphate (118 mg) was added, and the mixture was stirred at room temperature for 1 hr. To the reaction mixture was added a saturated aqueous sodium hydrogen carbonate solution, and the mixture was extracted with ethyl acetate. The extracts were combined, washed with water and saturated brine, dried over anhydrous sodium sulfate, and concentrated under reduced pressure. The obtained residue was purified by silica gel column chromatography (hexane/ethyl acetate), and concentrated under reduced pressure to give the title compound (83.1 mg).

MS (API+): [M−(tert-Bu)+H]$^+$ 383.3.

B) 5-(trans-2-((cyclopropylmethyl)amino)cyclopropyl)-N-(3,3-difluorocyclobutyl)-2-fluorobenzamide hydrochloride tert-Butyl (cyclopropylmethyl)(trans-2-(3-((3,3-difluorocyclobutyl)carbamoyl)-4-fluorophenyl)cyclopropyl)carbamate (83.1 mg) was dissolved in methanol (4.00 mL), a 2 mol/L hydrogen chloride/methanol solution (1.42 mL) was added, and the mixture was stirred at room temperature overnight. The reaction mixture was concentrated under reduced pressure, and the residue was crystallized from ethanol/heptane to give the title compound (64.1 mg).

$^1$H NMR (300 MHz, DMSO-d$_6$) δ0.31-0.41 (2H, m), 0.52-0.60 (2H, m), 0.98-1.14 (1H, m), 1.26-1.37 (1H, m), 1.48-1.59 (1H, m), 2.53-2.59 (1H, m), 2.61-2.81 (2H, m), 2.87-3.04 (5H, m), 4.16-4.31 (1H, m), 7.18-7.28 (1H, m), 7.31-7.45 (2H, m), 8.81 (1H, d, J=6.8 Hz), 9.25 (2H, brs).

Example 242

3-(trans-2-((4,4-difluorocyclohexyl)amino)cyclopropyl)-N-(1,3-dimethyl-1H-pyrazol-4-yl)benzamide dihydrochloride 3-(trans-2-((tert-Butoxycarbonyl)amino)cyclopropyl) benzoic acid (200 mg), 1,3-dimethyl-1H-pyrazol-4-amine dihydrochloride (146 mg) and triethylamine (0.402 mL) were dissolved in anhydrous DMF (2.00 mL), O-(7-azabenzotriazol-1-yl)-N,N,N',N'-tetramethyluronium hexafluorophosphate (302 mg) was added, and the mixture was stirred at room temperature for 3 hr. To the reaction mixture was added a saturated aqueous sodium hydrogen carbonate solution, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate), and concentrated under reduced pressure. The obtained residue was dissolved in TFA (3.00 mL), and the mixture was stirred at room temperature overnight. To the reaction mixture was added a saturated aqueous sodium hydrogen carbonate solution under ice-cooling, and the mixture was extracted with ethyl acetate. The extract was washed with water and saturated brine, dried over anhydrous magnesium sulfate, and concentrated under reduced pressure. The obtained residue and borane-2-methylpyridine complex (19.6 mg) were dissolved in methanol (2.00 mL)/acetic acid (0.20 mL), 4,4-difluorocyclohexanone (49.2 mg) was added, and the mixture was stirred at room temperature overnight. To the reaction mixture was added a saturated aqueous sodium hydrogen carbonate solution under ice-cooling, and the mixture was extracted with ethyl acetate. The extract was washed with water and saturated brine, dried over anhydrous magnesium sulfate, and concentrated under reduced pressure. The residue was purified by NH silica gel column chromatography (ethyl acetate/hexane), and concentrated under reduced pressure. The obtained residue was separated by HPLC (C18, mobile phase: water/acetonitrile (with 0.1% TFA)). To the obtained fraction was added a saturated aqueous sodium hydrogen carbonate solution, and the mixture was extracted with ethyl acetate, and dried over anhydrous magnesium sulfate. A 4 mol/L hydrogen chloride/ethyl acetate solution (2.00 mL) was added, and the solvent was evaporated under reduced pressure to give the title compound (3.00 mg).

$^1$H NMR (300 MHz, CD$_3$OD) δ1.47-2.09 (6H, m), 2.11-2.34 (4H, m), 2.37 (3H, s), 2.61 (1H, ddd, J=10.3, 6.7, 3.8 Hz), 3.12-3.17 (1H, m), 3.42-3.63 (1H, m), 3.99 (3H, s), 7.41-7.55 (2H, m), 7.76-7.88 (2H, m), 8.18 (1H, s).

Example 243

3-(trans-2-aminocyclopropyl)-N-(5-methyl-1,3,4-thiadiazol-2-yl)benzamide dihydrochloride [optical isomer, compound derived from methyl 3-(trans-2-((tert-Butoxycarbonyl) amino) cyclopropyl)benzoate (optical isomer, retention time long)]

A) methyl 3-(trans-2-((tert-butoxycarbonyl) amino) cyclopropyl)benzoate (optical isomer, retention time long)

A racemate (20.8 g) of methyl 3-(trans-2-((tert-butoxycarbonyl)amino)cyclopropyl)benzoate was fractionated by HPLC (column: CHIRALPAK IC (MD026) (trade name), 4.6 mmID×250 mmL manufactured by Daicel Corporation, mobile phase: hexane/2-propanol=650/350) to give the title compound with a longer retention time (10.0 g).

$^1$H NMR (300 MHz, CDCl$_3$) δ1.13-1.27 (2H, m), 1.45 (9H, s), 2.02-2.14 (1H, m), 2.68-2.82 (1H, m), 3.90 (3H, s), 4.57-5.01 (1H, m), 7.29-7.41 (2H, m), 7.73-7.78 (1H, m), 7.81-7.87 (1H, m). HPLC retention time 16.062 min (column: CHIRALPAK IC (trade name), 4.6mmID×250 mmL manufactured by Daicel Corporation, mobile phase: hexane/2-propanol=650/350/1, flow rate: 0.5 mL/min, temperature: 30° C., detection: UV 220 nm, concentration: 0.5 mg/mL, injection volume: 0.010 mL)

B) 3-(trans-2-((tert-butoxycarbonyl)amino)cyclopropyl)benzoic acid [optical isomer, compound derived from methyl 3-(trans-2-((tert-Butoxycarbonyl) amino)cyclopropyl)benzoate (optical isomer, retention time long)]

Methyl 3-(trans-2-((tert-butoxycarbonyl)amino)cyclopropyl)benzoate (optical isomer, retention time long) (10.0 g) was dissolved in ethanol (150 mL), a 8 mol/L aqueous sodium hydroxide solution (8.58 mL) was added, and the mixture was stirred at room temperature overnight. The reaction mixture was neutralized with 6 mol/L hydrochloric acid, and extracted with ethyl acetate. The extract was washed successively with water and saturated brine, dried over anhydrous magnesium sulfate, and concentrated under reduced pressure to give the title compound (9.42 g).

MS (API-): [M-H]$^-$ 276.2.

C) tert-butyl (trans-2-(3-((5-methyl-1,3,4-thiadiazol-2-yl)carbamoyl)phenyl)cyclopropyl)carbamate [optical isomer, compound derived from methyl 3-(trans-2-((tert-butoxycarbonyl)amino)cyclopropyl) benzoate (optical isomer, retention time long)]

3-(trans-2-((tert-Butoxycarbonyl)amino)cyclopropyl)benzoic acid [optical isomer, compound derived from methyl 3-(trans-2-((tert-butoxycarbonyl) amino)cyclopropyl)benzoate (optical isomer, retention time long)] (1.00 g), 5-methyl-1,3,4-thiadiazol-2-amine (481 mg) and triethylamine (2.01 mL) were dissolved in anhydrous DMF (10.0 mL), O-(7-azabenzotriazol-1-yl)-N,N,N',N'-tetramethyluronium hexafluorophosphate (1.65 g) was added at 0° C., and the mixture was stirred at room temperature for 30 min, at 50° C. for 1 hr and at room temperature overnight. The reaction mixture was poured into water, and the mixture was extracted with ethyl acetate. The extract was washed successively with saturated sodium hydrogen carbonate and saturated brine, and dried over anhydrous sodium sulfate. This was purified by short silica gel column chromatography (ethyl acetate), and concentrated under reduced pressure. The residue was washed with diisopropy ether to give the title compound (1.10 g).

MS (API+): [M+H]$^+$ 375.2.

D) 3-(trans-2-aminocyclopropyl)-N-(5-methyl-1,3,4-thiadiazol-2-yl)benzamide dihydrochloride [optical isomer, compound derived from methyl 3-(trans-2-((tert-butoxycarbonyl)amino)cyclopropyl)benzoate (optical isomer, retention time long)]

tert-Butyl (trans-2-(3-((5-methyl-1,3,4-thiadiazol-2-yl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (1.10 g) was suspended in ethyl acetate (10.0 mL)/methanol (5.00 mL), a 4 mol/L hydrogen chloride/ethyl acetate solution (14.7 mL) was added at room temperature, and the mixture was stirred at room temperature for 2 hr. The resulting precipitate was collected by filtration to give the title compound (1.02 g).

$^1$H NMR (300 MHz, DMSO-d$_6$) δ1.31-1.40 (1H, m), 1.43-1.53 (1H, m), 2.40-2.48 (1H, m), 2.65 (3H, s), 2.89-3.00 (1H, m), 7.43-7.58 (2H, m), 7.79-7.86 (1H, m), 7.88-7.95 (1H, m), 8.57 (3H, brs), 12.85 (1H, brs).

Example 244

3-(trans-2-aminocyclopropyl)-N-(5-methyl-1,3,4-thiadiazol-2-yl)benzamide dihydrochloride [optical isomer, compound derived from methyl 3-(trans-2-((tert-butoxycarbonyl)amino)cyclopropyl)benzoate (optical isomer, retention time short)]

A) methyl 3-(trans-2-((tert-butoxycarbonyl)amino) cyclopropyl)benzoate (optical isomer, retention time short)

A racemate (20.8 g) of methyl 3-(trans-2-((tert-butoxycarbonyl)amino)cyclopropyl)benzoate was fractionated by HPLC (column: CHIRALPAK IC (MD026)(trade name), 4.6 mmID×250 mmL, manufactured by Daicel Corporation, mobile phase: hexane/2-propanol=650/350) to give the title compound with a shorter retention time (10.0 g).

$^1$H NMR (300 MHz, CDCl$_3$) δ1.09-1.28 (2H, m), 1.45 (9H, s), 1.93-2.23 (1H, m), 2.58-2.90 (1H, m), 3.90 (3H, s), 4.82 (1H, brs), 7.28-7.43 (2H, m), 7.72-7.78 (1H, m), 7.80-7.90 (1H, m).

B) 3-(trans-2-((tert-butoxycarbonyl)amino)cyclopropyl)benzoic acid [optical isomer, compound derived from methyl 3-(trans-2-((tert-butoxycarbonyl)amino)cyclopropyl)benzoate (optical isomer, retention time short)]

The title compound was obtained by a method similar to that in Example 243, step B.
MS (API−): [M−H]$^-$ 276.1.

C) 3-(trans-2-aminocyclopropyl)-N-(5-methyl-1,3,4-thiadiazol-2-yl)benzamide dihydrochloride [optical isomer, compound derived from methyl 3-(trans-2-((tert-butoxycarbonyl) amino)cyclopropyl)benzoate (optical isomer, retention time short)]

The title compound was obtained by a method similar to that in Example 243, steps C-D.

Example 245

3-(trans-2-aminocyclopropyl)-N-(tetrahydro-2H-pyran-4-yl)benzamide hydrochloride [optical isomer, compound derived from methyl 3-(trans-2-((tert-butoxycarbonyl)amino)cyclopropyl)benzoate (optical isomer, retention time long)]

A) tert-butyl (trans-2-(3-((tetrahydro-2H-pyran-4-yl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)]

3-(trans-2-((tert-Butoxycarbonyl)amino)cyclopropyl)benzoic acid [optical isomer, compound derived from methyl 3-(trans-2-((tert-butoxycarbonyl)amino)cyclopropyl)benzoate (optical isomer, retention time long)] (700 mg), tetrahydro-2H-pyran-4-amine (323 mg) and triethylamine (1.06 mL) were dissolved in anhydrous DMF (7.00 mL), O-(7-azabenzotriazol-1-yl)-N,N,N',N'-tetramethyluronium hexafluorophosphate (1.15 g) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was washed with diisopropy ether to give the title compound (880 mg).
MS (API+): [M+H]$^+$ 361.3.

B) 3-(trans-2-aminocyclopropyl)-N-(tetrahydro-2H-pyran-4-yl)benzamide hydrochloride [optical isomer, compound derived from methyl 3-(trans-2-((tert-butoxycarbonyl)amino)cyclopropyl)benzoate (optical isomer, retention time long)]

To tert-butyl (trans-2-(3-((tetrahydro-2H-pyran-4-yl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (880 mg) was added a 4 mol/L hydrogen chloride/ethyl acetate solution (5.00 mL) at room temperature, and the mixture was stirred at room temperature overnight. The reaction mixture was concentrated under reduced pressure to give the title compound (725 mg).
$^1$H NMR (300 MHz, DMSO-d$_6$) δ1.22-1.33 (1H, m), 1.37-1.48 (1H, m), 1.50-1.67 (2H, m), 1.69-1.80 (2H, m), 2.34-2.45 (1H, m), 2.81-2.94 (1H, m), 3.32-3.44 (2H, m), 3.83-3.93 (2H, m), 3.94-4.06 (1H, m), 7.28-7.43 (2H, m), 7.61 (1H, s), 7.66-7.73 (1H, m), 8.27-8.35 (1H, m), 8.47 (3H, brs).

Example 246

3-(trans-2-aminocyclopropyl)-N-(tetrahydro-2H-pyran-4-yl)benzamide hydrochloride [optical isomer, compound derived from methyl 3-(trans-2-((tert-butoxycarbonyl)amino)cyclopropyl)benzoate (optical isomer, retention time short)]

By a method similar to that in Example 245, the compound of Example 246 was produced.

Example 247

3-(trans-2-aminocyclopropyl)-N-cyclopentylbenzamide hydrochloride [optical isomer, compound derived from methyl 3-(trans-2-((tert-butoxycarbonyl)amino)cyclopropyl)benzoate (optical isomer, retention time long)]

A) tert-butyl (trans-2-(3-(cyclopentylcarbamoyl)phenyl)cyclopropyl)carbamate [optical isomer, compound derived from methyl 3-(trans-2-((tert-butoxycarbonyl) amino) cyclopropyl)benzoate (optical isomer, retention time long)]

3-(trans-2-((tert-Butoxycarbonyl)amino)cyclopropyl)benzoic acid [optical isomer, compound derived from methyl 3-(trans-2-((tert-butoxycarbonyl) amino)cyclopropyl)benzoate (optical isomer, retention time long)] (310 mg), cyclopentanamine (0.134 mL) and triethylamine (0.234 mL) were dissolved in anhydrous DMF (3.00 mL), O-(7-azabenzotriazol-1-yl)-N,N,N',N'-tetramethyluronium hexafluorophosphate (510 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The residue was washed with diisopropy ether to give the title compound (380 mg).
MS (API+): [M+H]$^-$ 345.2.

B) 3-(trans-2-aminocyclopropyl)-N-cyclopentylbenzamide hydrochloride [optical isomer, compound derived from methyl 3-(trans-2-((tert-butoxycarbonyl)amino)cyclopropyl)benzoate (optical isomer, retention time long)]

To tert-butyl (trans-2-(3-(cyclopentylcarbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (380 mg) was added a 4 mol/L hydrogen chloride/ethyl acetate solution (3.00 mL) at room temperature, and the mixture was stirred at room temperature overnight. The reaction mixture was concentrated under reduced pressure to give the title compound (310 mg).

¹H NMR (300 MHz, DMSO-d₆) δ1.23-1.33 (1H, m), 1.34-1.44 (1H, m), 1.44-1.78 (6H, m), 1.82-1.94 (2H, m), 2.29-2.40 (1H, m), 2.82-2.93 (1H, m), 4.14-4.31 (1H, m), 7.27-7.41 (2H, m), 7.56-7.61 (1N, m), 7.65-7.72 (1H, m), 8.20-8.27 (1H, m), 8.28-8.40 (3H, m).

Example 248

3-(trans-2-aminocyclopropyl)-N-cyclopentylbenzamide hydrochloride [optical isomer, compound derived from methyl 3-(trans-2-((tert-butoxycarbonyl)amino)cyclopropyl)benzoate (optical isomer, retention time short)]

By a method similar to that in Example 247, the compound of Example 248 was produced.

Example 249

3-(trans-2-aminocyclopropyl)-N-(4,4-difluorocyclohexyl)benzamide hydrochloride [optical isomer, compound derived from methyl 3-(trans-2-((tert-butoxycarbonyl)amino)cyclopropyl)benzoate (optical isomer, retention time long)]

A) tert-butyl (trans-2-(3-((4,4-difluorocyclohexyl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)]

3-(trans-2-((tert-Butoxycarbonyl)amino)cyclopropyl)benzoic acid [optical isomer, compound derived from methyl 3-(trans-2-((tert-butoxycarbonyl)amino)cyclopropyl)benzoate (optical isomer, retention time long)] (600 mg), 4,4-difluorocyclohexanamine (351 mg) and triethylamine (0.905 mL) were dissolved in anhydrous DMF (20.0 mL), O-(7-azabenzotriazol-1-yl)-N,N,N',N'-tetramethyluronium hexafluorophosphate (987 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The obtained residue was purified by silica gel column chromatography (hexane/ethyl acetate) to give the title compound (721 mg).

¹H NMR (300 MHz, CDCl₃) δ1.14-1.26 (2H, m), 1.45 (9H, s), 1.60-1.71 (2H, m), 1.80-2.04 (2H, m), 2.05-2.22 (5H, m), 2.70-2.79 (1H, m), 4.02-4.19 (1H, m), 4.83 (1H, brs), 6.00 (1H, d, J=6.4 Hz), 7.25-7.29 (1H, m), 7.29-7.36 (1H, m), 7.49-7.55 (2H, m).

B) 3-(trans-2-aminocyclopropyl)-N-(4,4-difluorocyclohexyl)benzamide hydrochloride [optical isomer, compound derived from methyl 3-(trans-2-((tert-butoxycarbonyl)amino)cyclopropyl)benzoate (optical isomer, retention time long)]

tert-Butyl (trans-2-(3-((4,4-difluorocyclohexyl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (704 mg) was dissolved in methanol (42.2 mL)/THF (16.9 mL), and the mixture was cooled to 0° C. A 4 mol/L hydrogen chloride/ethyl acetate solution (6.70 mL) was added at room temperature, and the mixture was stirred at room temperature for 18 hr. The reaction mixture was concentrated under reduced pressure, and the residue was crystallized from methanol/ethyl acetate to give the title compound (536 mg).

¹H NMR (300 MHz, DMSO-d₆) δ1.23-1.32 (1H, m), 1.43 (1H, dt, J=9.8, 4.9 Hz), 1.56-1.73 (2H, m), 1.81-1.98 (3H, m), 1.99-2.13 (3H, m), 2.35-2.45 (1H, m), 2.82-2.92 (1H, m), 3.94-4.04 (1H, m), 7.29-7.34 (1H, m), 7.35-7.41 (1H, m), 7.60 (1H, s), 7.69 (1H, dt, J=7.6, 1.5 Hz), 8.29 (1H, d, J=7.6 Hz), 8.49 (3H, brs).

Example 250

3-(trans-2-aminocyclopropyl)-N-(4,4-difluorocyclohexyl)benzamide hydrochloride [optical isomer, compound derived from methyl 3-(trans-2-((tert-butoxycarbonyl)amino)cyclopropyl)benzoate (optical isomer, retention time short)]

By a method similar to that in Example 249, the compound of Example 250 was produced.

Example 251

3-(trans-2-aminocyclopropyl)-N-(1-(2,2,2-trifluoroethyl)piperidin-4-yl)benzamide dihydrochloride [optical isomer, compound derived from methyl 3-(trans-2-((tert-butoxycarbonyl)amino)cyclopropyl)benzoate (optical isomer, retention time long)]

A) tert-butyl (trans-2-(3-((1-(2,2,2-trifluoroethyl)piperidin-4-yl)carbamoyl)phenyl)cyclopropyl)carbamate [optical isomer, compound derived from methyl 3-(trans-2-((tert-butoxycarbonyl) amino)cyclopropyl)benzoate (optical isomer, retention time long)]

3-(trans-2-((tert-butoxycarbonyl)amino)cyclopropyl)benzoic acid [optical isomer, compound derived from methyl 3-(trans-2-((tert-butoxycarbonyl)amino)cyclopropyl)benzoate (optical isomer, retention time long)] (300 mg), 1-(2,2,2-trifluoroethyl)piperidin-4-amine dihydrochloride (276 mg) and triethylamine (0.603 mL) were dissolved in anhydrous DMF (10.0 mL), O-(7-azabenzotriazol-1-yl)-N,N,N',N'-tetramethyluronium hexafluorophosphate (494 mg) was added, and the mixture was stirred at room temperature for 18 hr. Water was added to the reaction mixture, and the mixture was extracted with ethyl acetate. The extract was washed successively with water and saturated brine, dried over anhydrous sodium sulfate, and concentrated under reduced pressure. The obtained residue was purified by silica gel column chromatography (hexane/ethyl acetate) to give the title compound (331 mg).

MS (API+): [M+H]⁺ 442.1.

B) 3-(trans-2-aminocyclopropyl)-N-(1-(2,2,2-trifluoroethyl)piperidin-4-yl)benzamide dihydrochloride [optical isomer, compound derived from methyl 3-(trans-2-((tert-butoxycarbonyl)amino)cyclopropyl)benzoate (optical isomer, retention time long)]

tert-Butyl (trans-2-(3-((1-(2,2,2-trifluoroethyl)piperidin-4-yl)carbamoyl)phenyl)cyclopropyl)carbamate [optical isomer, compound derived from methyl 3-(trans-2-((tert-butoxycarbonyl) amino)cyclopropyl)benzoate (optical isomer, retention time long)] (314 mg) was dissolved in methanol (18.8 mL)/THF (7.53 mL), and the mixture was cooled to 0°

C. A 4 mol/L hydrogen chloride/ethyl acetate solution (2.67 mL) was added at room temperature, and the mixture was stirred at room temperature for 18 hr. The reaction mixture was concentrated under reduced pressure to give the title compound (312 mg).

$^1$H NMR (300 MHz, DMSO-d$_6$)δ1.22-1.32 (1H, m), 1.39-1.48 (1H, m), 1.67-1.98 (4H, m), 2.36-2.44 (1H, m), 2.64-2.94 (3H, m), 3.10-3.27 (2H, m), 3.82-3.94 (3H, m), 7.29-7.35 (1H, m), 7.35-7.41 (1H, m), 7.63 (1H, s), 7.70 (1H, d, J=7.2 Hz), 8.37 (1H, d, J=4.9 Hz), 8.49 (3H, brs).

Example 252

3-(trans-2-aminocyclopropyl)-N-(1-(2,2,2-trifluoroethyl)piperidin-4-yl)benzamide dihydrochloride [optical isomer, compound derived from methyl 3-(trans-2-((tert-butoxycarbonyl)amino)cyclopropyl) benzoate (optical isomer, retention time short)]

By a method similar to that in Example 251, the compound of Example 252 was produced.

Example 253

3-(trans-2-(cyclobutylamino)cyclopropyl)-N-(5-methyl-1,3,4-thiadiazol-2-yl)benzamide 1/2 fumarate (optical isomer, retention time long)

3-(trans-2-Aminocyclopropyl)-N-(5-methyl-1,3,4-thiadiazol-2-yl)benzamide dihydrochloride [optical isomer, compound derived from methyl 3-(trans-2-((tert-butoxycarbonyl)amino)cyclopropyl)benzoate (optical isomer, retention time long)] (250 mg) and sodium hydrogen carbonate (242 mg) were dissolved in methanol (3.80 mL)/THF (3.80 mL), cyclobutanone (0.065 mL) was added, and the mixture was stirred at 60° C. for 1 hr. Furthermore, cyclobutanone (0.065 mL) was added at room temperature, and the mixture was stirred at 60° C. for 1 hr. To the reaction mixture was added sodium borohydride (32.7 mg) under ice-cooling, and the mixture was stirred at room temperature for 1 hr. Under ice-cooling, to the reaction mixture was added a saturated aqueous sodium hydrogen carbonate solution, and the mixture was extracted with an ethyl acetate/THF mixture. The extracts were combined, washed successively with water and saturated brine, dried over anhydrous sodium sulfate, and concentrated under reduced pressure. The residue was purified by silica gel column chromatography (ethyl acetate/methanol), to the obtained fraction was added a 2 mol/L hydrogen chloride/methanol solution (3.00 mL), and the reaction mixture was concentrated under reduced pressure. The residue was crystallized from ethanol/heptane to give 3-(trans-2-(cyclobutylamino)cyclopropyl)-N-(5-methyl-1,3,4-thiadiazol-2-yl)benzamide hydrochloride [optical isomer, compound derived from methyl 3-(trans-2-((tert-butoxycarbonyl)amino)cyclopropyl)benzoate (optical isomer, retention time long)] (139 mg). 3-(trans-2-(Cyclobutylamino) cyclopropyl)-N-(5-methyl-1,3,4-thiadiazol-2-yl)benzamide hydrochloride [optical isomer, compound derived from methyl 3-(trans-2-((tert-butoxycarbonyl)amino)cyclopropyl)benzoate (optical isomer, retention time long)] (139 mg) was dissolved in water, a saturated aqueous sodium hydrogen carbonate solution was added, and the mixture was extracted with an ethyl acetate/THF mixture. The extracts were combined, washed with saturated brine, dried over anhydrous sodium sulfate, and concentrated under reduced pressure. The residue was dissolved in methanol (7.00 mL)/ethyl acetate (3.00 mL), a solution of fumaric acid (41.8 mg) in methanol (3.00 mL) was added, and the mixture was stirred at room temperature for 40 min. The reaction mixture was concentrated under reduced pressure, and the residue was recrystallized from methanol/diisopropy ether to give the title compound (81.3 mg).

$^1$H NMR (300 MHz, DMSO-d$_6$) δ0.97-1.13 (2H, m), 1.49-1.66 (2H, m), 1.68-1.82 (2H, m), 1.85-1.93 (1H, m), 2.00-2.17 (2H, m), 2.29-2.35 (1H, m), 2.40-2.46 (1H, m), 2.64 (3H, s), 6.59 (1H, s), 7.33-7.44 (2H, m), 7.68-7.73 (1H, m), 7.79-7.87 (1H, m). HPLC retention time 9.640 min (column: CHIROBIOTIC V2 (trade name), 4.6 mmID×250 mmL, manufactured by Sigma-Aldrich Co. LLC, mobile phase: methanol/triethylammonium acetate=1000/1, flow rate: 1.0 mL/min, temperature: 30° C., detection: UV 254 nm, concentration: 0.5 mg/mL, injection volume: 0.010 mL)

Example 254

3-(trans-2-(cyclobutylamino)cyclopropyl)-N-(5-methyl-1,3,4-thiadiazol-2-yl)benzamide 1/2 fumarate (optical isomer, retention time short)

By a method similar to that in Example 253, the compound of Example 254 was produced.

Example 255

3-(trans-2-((1-cyclopropylpiperidin-4-yl)amino)cyclopropyl)-N-(5-methyl-1,3,4-thiadiazol-2-yl)benzamide acetate [optical isomer, compound derived from methyl 3-(trans-2-((tert-butoxycarbonyl) amino)cyclopropyl)benzoate (optical isomer, retention time long)]

3-(trans-2-Aminocyclopropyl)-N-(5-methyl-1,3,4-thiadiazol-2-yl)benzamide dihydrochloride [optical isomer, compound derived from methyl 3-(trans-2-((tert-butoxycarbonyl)amino)cyclopropyl)benzoate (optical isomer, retention time long)] (250 mg) and borane-2-methylpyridine complex (116 mg) were dissolved in methanol (15.0 mL)/acetic acid (1.50 mL), 1-cyclopropylpiperidin-4-one (0.174 mL) was added under ice-cooling, and the mixture was stirred at room temperature overnight. To the reaction mixture was added diisopropy ether, and the resulting precipitate was filtrated to give the title compound (300 mg).

$^1$H NMR (300 MHz, DMSO-d$_6$) δ0.68-0.88 (2H, m), 1.01-1.16 (2H, m), 1.41-1.53 (1H, m), 1.57-1.68 (1H, m), 1.91 (3H, s), 1.95-2.13 (2H, m), 2.19-2.34 (2H, m), 2.58-2.68 (4H, m), 2.71-2.78 (1H, m), 3.05-3.23 (3H, m), 3.45-3.67 (3H, m), 7.46-7.58 (2H, m), 7.82-7.90 (1H, m), 7.91-7.98 (1H, m), 9.82-10.34 (2H, m), 12.84 (1H, brs).

Example 256

3-(trans-2-((1-cyclopropylpiperidin-4-yl)amino)cyclopropyl)-N-(5-methyl-1,3,4-thiadiazol-2-yl)benzamide acetate [optical isomer, compound derived from methyl 3-(trans-2-((tert-butoxycarbonyl) amino)cyclopropyl)benzoate (optical isomer, retention time short)]

By a method similar to that in Example 255, the compound of Example 256 was produced.

Example 257

3-(trans-2-((1-cyclopropylpiperidin-4-yl)amino)cyclopropyl)-N-(5-methyl-1,3,4-thiadiazol-2-yl)benzamide difumarate (optical isomer, retention time long)

3-(trans-2-((1-Cyclopropylpiperidin-4-yl)amino)cyclopropyl)-N-(5-methyl-1,3,4-thiadiazol-2-yl)benzamide acetate [optical isomer, compound derived from methyl 3-(trans-2-((tert-butoxycarbonyl)amino)cyclopropyl)-benzoate (optical isomer, retention time long)] (250 mg) was dissolved in water, a saturated aqueous sodium hydrogen carbonate solution was added, and the mixture was extracted with an ethyl acetate/THF mixture. The extracts were combined, washed with saturated brine, dried over anhydrous sodium sulfate, and concentrated under reduced pressure. The residue was dissolved in methanol (8.00 mL)/ethyl acetate (4.00 mL), a solution of fumaric acid (51.7 mg) in methanol (4.00 mL) was added, and the mixture was stirred at room temperature for 40 min. The reaction mixture was concentrated under reduced pressure, and the residue was recrystallized from ethanol/heptane to give the title compound (110 mg).

$^1$H NMR (300 MHz, DMSO-$d_6$) δ0.22-0.30 (2H, m), 0.34-0.43 (2H, m), 1.07-1.18 (2H, m), 1.24-1.32 (2H, m), 1.51-1.62 (1H, m), 1.71-1.83 (2H, m), 1.89-1.97 (1H, m), 2.10-2.23 (1H, m), 2.39-2.44 (1H, m), 2.56-2.62 (1H, m), 2.65 (3H, s), 2.82-2.92 (2H, m), 6.59 (4H, s), 7.34-7.45 (2H, m), 7.69-7.74 (1H, m), 7.80-7.87 (1H, m).

HPLC retention time 20.804 min (column: CHIROBIOTIC V2 (trade name), 4.6 mmID×250 mmL, manufactured by Sigma-Aldrich Co. LLC, mobile phase: methanol/triethylamine/acetic acid=1000/0.1/0.1, flow rate: 1.0 mL/min, temperature: 30° C., detection: UV 254 nm, concentration: 0.5 mg/mL, injection volume: 0.010 mL)

Example 258

3-(trans-2-((1-cyclopropylpiperidin-4-yl)amino)cyclopropyl)-N-(5-methyl-1,3,4-thiadiazol-2-yl)benzamide difumarate (optical isomer, retention time short)

By a method similar to that in Example 257, the compound of Example 258 was produced.

Example 259

3-(trans-2-((4,4-difluorocyclohexyl)amino)cyclopropyl)-N-(tetrahydro-2H-pyran-4-yl)benzamide hydrochloride (optical isomer, retention time long)

3-(trans-2-Aminocyclopropyl)-N-(tetrahydro-2H-pyran-4-yl)benzamide hydrochloride [optical isomer, compound derived from methyl 3-(trans-2-((tert-butoxycarbonyl)amino) cyclopropyl)benzoate (optical isomer, retention time long)] (200 mg) and borane-2-methylpyridine complex (108 mg) were dissolved in methanol (2.00 mL)/acetic acid (0.20 mL), 4,4-difluorocyclohexanone (136 mg) was added, and the mixture was stirred at room temperature overnight. To the reaction mixture was added a saturated aqueous sodium hydrogen carbonate solution, and the mixture was extracted with ethyl acetate. The extracts were combined, washed successively with water and saturated brine, dried over anhydrous magnesium sulfate, and concentrated under reduced pressure. The residue was purified by NH silica gel column chromatography (hexane/ethyl acetate), and a 4 mol/L hydrogen chloride/ethyl acetate solution was added to the obtained fraction. The solvent was evaporated under reduced pressure, and the residue was recrystallized from ethanol/heptane to give the title compound (229 mg).

$^1$H NMR (300 MHz, DMSO-$d_6$) δ1.32-1.45 (1H, m), 1.49-2.24 (13H, m), 2.53-2.64 (1H, m), 2.96-3.12 (1H, m), 3.33-3.47 (3H, m), 3.83-4.08 (3H, m), 7.31-7.44 (2H, m), 7.63 (1H, s), 7.67-7.74 (1H, m), 8.26-8.35 (1H, m), 9.29-9.63 (2H, m).

mp 204-205° C.

Anal. Calcd for $C_{21}H_{28}N_2O_2F_2$-HCl: C, 60.79; H, 7.04; N, 6.75.

Found: C, 60.74; H, 6.98; N, 6.76.

HPLC retention time 25.020 min (column: CHIROBIOTIC V2 (trade name), 4.6 mmID×250 mmL, manufactured by Sigma-Aldrich Co. LLC, mobile phase: methanol/triethylamine/acetic acid=1000/0.125/0.375, flow rate: 0.5 mL/min, temperature: 30° C., detection: UV 220 nm, concentration: 0.5 mg/mL injection volume: 0.010 mL)

Example 260

3-(trans-2-((4,4-difluorocyclohexyl)amino)cyclopropyl)-N-(tetrahydro-2H-pyran-4-yl)benzamide hydrochloride (optical isomer, retention time short)

By a method similar to that in Example 259, the compound of Example 260 was produced.

Example 261

3-(trans-2-(cyclobutylamino)cyclopropyl)-N-(tetrahydro-2H-pyran-4-yl)benzamide hydrochloride (optical isomer, retention time long)

3-(trans-2-Aminocyclopropyl)-N-(tetrahydro-2H-pyran-4-yl)benzamide hydrochloride [optical isomer, compound derived from methyl 3-(trans-2-((tert-butoxycarbonyl) amino)cyclopropyl)benzoate (optical isomer, retention time long)] (350 mg) and borane-2-methylpyridine complex (189 mg) were dissolved in methanol (4.00 mL)/acetic acid (0.40 mL), cyclobutanone (0.097 mL) was added, and the mixture was stirred at room temperature for 18 hr. Under ice-cooling, to the reaction mixture was added a saturated aqueous sodium hydrogen carbonate solution, and the mixture was extracted with ethyl acetate. The extracts were combined, washed successively with water and saturated brine, dried over anhydrous sodium sulfate, and concentrated under reduced pressure. The residue was purified by silica gel column chromatography (ethyl acetate/methanol), and a 4 mol/L hydrogen chloride/ethyl acetate solution was added to the obtained fraction. The solvent was evaporated under reduced pressure, and the residue was recrystallized from ethanol/heptane to give the title compound (275 mg).

$^1$H NMR (300 MHz, DMSO-$d_6$) δ1.25-1.39 (1H, m), 1.43-1.67 (3H, m), 1.68-1.90 (4H, m), 2.12-2.30 (4H, m), 2.42-2.48 (1H, m), 2.84-2.94 (1H, m), 3.33-3.44 (2H, m), 3.77-4.07 (4H, m), 7.28-7.43 (2H, m), 7.58-7.63 (1H, m), 7.66-7.73 (1H, m), 8.23-8.33 (1H, m), 9.22-9.55 (2H, m).

mp 188-190° C.

Anal. Calcd for $C_{19}H_{26}N_2O_2$-HCl: C, 65.04; H, 7.76; N, 7.98.

Found: C, 64.97; H, 7.69; N, 7.95.

HPLC retention time 16.273 min (column: CHIROBIOTIC V2 (trade name), 4.6 mmID×250 mmL manufactured by Sigma-Aldrich Co. LLC, mobile phase: methanol/triethylamine/acetic acid=1000/0.25/0.75, flow rate: 1.0 mL/min, temperature: 30° C., detection: UV 220 nm, concentration: 0.5 mg/mL, injection volume: 0.010 mL)

Example 262

3-(trans-2-(cyclobutylamino)cyclopropyl)-N-(tetrahydro-2H-pyran-4-yl)benzamide hydrochloride (optical isomer, retention time short)

By a method similar to that in Example 261, the compound of Example 262 was produced.

Example 263

N-cyclopentyl-3-(trans-2-(tetrahydro-2H-pyran-4-ylamino)cyclopropyl)benzamide hydrochloride (optical isomer, retention time long)

3-(trans-2-Aminocyclopropyl)-N-cyclopentylbenzamide hydrochloride [optical isomer, compound derived from methyl 3-(trans-2-((tert-butoxycarbonyl)amino)cyclopropyl)benzoate (optical isomer, retention time long)] (300 mg) and borane-2-methylpyridine complex (171 mg) were dissolved in methanol (3.00 mL)/acetic acid (mL), dihydro-2H-pyran-4(3H)-one (0.310 mL) was added, and the mixture was stirred at room temperature for 18 hr. To the reaction mixture was added a saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (ethyl acetate/hexane), and a 4 mol/L hydrogen chloride/ethyl acetate solution (0.534 mL) was added to the obtained fraction. The solvent was evaporated under reduced pressure, and the residue was recrystallized from ethanol/heptane to give the title compound (300 mg).
$^1$H NMR (300 MHz, DMSO-d$_6$) δ1.32-1.43 (1H, m), 1.45-1.78 (9H, m), 1.81-2.03 (4H, m), 2.38-2.59 (1H, m), 2.96-3.09 (1H, m), 3.24-3.38 (2H, m), 3.39-3.55 (1H, m), 3.85-3.98 (2H, m), 4.14-4.29 (1H, m), 7.30-7.42 (2H, m), 7.58-7.65 (1H, m), 7.66-7.72 (1H, m), 8.17-8.32 (1H, m), 9.14-9.50 (2H, m).
mp 195-196° C.
Anal. Calcd for $C_{20}H_{28}N_2O_2$—HCl: C, 65.83; H, 8.01; N, 7.68.
Found: C, 65.78; H, 7.97; N, 7.65.
HPLC retention time 4.542 min (column: CHIRALCEL ODRH (trade name), 4.6 mmID×250 mmL, manufactured by Daicel Corporation, mobile phase: water/acetonitrile/TFA=800/200/1, flow rate: 1.0 mL/min, temperature: 30° C., detection: UV 254 nm, concentration: 0.5 mg/mL, injection volume: 0.010 mL)

Example 264

N-cyclopentyl-3-(trans-2-(tetrahydro-2H-pyran-4-ylamino)cyclopropyl)benzamide hydrochloride (optical isomer, retention time short)

By a method similar to that in Example 263, the compound of Example 264 was produced.

Example 265

N-(4,4-difluorocyclohexyl)-3-(trans-2-(tetrahydro-2H-pyran-4-ylamino)cyclopropyl)benzamide hydrochloride (optical isomer, retention time long)

3-(trans-2-Aminocyclopropyl)-N-(4,4-difluorocyclohexyl)benzamide hydrochloride [optical isomer, compound derived from methyl 3-(trans-2-((tert-butoxycarbonyl)amino)cyclopropyl)benzoate (optical isomer, retention time long)] (200 mg) and borane-2-methylpyridine complex (97.0 mg) were dissolved in methanol (20.0 mL)/acetic acid (2.00 mL), dihydro-2H-pyran-4(3H)-one (0.175 mL) was added, and the mixture was stirred at room temperature for 18 hr. To the reaction mixture was added a saturated aqueous sodium hydrogen carbonate solution under ice-cooling, and the mixture was extracted with ethyl acetate. The extract was washed successively with water and saturated brine, dried over anhydrous sodium sulfate, and concentrated under reduced pressure. The residue was purified by NH silica gel column chromatography (hexane/ethyl acetate) and concentrated under reduced pressure. The obtained residue was dissolved in methanol (5.00 mL) a 4 mol/L hydrogen chloride/ethyl acetate solution (0.756 mL) was added, and the mixture was stirred at 0° C. for 16 hr. The solvent was evaporated under reduced pressure, and the residue was recrystallized from ethanol/heptane to give the title compound (111 mg).
$^1$H NMR (300 MHz, DMSO-d$_6$) δ1.33-1.44 (1H, m), 1.47-1.55 (1H, m), 1.57-1.72 (4H, m), 1.79-2.15 (9H, m), 2.98-3.09 (1H, m), 3.26-3.38 (2H, m), 3.41-3.57 (1H, m), 3.87-4.06 (3H, m), 7.32-7.37 (1H, m), 7.37-7.43 (1H, m), 7.61 (1H, s), 7.70 (1H, d, J=7.2 Hz), 8.26 (1H, d, J=8.0 Hz), 9.19 (2H, brs).
mp 199-201° C.
Anal. Calcd for $C_{21}H_{28}N_2O_2F_2$-HCl: C, 60.79; H, 7.04; N, 6.75.
Found: C, 60.81; H, 7.08; N, 6.78.
HPLC retention time 6.404 min (column: CHIRALCEL ODRH (trade name), 4.6 mmID×250 mmL, manufactured by Daicel Corporation, mobile phase: water/acetonitrile/TFA=800/200/1, flow rate: 1.0 mL/min, temperature: 30° C., detection: UV 254 nm, concentration: 0.5 mg/mL, injection volume: 0.010 mL)

Example 266

N-(4,4-difluorocyclohexyl)-3-(trans-2-(tetrahydro-2H-pyran-4-ylamino)cyclopropyl)benzamide hydrochloride (optical isomer, retention time short)

By a method similar to that in Example 265, the compound of Example 266 was produced.

Example 267

3-(trans-2-((cyclopropylmethyl)amino)cyclopropyl)-N-(4,4-difluorocyclohexyl)benzamide hydrochloride (optical isomer, retention time long)

A) tert-butyl (cyclopropylmethyl) (trans-2-(3-((4,4-difluorocyclohexyl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)]

3-(trans-2-Aminocyclopropyl)-N-(4,4-difluorocyclohexyl)benzamide hydrochloride [optical isomer, compound derived from methyl 3-(trans-2-((tert-butoxycarbonyl)amino)cyclopropyl)benzoate (optical isomer, retention time long)] (200 mg) and sodium hydrogen carbonate (152 mg) were dissolved in THF (5.00 mL)/methanol (5.00 mL), and cyclopropanecarbaldehyde (0.056 mL) was added. The reaction mixture was stirred at 60° C. for 2 hr under a nitrogen atmosphere, and sodium borohydride (45.7 mg) was added under ice-cooling. The reaction mixture was stirred at room temperature for 2 hr, to the reaction mixture was added di-tert-butyl dicarbonate (0.211 mL), and the mixture was stirred at room temperature for 16 hr. The reaction mixture was poured into water, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (128 mg).

$^1$H NMR (300 MHz, CDCl$_3$) δ0.11-0.19 (1H, m), 0.21-(1H, m), 0.38-0.54 (2H, m), 0.94-1.08 (1H, m), 1.20-1.33 (2H, m), 1.43 (9H, s), 1.54-1.76 (4H, m), 1.78-2.04 (2H, m), 2.12-2.20 (3H, m), 2.84-2.91 (1H, m), 3.01 (1H, dd, J=14.4, 7.2 Hz), 3.29 (1H, dd, J=14.4, 6.8 Hz), 4.03-4.17 (1H, m), 6.04 (1H, brs), 7.26-7.30 (1H, m), 7.30-7.36 (1H, m), 7.50 (1H, dt, J=7.2, 1.7 Hz), 7.55 (1H, s).

B) 3-(trans-2-((cyclopropylmethyl)amino)cyclopropyl)-N-(4,4-difluorocyclohexyl)benzamide hydrochloride (optical isomer, retention time long)

tert-Butyl (cyclopropylmethyl)(trans-2-(3-((4,4-difluorocyclohexyl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (128 mg) was dissolved in THF (2.50 mL)/methanol (2.50 mL), a 4 mol/L hydrogen chloride/ethyl acetate solution (1.07 mL) was added at 0° C., and the mixture was stirred at room temperature for 18 hr. The reaction mixture was concentrated under reduced pressure, and the residue was crystallized from ethanol/heptane to give the title compound (79.1 mg).

$^1$H NMR (300 MHz, DMSO-d$_6$) δ0.31-0.41 (2H, m), 0.54-0.62 (2H, m), 0.99-1.12 (1H, m), 1.31-1.40 (1H, m), 1.49-1.59 (1H, m), 1.60-1.72 (2H, m), 1.81-1.97 (3H, m), 1.98-2.12 (3H, m), 2.53-2.59 (1H, m), 2.93-3.05 (3H, m), 3.99 (1H, q, J=8.7 Hz), 7.31-7.36 (1H, m), 7.36-7.42 (1H, m), 7.61 (1H, s), 7.67-7.73 (1H, m), 8.27 (1H, d, J=7.2 Hz), 9.16 (2H, brs).

mp 179-181° C.

Anal. Calcd for C$_{20}$H$_{26}$N$_2$OF$_2$—HCl: C, 62.41; H, 7.07; N, 7.28.

Found: C, 62.41; H, 7.20; N, 7.27.

HPLC retention time 40.244 min (column: CHIROBIOTIC V2 (trade name), 4.6 mmID×250 mmL manufactured by Sigma-Aldrich Co. LLC, mobile phase: methanol/triethylamine/acetic acid=1000/0.25/0.75, flow rate: 1.0 mL/min, temperature: 30° C., detection: UV 220 nm, concentration: 0.5 mg/mL, injection volume: 0.010 mL)

Example 268

3-(trans-2-((cyclopropylmethyl)amino)cyclopropyl)-N-(4,4-difluorocyclohexyl)benzamide hydrochloride (optical isomer, retention time short)

By a method similar to that in Example 267, the compound of Example 268 was produced.

Example 269

3-(trans-2-((cyclopropylmethyl)amino)cyclopropyl)-N-(1-(2,2,2-trifluoroethyl)piperidin-4-yl)benzamide dihydrochloride (optical isomer, retention time long)

A) tert-butyl (cyclopropylmethyl) (trans-2-(3-((1-(2,2,2-trifluoroethyl)piperidin-4-yl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)]

3-(trans-2-Aminocyclopropyl)-N-(1-(2,2,2-trifluoroethyl)piperidin-4-yl)benzamide dihydrochloride [optical isomer, compound derived from methyl 3-(trans-2-((tert-butoxycarbonyl)amino)cyclopropyl)benzoate (optical isomer, retention time long)] (302 mg) and sodium hydrogen carbonate (184 mg) were dissolved in THF (5.00 mL)/methanol (5.00 mL), and cyclopropanecarbaldehyde (0.068 mL) was added. The reaction mixture was stirred at 60° C. for 3 hr under a nitrogen atmosphere, and sodium borohydride (55.2 mg) was added under ice-cooling. The reaction mixture was stirred at room temperature for 2 hr, to the reaction mixture was added di-tert-butyl dicarbonate (0.254 mL), and the mixture was stirred at room temperature for 16 hr. The reaction mixture was poured into water, and the mixture was extracted with ethyl acetate. The extract was washed with water and saturated brine, dried over anhydrous sodium sulfate, and concentrated under reduced pressure. The residue was purified by silica gel column chromatography (hexane/ethyl acetate) to give the title compound (177 mg).

MS (API+): [M+H]$^+$ 496.3.

B) 3-(trans-2-((cyclopropylmethyl)amino)cyclopropyl)-N-(1-(2,2,2-trifluoroethyl)piperidin-4-yl)benzamide dihydrochloride (optical isomer, retention time long)

tert-Butyl (cyclopropylmethyl) (trans-2-(3-((1-(2,2,2-trifluoroethyl)piperidin-4-yl)carbamoyl)phenyl)cyclopropyl)carbamate [optical isomer, compound derived from methyl 3-(trans-2-((tert-butoxycarbonyl)amino)cyclopropyl)benzoate (optical isomer, retention time long)] (177 mg) was dissolved in THF (2.50 mL)/methanol (2.50 mL), and the mixture was cooled to 0° C. A 4 mol/L hydrogen chloride/ethyl acetate solution (1.34 mL) was added, and the mixture was stirred at room temperature for 18 hr. The reaction mixture was concentrated under reduced pressure to give the title compound (192 mg).

$^1$H NMR (300 MHz, DMSO-d$_6$) δ0.33-0.41 (2H, m), 0.52-0.61 (2H, In), 1.02-1.17 (1H, m), 1.30-1.39 (1H, m), 1.47-1.55 (1H, m), 1.56-1.65 (1H, m), 1.69-1.81 (1H, m), 1.84-2.02 (3H, m), 2.61 (1H, ddd, J=9.9, 6.3, 3.4 Hz), 2.86-3.09 (4H, m), 3.26-3.36 (1H, m), 3.41 (1H, t, J=6.4 Hz), 3.64 (1H, t, J=6.6 Hz), 7.31-7.36 (1H, m), 7.36-7.41 (1H, m), 7.67 (1H, s), 7.69-7.73 (1H, m), 8.47 (1H, d, J=7.2 Hz), 9.52 (2H, brs).

HPLC retention time 9.514 min (column: CHIROBTOTIC V2 (trade name), 4.6 mmID×250 mmL, manufactured by Sigma-Aldrich Co. LLC, mobile phase: methanol/triethylamine/acetic acid=1000/1/1, flow rate: 1.0 mL/min, temperature: 30° C., detection: UV 220 nm, concentration: 0.5 mg/mL, injection volume: 0.010 mL)

Example 270

3-(trans-2-((cyclopropylmethyl)amino)cyclopropyl)-N-(1-(2,2,2-trifluoroethyl)piperidin-4-yl)benzamide dihydrochloride (optical isomer, retention time short)

By a method similar to that in Example 269, the compound of Example 270 was produced.

Example 271

3-(trans-2-((cyclopropylmethyl) amino) cyclopropyl)-N-(1-(2,2,2-trifluoroethyl)piperidin-4-yl)benzamide 3/2 fumarate (optical isomer, retention time long) 3-(trans-2-((Cyclopropylmethyl)amino)cyclopropyl)-N-(1-(2,2,2-trifluoroethyl)piperidin-4-yl)benzamide dihydrochloride (optical isomer, retention time long) (167 mg) was dissolved in methanol, a saturated aqueous sodium hydrogen carbonate solution was added under ice-cooling, and the mixture was extracted with ethyl acetate. The extracts were combined, washed successively with water and saturated brine, dried over anhydrous sodium sulfate, and concentrated under reduced pressure. The residue was purified by NH silica gel column chromatography (hexane/ethyl acetate) and concentrated under reduced pressure. The obtained residue was dissolved in ethanol (2.00 mL), a solution of fumaric acid (52.2 mg) in ethanol (3.00 mL) was added, and the mixture was stirred at room temperature for 10 min. The reaction mixture was concentrated under reduced pressure, and the residue was recrystallized from ethanol/heptane to give the title compound (65.4 mg).

$^1$H NMR (300 MHz, DMSO-d$_6$) δ0.09-0.18 (2H, m), 0.37-0.46 (2H, m), 0.82-0.96 (1H, m), 1.02-1.19 (2H, m), 1.50-1.66 (2H, m), 1.70-1.81 (2H, m), 2.01 (1H, dd, J=9.1, 4.9 Hz), 2.36-2.47 (2H, m), 2.58 (2H, d, J=6.8 Hz), 2.88-2.98 (2H, m), 3.16 (2H, q, J 10.2 Hz), 3.25-3.45 (2H, m), 3.68-3.84 (1H, m), 6.58 (3H, s), 7.18-7.24 (1H, m), 7.28-7.35 (1H, m), 7.48 (1H, s), 7.59 (1H, d, J=7.2 Hz), 8.16 (1H, d, J=8.0 Hz).

mp 120-122° C.

Anal. Calcd for $C_{21}H_{28}N_3OF_3 \cdot 1.5C_4H_4O_4$: C, 56.94; H, 6.02; N, 7.38.

Found: C, 56.74; H, 6.09; N, 7.35.

HPLC retention time 9.579 min (column: CHIROBIOTIC V2 (trade name), 4.6 mmID×250 mmL, manufactured by Sigma-Aldrich Co. LLC, mobile phase: methanol/triethylammonium acetate=1000/1, flow rate: 1.0 mL/min, temperature: 30° C., detection: UV 220 nm, concentration: 0.5 mg/mL, injection volume: 0.010 mL)

Example 272

2-(trans-2-aminocyclopropyl)-5-fluoro-N-(5-methyl-1,3,4-thiadiazol-2-yl)benzamide dihydrochloride A) (E)-methyl 3-(2-bromo-4-fluorophenyl)acrylate To a solution of 2-bromo-4-fluorobenzaldehyde (7.68 g) in toluene (20.0 mL) was added methyl 2-(triphenylphosphoranylidene)acetate (3.11 g), and the mixture was stirred at room temperature for 5 hr. To the reaction mixture was added toluene, and the mixture was purified by silica gel column chromatography (hexane/ethyl acetate) to give the title compound (3.90 g).

$^1$H NMR (300 MHz, CDCl$_3$) δ3.82 (3H, s), 6.33 (1H, d, J=16.3 Hz), 7.02-7.10 (1H, m), 7.34-7.39 (1H, m), 7.60 (1H, dd, J=8.9, 5.9 Hz), 7.99 (1H, d, J=16.3 Hz).

B) methyl trans-2-(2-bromo-4-fluorophenyl)cyclopropanecarboxylate

The title compound was obtained by a method similar to that in Example 63, step A.

$^1$H NMR (300 MHz, CDCl$_3$) δ1.28-1.33 (1H, m), 1.59-1.66 (1H, m), 1.73-1.81 (1H, m), 2.60-2.68 (1H, m), 3.75 (3H, s), 6.90-7.04 (2H, m), 7.32 (1H, dd, J=8.3, 2.7 Hz).

C) trans-2-(2-bromo-4-fluorophenyl)cyclopropanecarboxylic acid

Methyl trans-2-(2-bromo-4-fluorophenyl)cyclopropanecarboxylate (840 mg) was dissolved in methanol (15.0 mL)/THF (10.0 mL), a 2 mol/L aqueous sodium hydroxide solution (4.61 mL) was added, and the mixture was stirred at room temperature overnight. To the reaction mixture was added water, and the mixture was washed with diethyl ether. The aqueous layer was neutralized with 6 mol/L hydrochloric acid under ice-cooling, and extracted with ethyl acetate. The extract was washed with saturated brine, dried over anhydrous sodium sulfate, and concentrated under reduced pressure to give the title compound (625 mg).

$^1$H NMR (300 MHz, CDCl$_3$) δ1.35-1.43 (1H, m), 1.64-1.73 (1H, m), 1.74-1.81 (1H, m), 2.66-2.76 (1H, m), 6.91-7.07 (2H, m), 7.33 (1H, dd, J=8.0, 2.7 Hz).

D) methyl 2-(trans-2-((tert-butoxycarbonyl)amino) cyclopropyl)-5-fluorobenzoate

The title compound was obtained by a method similar to that in Example 109, steps A and B.

$^1$H NMR (300 MHz, CDCl$_3$) δ1.17-1.26 (2H, m), 1.46 (9H, s), 2.48-2.58 (2H, m), 3.92 (3H, s), 5.18 (1H, brs), 7.08-7.21 (2H, m), 7.56-7.65 (1H, m).

E) 2-(trans-2-aminocyclopropyl)-5-fluoro-N-(5-methyl-1,3,4-thiadiazol-2-yl)benzamide dihydrochloride The title compound was obtained by a method similar to that in Example 63, steps D-F.

Example 273

2-(trans-2-((1-cyclopropylpiperidin-4-yl)amino)cyclopropyl)-5-fluoro-N-(5-methyl-1,3,4-thiadiazol-2-yl)benzamide dihydrochloride By a method similar to that in Example 175, the compound of Example 273 was produced.

Compounds produced according to the method described in the above-mentioned Examples or a method analogous thereto are shown in the following Tables. In the Tables, MS shows measured values.

TABLE 1-1

| Ex. No. | IUPAC name | structure | salt | MS |
|---|---|---|---|---|
| 1 | 4-(trans-2-aminocyclopropyl)-N-phenylbenzamide hydrochloride | 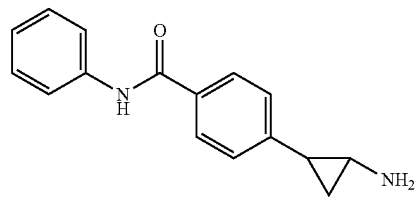 [SMILES: NC1CC1c1ccc(C(=O)Nc2ccccc2)cc1] | HCl | 253.1 |
| 2 | 4-(trans-2-aminocyclopropyl)-N-benzylbenzamide hydrochloride | 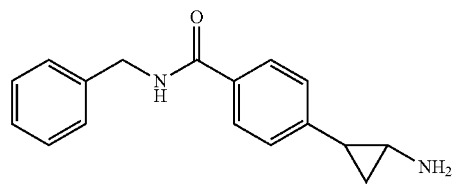 [SMILES: NC1CC1c1ccc(C(=O)NCc2ccccc2)cc1] | HCl | 267.2 |
| 3 | 4-(trans-2-aminocyclopropyl)-N-methyl-N-phenylbenzamide hydrochloride | 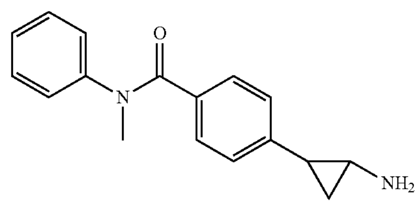 [SMILES: CN(C(=O)c1ccc(C2CC2N)cc1)c1ccccc1] | HCl | 267.2 |
| 4 | 4-(trans-2-aminocyclopropyl)-N-(3-(trifluoromethyl)-phenyl)benzamide hydrochloride | 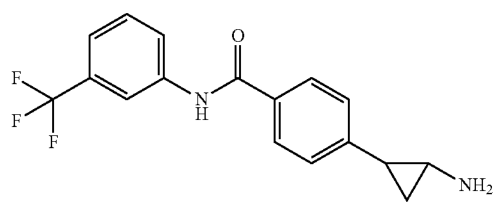 [SMILES: NC1CC1c1ccc(C(=O)Nc2cccc(C(F)(F)F)c2)cc1] | HCl | 321.2 |
| 5 | 4-(trans-2-aminocyclopropyl)-N-(1H-pyrazol-4-yl)benzamide dihydrochloride | 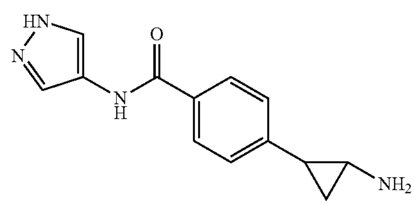 [SMILES: NC1CC1c1ccc(C(=O)Nc2cn[nH]c2)cc1] | 2HCl | 243.2 |
| 6 | 4-(trans-2-aminocyclopropyl)-N-cyclohexylbenzamide hydrochloride | 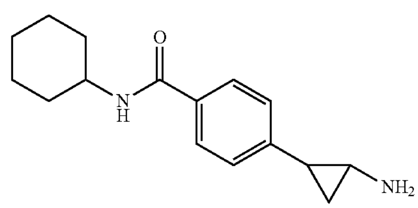 [SMILES: NC1CC1c1ccc(C(=O)NC2CCCCC2)cc1] | HCl | 259.3 |
| 7 | (4-(trans-2-aminocyclopropyl)-phenyl)(piperidin-1-yl)methanone hydrochloride | 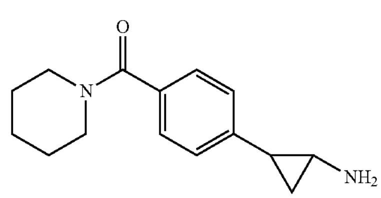 [SMILES: NC1CC1c1ccc(C(=O)N2CCCCC2)cc1] | HCl | 245.3 |

TABLE 1-1-continued

| Ex. No. | IUPAC name | structure | salt | MS |
|---|---|---|---|---|
| 8 | 4-(trans-2-((cyclopropylmethyl)-amino)cyclopropyl)-N-phenylbenzamide hydrochloride | 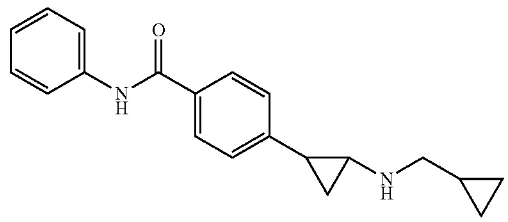 [SMILES: O=C(Nc1ccccc1)c1ccc(C2CC2NCC2CC2)cc1] | HCl | 307.3 |
| 9 | 4-(trans-2-aminocyclopropyl)-N-benzyl-N-methylbenzamide hydrochloride | 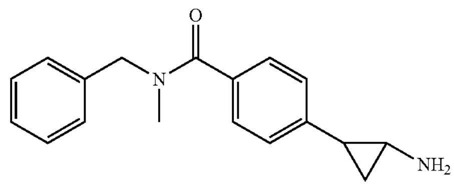 [SMILES: CN(Cc1ccccc1)C(=O)c1ccc(C2CC2N)cc1] | HCl | 281.2 |

TABLE 1-2

| Ex. No. | IUPAC name | structure | salt | MS |
|---|---|---|---|---|
| 10 | N-benzyl-4-(trans-2-((cyclopropylmethyl)-amino)cyclopropyl)-N-methylbenzamide hydrochloride | 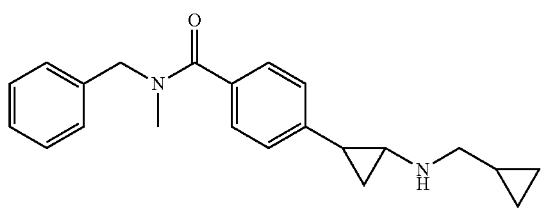 | HCl | 335.2 |
| 11 | 3-(trans-2-aminocyclopropyl)-N-phenylbenzamide hydrochloride | 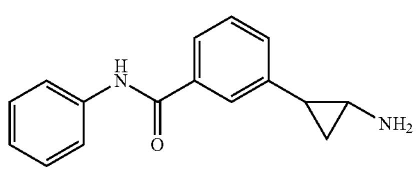 | HCl | 253.3 |
| 12 | 3-(trans-2-aminocyclopropyl)-N-benzylbenzamide hydrochloride | 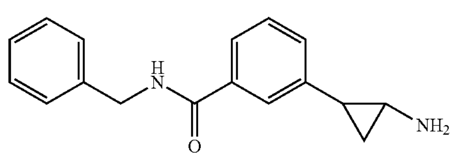 [SMILES: NC1CC1c1cccc(C(=O)NCc2ccccc2)c1] | HCl | 267.2 |
| 13 | 3-(trans-2-((cyclopropylmethyl)-amino)cyclopropyl)-N-phenylbenzamide hydrochloride | 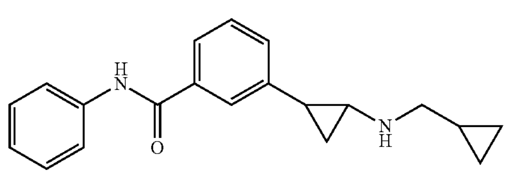 [SMILES: O=C(Nc1ccccc1)c1cccc(C2CC2NCC2CC2)c1] | HCl | 307.3 |
| 14 | N-benzyl-3-(trans-2-((cyclopropylmethyl)-amino)cyclopropyl)-benzamide hydrochloride | 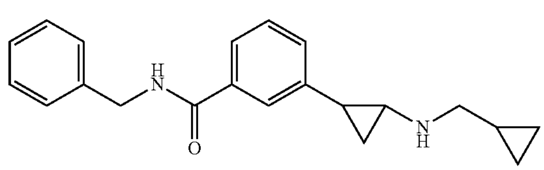 [SMILES: O=C(NCc1ccccc1)c1cccc(C2CC2NCC2CC2)c1] | HCl | 321.2 |

TABLE 1-2-continued

| Ex. No. | IUPAC name | structure | salt | MS |
|---|---|---|---|---|
| 15 | 4-(trans-2-((cyclopropylmethyl)-amino)cyclopropyl)-N-((5-methylpyrazin-2-yl)methyl)benzamide bis(trifluoroacetate) | 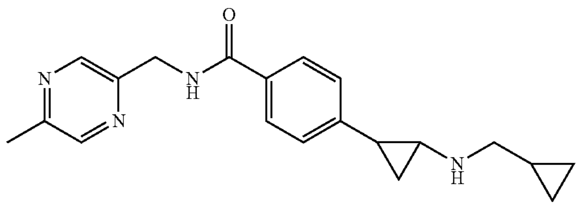 [SMILES: Cc1cnc(CNC(=O)c2ccc(C3CC3NCC3CC3)cc2)cn1] | 2CF3COOH | 337.0 |
| 16 | 4-(trans-2-((cyclopropylmethyl)-amino)cyclopropyl)-N-(pyridin-2-ylmethyl)benzamide bis(trifluoroacetate) | 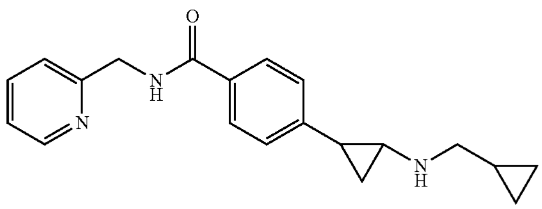 [SMILES: O=C(NCc1ccccn1)c1ccc(C2CC2NCC2CC2)cc1] | 2CF3COOH | 322.0 |
| 17 | 4-(trans-2-((cyclopropylmethyl)-amino)cyclopropyl)-N-(pyridin-4-ylmethyl)benzamide bis(trifluoroacetate) | 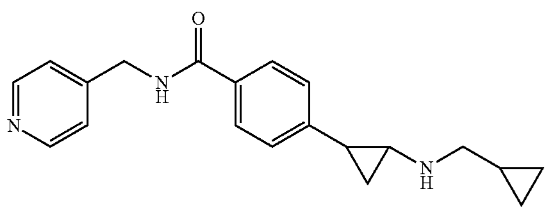 [SMILES: O=C(NCc1ccncc1)c1ccc(C2CC2NCC2CC2)cc1] | 2CF3COOH | 322.4 |
| 18 | 4-(trans-2-((cyclopropylmethyl)-amino)cyclopropyl)-N-(pyridin-3-ylmethyl)benzamide bis(trifluoroacetate) | 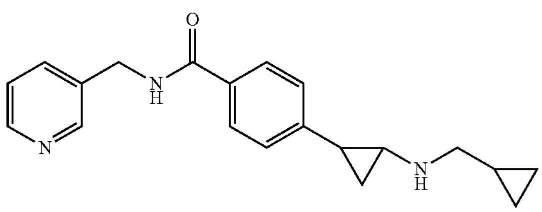 | 2CF3COOH | 322.4 |

TABLE 1-3

| Ex. No. | IUPAC name | structure | salt | MS |
|---|---|---|---|---|
| 19 | 4-(trans-2-((cyclopropylmethyl)-amino)cyclopropyl)-N-(2-(pyridin-2-yl)ethyl)benzamide bis(trifluoroacetate) | 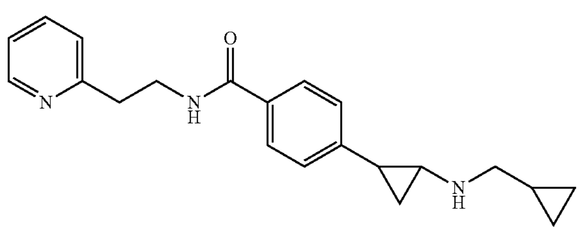 [SMILES: O=C(NCCc1ccccn1)c1ccc(C2CC2NCC2CC2)cc1] | 2CF3COOH | 336.3 |
| 20 | (4-(trans-2-((cyclopropylmethyl)-amino)cyclopropyl)phenyl)(5,7-dihydro-6H-pyrrolo[3,4-b]pyridin-6-yl)methanone bis(trifluoroacetate) | 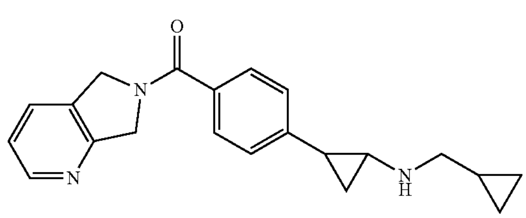 [SMILES: O=C(c1ccc(C2CC2NCC2CC2)cc1)N1Cc2cccnc2C1] | 2CF3COOH | 334.0 |

TABLE 1-3-continued

| Ex. No. | IUPAC name | structure | salt | MS |
|---|---|---|---|---|
| 21 | 4-(trans-2-((cyclopropylmethyl)-amino)cyclopropyl)-N-(3-phenoxybenzyl)benzamide trifluoroacetate | 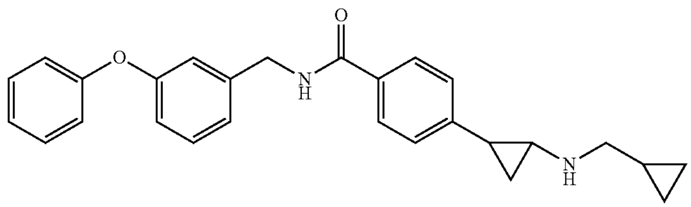 [SMILES: O=C(NCc1cccc(Oc2ccccc2)c1)c1ccc(C2CC2NCC2CC2)cc1] | CF3COOH | 413.4 |
| 22 | N-benzyl-N-(cyanomethyl)-4-(trans-2-((cyclopropyl-methyl)amino)cyclopropyl) benzamide trifluoroacetate | 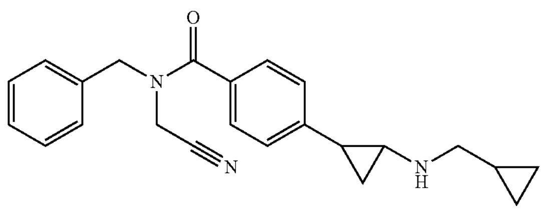 [SMILES: N#CCN(Cc1ccccc1)C(=O)c1ccc(C2CC2NCC2CC2)cc1] | CF3COOH | 360.1 |
| 23 | 4-(trans-2-((cyclopropylmethyl)-amino)cyclopropyl)-N-(4-(4-methylpiperazin-1-yl)phenyl)benzamide tris(trifluoroacetate) | 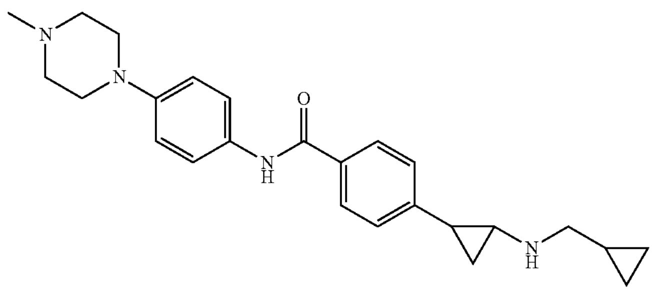 [SMILES: CN1CCN(c2ccc(NC(=O)c3ccc(C4CC4NCC4CC4)cc3)cc2)CC1] | 3CF3COOH | 405.1 |
| 24 | 4-(trans-2-((cyclopropylmethyl)-amino)cyclopropyl)-N-(2-(morpholin-4-yl)-2-phenylethyl)benzamide bis(trifluoroacetate) | 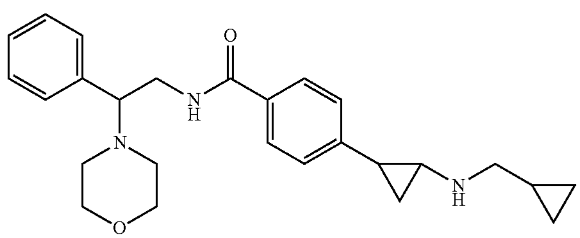 [SMILES: O=C(NCC(c1ccccc1)N1CCOCC1)c1ccc(C2CC2NCC2CC2)cc1] | 2CF3COOH | 420.1 |
| 25 | N-(3-cyanobenzyl)-4-(trans-2-((cyclopropyl-methyl)amino)cyclopropyl) benzamide trifluoroacetate | 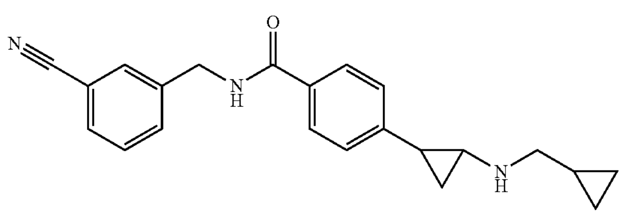 [SMILES: N#Cc1cccc(CNC(=O)c2ccc(C3CC3NCC3CC3)cc2)c1] | CF3COOH | 346.0 |
| 26 | 4-(trans-2-((cyclopropylmethyl)-amino)cyclopropyl)-N-((3-(trifluoromethyl)pyridin-2-yl)methyl)benzamide bis(trifluoroacetate) | 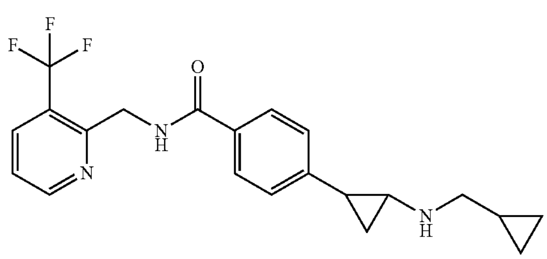 [SMILES: O=C(NCc1ncccc1C(F)(F)F)c1ccc(C2CC2NCC2CC2)cc1] | 2CF3COOH | 390.1 |

TABLE 1-3-continued

| Ex. No. | IUPAC name | structure | salt | MS |
|---|---|---|---|---|
| 27 | 4-(trans-2-((cyclopropylmethyl)-amino)cyclopropyl)-N-(4-(2-oxopyrrolidin-1-yl)benzyl)benzamide trifluoroacetate | 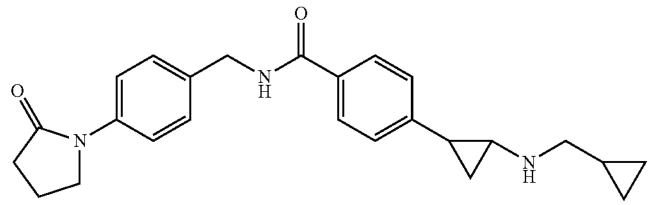 [SMILES: O=C(NCc1ccc(N2CCCC2=O)cc1)c1ccc(C2CC2NCC2CC2)cc1] | CF3COOH | 404.1 |

TABLE 1-4

| Ex. No. | IUPAC name | structure | salt | MS |
|---|---|---|---|---|
| 28 | 4-(trans-2-((cyclopropylmethyl)-amino)cyclopropyl)-N-(4-(morpholin-4-yl)benzyl)benzamide bis(trifluoroacetate) | 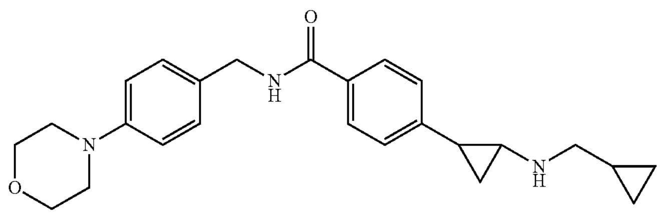 [SMILES: O=C(NCc1ccc(N2CCOCC2)cc1)c1ccc(C2CC2NCC2CC2)cc1] | 2CF3COOH | 406.1 |
| 29 | 4-(trans-2-((cyclopropylmethyl)-amino)cyclopropyl)-N-(3-(pyrazin-2-yloxy)benzyl)benzamide bis(trifluoroacetate) | 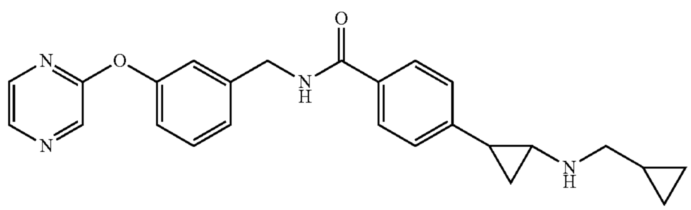 [SMILES: O=C(NCc1cccc(Oc2cnccn2)c1)c1ccc(C2CC2NCC2CC2)cc1] | 2CF3COOH | 415.1 |
| 30 | 4-(trans-2-((cyclopropylmethyl)-amino)cyclopropyl)-N-(2,3-dihydro-1,4-benzodioxin-5-ylmethyl)benzamide trifluoroacetate | 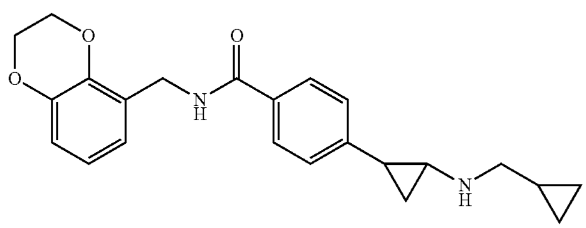 [SMILES: O=C(NCc1cccc2c1OCCO2)c1ccc(C2CC2NCC2CC2)cc1] | CF3COOH | 379.1 |
| 31 | N-benzyl-4-(trans-2-((4-tert-butylbenzyl)-amino)cyclopropyl)-benzamide trifluoroacetate | 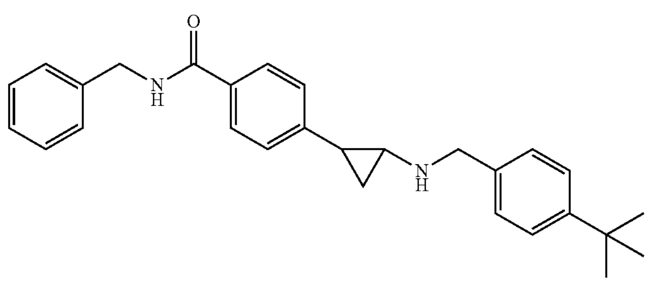 [SMILES: CC(C)(C)c1ccc(CNC2CC2c2ccc(C(=O)NCc3ccccc3)cc2)cc1] | CF3COOH | 413.4 |
| 32 | N-benzyl-4-(trans-2-((2-methoxybenzyl)-amino)cyclopropyl)-benzamide trifluoroacetate | 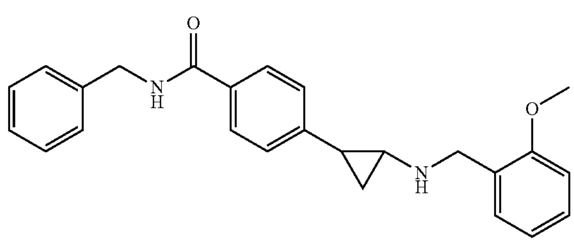 [SMILES: COc1ccccc1CNC1CC1c1ccc(C(=O)NCc2ccccc2)cc1] | CF3COOH | 387.4 |

TABLE 1-4-continued

| Ex. No. | IUPAC name | structure | salt | MS |
|---|---|---|---|---|
| 33 | N-benzyl-4-(trans-2-((2-methylbenzyl)-amino)cyclopropyl)-benzamide trifluoroacetate | 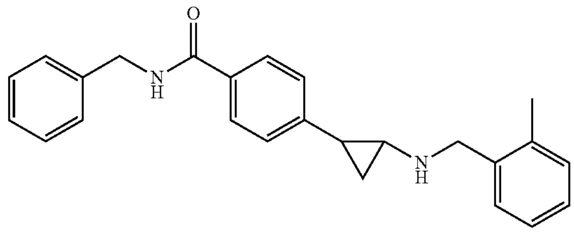 | CF3COOH | 371.4 |
| 34 | N-benzyl-4-(trans-2-((4-methylbenzyl)-amino)cyclopropyl)-benzamide trifluoroacetate | 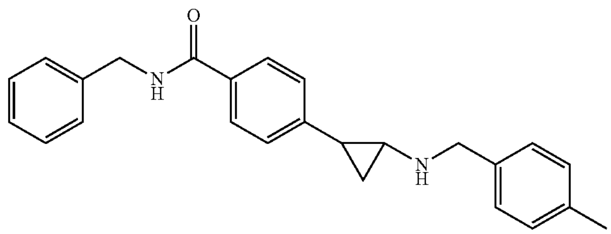 [SMILES: Cc1ccc(CNC2CC2c2ccc(C(=O)NCc3ccccc3)cc2)cc1] | CF3COOH | 371.4 |
| 35 | N-benzyl-4-(trans-2-((4-methoxybenzyl)-amino)cyclopropyl)-benzamide trifluoroacetate | 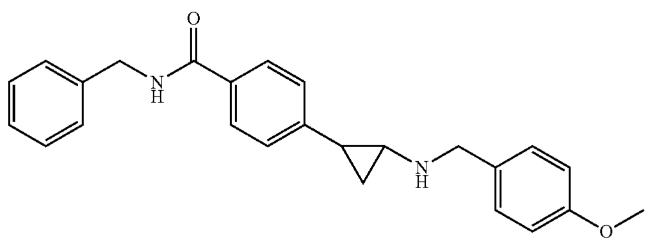 [SMILES: COc1ccc(CNC2CC2c2ccc(C(=O)NCc3ccccc3)cc2)cc1] | CF3COOH | 387.4 |
| 36 | N-benzyl-4-(trans-2-((4-cyanobenzyl)-amino)cyclopropyl)-benzamide trifluoroacetate | 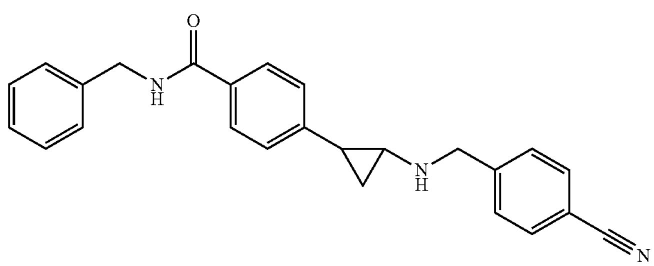 [SMILES: N#Cc1ccc(CNC2CC2c2ccc(C(=O)NCc3ccccc3)cc2)cc1] | CF3COOH | 382.4 |

TABLE 1-5

| Ex. No. | IUPAC name | structure | salt | MS |
|---|---|---|---|---|
| 37 | N-benzyl-4-(trans-2-((3-methoxybenzyl)-amino)cyclopropyl)-benzamide trifluoroacetate | 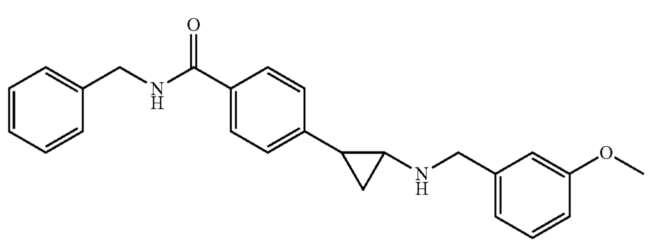 [SMILES: COc1cccc(CNC2CC2c2ccc(C(=O)NCc3ccccc3)cc2)c1] | CF3COOH | 387.4 |

TABLE 1-5-continued

| Ex. No. | IUPAC name | structure | salt | MS |
|---|---|---|---|---|
| 38 | N-benzyl-4-(trans-2-((4-(trifluoromethyl)benzyl)amino)cyclopropyl)benzamide trifluoroacetate | 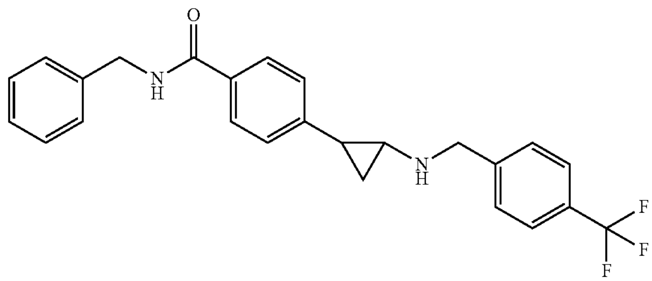 [SMILES: O=C(NCc1ccccc1)c1ccc(C2CC2NCc2ccc(C(F)(F)F)cc2)cc1] | CF3COOH | 425.4 |
| 39 | N-benzyl-4-(trans-2-((2-fluorobenzyl)amino)cyclopropyl)benzamide trifluoroacetate | 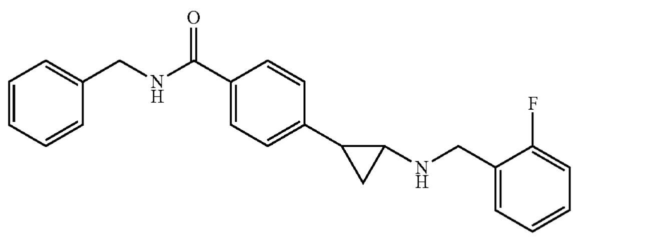 [SMILES: O=C(NCc1ccccc1)c1ccc(C2CC2NCc2ccccc2F)cc1] | CF3COOH | 375.4 |
| 40 | N-benzyl-4-(trans-2-((2-fluoro-5-methoxybenzyl)amino)cyclopropyl)benzamide trifluoroacetate | 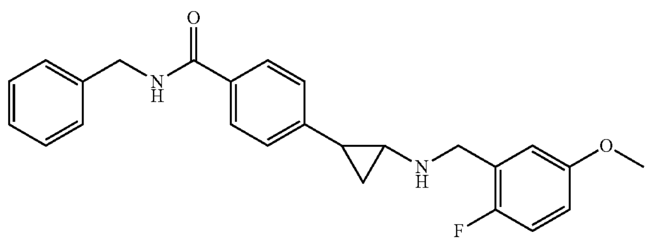 [SMILES: COc1ccc(F)c(CNC2CC2c2ccc(C(=O)NCc3ccccc3)cc2)c1] | CF3COOH | 405.4 |
| 41 | N-benzyl-4-(trans-2-((4-chloro-2-methoxybenzyl)amino)cyclopropyl)benzamide trifluoroacetate | 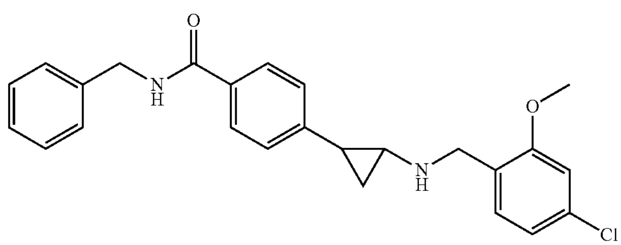 [SMILES: COc1cc(Cl)ccc1CNC1CC1c1ccc(C(=O)NCc2ccccc2)cc1] | CF3COOH | 421.4 |
| 42 | N-benzyl-4-(trans-2-((2-(dimethylamino)benzyl)amino)cyclopropyl)benzamide bis(trifluoroacetate) | 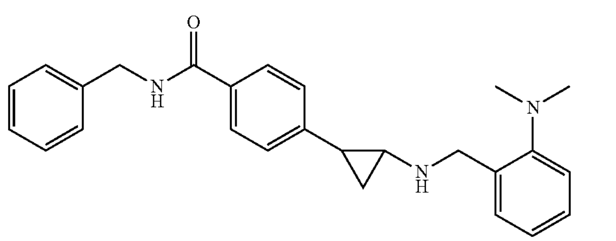 [SMILES: CN(C)c1ccccc1CNC1CC1c1ccc(C(=O)NCc2ccccc2)cc1] | 2CF3COOH | 400.4 |
| 43 | N-benzyl-4-(trans-2-((3-cyanobenzyl)amino)cyclopropyl)benzamide trifluoroacetate | 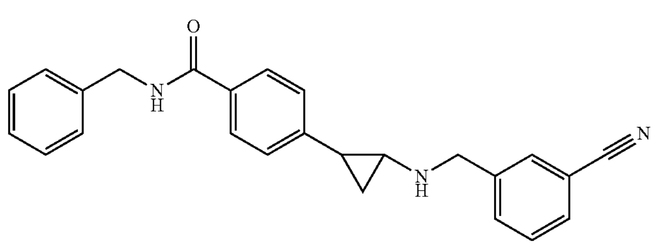 [SMILES: N#Cc1cccc(CNC2CC2c2ccc(C(=O)NCc3ccccc3)cc2)c1] | CF3COOH | 382.4 |

TABLE 1-5-continued

| Ex. No. | IUPAC name | structure | salt | MS |
|---|---|---|---|---|
| 44 | N-benzyl-4-(trans-2-(((3-oxo-3,4-dihydro-2H-1,4-benzoxazin-6-yl)methyl)amino)cyclopropyl)benzamide trifluoroacetate | 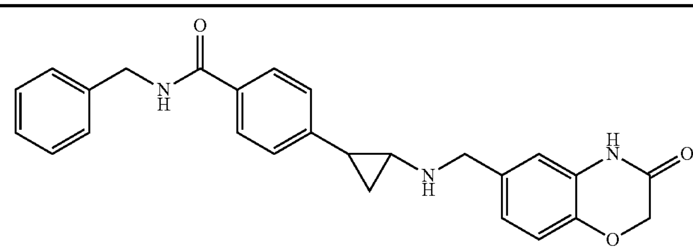 | CF3COOH | 428.4 |
| 45 | N-benzyl-4-(trans-2-((4-(pyrazin-2-yl)benzyl)amino)cyclopropyl)benzamide bis(trifluoroacetate) | 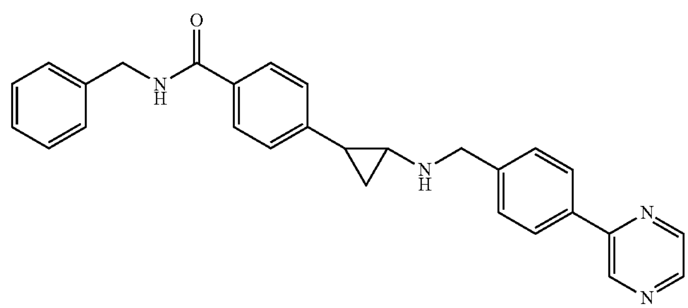 [SMILES: O=C(NCc1ccccc1)c1ccc(C2CC2NCc2ccc(-c3cnccn3)cc2)cc1] | 2CF3COOH | 435.4 |

TABLE 1-6

| Ex. No. | IUPAC name | structure | salt | MS |
|---|---|---|---|---|
| 46 | N-benzyl-4-(trans-2-((2-thienylmethyl)amino)cyclopropyl)benzamide trifluoroacetate | 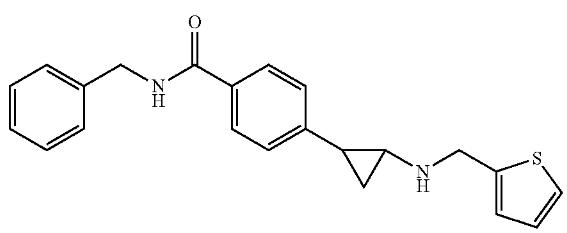 [SMILES: O=C(NCc1ccccc1)c1ccc(C2CC2NCc2cccs2)cc1] | CF3COOH | 363.3 |
| 47 | N-benzyl-4-(trans-2-(((3-methyl-2-thienyl)methyl)amino)cyclopropyl)benzamide trifluoroacetate | 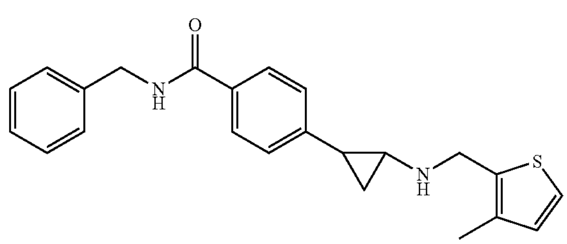 [SMILES: Cc1ccsc1CNC1CC1c1ccc(C(=O)NCc2ccccc2)cc1] | CF3COOH | 377.4 |
| 48 | N-benzyl-4-(trans-2-(((5-methyl-2-thienyl)methyl)amino)cyclopropyl)benzamide trifluoroacetate | 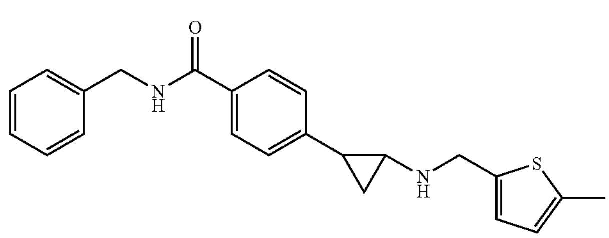 [SMILES: Cc1ccc(CNC2CC2c2ccc(C(=O)NCc3ccccc3)cc2)s1] | CF3COOH | 377.4 |

TABLE 1-6-continued

| Ex. No. | IUPAC name | structure | salt | MS |
|---|---|---|---|---|
| 49 | N-benzyl-4-(trans-2-(((4-methyl-2-thienyl)methyl)amino)cyclopropyl)benzamide trifluoroacetate | 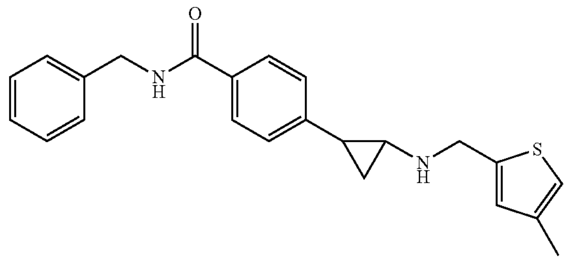 [SMILES: Cc1csc(CNC2CC2c2ccc(C(=O)NCc3ccccc3)cc2)c1] | CF3COOH | 377.4 |
| 50 | 4-(trans-2-aminocyclopropyl)-N-(4-(pyrimidin-2-yl)phenyl)benzamide dihydrochloride | 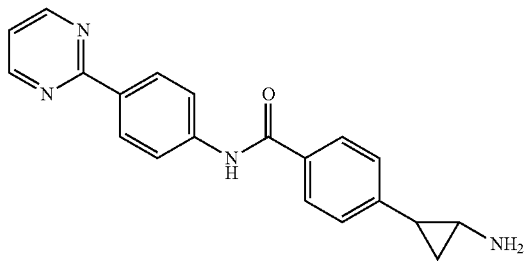 [SMILES: NC1CC1c1ccc(C(=O)Nc2ccc(-c3ncccn3)cc2)cc1] | 2HCl | 331.1 |
| 51 | 4-(trans-2-aminocyclopropyl)-N-(1-methyl-1H-pyrazol-4-yl)benzamide dihydrochloride | 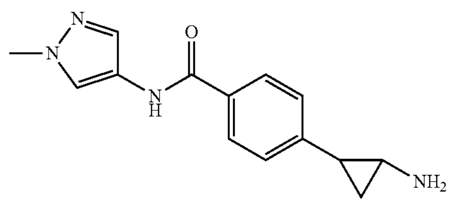 [SMILES: Cn1cc(NC(=O)c2ccc(C3CC3N)cc2)cn1] | 2HCl | 257.2 |
| 52 | 4-(trans-2-((cyclopropylmethyl)amino)cyclopropyl)-N-(4-(pyrimidin-2-yl)phenyl)benzamide dihydrochloride | 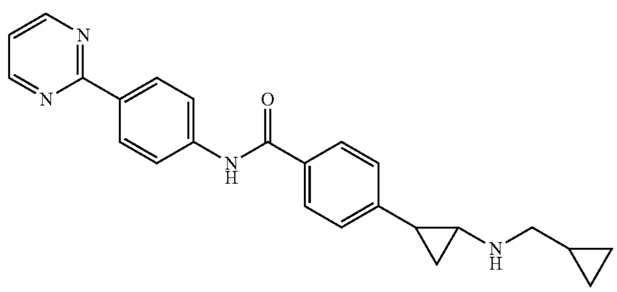 [SMILES: O=C(Nc1ccc(-c2ncccn2)cc1)c1ccc(C2CC2NCC2CC2)cc1] | 2HCl | 385.3 |
| 53 | 4-(trans-2-((cyclopropylmethyl)amino)cyclopropyl)-N-(1-methyl-1H-pyrazol-4-yl)benzamide dihydrochloride | 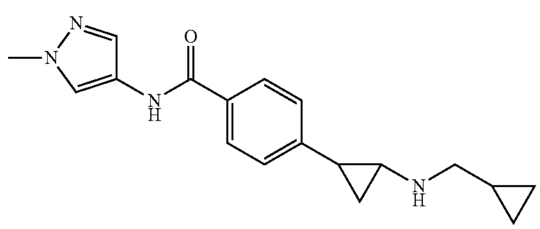 [SMILES: Cn1cc(NC(=O)c2ccc(C3CC3NCC3CC3)cc2)cn1] | 2HCl | 311.2 |
| 54 | 3-(trans-2-aminocyclopropyl)-N-(4-(pyrimidin-2-yl)phenyl)benzamide dihydrochloride | 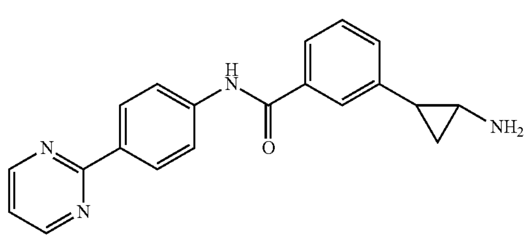 [SMILES: NC1CC1c1cccc(C(=O)Nc2ccc(-c3ncccn3)cc2)c1] | 2HCl | 331.1 |

TABLE 1-7

| Ex. No. | IUPAC name | structure | salt | MS |
|---|---|---|---|---|
| 55 | 3-(trans-2-aminocyclopropyl)-N-(1-methyl-1H-pyrazol-4-yl)benzamide dihydrochloride | 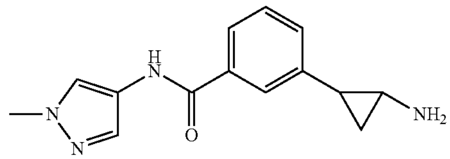 [SMILES: Cn1cc(NC(=O)c2cccc(C3CC3N)c2)cn1] | 2HCl | 257.2 |
| 56 | 3-(trans-2-aminocyclopropyl)-N-cyclopentylbenzamide hydrochloride | 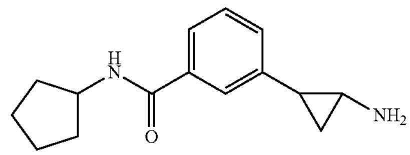 [SMILES: NC1CC1c1cccc(C(=O)NC2CCCC2)c1] | HCl | 245.2 |
| 57 | (3-(trans-2-aminocyclopropyl)phenyl)-(pyrrolidin-1-yl)methanone hydrochloride | 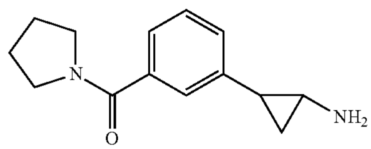 [SMILES: NC1CC1c1cccc(C(=O)N2CCCC2)c1] | HCl | 231.2 |
| 58 | 3-(trans-2-((cyclopropylmethyl)-amino)cyclopropyl)-N-(4-(pyrimidin-2-yl)phenyl)benzamide dihydrochloride | 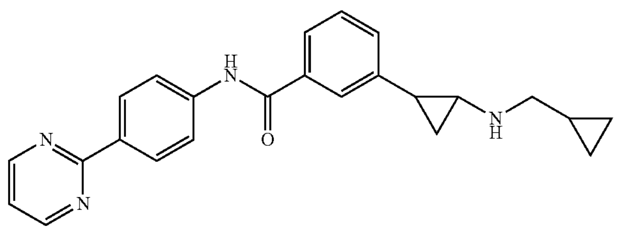 [SMILES: O=C(Nc1ccc(-c2ncccn2)cc1)c1cccc(C2CC2NCC2CC2)c1] | 2HCl | 385.3 |
| 59 | 3-(trans-2-((cyclopropylmethyl)-amino)cyclopropyl)-N-(1-methyl-1H-pyrazol-4-yl)benzamide dihydrochloride | 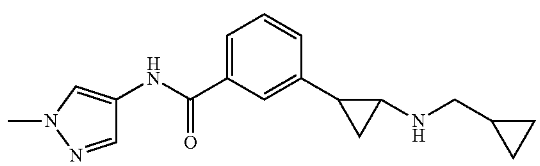 [SMILES: Cn1cc(NC(=O)c2cccc(C3CC3NCC3CC3)c2)cn1] | 2HCl | 311.2 |
| 60 | N-cyclopentyl-3-(trans-2-((cyclopropylmethyl)-amino)cyclopropyl)-benzamide hydrochloride | 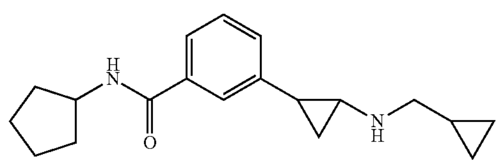 [SMILES: O=C(NC1CCCC1)c1cccc(C2CC2NCC2CC2)c1] | HCl | 299.2 |
| 61 | (3-(trans-2-((cyclopropylmethyl)-amino)cyclopropyl)-phenyl) (pyrrolidin-1-yl)methanone hydrochloride | 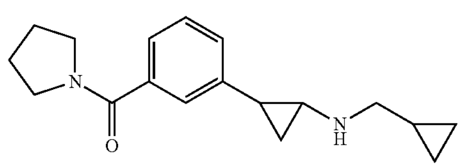 [SMILES: O=C(c1cccc(C2CC2NCC2CC2)c1)N1CCCC1] | HCl | 285.2 |
| 62 | 4-(trans-2-((1,1-dioxidotetrahydro-2H-thiopyran-4-yl)amino)-cyclopropyl)-N-(3-(trifluoromethyl)-phenyl)benzamide hydrochloride | 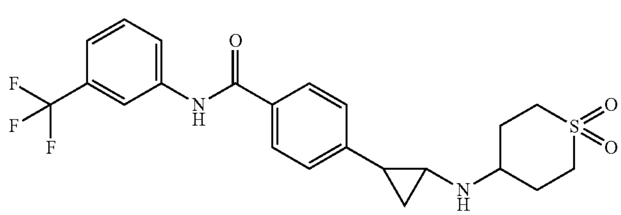 [SMILES: O=C(Nc1cccc(C(F)(F)F)c1)c1ccc(C2CC2NC2CCS(=O)(=O)CC2)cc1] | HCl | 453.2 |

TABLE 1-8

| Ex. No. | IUPAC name | structure | salt | MS |
|---|---|---|---|---|
| 63 | 3-(trans-2-aminocyclopropyl)-N-(1-(cyclopropylmethyl)-1H-pyrazol-4-yl)benzamide dihydrochloride | 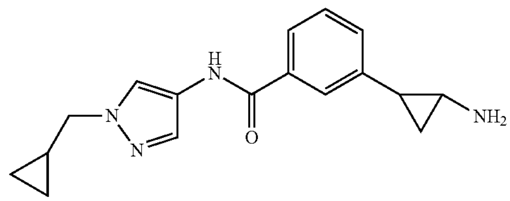 [SMILES: NC1CC1c1cccc(C(=O)Nc2cnn(CC3CC3)c2)c1] | 2HCl | 297.2 |
| 64 | 3-(trans-2-aminocyclopropyl)-N-(5-methyl-1,3,4-thiadiazol-2-yl)benzamide dihydrochloride | 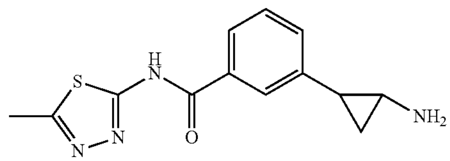 [SMILES: Cc1nnc(NC(=O)c2cccc(C3CC3N)c2)s1] | 2HCl | 275.0 |
| 65 | 3-(trans-2-aminocyclopropyl)-N-(1-tert-butyl-1H-pyrazol-4-yl)benzamide dihydrochloride | 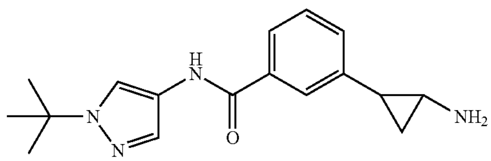 [SMILES: CC(C)(C)n1cc(NC(=O)c2cccc(C3CC3N)c2)cn1] | 2HCl | 299.3 |
| 66 | 3-(trans-2-aminocyclopropyl)-N-(4,4-difluorocyclohexyl)benzamide hydrochloride | 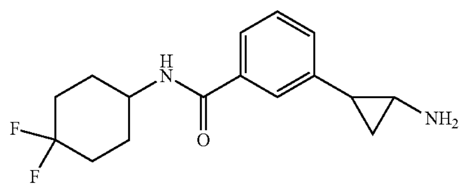 [SMILES: NC1CC1c1cccc(C(=O)NC2CCC(F)(F)CC2)c1] | HCl | 295.1 |
| 67 | 3-(trans-2-aminocyclopropyl)-N-(tetrahydro-2H-pyran-4-yl)benzamide hydrochloride | 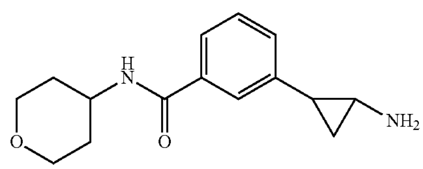 [SMILES: NC1CC1c1cccc(C(=O)NC2CCOCC2)c1] | HCl | 261.1 |
| 68 | 3-(trans-2-aminocyclopropyl)-N-methyl-N-phenylbenzamide hydrochloride | 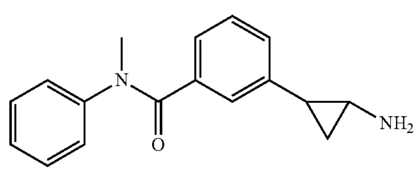 [SMILES: CN(C(=O)c1cccc(C2CC2N)c1)c1ccccc1] | HCl | 267.2 |
| 69 | 3-(trans-2-aminocyclopropyl)-N-(3-(pyrimidin-2-yl)phenyl)benzamide dihydrochloride | 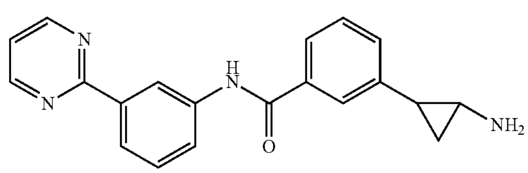 [SMILES: NC1CC1c1cccc(C(=O)Nc2cccc(-c3ncccn3)c2)c1] | 2HCl | 331.2 |
| 70 | 3-(trans-2-aminocyclopropyl)-N-(4-(2-oxopyrrolidin-1-yl)phenyl)benzamide hydrochloride | 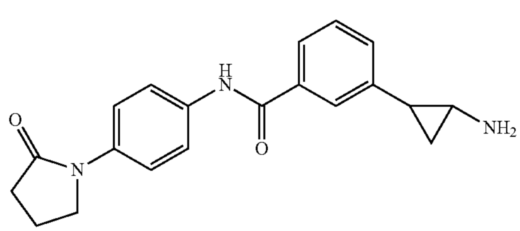 [SMILES: NC1CC1c1cccc(C(=O)Nc2ccc(N3CCCC3=O)cc2)c1] | HCl | 336.1 |

TABLE 1-8-continued

| Ex. No. | IUPAC name | structure | salt | MS |
|---|---|---|---|---|
| 71 | 3-(trans-2-aminocyclopropyl)-N-(1-(4-fluorophenyl)-1H-pyrazol-4-yl)benzamide dihydrochloride | 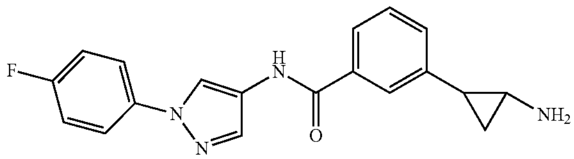 [SMILES: NC1CC1c1cccc(C(=O)Nc2cnn(-c3ccc(F)cc3)c2)c1] | 2HCl | 337.1 |

TABLE 1-9

| Ex. No. | IUPAC name | structure | salt | MS |
|---|---|---|---|---|
| 72 | 3-(trans-2-aminocyclopropyl)-N-(4-fluorophenyl)benzamide hydrochloride | 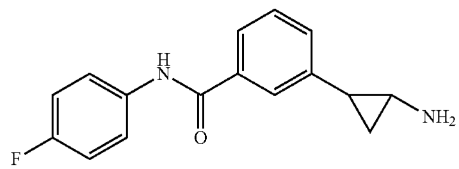 [SMILES: NC1CC1c1cccc(C(=O)Nc2ccc(F)cc2)c1] | HCl | 271.1 |
| 73 | 3-(trans-2-aminocyclopropyl)-N-(1,1-dioxidotetrahydro-2H-thiopyran-4-yl)benzamide hydrochloride | 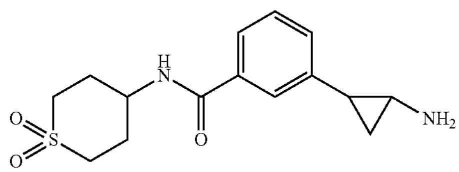 [SMILES: NC1CC1c1cccc(C(=O)NC2CCS(=O)(=O)CC2)c1] | HCl | 309.1 |
| 74 | 3-(trans-2-aminocyclopropyl)-N-(1-ethyl-1H-pyrazol-4-yl)benzamide dihydrochloride | 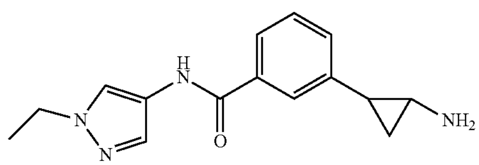 [SMILES: CCn1cc(NC(=O)c2cccc(C3CC3N)c2)cn1] | 2HCl | 271.1 |
| 75 | 5-(trans-2-aminocyclopropyl)-N-cyclopentyl-2-fluorobenzamide hydrochloride | 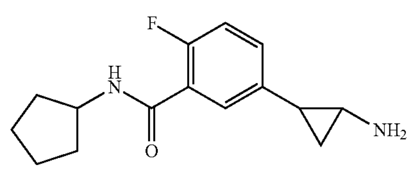 [SMILES: NC1CC1c1ccc(F)c(C(=O)NC2CCCC2)c1] | HCl | 263.1 |
| 76 | 5-(trans-2-aminocyclopropyl)-N-cyclopentyl-2-methoxybenzamide hydrochloride | 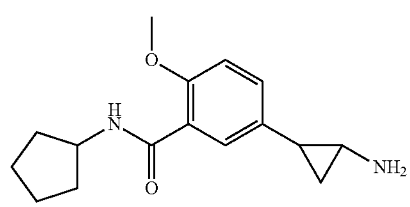 [SMILES: COc1ccc(C2CC2N)cc1C(=O)NC1CCCC1] | HCl | 275.1 |
| 77 | 3-(trans-2-((cyclopropylmethyl)amino)-cyclopropyl)-N-(1-(cyclopropylmethyl)-1H-pyrazol-4-yl)benzamide dihydrochloride | 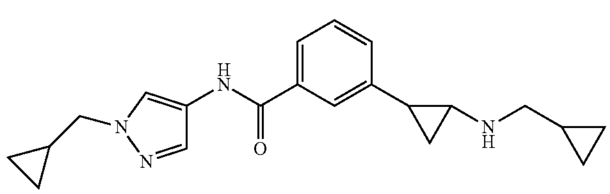 [SMILES: O=C(Nc1cnn(CC2CC2)c1)c1cccc(C2CC2NCC2CC2)c1] | 2HCl | 351.1 |

TABLE 1-9-continued

| Ex. No. | IUPAC name | structure | salt | MS |
|---|---|---|---|---|
| 78 | N-(1-tert-butyl-1H-pyrazol-4-yl)-3-(trans-2-((cyclopropylmethyl)-amino)cyclopropyl)-benzamide dihydrochloride | 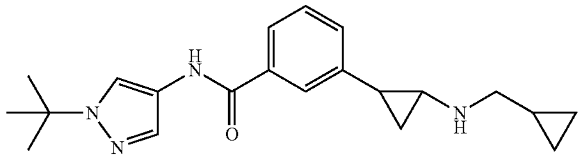 [SMILES: CC(C)(C)n1cc(NC(=O)c2cccc(C3CC3NCC3CC3)c2)cn1] | 2HCl | 353.2 |
| 79 | 3-(trans-2-((cyclopropylmethyl)-amino)cyclopropyl)-N-(2-methyl-1,3-thiazol-5-yl)benzamide dihydrochloride | 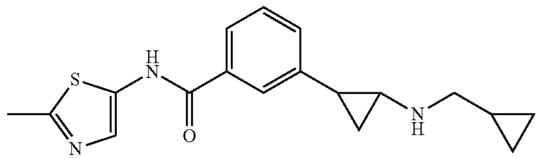 [SMILES: Cc1ncc(NC(=O)c2cccc(C3CC3NCC3CC3)c2)s1] | 2HCl | 328.2 |
| 80 | 3-(trans-2-((cyclopropylmethyl)-amino)cyclopropylmethyl)-methyl-N-phenylbenzamide hydrochloride | 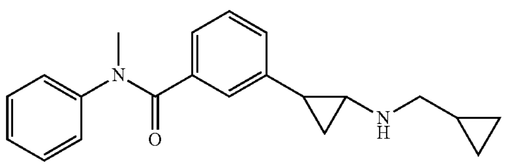 [SMILES: CN(C(=O)c1cccc(C2CC2NCC2CC2)c1)c1ccccc1] | HCl | 321.2 |

TABLE 1-10

| Ex. No. | IUPAC name | structure | salt | MS |
|---|---|---|---|---|
| 81 | 3-(trans-2-((cyclopropyimethyl)amino)-cyclopropyl)-N-(3-(pyrimidin-2-yl)phenyl)benzamide dihydrochloride | 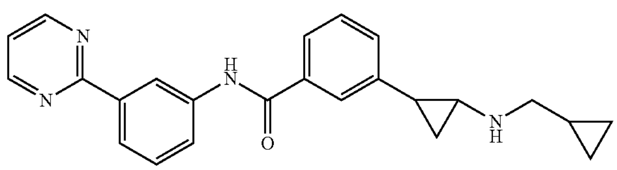 [SMILES: O=C(Nc1cccc(-c2ncccn2)c1)c1cccc(C2CC2NCC2CC2)c1] | 2HCl | 385.1 |
| 82 | 3-(trans-2-((cyclopropylmethyl)amino)-cyclopropyl)-N-(4-(2-oxopyrrolidin-1-yl)phenyl)benzamide hydrochloride | 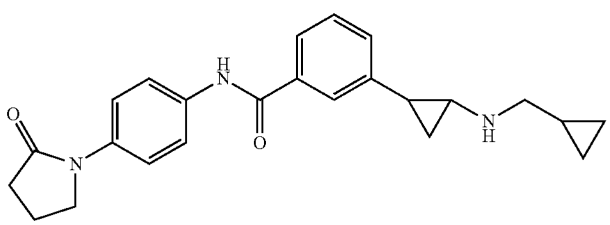 [SMILES: O=C(Nc1ccc(N2CCCC2=O)cc1)c1cccc(C2CC2NCC2CC2)c1] | HCl | 390.1 |
| 83 | N-cyclopentyl-3-(trans-2-((tetrahydro-2H-pyran-4-ylmethyl)amino)cyclopropyl)-benzamide hydrochloride | 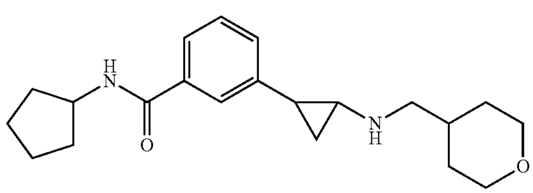 [SMILES: O=C(NC1CCCC1)c1cccc(C2CC2NCC2CCOCC2)c1] | HCl | 343.2 |
| 84 | N-(4,4-difluorocyclohexyl)-3-(trans-2-((tetrahydro-2H-pyran-4-ylmethyl)amino)-cyclopropyl)benzamide hydrochloride | 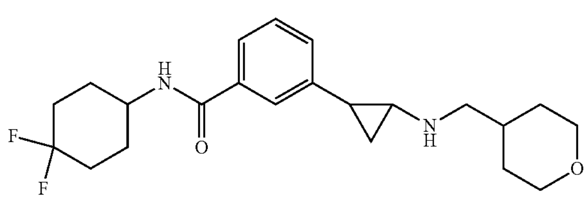 [SMILES: O=C(NC1CCC(F)(F)CC1)c1cccc(C2CC2NCC2CCOCC2)c1] | HCl | 393.2 |

TABLE 1-10-continued

| Ex. No. | IUPAC name | structure | salt | MS |
|---|---|---|---|---|
| 85 | 3-(trans-2-((2,2-dimethylpropyl)amino)cyclopropyl)-N-(1,1-dioxidotetrahydro-2H-thiopyran-4-yl)benzamide hydrochloride | 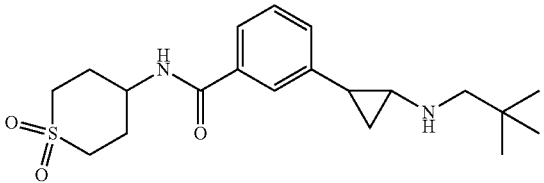 [SMILES: CC(C)(C)CNC1CC1c1cccc(C(=O)NC2CCS(=O)(=O)CC2)c1] | HCl | 379.2 |
| 86 | N-(1-ethyl-1H-pyrazol-4-yl)-3-(trans-2-((tetrahydro-2H-pyran-4-ylmethyl)amino)cyclopropyl)benzamide dihydrochloride | 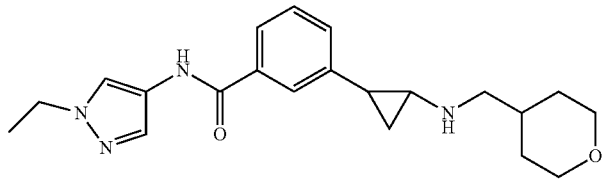 [SMILES: CCn1cc(NC(=O)c2cccc(C3CC3NCC3CCOCC3)c2)cn1] | 2HCl | 369.1 |
| 87 | N-(1-(cyclopropylmethyl)-1H-pyrazol-4-yl)-3-(trans-2-((tetrahydro-2H-pyran-4-ylmethyl)amino)cyclopropyl)-benzamide dihydrochloride | 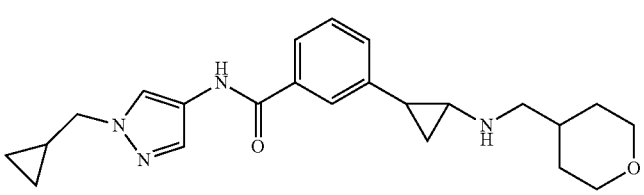 [SMILES: O=C(Nc1cnn(CC2CC2)c1)c1cccc(C2CC2NCC2CCOCC2)c1] | 2HCl | 395.2 |
| 88 | N-(1-tert-butyl-1H-pyrazol-4-yl)-3-(trans-2-((2,2-dimethylpropyl)amino)cyclopropyl)benzamide dihydrochloride | 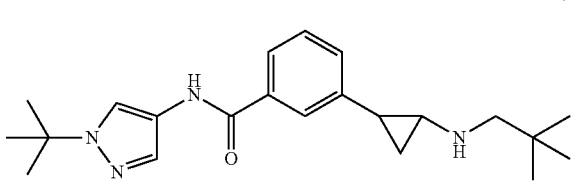 [SMILES: CC(C)(C)CNC1CC1c1cccc(C(=O)Nc2cnn(C(C)(C)C)c2)c1] | 2HCl | 369.2 |
| 89 | N-(1-tert-butyl-1H-pyrazol-4-yl)-3-(trans-2-((tetrahydro-2H-pyran-4-ylmethyl)amino)cyclopropyl)-benzamide dihydrochloride | 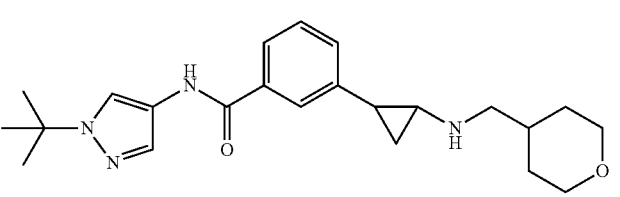 [SMILES: CC(C)(C)n1cc(NC(=O)c2cccc(C3CC3NCC3CCOCC3)c2)cn1] | 2HCl | 397.2 |

TABLE 1-11

| Ex. No. | IUPAC name | structure | salt | MS |
|---|---|---|---|---|
| 90 | N-(2-methyl-1,3-thiazol-5-yl)-3-(trans-2-((tetrahydro-2H-pyran-4-ylmethyl)amino)cyclopropyl)benzamide dihydrochloride | 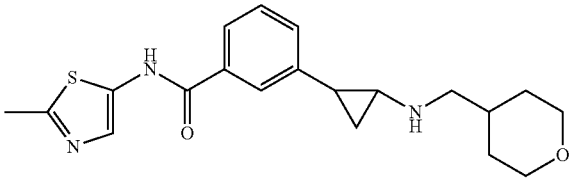 [SMILES: Cc1ncc(NC(=O)c2cccc(C3CC3NCC3CCOCC3)c2)s1] | 2HCl | 372.1 |
| 91 | 5-(trans-2-((cyclopropylmethyl)amino)cyclopropyl)-2-fluoro-N-(1-methyl-1H-pyrazol-4-yl)benzamide dihydrochloride | 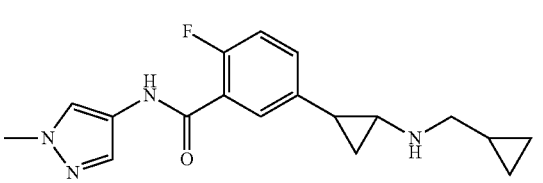 [SMILES: Cn1cc(NC(=O)c2cc(C3CC3NCC3CC3)ccc2F)cn1] | 2HCl | 329.2 |

TABLE 1-11-continued

| Ex. No. | IUPAC name | structure | salt | MS |
|---|---|---|---|---|
| 92 | N-(3-methyl-1,2-oxazol-5-yl)-3-(trans-2-((tetrahydro-2H-pyran-4-ylmethyl)amino)cyclopropyl)benzamide hydrochloride | 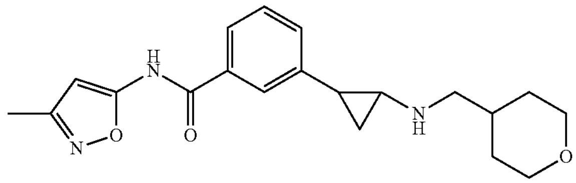 | HCl | 356.2 |
| 93 | N-(3-methyl-1,2-thiazol-5-yl)-3-(trans-2-((tetrahydro-2H-pyran-4-ylmethyl)amino)cyclopropyl)benzamide dihydrochloride | 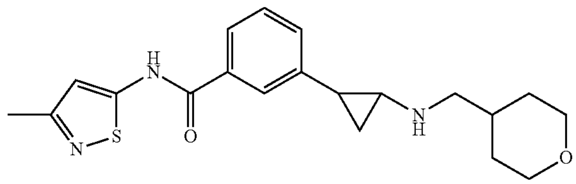 [SMILES: Cc1cc(NC(=O)c2cccc(C3CC3NCC3CCOCC3)c2)on1] | 2HCl | 369.9 |
| 94 | 5-(trans-2-((cyclopropylmethyl)-amino)cyclopropyl)-2-methoxy-N-(1-methyl-1H-pyrazol-4-yl)benzamide dihydrochloride | 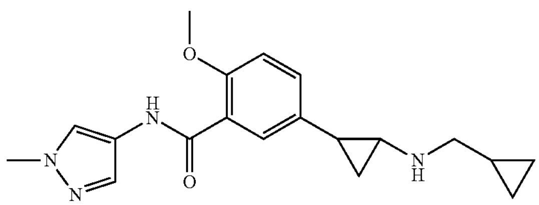 [SMILES: COc1ccc(C2CC2NCC2CC2)cc1C(=O)Nc1cnn(C)c1] | 2HCl | 341.2 |
| 95 | 3-(trans-2-((cyclopropylmethyl)-amino)cyclopropyl)-N-(5-methyl-1,3,4-thiadiazol-2-yl)benzamide dihydrochloride | 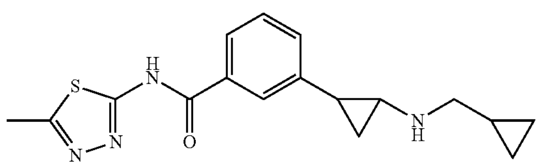 [SMILES: Cc1nnc(NC(=O)c2cccc(C3CC3NCC3CC3)c2)s1] | 2HCl | 329.2 |
| 96 | 3-(trans-2-((cyclopropylmethyl)-amino)cyclopropyl)-N-(5-methyl-1,3,4-thiadiazol-2-yl)benzamide hydrochloride | 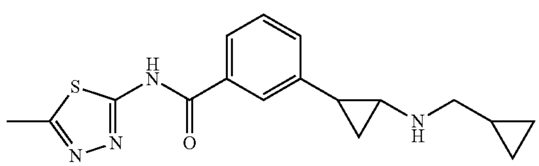 [SMILES: Cc1nnc(NC(=O)c2cccc(C3CC3NCC3CC3)c2)s1] | HCl | 329.2 |
| 97 | 3-(trans-2-((cyclopropylmethyl)-amino)cyclopropyl)-N-(5-methyl-1,3,4-thiadiazol-2-yl)benzamide hydrochloride (optical isomer, retention time short) | 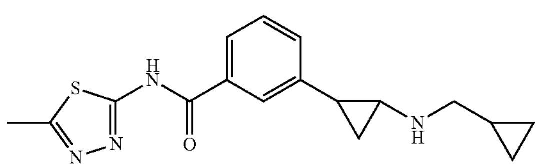 [SMILES: Cc1nnc(NC(=O)c2cccc(C3CC3NCC3CC3)c2)s1] | HCl | 326.9 |
| 98 | 3-(trans-2-((cyclopropylmethyl)-amino)cyclopropyl)-N-(5-methyl-1,3,4-thiadiazol-2-yl)benzamide hydrochloride (optical isomer, retention time long) | 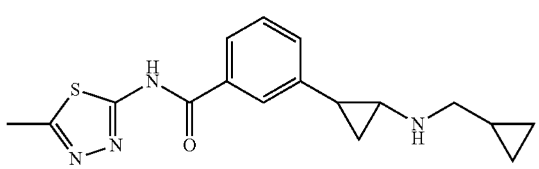 [SMILES: Cc1nnc(NC(=O)c2cccc(C3CC3NCC3CC3)c2)s1] | HCl | 326.9 |

TABLE 1-12

| Ex. No. | IUPAC name | structure | salt | MS |
|---|---|---|---|---|
| 99 | 3-(trans-2-((cyclo-propylmethyl)amino)-cyclopropyl)-N-(3,3-difluorocyclobutyl)-benzamide hydrochloride | 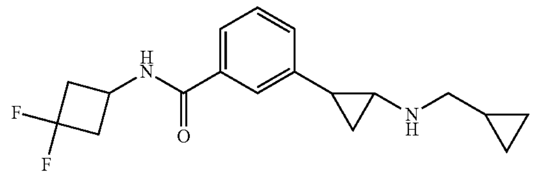 [SMILES: O=C(NC1CC(F)(F)C1)c1cccc(C2CC2NCC2CC2)c1] | HCl | 321.1 |
| 100 | 3-(trans-2-((cyclo-propylmethyl)amino)-cyclopropyl)-N-(tetrahydro-2H-pyran-4-yl)benzamide hydrochloride | 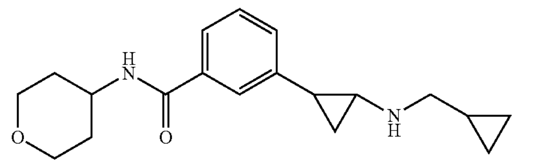 [SMILES: O=C(NC1CCOCC1)c1cccc(C2CC2NCC2CC2)c1] | HCl | 315.2 |
| 101 | 3-(trans-2-((cyclopropylmethyl)-amino)cyclopropyl)-N-(1-ethyl-1H-pyrazol-4-yl)benzamide dihydrochloride | 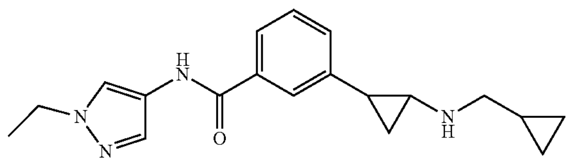 [SMILES: CCn1cc(NC(=O)c2cccc(C3CC3NCC3CC3)c2)cn1] | 2HCl | 325.2 |
| 102 | 3-(trans-2-((cyclopropylmethyl)-amino)cyclopropyl)-N-(4,4-difluorocyclohexyl)-benzamide hydrochloride | 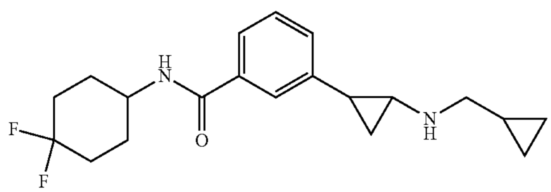 [SMILES: O=C(NC1CCC(F)(F)CC1)c1cccc(C2CC2NCC2CC2)c1] | HCl | 349.1 |
| 103 | 3-(trans-2-((cyclopropylmethyl)-amino)cyclopropyl)-N-(5-methyl-1,2-oxazol-3-yl)benzamide hydrochloride | 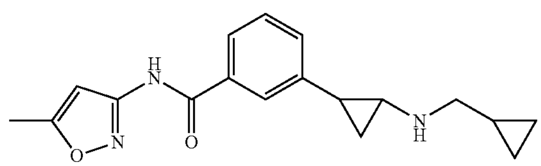 [SMILES: Cc1cc(NC(=O)c2cccc(C3CC3NCC3CC3)c2)no1] | HCl | 312.2 |
| 104 | 3-(trans-2-((cyclopropylmethyl)-amino)cyclopropyl)-N-(5-methyl-1,2-oxazol-3-yl)benzamide hydrochloride (optical isomer, retention time short) | 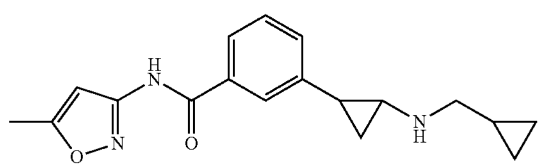 [SMILES: Cc1cc(NC(=O)c2cccc(C3CC3NCC3CC3)c2)no1] | HCl | 312.2 |
| 105 | 3-(trans-2-((cyclopropylmethyl)-amino)cyclopropyl)-N-(5-methyl-1,2-oxazol-3-yl)benzamide hydrochloride (optical isomer, retention time long) | 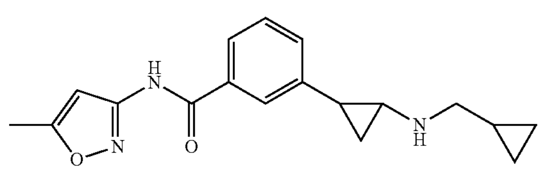 | HCl | 312.2 |
| 106 | 3-(trans-2-((cyclopropylmethyl)-amino)cyclopropyl)-N-(3-methyl-1,2-oxazol-5-yl)benzamide hydrochloride | 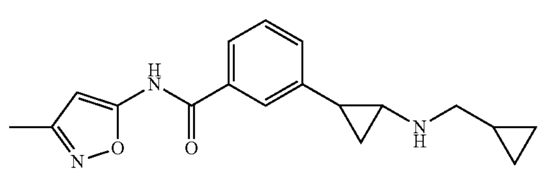 | HCl | 312.2 |
| 107 | 3-(trans-2-((cyclo-propylmethyl)amino)-cyclopropyl)-N-(1,3-dimethyl-1H-pyrazol-5-yl)benzamide dihydrochloride | 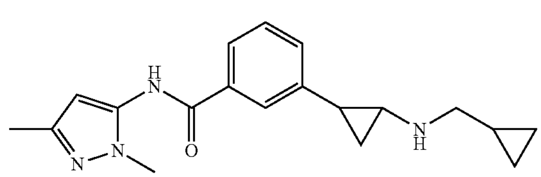 [SMILES: Cc1cc(NC(=O)c2cccc(C3CC3NCC3CC3)c2)n(C)n1] | 2HCl | 325.2 |

US 9,751,885 B2

TABLE 1-12-continued

| Ex. No. | IUPAC name | structure | salt | MS |
|---|---|---|---|---|

TABLE 1-13

| Ex. No. | IUPAC name | structure | salt | MS |
|---|---|---|---|---|
| 108 | 3-(trans-2-((cyclopropylmethyl)amino)-cyclopropyl)-N-(1-(2,2,2-trifluoroethyl)piperidin-4-yl)benzamide dihydrochloride | 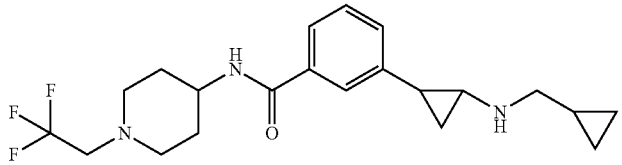 [SMILES: O=C(NC1CCN(CC(F)(F)F)CC1)c1cccc(C2CC2NCC2CC2)c1] | 2HCl | 396.2 |
| 109 | 3-(trans-2-((cyclopropylmethyl)-amino)cyclopropyl)-4-fluoro-N-(5-methyl-1,3,4-thiadiazol-2-yl)benzamide dihydrochloride | 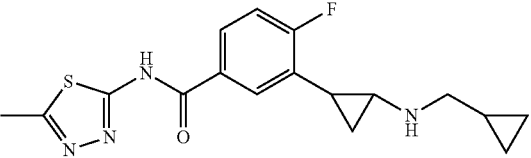 [SMILES: Cc1nnc(NC(=O)c2ccc(F)c(C3CC3NCC3CC3)c2)s1] | 2HCl | 347.2 |
| 110 | 5-(trans-2-((cyclopropylmethyl)-amino)cyclopropyl)-2-fluoro-N-(5-methyl-1,3,4-thiadiazol-2-yl)benzamide dihydrochloride | 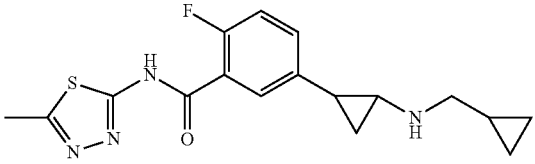 [SMILES: Cc1nnc(NC(=O)c2cc(C3CC3NCC3CC3)ccc2F)s1] | 2HCl | 347.2 |
| 111 | 5-(trans-2-((cyclopropylmethyl)-amino)cyclopropyl)-2-fluoro-N-(tetrahydro-2H-pyran-4-yl)benzamide hydrochloride | 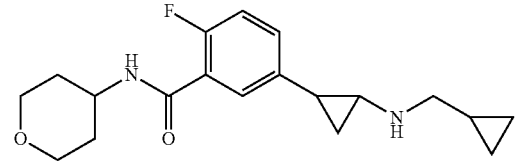 [SMILES: O=C(NC1CCOCC1)c1cc(C2CC2NCC2CC2)ccc1F] | HCl | 333.1 |
| 112 | N-(5-methyl-1,3,4-thiadiazol-2-yl)-3-(trans-2-((tetrahydro-2H-pyran-4-ylmethyl)-amino)cyclopropyl)-benzamide dihydrochloride | 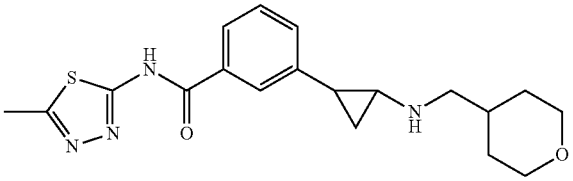 | 2HCl | 373.1 |
| 113 | (3-(trans-2-((cyclopropylmethyl)-amino)cyclopropyl)-phenyl) (1,3-dihydro-2H-isoindol-2-yl)methanone trifluoroacetate | 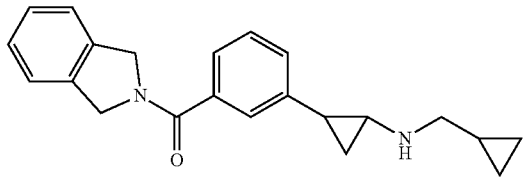 [SMILES: O=C(c1cccc(C2CC2NCC2CC2)c1)N1Cc2ccccc2C1] | CF3COOH | 333.1 |
| 114 | N-tert-butyl-3-(trans-2-((cyclopropylmethyl)-amino)cyclopropyl)-benzamide trifluoroacetate | 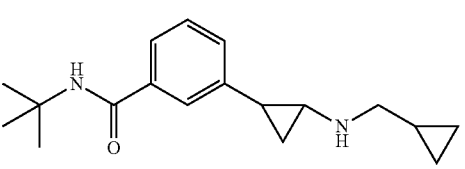 [SMILES: CC(C)(C)NC(=O)c1cccc(C2CC2NCC2CC2)c1] | CF3COOH | 287.2 |

TABLE 1-13-continued

| Ex. No. | IUPAC name | structure | salt | MS |
|---|---|---|---|---|
| 115 | 3-(trans-2-((cyclopropylmethyl)amino)-cyclopropyl)-N-(3,3-difluorocyclobutyl)-benzamide trifluoroacetate | 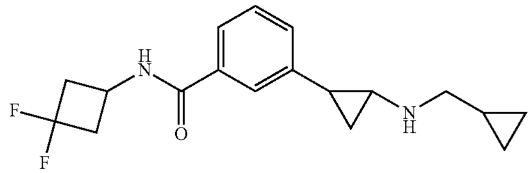 [SMILES: O=C(NC1CC(F)(F)C1)c1cccc(C2CC2NCC2CC2)c1] | CF3COOH | 321.1 |
| 116 | 3-(trans-2-((cyclopropylmethyl)amino)-cyclopropyl)-N-((3,3-difluorocyclobutyl)methyl)benzamide trifluoroacetate | 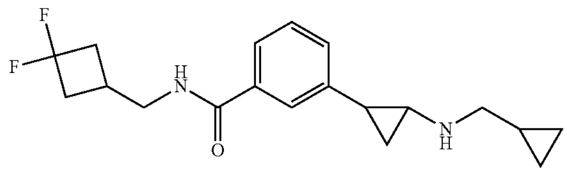 [SMILES: O=C(NCC1CC(F)(F)C1)c1cccc(C2CC2NCC2CC2)c1] | CF3COOH | 335.2 |

TABLE 1-14

| Ex. No. | IUPAC name | structure | salt | MS |
|---|---|---|---|---|
| 117 | 3-(trans-2-((cyclopropylmethyl)-amino)cyclopropyl)-N-(2-oxoazepan-3-yl)benzamide trifluoroacetate | 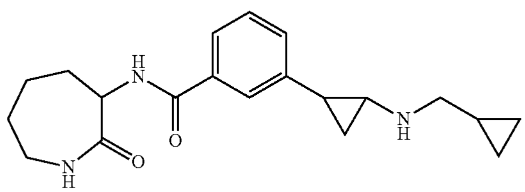 [SMILES: O=C(NC1CCCCNC1=O)c1cccc(C2CC2NCC2CC2)c1] | CF3COOH | 342.2 |
| 118 | N-(1-benzylpyrrolidin-3-yl)-3-(trans-2-((cyclopropylmethyl)amino)-cyclopropyl)benzamide bis(trifluoroacetate) | 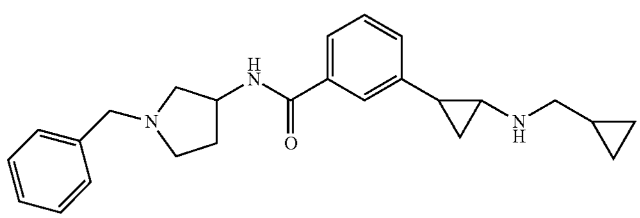 [SMILES: O=C(NC1CCN(Cc2ccccc2)C1)c1cccc(C2CC2NCC2CC2)c1] | 2CF3COOH | 390.2 |
| 119 | N-(1-benzylpiperidin-4-yl)-3-(trans-2-((cyclopropylmethyl)-amino)cyclopropyl)benzamide bis(trifluoroacetate) | 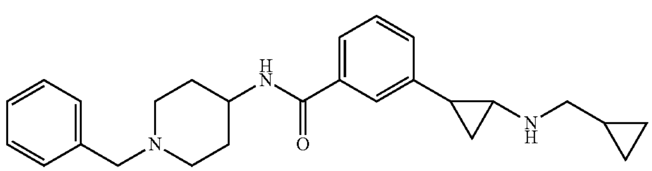 [SMILES: O=C(NC1CCN(Cc2ccccc2)CC1)c1cccc(C2CC2NCC2CC2)c1] | 2CF3COOH | 404.2 |
| 120 | 3-(trans-2-((cyclopropylmethyl)-amino)cyclopropyl)-N-(2-phenylethyl)benzamide trifluoroacetate | 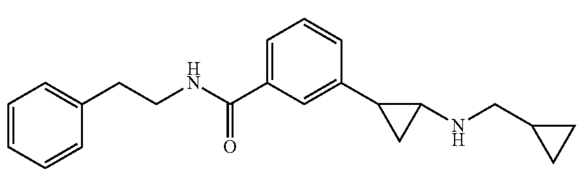 [SMILES: O=C(NCCc1ccccc1)c1cccc(C2CC2NCC2CC2)c1] | CF3COOH | 335.2 |
| 121 | 3-(trans-2-((cyclopropylmethyl)amino)-cyclopropyl)-N-(2-fluorophenyl)benzamide trifluoroacetate | 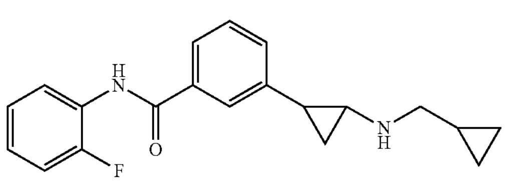 [SMILES: O=C(Nc1ccccc1F)c1cccc(C2CC2NCC2CC2)c1] | CF3COOH | 325.2 |

TABLE 1-14-continued

| Ex. No. | IUPAC name | structure | salt | MS |
|---|---|---|---|---|
| 122 | 3-(trans-2-((cyclopropyl-methyl)-amino)cyclopropyl)-N-(3-fluorophenyl)benzamide trifluoroacetate | 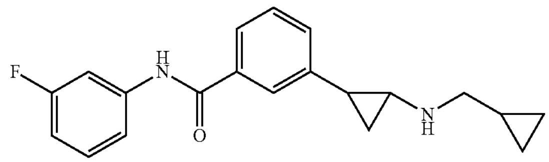 [SMILES: O=C(Nc1cccc(F)c1)c1cccc(C2CC2NCC2CC2)c1] | CF3COOH | 325.2 |
| 123 | 3-(trans-2-((cyclo-propylmethyl)amino)cyclo-propyl)-N-(4-(trifluoro-methoxy)phenyl)benzamide trifluoroacetate | 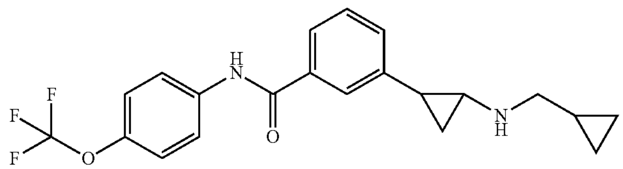 [SMILES: O=C(Nc1ccc(OC(F)(F)F)cc1)c1cccc(C2CC2NCC2CC2)c1] | CF3COOH | 391.1 |
| 124 | 3-(trans-2-((cyclo-propylmethyl)amino)cyclo-propyl)-N-(4-(methylsulfonyl)phenyl)-benzamide trifluoroacetate | 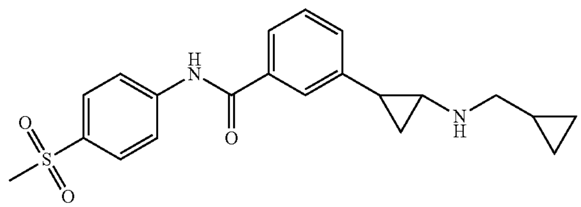 [SMILES: CS(=O)(=O)c1ccc(NC(=O)c2cccc(C3CC3NCC3CC3)c2)cc1] | CF3COOH | 385.1 |
| 125 | 3-(trans-2-((cyclopropyl-methyl)amino)-cyclopropyl)-N-(4-(morpholin-4-yl)phenyl)benzamide bis(trifluoroacetate) | 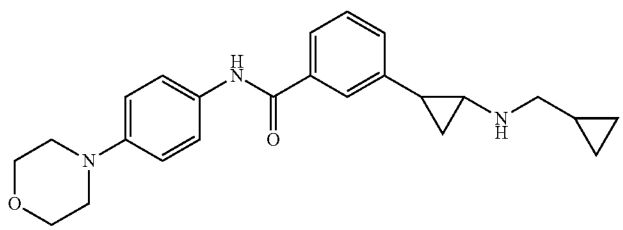 [SMILES: O=C(Nc1ccc(N2CCOCC2)cc1)c1cccc(C2CC2NCC2CC2)c1] | 2CF3COOH | 392.2 |

TABLE 1-15

| Ex. No. | IUPAC name | structure | salt | MS |
|---|---|---|---|---|
| 126 | 3-(trans-2-((cyclo-propylmethyl)amino) cyclopropyl)-N-(4-((1,1-dioxidothiomorpholin-4-yl)methyl)phenyl) benzamide bis(trifluoroacetate) | 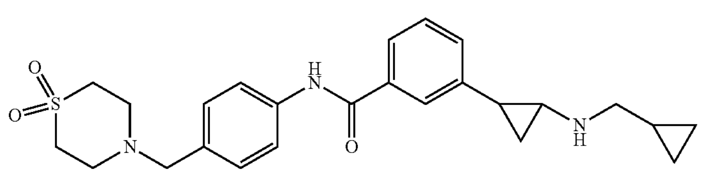 [SMILES: O=C(Nc1ccc(CN2CCS(=O)(=O)CC2)cc1)c1cccc(C2CC2NCC2CC2)c1] | 2CF3COOH | 454.1 |
| 127 | 3-(trans-2-((cyclo-propylmethyl)amino) cyclopropyl)-N-(4-(2,3-dihydroimidazo[2,1-b] [1,3]thiazol-6-yl)phenyl)benzamide bis(trifluoroacetate) | 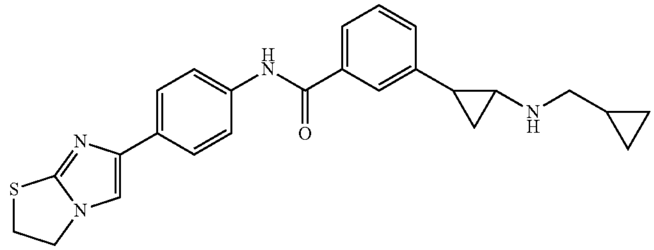 [SMILES: O=C(Nc1ccc(-c2cn3c(n2)SCC3)cc1)c1cccc(C2CC2NCC2CC2)c1] | 2CF3COOH | 431.1 |

TABLE 1-15-continued

| Ex. No. | IUPAC name | structure | salt | MS |
|---|---|---|---|---|
| 128 | 3-(trans-2-((cyclopropylmethyl)amino)cyclopropyl)-N-(4-(4,6-dimethoxypyrimidin-2-yl)phenyl)benzamide trifluoroacetate | 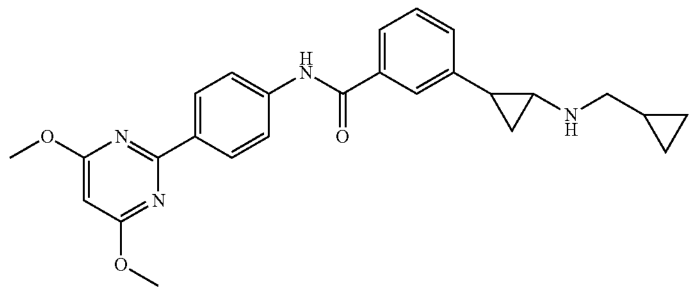 [SMILES: COc1cc(OC)nc(-c2ccc(NC(=O)c3cccc(C4CC4NCC4CC4)c3)cc2)n1] | CF3COOH | 445.2 |
| 129 | N-(4-benzylphenyl)-3-(trans-2-((cyclopropylmethyl)-amino)cyclopropyl)benzamide trifluoroacetate | 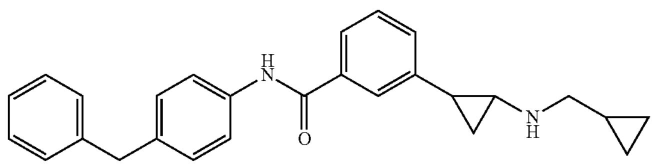 [SMILES: O=C(Nc1ccc(Cc2ccccc2)cc1)c1cccc(C2CC2NCC2CC2)c1] | CF3COOH | 397.1 |
| 130 | N-(biphenyl-3-yl)-3-(trans-2-((cyclopropylmethyl)amino)cyclopropyl)-benzamide trifluoroacetate | 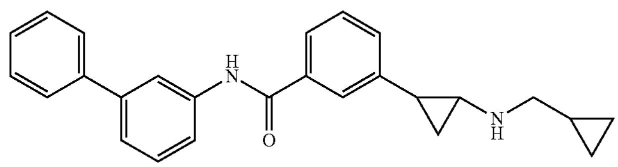 [SMILES: O=C(Nc1cccc(-c2ccccc2)c1)c1cccc(C2CC2NCC2CC2)c1] | CF3COOH | 383.1 |
| 131 | 3-(trans-2-((cyclopropylmethyl)amino)cyclopropyl)-N-(3-(2-methyl-1,3-thiazol-4-yl)phenyl)benzamide trifluoroacetate | 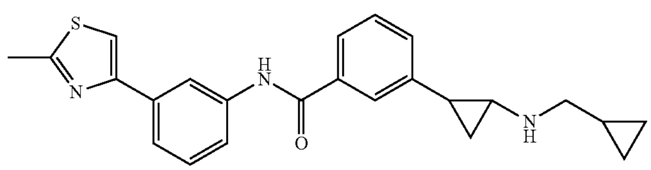 [SMILES: Cc1nc(-c2cccc(NC(=O)c3cccc(C4CC4NCC4CC4)c3)c2)cs1] | CF3COOH | 404.1 |
| 132 | 3-(trans-2-((cyclopropylmethyl)amino)cyclopropyl)-N-(3-((4,6-dimethylpyrimidin-2-yl)sulfanyl)phenyl)-benzamide trifluoroacetate | 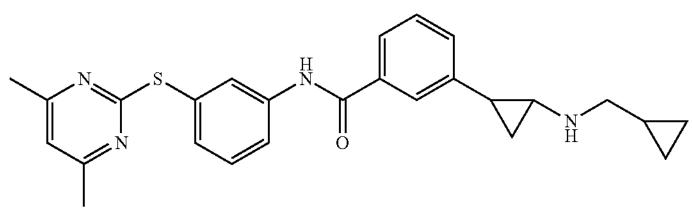 [SMILES: Cc1cc(C)nc(Sc2cccc(NC(=O)c3cccc(C4CC4NCC4CC4)c3)c2)n1] | CF3COOH | 445.1 |
| 133 | 3-(trans-2-((cyclopropylmethyl)amino)cyclopropyl)-N-(3-(6,7,8,9-tetrahydro-5H-[1,2,4]triazolo[4,3-a]azepin-3-yl)phenyl)-benzamide trifluoroacetate | 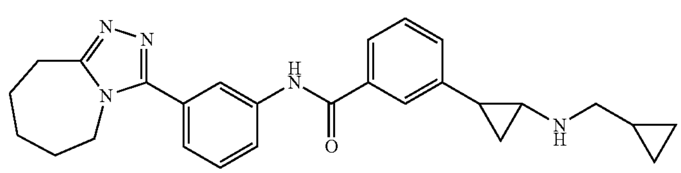 [SMILES: O=C(Nc1cccc(-c2nnc3n2CCCCC3)c1)c1cccc(C2CC2NCC2CC2)c1] | CF3COOH | 442.2 |
| 134 | 3-(trans-2-((cyclopropylmethyl)amino)cyclopropyl)-N-(6-(morpholin-4-yl)pyridin-3-yl)benzamide tris(trifluoroacetate) | 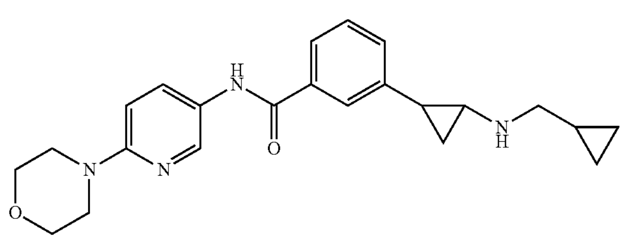 [SMILES: O=C(Nc1ccc(N2CCOCC2)nc1)c1cccc(C2CC2NCC2CC2)c1] | 3CF3COOH | 393.2 |

TABLE 1-16

| Ex. No. | IUPAC name | structure | salt | MS |
|---|---|---|---|---|
| 135 | 3-(trans-2-((cyclopropyl-methyl)amino)cyclo-propyl)-N-(6-phenoxy-1,3-benzothiazol-2-yl)benzamide trifluoroacetate | 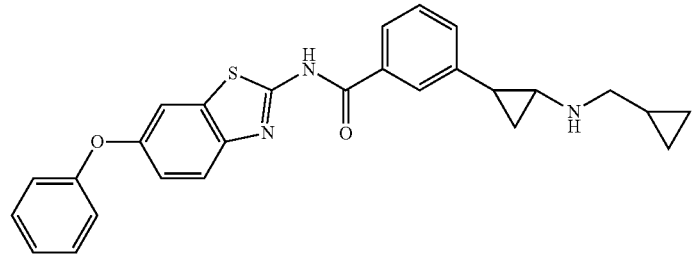 [SMILES: O=C(Nc1nc2ccc(Oc3ccccc3)cc2s1)c1cccc(C2CC2NCC2CC2)c1] | CF3COOH | 456.1 |
| 136 | 3-(trans-2-((cyclopropyl-methyl)amino)cyclo-propyl)-N-(1-methyl-3-(2-thienyl)-1H-pyrazol-5-yl)benzamide bis(trifluoroacetate) | 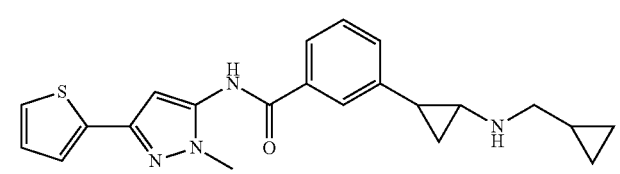 [SMILES: Cn1nc(-c2cccs2)cc1NC(=O)c1cccc(C2CC2NCC2CC2)c1] | 2CF3COOH | 393.2 |
| 137 | 3-(trans-2-((cyclopropyl-methyl)amino)cyclo-propyl)-N-(6-(4-fluorophenoxy)pyridin-3-yl)benzamide bis(trifluoroacetate) | 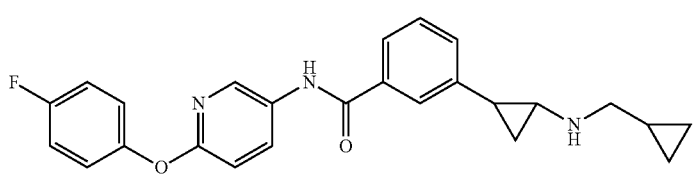 [SMILES: O=C(Nc1ccc(Oc2ccc(F)cc2)nc1)c1cccc(C2CC2NCC2CC2)c1] | 2CF3COOH | 418.1 |
| 138 | 3-(trans-2-((cyclopropyl-methyl)amino)cyclo-propyl)-N-(1,3-thiazol-2-yl)benzamide trifluoroacetate | 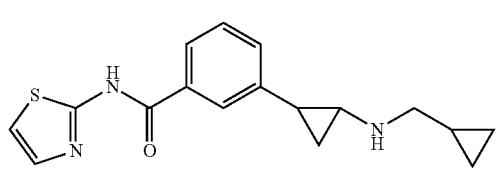 [SMILES: O=C(Nc1nccs1)c1cccc(C2CC2NCC2CC2)c1] | CF3COOH | 314.2 |
| 139 | 3-(trans-2-((cyclopropyl-methyl)amino)cyclo-propyl)-N-(5-methyl-1,3,4-thiadiazol-2-yl)benzamide trifluoroacetate | 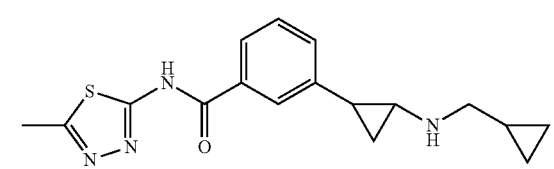 | CF3COOH | 329.1 |
| 140 | 3-(trans-2-((cyclopropyl-methyl)amino)cyclo-propyl)-N-(3-ethyl-1,2,4-thiadiazol-5-yl)benzamide trifluoroacetate | 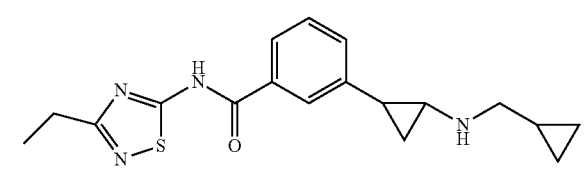 [SMILES: CCc1nsc(NC(=O)c2cccc(C3CC3NCC3CC3)c2)n1] | CF3COOH | 341.0 |
| 141 | N-(3-tert-butyl-1-methyl-1H-pyrazol-5-yl)-3-(trans-2-((cyclopropyl-methyl)amino)cyclopropyl)benzamide bis(trifluoroacetate) | 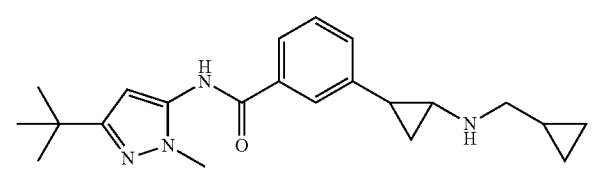 [SMILES: Cn1nc(C(C)(C)C)cc1NC(=O)c1cccc(C2CC2NCC2CC2)c1] | 2CF3COOH | 367.2 |
| 142 | 3-(trans-2-((cyclopropyl-methyl)amino)cyclo-propyl)-N-(3,5-dimethyl-1,2-oxazol-4-yl)benzamide trifluoroacetate | 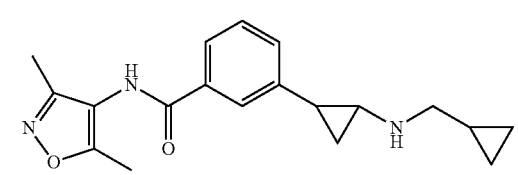 [SMILES: Cc1noc(C)c1NC(=O)c1cccc(C2CC2NCC2CC2)c1] | CF3COOH | 326.2 |

TABLE 1-16-continued

| Ex. No. | IUPAC name | structure | salt | MS |
|---|---|---|---|---|
| 143 | 3-(trans-2-((cyclopropyl-methyl)amino)cyclo-propyl)-N-(quinoxalin-6-yl)benzamide bis(trifluoroacetate) | 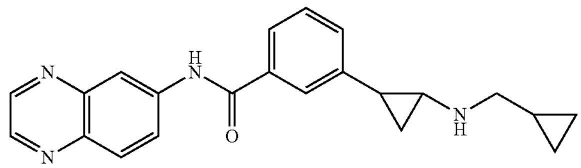 [SMILES: O=C(Nc1ccc2nccnc2c1)c1cccc(C2CC2NCC2CC2)c1] | 2CF3COOH | 359.1 |

TABLE 1-17

| Ex. No. | IUPAC name | structure | salt | MS |
|---|---|---|---|---|
| 144 | N-(1,3-benzothiazol-6-yl)-3-(trans-2-((cyclo-propylmethyl)amino)cyclo-propyl)benzamide trifluoroacetate | 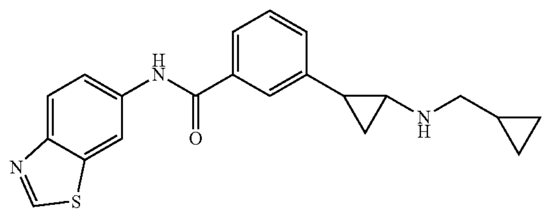 [SMILES: O=C(Nc1ccc2ncsc2c1)c1cccc(C2CC2NCC2CC2)c1] | CF3COOH | 364.2 |
| 145 | N-(1H-benzimidazol-5-yl)-3-(trans-2-((cyclopropyl-methyl)amino)cyclo-propyl)benzamide bis(trifluoroacetate) | 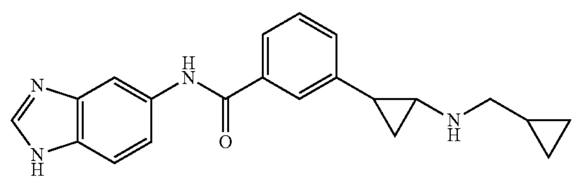 [SMILES: O=C(Nc1ccc2[nH]cnc2c1)c1cccc(C2CC2NCC2CC2)c1] | 2CF3COOH | 347.2 |
| 146 | 3-(trans-2-((cyclopropyl-methyl)amino)cyclo-propyl)-N-(1H-indazol-5-yl)benzamide trifluoroacetate | 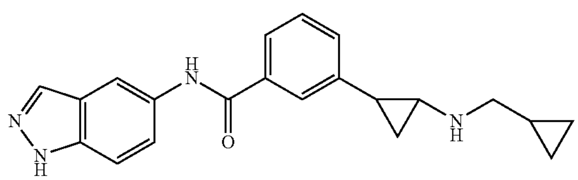 [SMILES: O=C(Nc1ccc2[nH]ncc2c1)c1cccc(C2CC2NCC2CC2)c1] | CF3COOH | 347.2 |
| 147 | 3-(trans-2-((cyclopropyl-methyl)amino)cyclo-propyl)-N-(2-oxo-2,3-dihydro-1,3-benzothiazol-6-yl)benzamide trifluoroacetate | 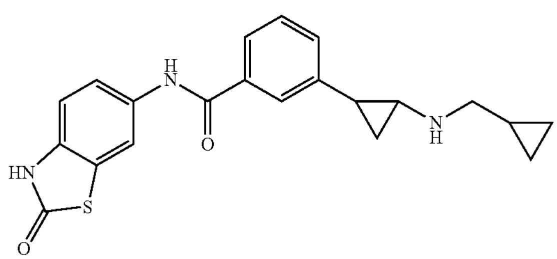 [SMILES: O=C(Nc1ccc2[nH]c(=O)sc2c1)c1cccc(C2CC2NCC2CC2)c1] | CF3COOH | 380.1 |
| 148 | 3-(trans-2-((cyclopropyl-methyl)amino)cyclo-propyl)-N-(7,8,9,10-tetrahydro-6H-azepino-[1,2-a]benzimidazol-3-yl)benzamide bis(trifluoroacetate) | 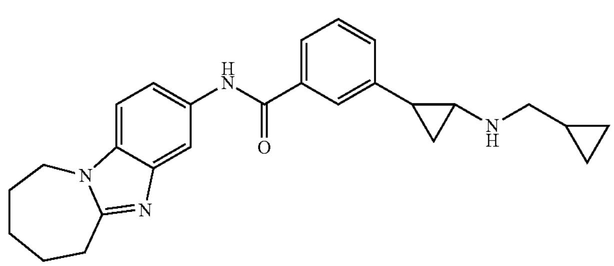 [SMILES: O=C(Nc1ccc2c(c1)nc1n2CCCCC1)c1cccc(C2CC2NCC2CC2)c1] | 2CF3COOH | 415.2 |

TABLE 1-17-continued

| Ex. No. | IUPAC name | structure | salt | MS |
|---|---|---|---|---|
| 149 | 3-(trans-2-((cyclopropyl-methyl)amino)cyclo-propyl)-N-(4-ethyl-3-oxo-3,4-dihydro-2H-1,4-benzoxazin-7-yl)benzamide trifluoroacetate | 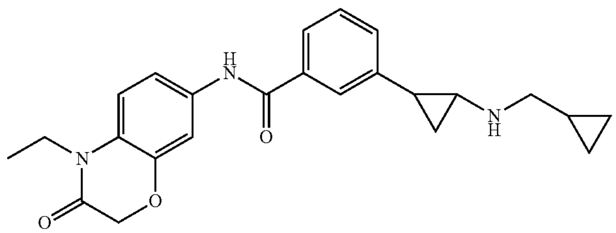 [SMILES: CCN1C(=O)COc2cc(NC(=O)c3cccc(C4CC4NCC4CC4)c3)ccc21] | CF3COOH | 406.2 |
| 150 | 3-(trans-2-((cyclopropyl-methyl)amino)cyclo-propyl)-N-(4-hydroxy-5,6,7,8-tetrahydro-quinazolin-2-yl)benzamide trifluoroacetate | 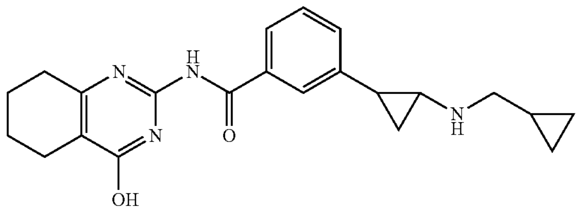 [SMILES: O=C(Nc1nc(O)c2c(n1)CCCC2)c1cccc(C2CC2NCC2CC2)c1] | CF3COOH | 379.2 |
| 151 | 3-(trans-2-((cyclopropyl-methyl)amino)cyclo-propyl)-N-(1-(2,2,2-trifluoroethyl)-1H-pyrazol-4-yl)benzamide hydrochloride | 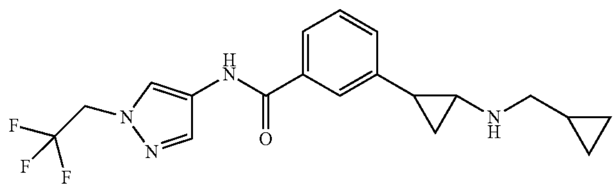 [SMILES: O=C(Nc1cnn(CC(F)(F)F)c1)c1cccc(C2CC2NCC2CC2)c1] | HCl | 379.2 |
| 152 | 3-(trans-2-((cyclopropyl-methyl)amino)cyclo-propyl)-N-(3-methyl-1,2-thiazol-5-yl)benzamide hydrochloride | 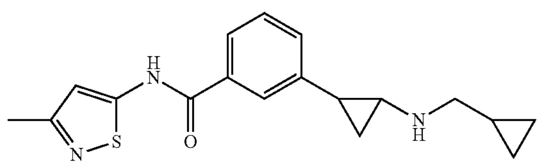 [SMILES: Cc1cc(NC(=O)c2cccc(C3CC3NCC3CC3)c2)sn1] | HCl | 328.1 |

TABLE 1-18

| Ex. No. | IUPAC name | structure | salt | |
|---|---|---|---|---|
| 153 | 3-(trans-2-((2,2-dimethylpropyl)amino)-cyclopropyl)-N-(tetrahydro-2H-pyran-4-yl)benzamide hydrochloride | 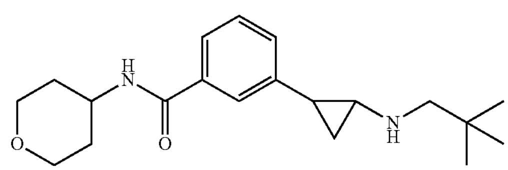 [SMILES: CC(C)(C)CNC1CC1c1cccc(C(=O)NC2CCOCC2)c1] | HCl | 331.3 |
| 154 | N-(3,3-difluorocyclobutyl)-3-(trans-2-((2,2-dimethylpropyl)amino)-cyclopropyl)benzamide hydrochloride | 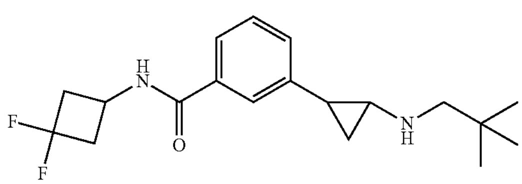 [SMILES: CC(C)(C)CNC1CC1c1cccc(C(=O)NC2CC(F)(F)C2)c1] | HCl | 337.2 |
| 155 | 3-(trans-2-((2,2-dimethylpropyl)amino)-cyclopropyl)-N-(1-methyl-1H-pyrazol-4-yl)benzamide dihydrochloride | 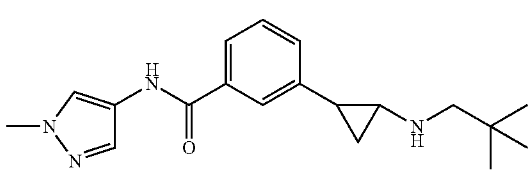 [SMILES: Cn1cc(NC(=O)c2cccc(C3CC3NCC(C)(C)C)c2)cn1] | 2HCl | 327.2 |

TABLE 1-18-continued

| Ex. No. | IUPAC name | structure | salt | MS |
|---|---|---|---|---|
| 156 | 3-(trans-2-((2,2-dimethylpropyl)amino)-cyclopropyl)-N-(1,5-dimethyl-1H-pyrazol-4-yl)benzamide dihydrochloride | 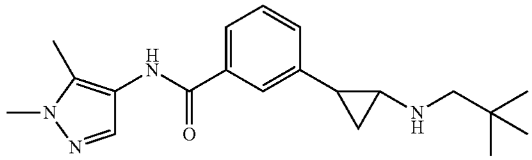 [SMILES: Cc1c(NC(=O)c2cccc(C3CC3NCC(C)(C)C)c2)cnn1C] | 2HCl | 341.2 |
| 157 | 3-(trans-2-((2,2-dimethylpropyl)amino)-cyclopropyl)-N-(1,3-dimethyl-1H-pyrazol-4-yl)benzamide dihydrochloride | 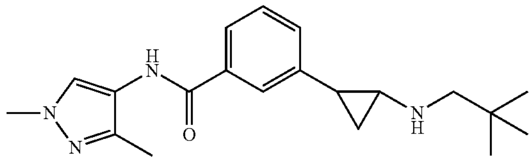 [SMILES: Cc1nn(C)cc1NC(=O)c1cccc(C2CC2NCC(C)(C)C)c1] | 2HCl | 341.2 |
| 158 | 3-(trans-2-((2,2-dimethylpropyl)amino)-cyclopropyl)-N-(5-methyl-1,3,4-thiadiazol-2-yl)benzamide dihydrochloride | 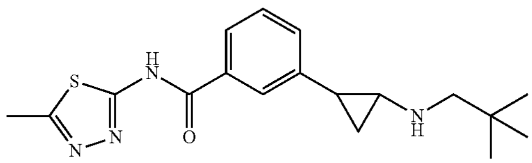 [SMILES: Cc1nnc(NC(=O)c2cccc(C3CC3NCC(C)(C)C)c2)s1] | 2HCl | 345.2 |
| 159 | 5-(trans-2-((cyclopropylmethyl)amino)-cyclopropyl)-2-methoxy-N-(5-methyl-1,3,4-thiadiazol-2-yl)benzamide dihydrochloride | 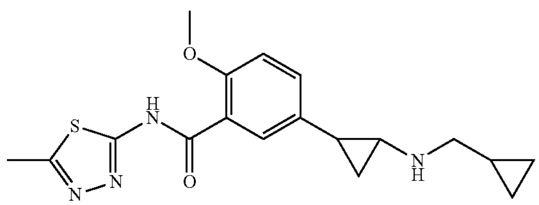 [SMILES: COc1ccc(C2CC2NCC2CC2)cc1C(=O)Nc1nnc(C)s1] | 2HCl | 359.0 |
| 160 | 5-(trans-2-((cyclopropylmethyl)amino)-cyclopropyl)-2-methoxy-N-(tetrahydro-2H-pyran-4-yl)benzamide hydrochloride | 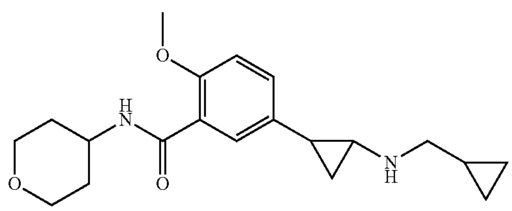 [SMILES: COc1ccc(C2CC2NCC2CC2)cc1C(=O)NC1CCOCC1] | HCl | 345.2 |
| 161 | 3-(trans-2-((cyclopropylmethyl)amino)-cyclopropyl)-4-methyl-N-(5-methyl-1,3,4-thiadiazol-2-yl)benzamide dihydrochloride | 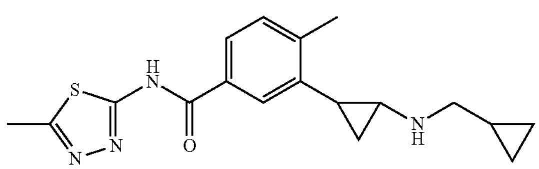 [SMILES: Cc1nnc(NC(=O)c2ccc(C)c(C3CC3NCC3CC3)c2)s1] | 2HCl | 343.2 |

TABLE 1-19

| Ex. No. | IUPAC name | structure | salt | MS |
|---|---|---|---|---|
| 162 | 3-(trans-2-((cyclopropylmethyl)amino)-cyclopropyl)-4-methoxy-N-(5-methyl-1,3,4-thiadiazol-2-yl)benzamide dihydrochloride | 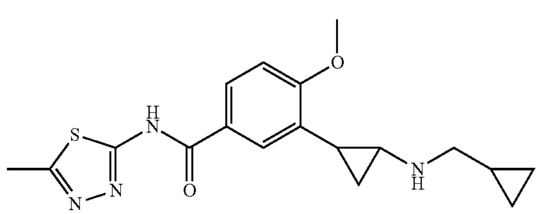 [SMILES: COc1ccc(C(=O)Nc2nnc(C)s2)cc1C1CC1NCC1CC1] | 2HCl | 359.0 |

TABLE 1-19-continued

| Ex. No. | IUPAC name | salt | MS |
|---|---|---|---|
| 163 | 3-(trans-2-((cyclopropylmethyl)amino)cyclopropyl)-5-methoxy-N-(5-methyl-1,3,4-thiadiazol-2-yl)-benzamide dihydrochloride | 2HCl | 359.1 |
| 164 | N-(5-methyl-1,3,4-thiadiazol-2-yl)-3-(trans-2-(tetrahydro-2H-pyran-4-ylamino)cyclopropyl)-benzamide dihydrochloride | 2HCl | 359.1 |
| 165 | N-(5-methyl-1,3,4-thiadiazol-2-yl)-3-(trans-2-(tetrahydro-2H-pyran-4-ylamino)-cyclopropyl)benzamide fumarate | fumarate | 359.0 |
| 166 | 3-(trans-2-((4,4-difluorocyclohexyl)amino)cyclopropyl)-N-(5-methyl-1,3,4-thiadiazol-2-yl)benzamide dihydrochloride | 2HCl | 391.1 |
| 167 | 3-(trans-2-((4,4-difluorocyclohexyl)amino)cyclopropyl)-N-(5-methyl-1,3,4-thiadiazol-2-yl)benzamide hydrochloride | HCl | 393.1 |
| 168 | N-cyclopentyl-3-(trans-2-(tetrahydro-2H-pyran-4-ylamino)cyclopropyl)-benzamide hydrochloride | HCl | 329.3 |
| 169 | 3-(trans-2-(cyclobutylamino)cyclopropyl)-N-(1-methyl-1H-pyrazol-4-yl)benzamide dihydrochloride | 2HCl | 311.2 |
| 170 | 3-(trans-2-(dicyclobutylamino)cyclopropyl)-N-(1-methyl-1H-pyrazol-4-yl)benzamide dihydrochloride | 2HCl | 365.2 |

TABLE 1-20

| Ex. No. | IUPAC name | structure | salt | MS |
|---|---|---|---|---|
| 171 | N-(1-methyl-1H-pyrazol-4-yl)-3-(trans-2-((1-(2,2,2-trifluoroethyl)-piperidin-4-yl)amino)-cyclopropyl)benzamide trihydrochloride | 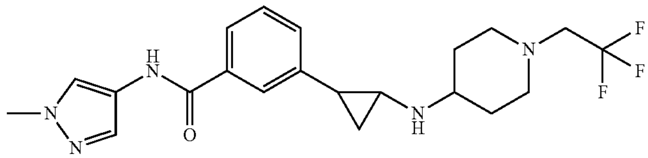 [SMILES: Cn1cc(NC(=O)c2cccc(C3CC3NC3CCN(CC(F)(F)F)CC3)c2)cn1] | 3HCl | 422.1 |
| 172 | 3-(trans-2-(cyclopentyl-amino)cyclopropyl)-N-(1-methyl-1H-pyrazol-4-yl)benzamide dihydrochloride | 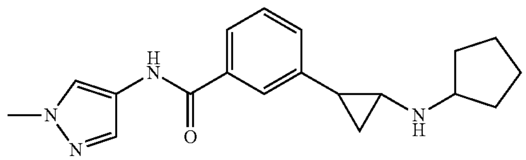 [SMILES: Cn1cc(NC(=O)c2cccc(C3CC3NC3CCCC3)c2)cn1] | 2HCl | 325.2 |
| 173 | 3-(trans-2-(cyclobutyl-amino)cyclopropyl)-N-(5-methyl-1,3,4-thiadiazol-2-yl)benzamide dihydrochloride | 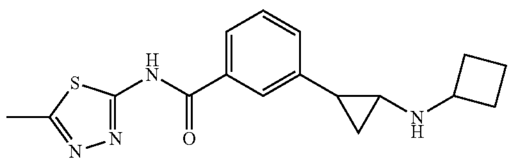 [SMILES: Cc1nnc(NC(=O)c2cccc(C3CC3NC3CCC3)c2)s1] | 2HCl | 329.2 |
| 174 | 3-(trans-2-(cyclobutyl-amino)cyclopropyl)-N-(5-methyl-1,3,4-thiadiazol-2-yl)benzamide hydrochloride | 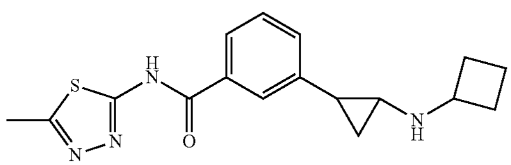 [SMILES: Cc1nnc(NC(=O)c2cccc(C3CC3NC3CCC3)c2)s1] | HCl | 329.2 |
| 175 | 3-(trans-2-((1-cyclo-propylpiperldin-4-yl)amino)cyclopropyl)-N-(5-methyl-1,3,4-thiadiazol-2-yl)benzamide trihydrochloride | 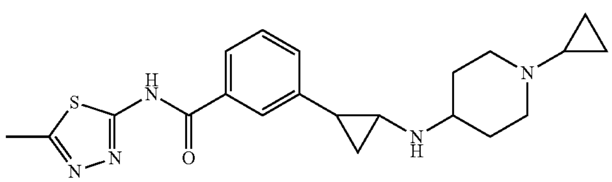 [SMILES: Cc1nnc(NC(=O)c2cccc(C3CC3NC3CCN(C4CC4)CC3)c2)s1] | 3HCl | 398.1 |
| 176 | 3-(trans-2-((1-cyclo-propylpiperidin-4-yl)amino)cyclopropyl)-N-(5-methyl-1,3,4-thiadiazol-2-yl)benzamide fumarate | 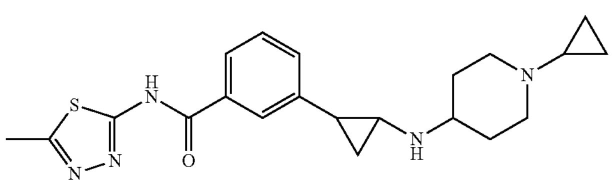 [SMILES: Cc1nnc(NC(=O)c2cccc(C3CC3NC3CCN(C4CC4)CC3)c2)s1] | fumarate | 398.2 |
| 177 | N-(4,4-difluoro-cyclohexyl)-3-(trans-2-(tetrahydro-2H-pyran-4-ylamino)cyclopropyl)-benzamide hydrochloride | 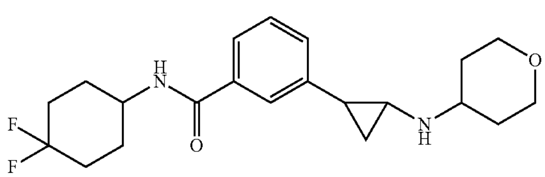 [SMILES: O=C(NC1CCC(F)(F)CC1)c1cccc(C2CC2NC2CCOCC2)c1] | HCl | 379.2 |
| 178 | 3-(trans-2-((4,4-difluorocyclohexyl)-amino)cyclopropyl)-N-(tetrahydro-2H-pyran-4-yl)benzamide hydrochloride | 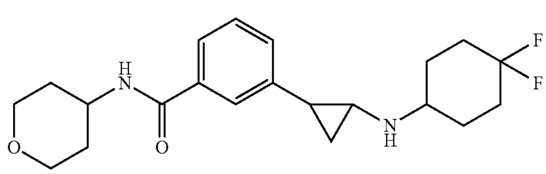 [SMILES: O=C(NC1CCOCC1)c1cccc(C2CC2NC2CCC(F)(F)CC2)c1] | HCl | 379.2 |

TABLE 1-20-continued

| Ex. No. | IUPAC name | structure | salt | MS |
|---|---|---|---|---|
| 179 | 3-(trans-2-(cyclobutyl-amino)cyclopropyl)-N-(tetrahydro-2H-pyran-4-yl)benzamide hydrochloride | 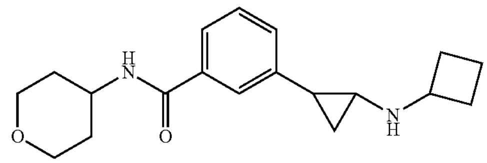 [SMILES: O=C(NC1CCOCC1)c1cccc(C2CC2NC2CCC2)c1] | HCl | 315.2 |

TABLE 1-21

| Ex. No. | IUPAC name | structure | salt | MS |
|---|---|---|---|---|
| 180 | 3-(trans-2-aminocyclopropyl)-N-(1,3-dimethyl-1H-pyrazol-5-yl)benzamide dihydrochloride | 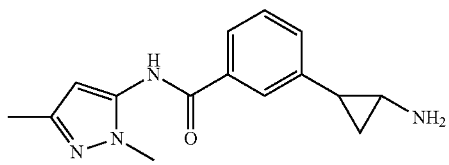 [SMILES: Cc1cc(NC(=O)c2cccc(C3CC3N)c2)n(C)n1] | 2HCl | 271.1 |
| 181 | 3-(trans-2-(cyclobutylamino)-cyclopropyl)-N-(1,3-dimethyl-1H-pyrazol-5-yl)benzamide dihydrochloride | 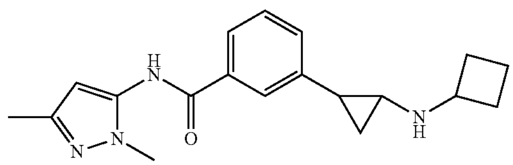 [SMILES: Cc1cc(NC(=O)c2cccc(C3CC3NC3CCC3)c2)n(C)n1] | 2HCl | 425.2 |
| 182 | 5-(trans-2-aminocyclopropyl)-2-fluoro-N-(5-methyl-1,3,4-thiadiazol-2-yl)benzamide dihydrochloride | 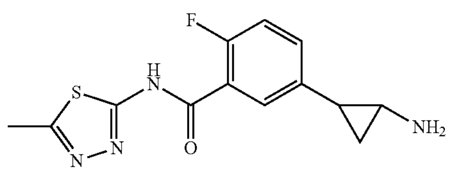 [SMILES: Cc1nnc(NC(=O)c2cc(C3CC3N)ccc2F)s1] | 2HCl | 293.0 |
| 183 | 5-(trans-2-(cyclobutylamino)-cyclopropyl)-2-fluoro-N-(5-methyl-1,3,4-thiadiazol-2-yl)benzamide dihydrochloride | 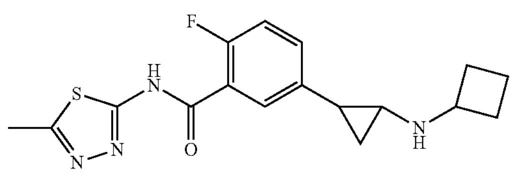 [SMILES: Cc1nnc(NC(=O)c2cc(C3CC3NC3CCC3)ccc2F)s1] | 2HCl | 347.2 |
| 184 | 4-methyl-N-(5-methyl-1,3,4-thiadiazol-2-yl)-3-(trans-2-(tetrahydro-2H-pyran-4-ylamino)cyclopropyl)-benzamide dihydrochloride | 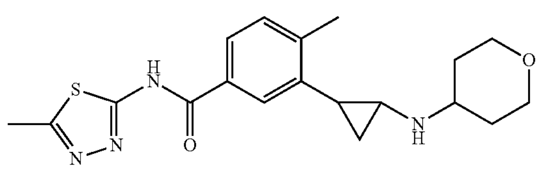 [SMILES: Cc1nnc(NC(=O)c2ccc(C)c(C3CC3NC3CCOCC3)c2)s1] | 2HCl | 373.1 |
| 185 | 4-methyl-N-(5-methyl-1,3,4-thiadiazol-2-yl)-3-(trans-2-(tetrahydro-2H-pyran-4-ylamino)cyclopropyl)-benzamide hydrochloride | 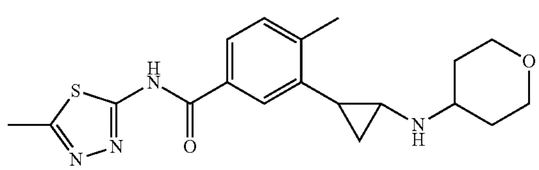 [SMILES: Cc1nnc(NC(=O)c2ccc(C)c(C3CC3NC3CCOCC3)c2)s1] | HCl | 371.0 |
| 186 | 5-(trans-2-((4,4-difluorocyclohexyl)-amino)cyclopropyl)-2-fluoro-N-(1-methyl-1H-pyrazol-4-yl)benzamide hydrochloride | 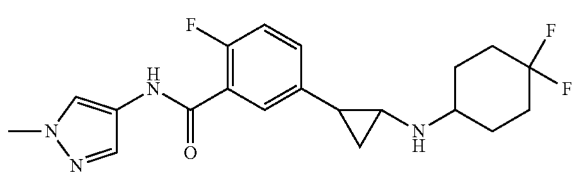 [SMILES: Cn1cc(NC(=O)c2cc(C3CC3NC3CCC(F)(F)CC3)ccc2F)cn1] | HCl | 393.2 |

TABLE 1-21-continued

| Ex. No. | IUPAC name | structure | salt | MS |
|---|---|---|---|---|
| 187 | N-(1-(cyclopropylmethyl)-1H-pyrazol-4-yl)-3-(trans-2-((1-cyclopropylpiperidin-4-yl)amino)cyclopropyl)-benzamide dihydrochloride | 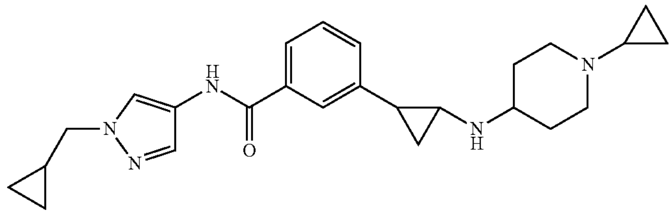 [SMILES: O=C(Nc1cnn(CC2CC2)c1)c1cccc(C2CC2NC2CCN(C3CC3)CC2)c1] | 2HCl | 420.2 |

15

TABLE 1-22

| Ex. No. | IUPAC name | structure | salt | MS |
|---|---|---|---|---|
| 188 | N-(1-(cyclopropylmethyl)-1H-pyrazol-4-yl)-3-(trans-2-((1-cyclopropyl-piperidin-4-yl)amino)-cyclopropyl)benzamide trihydrochloride [optical isomer, compound derived from N-(1-(cyclopropyl-methyl)-1H-pyrazol-4-yl)-3-(trans-2-((1-cyclo-propylpiperidin-4-yl)-amino)cyclopropyl)-benzamide (optical isomer, retention time short)] | 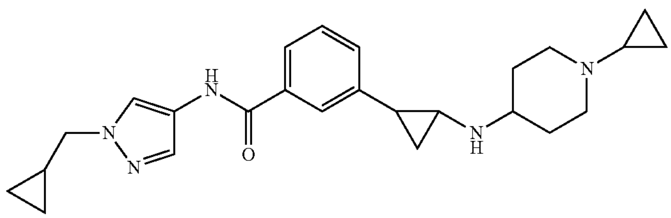 [SMILES: O=C(Nc1cnn(CC2CC2)c1)c1cccc(C2CC2NC2CCN(C3CC3)CC2)c1] | 3HCl | 420.2 |
| 189 | N-(1-(cyclopropylmethyl)-1H-pyrazol-4-yl)-3-(trans-2-((1-cyclopropyl-piperidin-4-yl)amino)-cyclopropyl)benzamide trihydrochloride [optical isomer, compound derived from N-(1-(cyclopropyl-methyl)-1H-pyrazol-4-yl)-3-(trans-2-((1-cyclo-propylpiperidin-4-yl)-amino)cyclopropyl)-benzamide (optical isomer, retention time long)] | 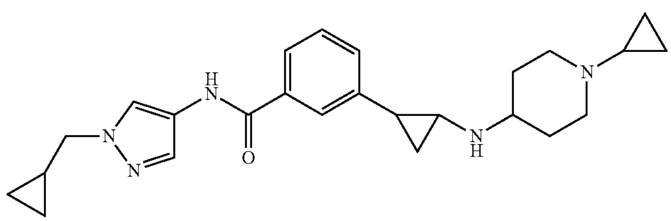 [SMILES: O=C(Nc1cnn(CC2CC2)c1)c1cccc(C2CC2NC2CCN(C3CC3)CC2)c1] | 3HCl | 420.2 |
| 190 | N-(1-(cyclopropylmethyl)-1H-pyrazol-4-yl)-3-(trans-2-(tetrahydro-2H-pyran-4-ylamino)cyclopropyl)-benzamide dihydrochloride | 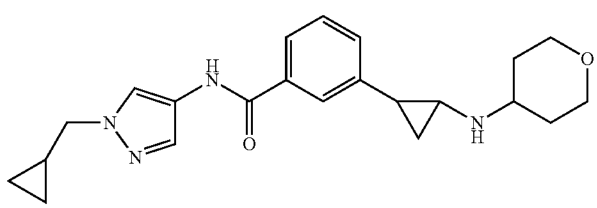 [SMILES: O=C(Nc1cnn(CC2CC2)c1)c1cccc(C2CC2NC2CCOCC2)c1] | 2HCl | 381.1 |
| 191 | N-(1-(cyclopropylmethyl)-1H-pyrazol-4-yl)-3-(trans-2-(tetrahydro-2H-pyran-4-ylamino)cyclopropyl)-benzamide dihydrochloride [optical isomer, compound derived from N-(1-(cyclopropylmethyl)-1H-pyrazol-4-yl)-3-(trans-2-(tetrahydro-2H-pyran-4-ylamino)cyclopropyl)-benzamide (optical isomer, retention time short)] | 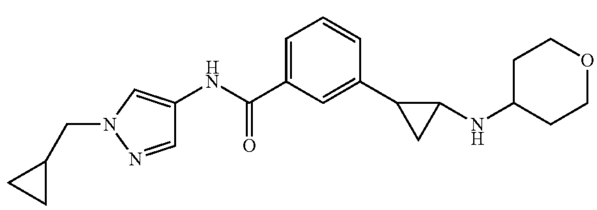 [SMILES: O=C(Nc1cnn(CC2CC2)c1)c1cccc(C2CC2NC2CCOCC2)c1] | 2HCl | 381.1 |

TABLE 1-23

| Ex. No. | IUPAC name | structure | salt | MS |
|---|---|---|---|---|
| 192 | N-(1-(cyclopropyl-methyl)-1H-pyrazol-4-yl)-3-(trans-2-(tetrahydro-2H-pyran-4-ylamino)cyclopropyl)-benzamide dihydrochloride [optical isomer, compound derived from N-(1-(cyclopropyl-methyl)-1H-pyrazol-4-yl)-3-(trans-2-(tetra-hydro-2H-pyran-4-ylamino)cyclopropyl)-benzamide (optical isomer, retention time long)] | 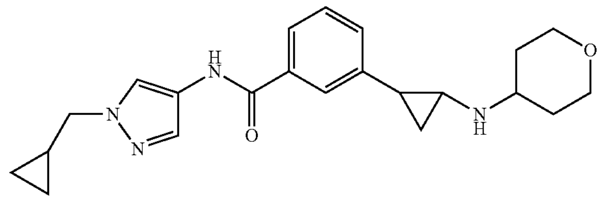 [SMILES: O=C(Nc1cnn(CC2CC2)c1)c1cccc(C2CC2NC2CCOCC2)c1] | 2HCl | 381.1 |
| 193 | 3-(trans-2-((1,1-dioxidotetrahydro-2H-thiopyran-4-yl)amino)-cyclopropyl)-N-(4-(pyrimidin-2-yl)phenyl)benzamide dihydrochloride | 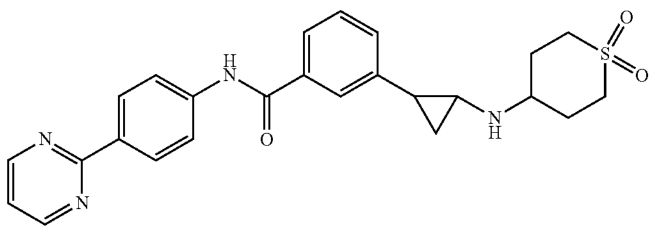 [SMILES: O=C(Nc1ccc(-c2ncccn2)cc1)c1cccc(C2CC2NC2CCS(=O)(=O)CC2)c1] | 2HCl | 463.1 |
| 194 | N-(1-tert-butyl-1H-pyrazol-4-yl)-3-(trans-2-(tetrahydro-2H-pyran-4-ylamino)cyclopropyl)-benzamide dihydrochloride | 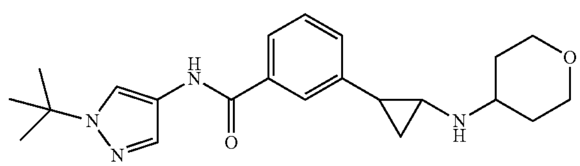 [SMILES: CC(C)(C)n1cc(NC(=O)c2cccc(C3CC3NC3CCOCC3)c2)cn1] | 2HCl | 383.2 |
| 195 | N-(1-tert-butyl-1H-pyrazol-4-yl)-3-(trans-2-((1-cyclopropyl-piperidin-4-yl)amino)-cyclopropyl)benzamide dihydrochloride | 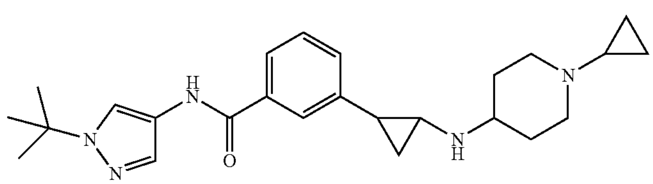 [SMILES: CC(C)(C)n1cc(NC(=O)c2cccc(C3CC3NC3CCN(C4CC4)CC3)c2)cn1] | 2HCl | 422.2 |
| 196 | N-(1-(4-fluorophenyl)-1H-pyrazol-4-yl)-3-(trans-2-(tetrahydro-2H-pyran-4-ylamino)cyclo-propyl)benzamide dihydrochloride | 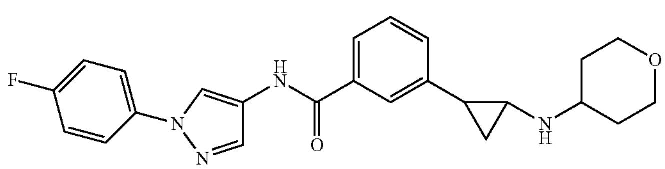 [SMILES: O=C(Nc1cnn(-c2ccc(F)cc2)c1)c1cccc(C2CC2NC2CCOCC2)c1] | 2HCl | 421.2 |
| 197 | 3-(trans-2-((1,1-dioxidotetrahydro-2H-thiopyran-4-yl)amino)cyclopropyl)-N-(1-(4-fluorophenyl)-1H-pyrazol-4-yl)benzamide dihydrochloride | 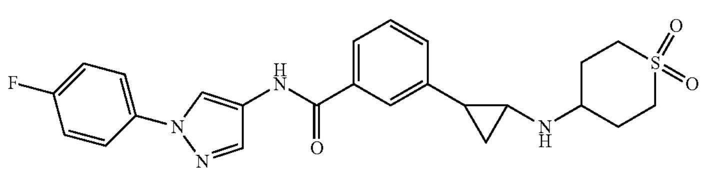 [SMILES: O=C(Nc1cnn(-c2ccc(F)cc2)c1)c1cccc(C2CC2NC2CCS(=O)(=O)CC2)c1] | 2HCl | 469.2 |
| 198 | N-cyclopentyl-3-(trans-2-((1,1-dioxidotetra-hydro-2H-thiopyran-4-yl)amino)cyclopropyl)-benzamide hydrochloride | 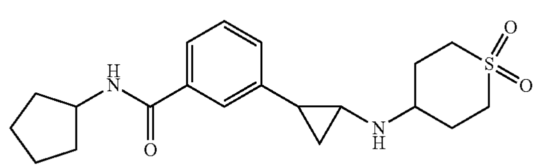 [SMILES: O=C(NC1CCCC1)c1cccc(C2CC2NC2CCS(=O)(=O)CC2)c1] | HCl | 377.2 |

TABLE 1-24

| Ex. No. | IUPAC name | structure | salt | MS |
|---|---|---|---|---|
| 199 | N-cyclopentyl-3-(trans-2-((1-cyclopropyl-piperidin-4-yl)amino)-cyclopropyl)benzamide dihydrochloride | 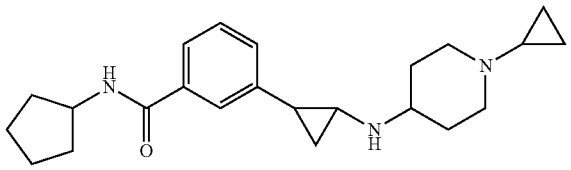 [SMILES: O=C(NC1CCCC1)c1cccc(C2CC2NC2CCN(C3CC3)CC2)c1] | 2HCl | 368.2 |
| 200 | N-cyclopentyl-3-(trans-2-((1-methylpiperidin-4-yl)amino)cyclo-propyl)benzamide dihydrochloride | 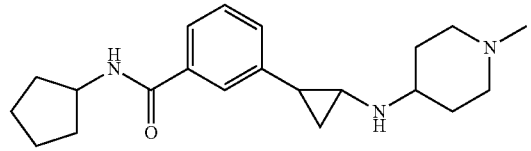 [SMILES: CN1CCC(NC2CC2c2cccc(C(=O)NC3CCCC3)c2)CC1] | 2HCl | 342.3 |
| 201 | 3-(trans-2-(cyclobbutyl-amino)cyclopropyl)-N-(1-(cyclopropylmethyl)-1H-pyrazol-4-yl)benzamide dihydrochloride | 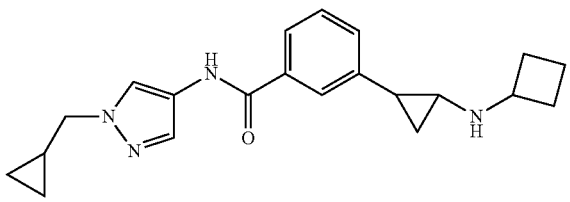 [SMILES: O=C(Nc1cnn(CC2CC2)c1)c1cccc(C2CC2NC2CCC2)c1] | 2HCl | 351.2 |
| 202 | N-(1-(cyclopropyl-methyl)-1H-pyrazol-4-yl)-3-(trans-2-((1-methylpiperidin-4-yl)amino)cyclopropyl)-benzamide trihydrochloride | 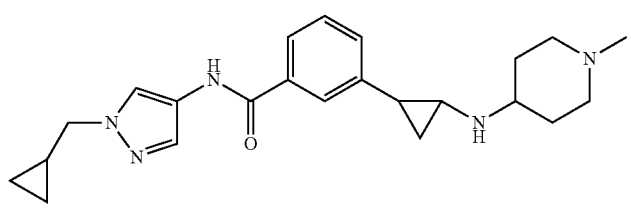 [SMILES: CN1CCC(NC2CC2c2cccc(C(=O)Nc3cnn(CC4CC4)c3)c2)CC1] | 3HCl | 394.2 |
| 203 | N-(1-(cyclopropyl-methyl)-1H-pyrazol-4-yl)-3-(trans-2-((1-(2,2,2-trifluoroethyl)-piperidin-4-yl)amino)cyclopropyl)-benzamide trihydrochloride | 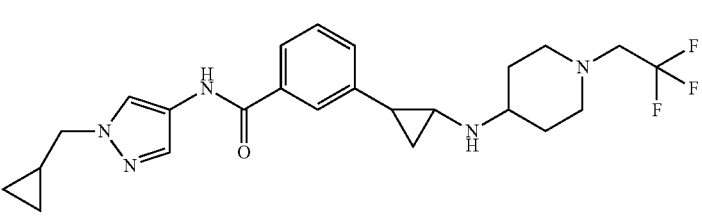 [SMILES: O=C(Nc1cnn(CC2CC2)c1)c1cccc(C2CC2NC2CCN(CC(F)(F)F)CC2)c1] | 3HCl | 462.2 |
| 204 | N-(1-(cyclopropyl-methyl)-1H-pyrazol-4-yl)-3-(trans-2-((4,4-difluorocyclohexyl)-amino)cyclopropyl)-benzamide dihydrochloride | 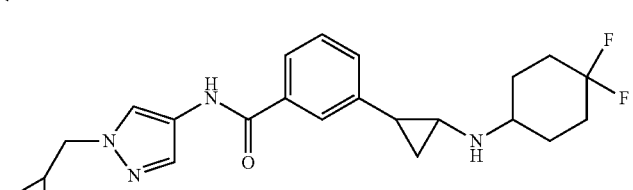 | 2HCl | 415.2 |
| 205 | 3-(trans-2-((4,4-difluorocyclohexyl-amino)cyclopropyl)-N-(1-methyl-1H-pyrazol-4-yl)benzamide dihydrochloride | 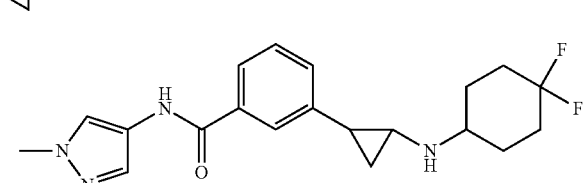 | 2HCl | 375.1 |
| 206 | 3-(trans-2-((1-acetylpiperidin-4-yl)amino)cyclopropyl)-N-(4-fluorophenyl)-benzamide hydrochloride | 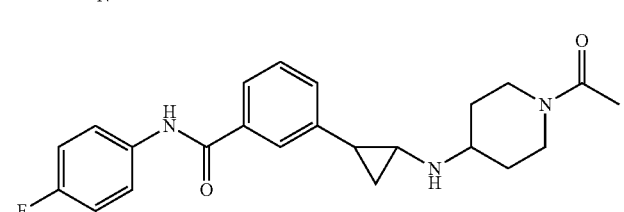 | HCl | 396.3 |

TABLE 1-25

| Ex. No. | IUPAC name | structure | salt | MS |
|---|---|---|---|---|
| 207 | N-(4-fluorophenyl)-3-(trans-2-(tetrahydro-2H-pyran-4-ylamino)cyclopropyl)-benzamide hydrochloride | 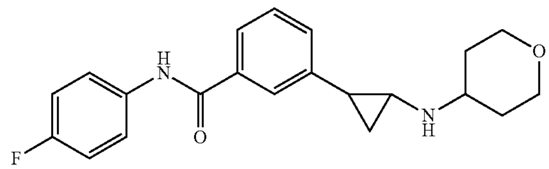 [SMILES: O=C(Nc1ccc(F)cc1)c1cccc(C2CC2NC2CCOCC2)c1] | HCl | 355.2 |
| 208 | 3-(trans-2-((1-cyclopropylpiperidin-4-yl)amino)cyclopropyl)-N-(4,4-difluorocyclohexyl)-benzamide dihydrochloride | 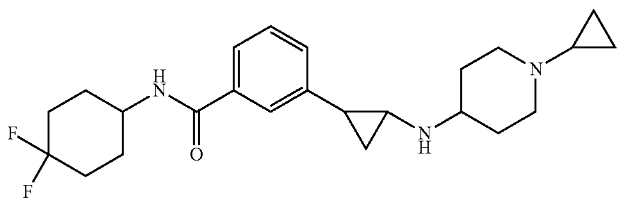 [SMILES: O=C(NC1CCC(F)(F)CC1)c1cccc(C2CC2NC2CCN(C3CC3)CC2)c1] | 2HCl | 418.2 |
| 209 | 3-(trans-2-((4,4-difluorocyclohexyl)-amino)cyclopropyl)-N-(1-ethyl-1H-pyrazol-4-yl)benzamide dihydrochloride | 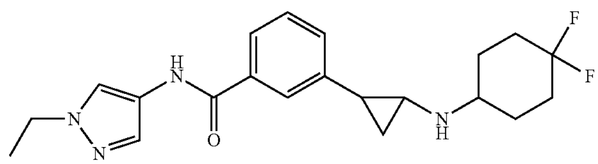 [SMILES: CCn1cc(NC(=O)c2cccc(C3CC3NC3CCC(F)(F)CC3)c2)cn1] | 2HCl | 389.2 |
| 210 | 3-(trans-2-(cyclobutyl-amino)cyclopropyl)-N-(2-methyl-1,3-thiazol-5-yl)benzamide dihydrochloride | 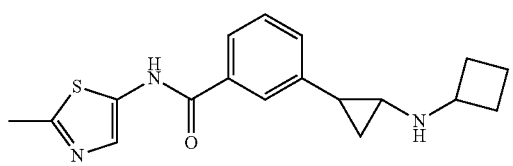 [SMILES: Cc1ncc(NC(=O)c2cccc(C3CC3NC3CCC3)c2)s1] | 2HCl | 328.2 |
| 211 | 3-(trans-2-((4,4-difluorocyclohexyl)-amino)cyclopropyl)-N-(2-methyl-1,3-thiazol-5-yl)benzamide dihydrochloride | 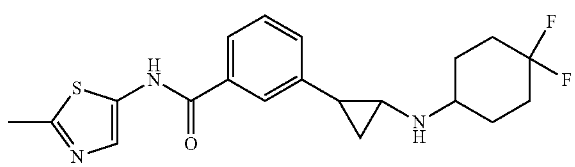 [SMILES: Cc1ncc(NC(=O)c2cccc(C3CC3NC3CCC(F)(F)CC3)c2)s1] | 2HCl | 392.1 |
| 212 | N-(2-methyl-1,3-thiazol-5-yl)-3-(trans-2-(tetrahydro-2H-pyran-4-ylamino)cyclopropyl)-benzamide dihydrochloride | 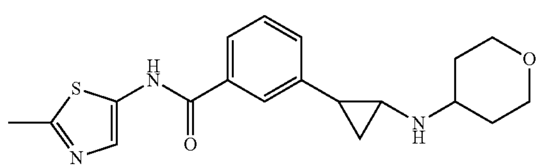 [SMILES: Cc1ncc(NC(=O)c2cccc(C3CC3NC3CCOCC3)c2)s1] | 2HCl | 358.1 |
| 213 | N-cyclopentyl-2-fluoro-5-(trans-2-(tetrahydro-2H-pyran-4-ylamino)cyclopropyl)-benzamide hydrochloride | 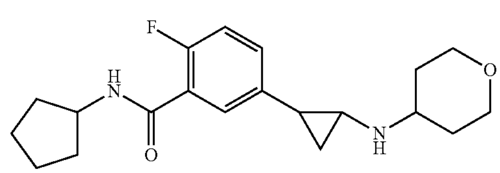 [SMILES: O=C(NC1CCCC1)c1cc(C2CC2NC2CCOCC2)ccc1F] | HCl | 347.3 |
| 214 | N-cyclopentyl-2-methoxy-5-(trans-2-(tetrahydro-2H-pyran-4-ylamino)cyclopropyl)-benzamide hydrochloride | 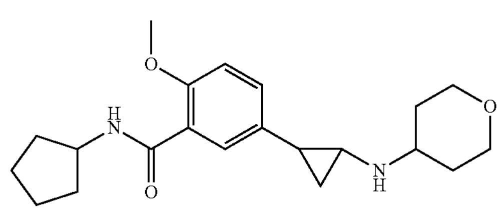 [SMILES: COc1ccc(C2CC2NC2CCOCC2)cc1C(=O)NC1CCCC1] | HCl | 359.2 |

TABLE 1-25-continued

| Ex. No. | IUPAC name | structure | salt | MS |
|---|---|---|---|---|
| 215 | 3-(trans-2-((4,4-difluorocyclohexyl)-amino)cyclopropyl)-N-(1,3-dimethyl-1H-pyrazol-5-yl)benzamide dihydrochloride | 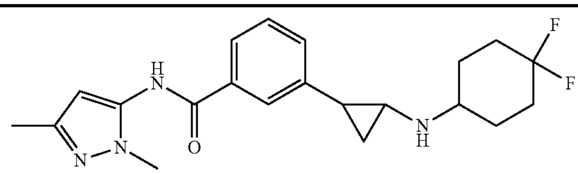 | 2HCl | 389.2 |

TABLE 1-26

| Ex. No. | IUPAC name | structure | salt | MS |
|---|---|---|---|---|
| 216 | 3-(trans-2-((4,4-difluorocyclohexyl)-amino)cyclopropyl)-N-(3-methyl-1,2-oxazol-5-yl)benzamide hydrochloride | 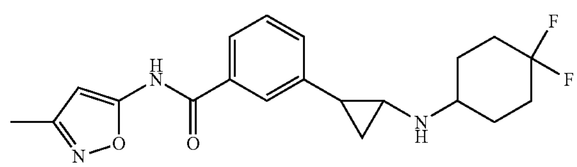 [SMILES: Cc1cc(NC(=O)c2cccc(C3CC3NC3CCC(F)(F)CC3)c2)on1] | HCl | 376.1 |
| 217 | N-(1-(4-fluorobenzyl)-1H-pyrazol-4-yl)-3-(trans-2-(tetrahydro-2H-pyran-4-ylamino)cyclopropyl)-benzamide dihydrochloride | 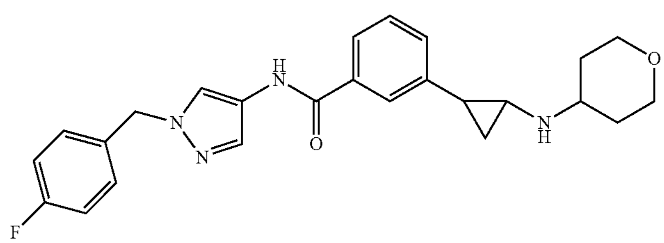 [SMILES: O=C(Nc1cnn(Cc2ccc(F)cc2)c1)c1cccc(C2CC2NC2CCOCC2)c1] | 2HCl | 435.1 |
| 218 | 3-(trans-2-((1-acetyl-piperidin-4-yl)amino)-cyclopropyl)-N-(1-(4-fluorobenzyl)-1H-pyrazol-4-yl)benzamide dihydrochloride | 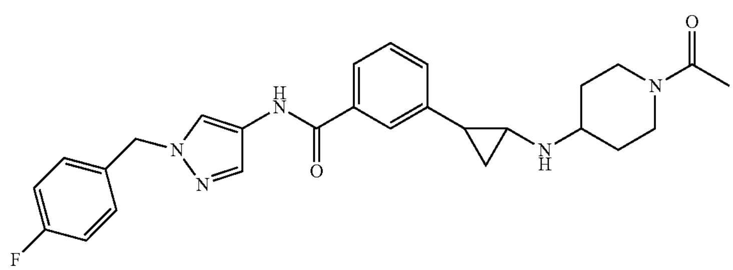 [SMILES: CC(=O)N1CCC(NC2CC2c2cccc(C(=O)Nc3cnn(Cc4ccc(F)cc4)c3)c2)CC1] | 2HCl | 476.3 |
| 219 | 3-(trans-2-((1-acetylpiperidin-4-yl)amino)cyclopropyl)-N-(2-(4-fluorophenyl)-1,3-thiazol-5-yl)benzamide dihydrochloride | 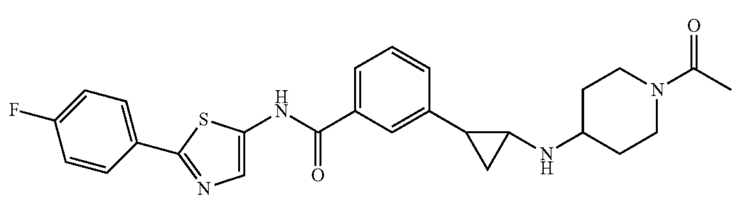 [SMILES: CC(=O)N1CCC(NC2CC2c2cccc(C(=O)Nc3cnc(-c4ccc(F)cc4)s3)c2)CC1] | 2HCl | 477.0 |
| 220 | N-(3-methyl-1,2-thiazol-5-yl)-3-(trans-2-(tetrahydro-2H-pyran-4-ylamino)cyclopropyl)-benzamide hydrochloride | 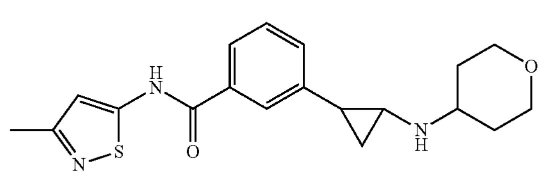 | HCl | 356.0 |

TABLE 1-26-continued

| Ex. No. | IUPAC name | structure | salt | MS |
|---|---|---|---|---|
| 221 | 2-methoxy-N-(5-methyl-1,3,4-thiadiazol-2-yl)-5-(trans-2-(tetrahydro-2H-pyran-4-ylamino)cyclopropyl)benzamide | 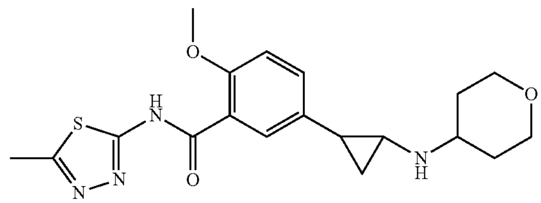 [SMILES: COc1ccc(C2CC2NC2CCOCC2)cc1C(=O)Nc1nnc(C)s1] | free base/ acid | 389.1 |
| 222 | 5-(trans-2-((4,4-difluorocyclohexyl)amino)cyclopropyl)-2-methoxy-N-(5-methyl-1,3,4-thiadiazol-2-yl)benzamide dihydrochloride | 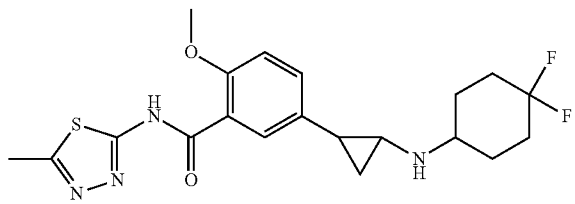 [SMILES: COc1ccc(C2CC2NC2CCC(F)(F)CC2)cc1C(=O)Nc1nnc(C)s1] | 2HCl | 423.1 |
| 223 | 5-(trans-2-((4,4-difluorocyclohexyl)amino)cyclopropyl)-2-fluoro-N-(5-methyl-1,3,4-thiadiazol-2-yl)benzamide dihydrochloride | 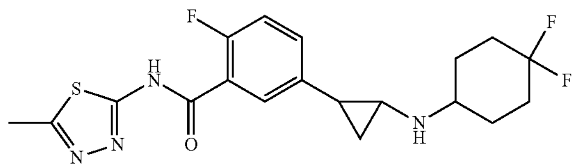 [SMILES: Cc1nnc(NC(=O)c2cc(C3CC3NC3CCC(F)(F)CC3)ccc2F)s1] | 2HCl | 411.1 |
| 224 | 4-fluoro-N-(5-methyl-1,3,4-thiadiazol-2-yl)-3-(trans-2-(tetrahydro-2H-pyran-4-ylamino)cyclopropyl)-benzamide fumarate | 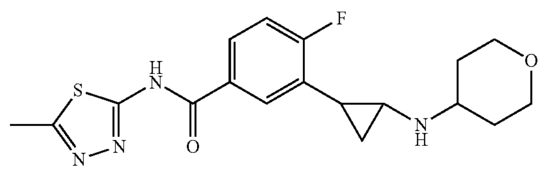 [SMILES: Cc1nnc(NC(=O)c2ccc(F)c(C3CC3NC3CCOCC3)c2)s1] | fumarate | 377.1 |

TABLE 1-27

| Ex. No. | IUPAC name | structure | salt | MS |
|---|---|---|---|---|
| 225 | 5-(trans-2-(cyclobutylamino)cyclopropyl)-2-fluoro-N-(1-methyl-1H-pyrazol-4-yl)benzamide dihydrochloride | 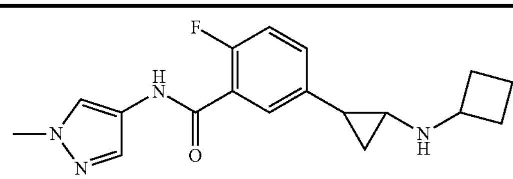 | 2HCl | 329.2 |
| 226 | 5-(trans-2-(cyclobutylamino)cyclopropyl)-2-methoxy-N-(1-methyl-1H-pyrazol-4-yl)benzamide dihydrochloride | 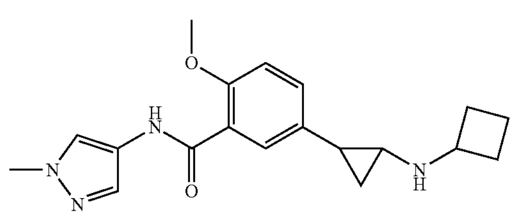 [SMILES: COc1ccc(C2CC2NC2CCC2)cc1C(=O)Nc1cnn(C)c1] | 2HCl | 341.2 |
| 227 | 5-(trans-2-((4,4-difluorocyclohexyl)amino)cyclopropyl)-2-methoxy-N-(1-methyl-1H-pyrazol-4-yl)benzamide dihydrochloride | 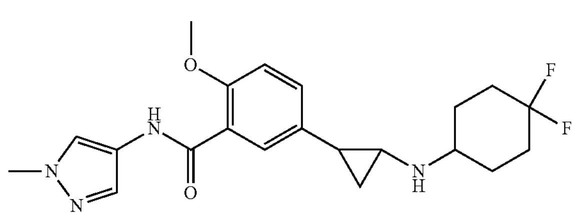 [SMILES: COc1ccc(C2CC2NC2CCC(F)(F)CC2)cc1C(=O)Nc1cnn(C)c1] | 2HCl | 405.1 |

TABLE 1-27-continued

| Ex. No. | IUPAC name | structure | salt | MS |
|---|---|---|---|---|
| 228 | 3-(trans-2-(cyclobutyl-amino)cyclopropyl)-4-fluoro-N-(1-methyl-1H-pyrazol-4-yl)benzamide hydrochloride | 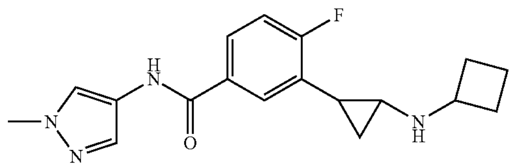 [SMILES: Cn1cc(NC(=O)c2ccc(F)c(C3CC3NC3CCC3)c2)cn1] | HCl | 329.2 |
| 229 | 3-(trans-2-((cyclo-propylmethyl)amino)-cyclopropyl)-4-fluoro-N-(tetrahydro-2H-pyran-4-yl)benzamide hydrochloride | 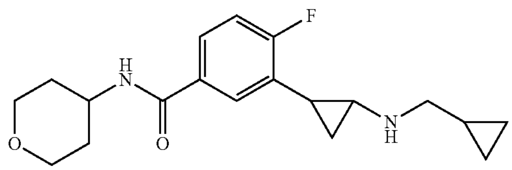 [SMILES: O=C(NC1CCOCC1)c1ccc(F)c(C2CC2NCC2CC2)c1] | HCl | 333.2 |
| 230 | 3-(trans-2-((cyclopropylmethyl)-amino)cyclopropyl)-4-methyl-N-(tetrahydro-2H-pyran-4-yl)benzamide hydrochloride | 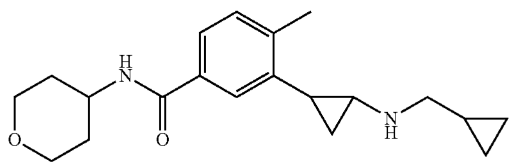 [SMILES: Cc1ccc(C(=O)NC2CCOCC2)cc1C1CC1NCC1CC1] | HCl | 329.2 |
| 231 | N-(5-methyl-1,2-oxazol-3-yl)-3-(trans-2-((tetrahydro-2H-pyran-4-ylmethyl)amino)-cyclopropyl)benzamide | 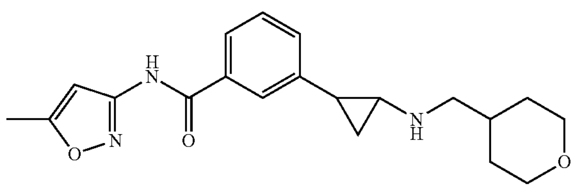 [SMILES: Cc1cc(NC(=O)c2cccc(C3CC3NCC3CCOCC3)c2)no1] | free base/ acid | 356.2 |
| 232 | 3-(trans-2-(cyclobutylamino)-cyclopropyl)-N-(5-methyl-1,2-oxazol-3-yl)benzamide hydrochloride | 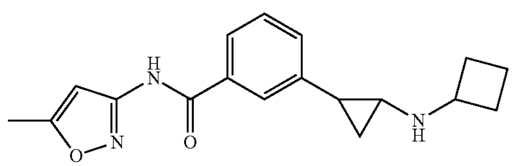 [SMILES: Cc1cc(NC(=O)c2cccc(C3CC3NC3CCC3)c2)no1] | HCl | 312.1 |
| 233 | 3-(trans-2-(dicyclobutylamino)-cyclopropyl)-N-(5-methyl-1,2-oxazol-3-yl)benzamide hydrochloride | 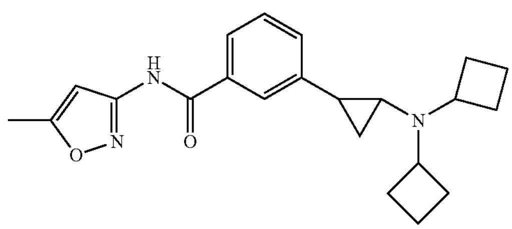 [SMILES: Cc1cc(NC(=O)c2cccc(C3CC3N(C3CCC3)C3CCC3)c2)no1] | HCl | 366.1 |

TABLE 1-28

| Ex. No. | IUPAC name | structure | salt | MS |
|---|---|---|---|---|
| 234 | N-(3,3-difluorocyclo-butyl)-3-(trans-2-((4,4-difluorocyclo-hexyl)amino)cyclo-propyl)benzamide hydrochloride | 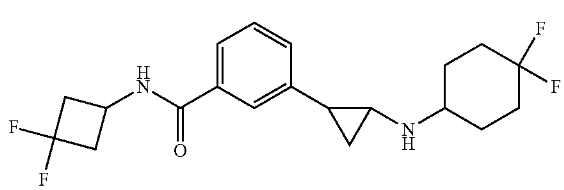 [SMILES: O=C(NC1CC(F)(F)C1)c1cccc(C2CC2NC2CCC(F)(F)CC2)c1] | HCl | 385.1 |

TABLE 1-28-continued

| Ex. No. | IUPAC name | salt | MS |
|---|---|---|---|
| 235 | N-(3-methyl-1,2-oxazol-5-yl)-3-(trans-2-(tetrahydro-2H-pyran-4-ylamino)cyclopropyl)-benzamide hydrochloride | HCl | 342.1 |
| 236 | 3-(trans-2-((cyclopropylmethyl)amino)cyclopropyl)-4-methyl-N-(1-methyl-2H-pyrazol-4-yl)benzamide dihydrochloride | 2HCl | 325.2 |
| 237 | 3-(trans-2-((cyclopropylmethyl)amino)cyclopropyl)-4-fluoro-N-(1-methyl-1H-pyrazol-4-yl)benzamide dihydrochloride | 2HCl | 329.2 |
| 238 | 3-(trans-2-(cyclobutylamino)cyclopropyl)-4-methyl-N-(1-methyl-1H-pyrazol-4-yl)benzamide hydrochloride | HCl | 325.2 |
| 239 | 3-(trans-2-(cyclopentylamino)cyclopropyl)-4-methyl-N-(1-methyl-1H-pyrazol-4-yl)benzamide hydrochloride | HCl | 339.2 |
| 240 | 3-(trans-2-((cyclopropylmethyl)amino)cyclopropyl)-N-(3,3-difluorocyclobutyl)-4-fluorobenzamide hydrochloride | HCl | 339.1 |
| 241 | 5-(trans-2-((cyclopropylmethyl)amino)cyclopropyl)-N-(3,3-difluorocyclobutyl)-2-fluorobenzamide hydrochloride | HCl | 339.1 |
| 242 | 3-(trans-2-((4,4-difluorocyclohexyl)amino)cyclopropyl)-N-(1,3-dimethyl-1H-pyrazol-4-yl)benzamide dihydrochloride | 2HCl | 389.2 |

TABLE 1-29

| Ex. No. | IUPAC name | structure | salt | MS |
|---|---|---|---|---|
| 243 | 3-(trans-2-aminocyclopropyl)-N-(5-methyl-1,3,4-thiadiazol-2-yl)benzamide dihydrochloride [optical isomer, compound derived from methyl 3-(trans-2-((tert-butoxycarbonyl)-amino)cyclopropyl)-benzoate (optical isomer, retention time long)] | 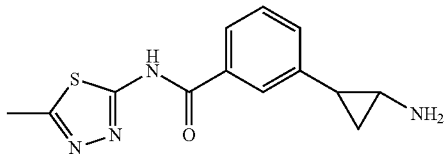 [SMILES: Cc1nnc(NC(=O)c2cccc(C3CC3N)c2)s1] | 2HCl | 275.0 |
| 244 | 3-(trans-2-aminocyclopropyl)-N-(5-methyl-1,3,4-thiadiazol-2-yl)benzamide dihydrochloride [optical isomer, compound derived from methyl 3-(trans-2-((tert-butoxycarbonyl)-amino)cyclopropyl)-benzoate (optical isomer, retention time short)] | 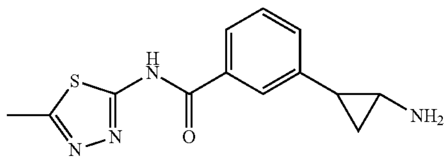 [SMILES: Cc1nnc(NC(=O)c2cccc(C3CC3N)c2)s1] | 2HCl | 275.1 |
| 245 | 3-(trans-2-aminocyclopropyl)-N-(tetrahydro-2H-pyran-4-yl))benzamide hydrochloride [optical isomer, compound derived from methyl 3-(trans-2-((tert-butoxycarbonyl)amino)-cyclopropyl)benzoate (optical isomer, retention time long)] | 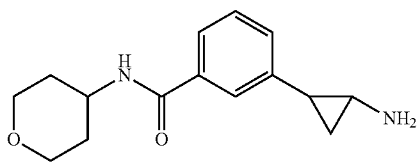 [SMILES: NC1CC1c1cccc(C(=O)NC2CCOCC2)c1] | HCl | 261.1 |
| 246 | 3-(trans-2-aminocyclopropyl)-N-(tetrahydro-2H-pyran-4-yl))benzamide hydrochloride [optical isomer, compound derived from methyl 3-(trans-2-((tert-butoxycarbonyl)amino)-cyclopropyl)benzoate (optical isomer, retention time short)] | 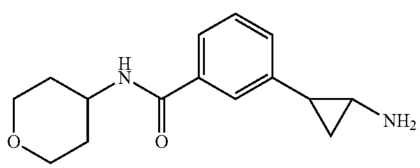 [SMILES: NC1CC1c1cccc(C(=O)NC2CCOCC2)c1] | HCl | 261.1 |

TABLE 1-30

| Ex. No. | IUPAC name | structure | salt | MS |
|---|---|---|---|---|
| 247 | 3-(trans-2-aminocyclopropyl)-N-cyclopentylbenzamide hydrochloride [optical isomer, compound derived from methyl 3-(trans-2-((tert- | 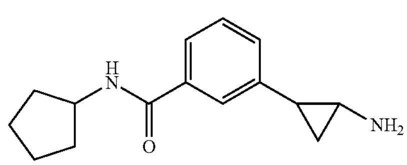 [SMILES: NC1CC1c1cccc(C(=O)NC2CCCC2)c1] | HCl | 245.1 |

TABLE 1-30-continued

| Ex. No. | IUPAC name | structure | salt | MS |
|---|---|---|---|---|
| | butoxycarbonyl)amino)-cyclopropyl)benzoate (optical isomer, retention time long)] | | | |
| 248 | 3-(trans-2-aminocyclopropyl)-N-cyclopentylbenzamide hydrochloride [optical isomer, compound derived from methyl 3-(trans-2-((tert-butoxycarbonyl)amino)-cyclopropyl)benzoate (optical isomer, retention time short)] | 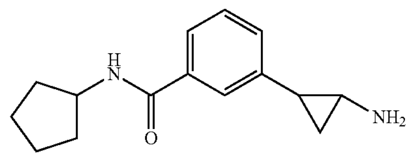 [SMILES: NC1CC1c1cccc(C(=O)NC2CCCC2)c1] | HCl | 245.1 |
| 249 | 3-(trans-2-aminocyclopropyl)-N-(4,4-difluorocyclohexyl)-benzamide hydrochloride [optical isomer, compound derived from methyl 3-(trans-2-((tert-butoxycarbonyl)amino)-cyclopropyl)benzoate (optical isomer, retention time long)] | 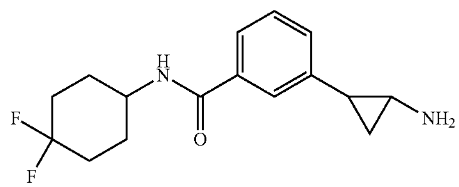 [SMILES: NC1CC1c1cccc(C(=O)NC2CCC(F)(F)CC2)c1] | HCl | 295.1 |
| 250 | 3-(trans-2-aminocyclopropyl)-N-(4,4-difluorocyclohexyl)-benzamide hydrochloride [optical isomer, compound derived from methyl 3-(trans-2-((tert-butoxycarbonyl)amino)-cyclopropyl)benzoate (optical isomer, retention time short)] | 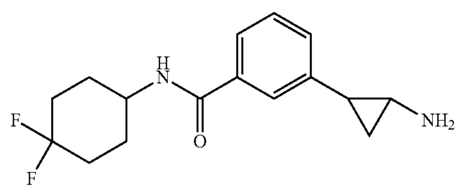 [SMILES: NC1CC1c1cccc(C(=O)NC2CCC(F)(F)CC2)c1] | HCl | 295.1 |

TABLE 1-31

| Ex. No. | IUPAC name | structure | salt | MS |
|---|---|---|---|---|
| 251 | 3-(trans-2-aminocyclopropyl)-N-(1-(2,2,2-trifluoro-ethyl)piperidin-4-yl)benzamide dihydrochloride [optical isomer, compound derived from methyl 3-(trans-2-((tert-butoxycarbonyl)amino)-cyclopropyl)benzoate (optical isomer, retention time long)] | 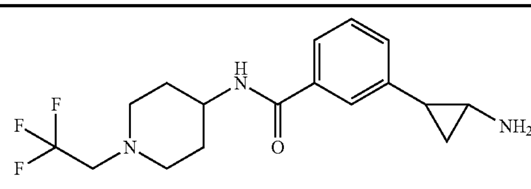 | 2HCl | 342.1 |
| 252 | 3-(trans-2-aminocyclopropyl)-N-(1-(2,2,2-trifluoro-ethyl)piperidin-4-yl)benzamide dihydrochloride [optical isomer, compound derived | 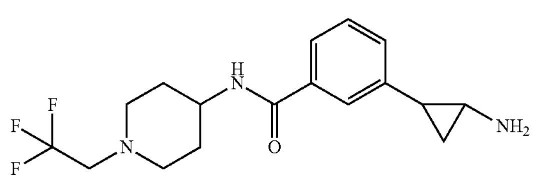 [SMILES: NC1CC1c1cccc(C(=O)NC2CCN(CC(F)(F)F)CC2)c1] | 2HCl | 342.1 |

TABLE 1-31-continued

| Ex. No. | IUPAC name | structure | salt | MS |
|---|---|---|---|---|
| | from methyl 3-(trans-2-((tert-butoxycarbonyl)amino)-cyclopropyl)benzoate (optical isomer, retention time short)] | | | |
| 253 | 3-(trans-2-(cyclobutylamino)-cyclopropyl)-N-(5-methyl-1,3,4-thiadiazol-2-yl)benzamide 1/2 fumarate (optical isomer, retention time long) | 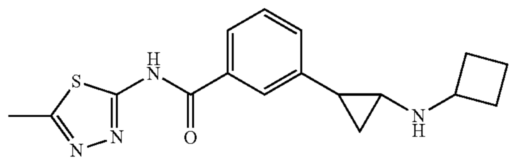 [SMILES: Cc1nnc(NC(=O)c2cccc(C3CC3NC3CCC3)c2)s1] | 1/2 fumarate | 329.1 |
| 254 | 3-(trans-2-(cyclobutylamino)-cyclopropyl)-N-(5-methyl-1,3,4-thiadiazol-2-yl)benzamide 1/2 fumarate (optical isomer, retention time short) | 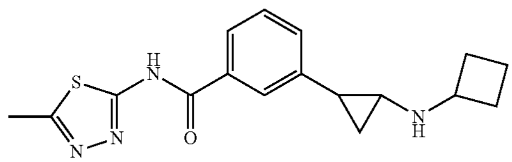 [SMILES: Cc1nnc(NC(=O)c2cccc(C3CC3NC3CCC3)c2)s1] | 1/2 fumarate | 329.1 |

TABLE 1-32

| Ex. No. | IUPAC name | structure | salt | MS |
|---|---|---|---|---|
| 255 | 3-(trans-2-((1-cyclopropylpiperidin-4-yl)amino)cyclopropyl)-N-(5-methyl-1,3,4-thiadiazol-2-yl)benzamide acetate [optical isomer, compound derived from methyl 3-(trans-2-((tert-butoxycarbonyl)amino)-cyclopropyl)benzoate (optical isomer, retention time long)] | 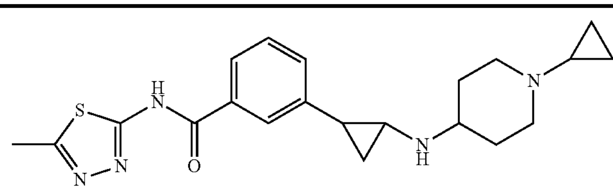 | CH3COOH | 398.1 |
| 256 | 3-(trans-2-((1-cyclopropylpiperidin-4-yl)amino)cyclopropyl)-N-(5-methyl-1,3,4-thiadiazol-2-yl)benzamide acetate [optical isomer, compound derived from methyl 3-(trans-2-((tert-butoxycarbonyl)amino)-cyclopropyl)benzoate (optical isomer, retention time short)] | 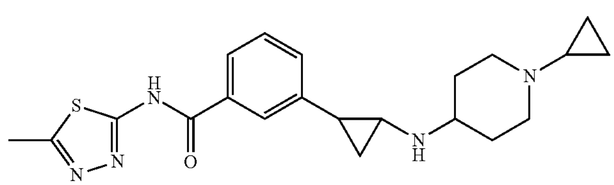 [SMILES: Cc1nnc(NC(=O)c2cccc(C3CC3NC3CCN(C4CC4)CC3)c2)s1] | CH3COOH | 398.1 |
| 257 | 3-(trans-2-((1-cyclopropylpiperidin-4-yl)amino)cyclopropyl)-N-(5-methyl-1,3,4-thiadiazol-2-yl)benzamide difumarate (optical isomer, retention time long) | 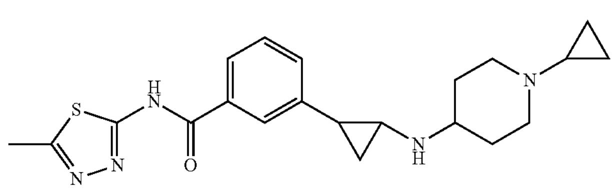 [SMILES: Cc1nnc(NC(=O)c2cccc(C3CC3NC3CCN(C4CC4)CC3)c2)s1] | 2 fumarate | 398.1 |

TABLE 1-32-continued

| Ex. No. | IUPAC name | structure | salt | MS |
|---|---|---|---|---|
| 258 | 3-(trans-2-((1-cyclopropylpiperidin-4-yl)amino)cyclopropyl)-N-(5-methyl-1,3,4-thiadiazol-2-yl)benzamide difumarate (optical isomer, retention time short) | 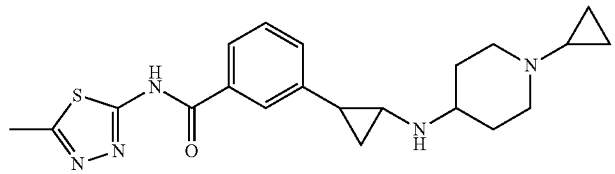 [SMILES: Cc1nnc(NC(=O)c2cccc(C3CC3NC3CCN(C4CC4)CC3)c2)s1] | 2 fumarate | 398.6 |

TABLE 1-33

| Ex. No. | IUPAC name | structure | salt | MS |
|---|---|---|---|---|
| 259 | 3-(trans-2-((4,4-difluorocyclohexyl)amino)cyclopropyl)-N-(tetrahydro-2H-pyran-4-yl)benzamide hydrochloride (optical isomer, retention time long) | 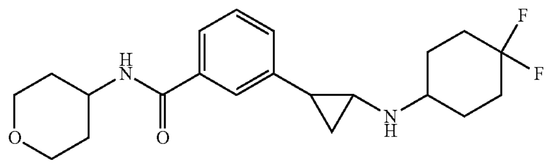 [SMILES: O=C(NC1CCOCC1)c1cccc(C2CC2NC2CCC(F)(F)CC2)c1] | HCl | 379.2 |
| 260 | 3-(trans-2-((4,4-difluorocyclohexyl)amino)cyclopropyl)-N-(tetrahydro-2H-pyran-4-yl)benzamide hydrochloride (optical isomer, retention time short) | 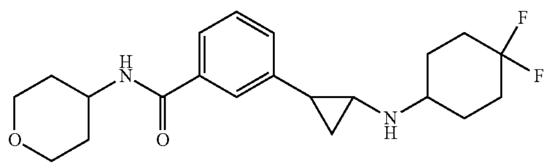 [SMILES: O=C(NC1CCOCC1)c1cccc(C2CC2NC2CCC(F)(F)CC2)c1] | HCl | 379.2 |
| 261 | 3-(trans-2-(cyclobutylamino)cyclopropyl)-N-(tetrahydro-2H-pyran-4-yl)benzamide hydrochloride (optical isomer, retention time long) | 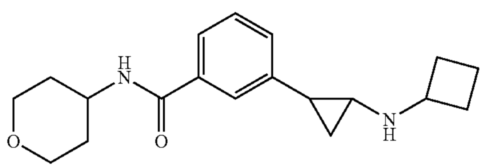 [SMILES: O=C(NC1CCOCC1)c1cccc(C2CC2NC2CCC2)c1] | HCl | 315.2 |
| 262 | 3-(trans-2-(cyclobutylamino)cyclopropyl)-N-(tetrahydro-2H-pyran-4-yl)benzamide hydrochloride (optical isomer, retention time short) | 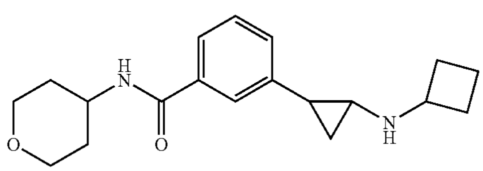 [SMILES: O=C(NC1CCOCC1)c1cccc(C2CC2NC2CCC2)c1] | HCl | 315.2 |
| 263 | N-cyclopentyl-3-(trans-2-(tetrahydro-2H-pyran-4-ylamino)cyclopropyl)benzamide hydrochloride (optical isomer, retention time long) | 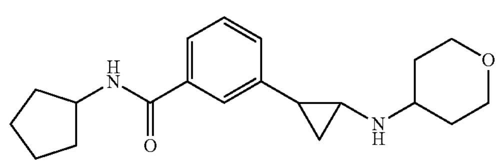 [SMILES: O=C(NC1CCCC1)c1cccc(C2CC2NC2CCOCC2)c1] | HCl | 329.1 |
| 264 | N-cyclopentyl-3-(trans-2-(tetrahydro-2H-pyran-4-ylamino)cyclopropyl)benzamide hydrochloride (optical isomer, retention time short) | 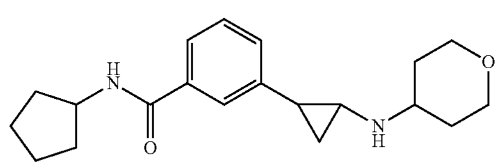 [SMILES: O=C(NC1CCCC1)c1cccc(C2CC2NC2CCOCC2)c1] | HCl | 329.2 |

TABLE 1-34

| Ex. No. | IUPAC name | salt | MS |
|---|---|---|---|
| 265 | N-(4,4-difluorocyclohexyl)-3-(trans-2-(tetrahydro-2H-pyran-4-ylamino)cyclopropyl)-benzamide hydrochloride (optical isomer, retention time long) | HCl | 379.2 |
| 266 | N-(4,4-difluorocyclohexyl)-3-(trans-2-(tetrahydro-2H-pyran-4-ylamino)cyclopropyl)-benzamide hydrochloride (optical isomer, retention time short) | HCl | 379.2 |
| 267 | 3-(trans-2-((cyclopropylmethyl)-amino)cyclopropyl)-N-(4,4-difluorocyclohexyl)-benzamide hydrochloride (optical isomer, retention time long) | HCl | 349.3 |
| 268 | 3-(trans-2-((cyclopropylmethyl)-amino)cyclopropyl)-N-(4,4-difluorocyclohexyl)-benzamide hydrochloride (optical isomer, retention time short) | HCl | 349.1 |
| 269 | 3-(trans-2-((cyclopropylmethyl)-amino)cyclopropyl)-N-(1-(2,2,2-trifluoroethyl)-piperidin-4-yl)benzamide dihydrochloride (optical isomer, retention time long) | 2HCl | 396.1 |
| 270 | 3-(trans-2-((cyclopropylmethyl)-amino)cyclopropyl)-N-(1-(2,2,2-trifluoroethyl)-piperidin-4-yl)benzamide dihydrochloride (optical isomer, retention time short) | 2HCl | 396.1 |

TABLE 1-35

| Ex. No. | IUPAC name | salt | MS |
|---|---|---|---|
| 271 | 3-(trans-2-((cyclopropylmethyl)-amino)cyclopropyl)-N-(1-(2,2,2-trifluoroethyl)piperidin-4-yl)benzamide 3/2 fumarate (optical isomer, retention time long) | 3/2 fumarate | 396.1 |

TABLE 1-35-continued

| Ex. No. | IUPAC name | structure | salt | MS |
|---|---|---|---|---|
| 272 | 2-(trans-2-aminocyclopropyl)-5-fluoro-N-(5-methyl-1,3,4-thiadiazol-2-yl)benzamide dihydrochloride | 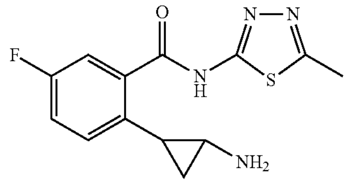 [SMILES: Cc1nnc(NC(=O)c2cc(F)ccc2C2CC2N)s1] | 2HCl | 290.9 |
| 273 | 2-(trans-2-((1-cyclopropylpiperidin-4-yl)amino)cyclopropyl)-5-fluoro-N-(5-methyl-1,3,4-thiadiazol-2-yl)benzamide dihydrochloride | 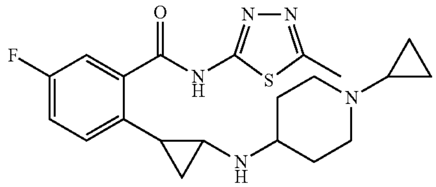 [SMILES: Cc1nnc(NC(=O)c2cc(F)ccc2C2CC2NC2CCN(C3CC3)CC2)s1] | 2HCl | 416.1 |

Experimental Example 1

The genetic engineering method described below was performed according to the method described in a book (Maniatis et al., Molecular Cloning, Cold Spring Harbor Laboratory, 1989) or the method described in the protocol attached to the reagent.

(1) Construction of GST-tagged expression vector having TEV Protease cleavage sequence A GST-tagged expression vector having TEV Protease cleavage sequence was constructed by successive 2 times of PCR method. Firstly, PCR was performed using pGEX6P1 (GE Healthcare) as a template, two primers GST-Sw-F:
[SEQ ID NO: 1]
5'-AGAATCATTTAAATGGTGATCATGTAACCCATCCT-3'

GST-Tv-R1:
[SEQ ID NO: 2]
5'-CGCCCTGAAAGTACAGGTTCTCATCCGATTTTGGAGGATGGTCG-3' and PrimeStar GXL DNA Polymerase (Takara Bio Inc.). Template DNA 0.5 µL, PrimeStar GXL DNA Polymerase Buffer 10 µL, 2.5 mM dNTP solution 4 µL, 10 µM primer solution each 1.5 µL, PrimeStar GXL DNA Polymerase 1 µL, and sterilized distilled water 31.5 µL were mixed. After a treatment at 98° C. for 1 min, the PCR was started with 35 repeats of reactions at 98° C. for 10 seconds, at 65° C. for 5 seconds, and at 72° C. for 25 seconds, followed by a reaction at 72° C. for 1 min. Then, PCR was performed using the obtained PCR product as a template, two primers GST-Sw-F:
[SEQ ID NO: 1]
5'-AGAATCATTTAAATGGTGATCATGTAACCCATCCT-3'

GST-Tv-R2:
[SEQ ID NO: 3]
5'-ATAATAGGATCCGCCCTGAAAGTACAGGTTCTC-3' and PrimeStar GXL DNA Polymerase. Template DNA 0.5 µL, PrimeStar GXL DNA Polymerase Buffer 10 µL, 2.5 mM dNTP solution 4 µL, 10 µM primer solution each 1.5 µL, PrimeStar GXL DNA Polymerase 1 µL, and sterilized distilled water 31.5 µL were mixed. After a treatment at 98° C. for 1 min, the PCR was started with 25 repeats of reactions at 98° C. for 10 seconds, at 65° C. for 5 seconds, and at 72° C. for 25 seconds, followed by a reaction at 72° C. for 1 min. The obtained PCR product was electrophoresed on agarose gel (1%), and an about 0.3 kbp DNA fragment containing a part of the GST gene was recovered from the gel. The recovered DNA fragment was cleaved with restriction enzymes Swa I (New England Biolabs) and Bam HI (Takara Bio Inc.), and inserted into the Swa I/Bam HI site of pGEX6P1 to construct an expression vector pGEX7V1.

(2) Cloning of Human LSD1 (AOF2) Gene

Human LSD1 gene was cloned by PCR method using brain cDNA Library (Takara Bio Inc.) as a template, two primers hLSD1-NheI-ko-F:
[SEQ ID NO: 4]
5'-TATTATGCTAGCGCCACCATGTTATCTGGGAAGAAGGCGGCAGC-3' hLSD1-St-NotI-R:
[SEQ ID NO: 5]
5'-TATTATGCGGCCGCTCACATGCTTGGGGACTGCTGTGC-3' and Pyrobest DNA Polymerase (Takara Bio Inc.). Template DNA 0.5 µL, Pyrobest DNA Polymerase Buffer 5 µL, 2.5 mM dNTP solution 4 µL, 10 µM primer solution each 2.5 µL, Pyrobest DNA Polymerase 0.5 µL, and sterilized distilled water 35 µL were mixed. After a reaction at 98° C. for 1 min, the PCR was started with 35 repeats of reactions at 98° C. for 10 seconds, at 68° C. for 5 seconds, and at 72° C. for 2.5 min, followed by a reaction at 72° C. for 1 min. The obtained PCR product was electrophoresed on agarose gel (1%), and an about 2.5 kbp DNA fragment containing the human LSD1 gene was recovered from the gel. The recovered DNA fragment was cleaved with restriction enzymes Nhe I and Not I (Takara Bio Inc.), and inserted into the Nhe I/Not I site of pcDNA3.1(+) (Invitrogen) to construct an expression plasmid pcDNA3.1/hLSD1.

(3) Construction of Expression Plasmid for Human LSD1 (172-833) in *Escherichia coli*

A plasmid for expression of human LSD1(172-B33) in *Escherichia coli* was constructed by PCR method using pcDNA3.1/hLSD1 as a template, two primers hLSD1-172aa-59-12-F:
[SEQ ID NO: 6]
5'-ATAATAAGATCTTCGGGTGTGGAGGGCGCAGCTT-3' hLSD1-833aa-St-NotI-R:

[SEQ ID NO: 7]
5'-ATAATAGCGGCCGCCATGGCCCCCAAAAACTGGTCTGCA-3' and PrimeStar MAX DNA Polymerase (Takara Bio Inc.). Template DNA 1 μL, PrimeStar MAX DNA Polymerase Enzyme PreMix 25 μL, 10 μM primer solution each 1.5 μL, and sterilized distilled water 21 μL were mixed. After a reaction at 98° C. for 1 min, the PCR was started with 25 repeats of reactions at 98° C. for 10 seconds and at 68° C. for 8 seconds, followed by a reaction at 72° C. for 1 min. The obtained PCR product was electrophoresed on agarose gel (1%), and an about 2 kbp DNA fragment containing human LSD1(172-833) gene was recovered from the gel. The recovered DNA fragment was cleaved with restriction enzymes Bgl II and Not I (Takara Bio Inc.), and inserted into the Bam HI/Not I site of pGEX7V1 to construct an expression plasmid pGEX7V1/GST-hLSD1(172-833).

(4) Preparation of LSD1

Escherichia coli C43(DE3) pLysS was transformed with the expression plasmid pGEX7V1/GST-hLSD1(172-833). The obtained recombinant Escherichia coli was inoculated in a TB medium (1.2% tryptone, 2.4% yeast extract, 0.4% glycerol, 17 mM potassium dihydrogen phosphate and 72 mM dipotassium hydrogen phosphate) added with 100 mg/L ampicillin and 35 mg/L chloramphenicol, and cultured at 37° C. When the turbidity reached 500 Klett units, the culture temperature was changed to 16° C., IPTG (Isopropyl β-D-1-thiogalactopyranoside) having a final concentration of 0.5 mM was added to induce expression, and the cells were cultured further for 14 hr. The culture medium was centrifuged at 6,000 g for 15 min, and Escherichia coil pellets were recovered.

Escherichia coli pellets for 12 L of the culture medium were suspended in 1000 mL of PBS (Immuno-Biological Laboratories Co., Ltd.), 0.15 M NaCl, 5%(V/V) Glycerol (Buffer A), and 5000 units Benzonase (Merck), 1000 mg Lysozyme, and 10 tablets of Protease Inhibitor (Roche) were added. Using Branson ultrasonic disintegrator, the suspension was disrupted by ultrasonication for 3 min, and centrifuged at 33,000 g for 60 min, and the supernatant was recovered. The supernatant was applied to two GSTrap 4B 5 mL columns (GE Healthcare) equilibrated in advance with 0.1 M Tris (pH 8.0), 0.15 M NaCl, 5%(V/V) Glycerol (Buffer 13), and the columns were each washed with 30 mL of Buffer B. GST-hLSD1(172-833) was eluted from each column with Buffer B added with 13 mL of GSH with the final concentration 20 mM, applied to two HiLoad 26/60 Superdex 200 pg columns (GE Healthcare) equilibrated in advance with Buffer B, and eluted with 380 mL of Buffer B. Total 60 mL of GST-hLSD1(172-833)-containing fraction was diluted 5-fold with 20 mM Tris (pH 8.0) (Buffer C), applied to Mono Q 10/100 GL column (GE Healthcare) equilibrated in advance with Buffer C, and 0-500 mM NaCl gradient elution was performed to give purified GST-hLSD1 (172-833). 3.4 mg of His-TEV protease was added to about 34 mg of GST-hLSD1(172-833), and the mixture was treated with 50 mM Tris (pH 8.0), 0.5 mM EDTA, 1 mM DTT at 4° C. for 16 hr to cleave the GST tag. The reaction mixture after the cleavage reaction was applied to two series-coupled columns with Ni-NTA Superflow Cartridges 1 mL (QIAGEN), and GSTrap 4B 5 mL column (GE Healthcare) equilibrated in advance with Buffer A added with Imidazole at a final concentration of 20 mM, and a flow-through fraction containing hLSD1(172-833) free of GST-tag was recovered. It was concentrated to 10 mL with AmiconUltra (NWCO 30K) (Millipore Japan), and purified with HiLoad 26/60 Superdex 200 pg column (GE Healthcare) equilibrated with Buffer A to give hLSD1 purified product (8.4 mg). The protein concentration of hLSD1 was measured by BCA Protein Assay Kit (Thermo Fisher Scientific K.K.) using bovine serum albumin as the standard.

(5) Measurement of LSD1 Inhibitory Activity

A test compound dissolved in 2.5% DMSO was added by 4 μL to 3 μL reaction solution (50 mM Tris-HCl (pH 8.0), 0.1% BSA, 1 mM DTT) containing 7.5 ng of LSD1, and the mixture was reacted at room temperature for 60 min. Biotin-histone H3 mono methylated K4 peptide solution (NH2-ART(me-K)QTARKSTGGKAPRKQLAGGK(Biotin)-CONH2) (3.3 μM) was added by 3 μL to start the reaction. After reaction at room temperature for 5 min, 1 mM 2-PCPA solution was added 5 μL to terminate the reaction. A detection solution (BOO mM potassium fluoride, 0.1% BSA) containing europium-labeled anti-histone H3 antibody (Wako Pure Chemical Industries, Ltd.) and Streptavidin-XL665 (Cisbio) was further added by 5 μL, and the mixture was left standing for 60 min. A time-resolved fluorescence (excitation 320 nm, emission 615 nm, 665 nm) was measured by Envision (PerkinElmer). The LSD1 inhibitory rate (%) of the test compound was calculated by the following formula.

inhibitory rate(%)=(1−(test compound count−blank)÷(control−blank))×100

The count of the LSD1 enzyme reaction mixture under compound non-addition conditions is indicated as control, and the count under compound non-addition and LSD1 enzyme non-addition conditions is indicated as blank. A concentration necessary for achieving 50% inhibitory rate was taken as $IC_{50}$ value. The results are shown in Table 2.

Experimental Example 2

(1) Measurement of MAO-A Inhibitory Activity

The MAO-A inhibitory activity evaluation described below followed the protocol of MAO-Glo (registered trademark) Assay of Promega KK.

A test compound dissolved in 4% DMSO was added by 12.5 μL to 25 μL reaction solution (100 mM HEPES (pH 7.5), 5% glycerol) containing 400 ng of MAO-A enzyme (Sigma-Aldrich Co. LLC.), and the mixture was reacted at room temperature for 10 min. MAO substrate (Promega KK) (160 μM) was added by 12.5 μL to start the reaction. After reaction at room temperature for 60 min, Luciferine detection reagent (Promega KK) (50 μL) was added to terminate the reaction. After reaction at room temperature for min with stirring, the luminescence was measured by Envision (PerkinElmer). The MAO-A inhibitory rate (%) of the test compound was calculated by the following formula.

inhibitory rate(%)=(1−(test compound count−blank)÷(control−blank))×100

The count of the MAO-A enzyme reaction mixture under compound non-addition conditions is indicated as control, and the count under compound non-addition and MAO-A enzyme non-addition conditions is indicated as blank. A concentration necessary for achieving 50% inhibitory rate was taken as $IC_{50}$ value. The results are shown in Table 2.

(2) Measurement of MAO-B Inhibitory Activity

The MAO-B inhibitory activity evaluation described below followed the protocol of MAO-Glo (registered trademark) Assay of Promega KK.

A test compound dissolved in 4% DMSO was added by 12.5 μL to 25 μL reaction solution (100 mM HEPES (pH 7.5), 5% glycerol, 10% DMSO) containing 400 ng of MAO-B enzyme (Sigma-Aldrich Co. LLC.), and the mixture was reacted at room temperature for 10 min. MAO substrate (Promega KK) (16 μM) was added by 12.5 μL to start the reaction. After reaction at room temperature for 60 min, Luciferine detection reagent (Promega KK) (50 μL) was added to terminate the reaction. After reaction at room temperature for 20 min with stirring, the luminescence was measured by Envision (PerkinElmer). The MAO-B inhibitory rate (%) of the test compound was calculated by the following formula.

inhibitory rate(%)=(1−(test compound count−blank)÷(control−blank))×100

The count of the MAO-B enzyme reaction mixture under compound non-addition conditions is indicated as control, and the count under compound non-addition and MAO-B enzyme non-addition conditions is indicated as blank. A concentration necessary for achieving 50% inhibitory rate was taken as $IC_{50}$ value. The results are shown in Table 2.

TABLE 2

| Example No. | LSD1 $IC_{50}$ value (μM) | MAO-A $IC_{50}$ value (μM) | MAO-B $IC_{50}$ value (μM) |
| --- | --- | --- | --- |
| 1 | <0.1 | 0.10 | 3.2 |
| 2 | <0.1 | 0.10 | >10 |
| 3 | <0.1 | 0.25 | >10 |
| 4 | <0.1 | 0.19 | 0.54 |
| 5 | 0.14 | 2.9 | >10 |
| 6 | <0.1 | 0.32 | 4.2 |
| 7 | <0.1 | 0.80 | >10 |
| 8 | <0.1 | 8.3 | 4.6 |
| 9 | <0.1 | 0.12 | >10 |
| 10 | <0.1 | 7.0 | >10 |
| 11 | 0.21 | 5.9 | >10 |
| 12 | 0.21 | 4.0 | >10 |
| 13 | <0.1 | >10 | >10 |
| 14 | <0.1 | 8.1 | >10 |
| 15 | <0.1 | >10 | >10 |
| 16 | <0.1 | >10 | >10 |
| 17 | <0.1 | >10 | >10 |
| 18 | <0.1 | >10 | >10 |
| 19 | <0.1 | >10 | >10 |
| 20 | <0.1 | >10 | >10 |
| 21 | <0.1 | 1.8 | >10 |
| 22 | <0.1 | >10 | >10 |
| 23 | <0.1 | >10 | >10 |
| 24 | <0.1 | >10 | >10 |
| 25 | <0.1 | >10 | >10 |
| 26 | <0.1 | >10 | >10 |
| 27 | <0.1 | >10 | >10 |
| 28 | <0.1 | >10 | >10 |
| 29 | <0.1 | 7.3 | >10 |
| 30 | <0.1 | >10 | >10 |
| 31 | <0.1 | 4.0 | >10 |
| 32 | <0.1 | >10 | >10 |
| 33 | <0.1 | >10 | >10 |
| 34 | <0.1 | 4.4 | >10 |
| 35 | <0.1 | 3.1 | >10 |
| 36 | <0.1 | 4.3 | >10 |
| 37 | <0.1 | 4.5 | >10 |
| 38 | <0.1 | 2.2 | >10 |
| 39 | <0.1 | 6.6 | >10 |
| 40 | <0.1 | >10 | >10 |
| 41 | <0.1 | 6.6 | >10 |
| 42 | <0.1 | 3.4 | >10 |
| 43 | <0.1 | 1.5 | >10 |
| 44 | <0.1 | 1.3 | >10 |
| 45 | <0.1 | 1.7 | >10 |
| 46 | <0.1 | 1.8 | >10 |
| 47 | <0.1 | 5.0 | >10 |
| 48 | <0.1 | 2.6 | >10 |
| 49 | <0.1 | 1.8 | >10 |
| 50 | <0.1 | 0.20 | >10 |
| 51 | <0.1 | 0.83 | >10 |
| 52 | <0.1 | >10 | >10 |
| 53 | <0.1 | >10 | >10 |
| 54 | 0.75 | >10 | 3.7 |
| 55 | 2.4 | >10 | >10 |
| 56 | 2.4 | >10 | >10 |
| 58 | <0.1 | >10 | >10 |
| 59 | 0.31 | >10 | >10 |
| 60 | 0.11 | >10 | >10 |
| 61 | 0.67 | >10 | >10 |
| 62 | <0.1 | >10 | 4.8 |
| 63 | 0.91 | >10 | >10 |
| 64 | 1.3 | >10 | >10 |
| 65 | 2.5 | >10 | >10 |
| 66 | 3.6 | >10 | >10 |
| 67 | 4.0 | >10 | >10 |
| 68 | 2.5 | 0.49 | 6.1 |
| 69 | 0.68 | 6.0 | 2.7 |
| 70 | 0.70 | >10 | 8.9 |
| 71 | 0.25 | 10 | 0.39 |
| 72 | 0.74 | >10 | 5.7 |
| 74 | 4.6 | >10 | >10 |
| 75 | 1.6 | 8.4 | >10 |
| 76 | 3.5 | >10 | >10 |
| 77 | <0.1 | >10 | >10 |
| 78 | 0.13 | >10 | >10 |
| 79 | <0.1 | >10 | >10 |
| 80 | <0.1 | 0.90 | >10 |
| 81 | <0.1 | 5.2 | >10 |
| 82 | <0.1 | >10 | >10 |
| 83 | <0.1 | >10 | >10 |
| 84 | 0.13 | >10 | >10 |
| 85 | 0.94 | >10 | >10 |
| 86 | <0.1 | >10 | >10 |
| 87 | <0.1 | >10 | >10 |
| 88 | 0.11 | >10 | >10 |
| 89 | <0.1 | >10 | >10 |
| 90 | <0.1 | >10 | >10 |
| 91 | 0.35 | >10 | >10 |
| 92 | <0.1 | >10 | >10 |
| 93 | <0.1 | 4.9 | 4.9 |
| 94 | 1.5 | >10 | >10 |
| 95 | 0.14 | >10 | >10 |
| 96 | <0.1 | >10 | >10 |
| 97 | 0.20 | >10 | >10 |
| 98 | 0.17 | >10 | >10 |
| 99 | 0.15 | >10 | >10 |
| 100 | 0.33 | >10 | >10 |
| 101 | 0.15 | >10 | >10 |
| 102 | 0.20 | >10 | >10 |
| 103 | <0.1 | >10 | >10 |
| 104 | <0.1 | >10 | >10 |
| 105 | 0.20 | >10 | >10 |
| 106 | <0.1 | >10 | >10 |
| 107 | 0.27 | >10 | >10 |
| 108 | 0.32 | >10 | >10 |
| 109 | <0.1 | >10 | >10 |
| 110 | 0.38 | >10 | >10 |
| 111 | 0.79 | >10 | >10 |
| 112 | 0.10 | >10 | >10 |
| 113 | 0.12 | 2.9 | >10 |
| 114 | 0.26 | >10 | >10 |
| 115 | 0.29 | >10 | >10 |
| 116 | 0.13 | >10 | >10 |
| 117 | 0.51 | >10 | >10 |
| 118 | 0.16 | >10 | >10 |
| 119 | 0.16 | >10 | >10 |
| 120 | <0.1 | 9.6 | >10 |
| 121 | 0.12 | >10 | >10 |
| 122 | <0.1 | >10 | >10 |
| 123 | <0.1 | >10 | >10 |
| 124 | <0.1 | >10 | >10 |
| 125 | 0.12 | >10 | >10 |
| 126 | 0.16 | >10 | >10 |

TABLE 2-continued

| Example No. | LSD1 IC$_{50}$ value (μM) | MAO-A IC$_{50}$ value (μM) | MAO-B IC$_{50}$ value (μM) |
|---|---|---|---|
| 127 | <0.1 | >10 | >10 |
| 128 | 0.14 | >10 | >10 |
| 129 | <0.1 | >10 | >10 |
| 130 | 0.12 | 7.2 | >10 |
| 131 | 0.13 | >10 | >10 |
| 132 | <0.1 | >10 | >10 |
| 133 | 0.21 | >10 | >10 |
| 134 | 0.17 | >10 | >10 |
| 135 | 0.30 | >10 | >10 |
| 136 | 0.11 | >10 | >10 |
| 137 | <0.1 | >10 | >10 |
| 138 | 0.15 | >10 | >10 |
| 139 | 0.29 | >10 | >10 |
| 140 | 0.80 | >10 | >10 |
| 141 | 0.38 | >10 | >10 |
| 142 | 0.42 | >10 | >10 |
| 143 | <0.1 | 2.1 | >10 |
| 144 | <0.1 | >10 | >10 |
| 145 | 0.28 | >10 | >10 |
| 146 | <0.1 | >10 | >10 |
| 147 | <0.1 | >10 | >10 |
| 148 | 0.19 | >10 | >10 |
| 149 | <0.1 | >10 | >10 |
| 150 | 0.46 | >10 | >10 |
| 151 | <0.1 | >10 | >10 |
| 152 | <0.1 | >10 | >10 |
| 153 | 0.14 | >10 | >10 |
| 154 | <0.1 | >10 | >10 |
| 155 | 0.14 | >10 | >10 |
| 156 | 0.14 | >10 | >10 |
| 157 | 0.17 | >10 | >10 |
| 158 | <0.1 | >10 | >10 |
| 159 | 1.1 | >10 | >10 |
| 160 | 2.3 | >10 | >10 |
| 161 | 0.17 | >10 | >10 |
| 162 | 0.22 | >10 | >10 |
| 163 | 1.7 | >10 | >10 |
| 164 | 0.32 | >10 | >10 |
| 165 | 0.27 | >10 | >10 |
| 166 | 0.18 | >10 | >10 |
| 167 | 0.24 | >10 | >10 |
| 168 | <0.1 | >10 | >10 |
| 169 | 0.21 | >10 | >10 |
| 170 | 9.6 | >10 | >10 |
| 171 | 0.33 | >10 | >10 |
| 172 | 0.23 | >10 | >10 |
| 173 | 0.17 | >10 | >10 |
| 174 | 0.36 | >10 | >10 |
| 175 | 0.23 | >10 | >10 |
| 176 | 0.46 | >10 | >10 |
| 177 | 0.16 | >10 | >10 |
| 178 | 0.19 | >10 | >10 |
| 179 | 0.58 | >10 | >10 |
| 180 | 3.4 | >10 | >10 |
| 181 | 0.32 | >10 | >10 |
| 183 | 0.82 | >10 | >10 |
| 184 | 0.21 | >10 | >10 |
| 185 | 0.20 | >10 | >10 |
| 186 | 0.36 | >10 | >10 |
| 187 | <0.1 | >10 | >10 |
| 188 | 0.21 | >10 | >10 |
| 189 | <0.1 | >10 | >10 |
| 190 | <0.1 | >10 | >10 |
| 191 | 0.11 | >10 | >10 |
| 192 | 0.10 | >10 | >10 |
| 193 | 0.17 | >10 | >10 |
| 194 | 0.21 | >10 | >10 |
| 195 | 0.49 | >10 | >10 |
| 196 | <0.1 | >10 | >10 |
| 197 | <0.1 | >10 | >10 |
| 198 | 0.12 | >10 | >10 |
| 199 | <0.1 | >10 | >10 |
| 200 | <0.1 | >10 | >10 |
| 201 | <0.1 | >10 | >10 |
| 202 | <0.1 | >10 | >10 |
| 203 | 0.10 | >10 | >10 |
| 204 | <0.1 | >10 | >10 |
| 205 | 0.19 | >10 | >10 |
| 206 | <0.1 | >10 | >10 |
| 207 | 0.10 | >10 | >10 |
| 208 | <0.1 | >10 | >10 |
| 209 | 0.19 | >10 | >10 |
| 210 | <0.1 | >10 | >10 |
| 211 | <0.1 | >10 | >10 |
| 212 | <0.1 | >10 | >10 |
| 213 | 0.10 | >10 | >10 |
| 214 | 0.35 | >10 | >10 |
| 215 | 0.26 | >10 | >10 |
| 216 | <0.1 | >10 | >10 |
| 217 | <0.1 | >10 | >10 |
| 218 | <0.1 | >10 | >10 |
| 219 | <0.1 | >10 | >10 |
| 220 | <0.1 | >10 | >10 |
| 221 | 2.3 | >10 | >10 |
| 222 | 1.0 | >10 | >10 |
| 223 | 0.45 | >10 | >10 |
| 224 | 4.6 | >10 | >10 |
| 225 | 0.59 | >10 | >10 |
| 226 | 1.1 | >10 | >10 |
| 227 | 1.4 | >10 | >10 |
| 228 | 0.11 | >10 | >10 |
| 229 | 0.14 | >10 | >10 |
| 230 | 0.79 | >10 | >10 |
| 231 | <0.1 | >10 | >10 |
| 232 | 0.14 | >10 | >10 |
| 234 | 0.20 | >10 | >10 |
| 235 | 0.13 | >10 | >10 |
| 236 | 0.64 | >10 | >10 |
| 237 | <0.1 | >10 | >10 |
| 238 | 0.37 | >10 | >10 |
| 239 | 0.55 | >10 | >10 |
| 240 | <0.1 | >10 | >10 |
| 241 | 0.32 | >10 | >10 |
| 242 | 0.38 | >10 | >10 |
| 243 | 1.3 | >10 | >10 |
| 244 | 3.4 | >10 | >10 |
| 245 | 4.4 | >10 | >10 |
| 247 | 1.3 | >10 | >10 |
| 248 | 2.3 | >10 | >10 |
| 249 | 3.3 | >10 | >10 |
| 250 | 4.5 | >10 | >10 |
| 251 | 9.6 | >10 | >10 |
| 252 | 7.9 | >10 | >10 |
| 253 | 0.16 | >10 | >10 |
| 254 | 0.45 | >10 | >10 |
| 255 | <0.1 | >10 | >10 |
| 256 | 0.75 | >10 | >10 |
| 257 | 0.14 | >10 | >10 |
| 258 | 0.66 | >10 | >10 |
| 259 | <0.1 | >10 | >10 |
| 260 | 4.9 | >10 | >10 |
| 261 | 0.19 | >10 | >10 |
| 262 | 2.4 | >10 | >10 |
| 263 | <0.1 | >10 | >10 |
| 264 | 0.70 | >10 | >10 |
| 265 | 0.16 | >10 | >10 |
| 266 | 0.56 | >10 | >10 |
| 267 | 0.23 | >10 | >10 |
| 268 | 0.36 | >10 | >10 |
| 269 | 0.25 | >10 | >10 |
| 270 | 0.87 | >10 | >10 |
| 271 | 0.29 | >10 | >10 |
| 273 | 3.8 | >10 | >10 |

As shown in Table 2, the compound of the present invention has a superior LSD1 inhibitory activity. In addition, the MAO-A inhibitory activity and MAO-B inhibitory activity of the compound of the present invention are low, and the compound of the present invention has a selective LSD1 inhibitory activity.

Experimental Example 3

Gad1 H3K4 Methylation Induction Activity in Rat Primary Culture Neurons

Experimental Method

Hippocampus and cerebral cortex were isolated from fetal SD rat at embryonic day 19, a cell suspension was prepared using Nerve Cell Dissociation Medium (SUMITOMO BAKELITE CO., LTD., #MB-X9901), and plated on a poly D-lysine-coated 6-well plate (Japan BD, #356413) at a density of 900000 cells/well. Under the conditions of 37° C. and 5% $CO_2$, the cells were cultured in a neurobasal medium (Invitrogen, #211103049) containing B27 supplement (Invitrogen, #17504044, 1:50 dilution), 2 mM L-glutamine (Lonza, #B76053), 100 U/mL penicillin/100 pg/mL streptomycin (Lonza, #17-602E), and 20 pg/mL gentamicin sulfate (Lonza, #17-519Z) for 9-12 days.

Thereafter, the compound was added to final concentrations of 1 or 10 µM, and the cells were further cultured for 3 days. The culture supernatant was aspirated, ice-cold PBS was added, and the cell suspension was collected on ice using CELL SCRAPER (IWAKI). The supernatant was removed by centrifugation at 3000 rpm, 4° C. for 5 min, and the pellet was suspended in cell lysis buffer 1 [60 mM KCl, 30 mM NaCl, 10 mM $MgCl_2$, 0.2 mM EGTA, 30 mM Tris-HCl (pH 7.6), 0.3 M sucrose, 0.5 mM DTT, protease inhibitor (Roche, #4693132)] (750 µL). Furthermore, 0.3% NP40/cell lysis buffer 1 (750 µL) was added, and the cells were lysed by incubating for 5 min on ice. Thereafter, the suspension was centrifuged at 10000 g, 4° C. for 10 min, the supernatant was removed, the pellet was suspended in cell lysis buffer 2 [60 mM KCl, 30 mM NaCl, 10 mM $MgCl_2$, 0.2 mM EGTA, 30 mM Tris-HCl (pH 7.6), 1.2 M sucrose, 0.5 mM DTT, protease inhibitor (Roche, #4693132)] (1 mL), and the suspension was centrifuged at 10000 g, 4° C. for 10 min. The supernatant was removed, the pellet was suspended in MNase buffer [50 mM Tris-HCl (pH 7.6), 4 mM $MgCl_2$, 1 mM $CaCl_2$, 0.3 M sucrose, protease inhibitor (Roche, #4693132)] (180 µL), MNase I (TheLmo #88216) was added to a final concentration of 5 U/mL, and the mixture was incubated at 37° C. for 20 min. 0.5 M EDTA (10 µL) was added, and the mixture was centrifuged at 13000 rpm, 4° C. for 5 min. The supernatant was collected as a chromatin fraction and subjected to chromatin immunoprecipitation.

Chromatin immunoprecipitation was performed using OneDay ChIP kit (Diagenode, #313-80461) and H3K4me2 antibody (Millipore, #07-030). Using the DNA obtained by the chromatin immunoprecipitation as a template, quantitative PCR of the Gad1 gene upstream genomic region was performed, and the measurement value was taken as the Gad1 H3K4me2 level. The quantitative PCR was performed by ABI PRISM 7900HT Sequence Detection System (Applied Biosystems) using forward primer: 5'-TCATCTTTTC-CCTCCTCTCA-3' (SEQ ID NO: 8), reverse primer: 5'-TC-CCATCACTAATCCACAACC-3' (SEQ ID NO: 9), and SYBR Green Realtime PCR Master Mix-Plus-(TOYOBO, #QPK-212). The Gad1 H3K4me2 induction by the compound was expressed by the H3K4me2 level when the compound was added, as compared to the H3K4me2 level of the control (without addition of the compound) as 100%.

Gad1 H3K4me2 induction activity(%)(H3K4me2 induction expressed as percentage of control)= (H3K4me2 level with addition of compound÷H3K4me2 level without addition of compound)×100

The Gad1 H3K4me2 induction activity by each compound as measured by the above-mentioned method is shown in Table 3.

TABLE 3

| Example | Gad1 H3K4me2 induction activity (%) | |
|---|---|---|
| No. | 1 µM | 10 µM |
| 58 | 126 | 116 |
| 59 | 206 | 161 |
| 77 | 165 | 163 |
| 96 | 122 | 151 |
| 97 | 100 | 111 |
| 98 | 114 | 133 |
| 99 | 174 | 181 |
| 101 | 128 | 135 |
| 103 | 139 | 134 |
| 106 | 139 | 132 |
| 108 | 384 | 268 |
| 109 | 117 | 96 |
| 110 | 172 | 208 |
| 155 | 104 | 106 |
| 165 | 272 | 373 |
| 166 | 98 | 147 |
| 168 | 227 | 263 |
| 172 | 145 | 204 |
| 176 | 139 | 116 |
| 177 | 340 | 200 |
| 179 | 175 | 123 |
| 184 | 136 | 122 |
| 186 | 239 | 191 |
| 212 | 201 | 289 |

From the above results, it was clarified that the compound of the present invention has an inductive effect on H3K4 methylation.

Experimental Example 4

Evaluation of Blood Cell Number in Mouse

Experimental method

Male ICR mice (hereinafter mice) were acclimated for at least one week in a rearing facility. The mice were raised in a rearing room with controlled temperature and humidity under a 12:12 hour light-dark cycle, and allowed free ingestion of feed and water.

The compounds were suspended in 0.5% methylcellulose/ 0.02% citric acid/distilled water and orally administered. All compounds were administered to the mice at a dose of 1 mg/kg, 10 mg/kg, 50 mg/kg or 100 mg/kg (body weight). On Day 2 after the administration of the compound, the whole blood was collected.

Using Sysmex XT-1800i (Sysmex Corporation), the white blood cell number, red blood cell number, and platelet number in the collected whole blood per unit volume were measured. The influence of each compound on each blood cell number was determined by comparing the number with the mean of each blood cell number of the mouse without administration of the compound (control group), and the numerical value of each blood cell number of a mouse with the administration of the compound is shown in percentage.

percentage (%) of blood cell number of compound administration group as compared to control group=(mean blood cell number of compound administration group mean blood cell number of compound non-administration group)×100

The percentages (%) of blood cell numbers of compound administration group compared to control group as measured by the above-mentioned method are shown in Table 4.

TABLE 4

| | percentage of blood cell numbers of compound administration group compared to control group (%) | | | | | | | | | | | |
|---|---|---|---|---|---|---|---|---|---|---|---|---|
| | white blood cell number | | | | red blood cell number | | | | platelet number | | | |
| | 10 mg/kg | | 100 mg/kg | | 10 mg/kg | | 100 mg/kg | | 10 mg/kg | | 100 mg/kg | |
| Example No. | mean | standard error | mean | standard error | mean | standard error | mean | standard error | mean | standard error | mean | standard error |
| 58 | 94.2 | 10.7 | 85.8[a] | 5.9[a] | 99.7 | 2.4 | 101.3[a] | 1.8[a] | 99.4 | 6.0 | 102.9[a] | 4.1[a] |
| 59 | 128.1 | 27.5 | 98.8 | 17.5 | 101.1 | 1.5 | 93.3 | 3.0 | 91.9 | 2.9 | 91.2 | 2.5 |
| 77 | 147.9 | 24.5 | 98.2 | 8.8 | 98.2 | 3.0 | 100.9 | 1.9 | 99.6 | 7.2 | 96.6 | 4.3 |
| 79 | 122.4 | 12.3 | 96.3 | 7.3 | 101.1 | 1.6 | 101.6 | 2.1 | 92.4 | 2.0 | 92.8 | 4.8 |
| 82 | 81.2 | 12.5 | 135.5 | 18.0 | 100.5 | 2.2 | 99.9 | 1.0 | 104.6 | 2.3 | 94.6 | 3.7 |
| 87 | 94.6 | 19.9 | 101.1 | 22.4 | 96.8 | 4.7 | 100.7 | 2.3 | 111.7 | 4.7 | 105.2 | 2.3 |
| 96 | 61.5 | 8.6 | 65.5 | 6.0 | 97.9 | 2.5 | 100.7 | 2.1 | 102.1 | 3.3 | 102.4 | 4.1 |
| 96 | 116.6[b] | 11.1[b] | 122.4[c] | 15.1[c] | 107.4[b] | 1.9[b] | 102.6[c] | 1.7[c] | 100.9[b] | 6.5[b] | 101.0[c] | 1.9[c] |
| 97 | 114.4[b] | 5.2[b] | 100.7[c] | 4.7[c] | 102.7[b] | 1.9[b] | 105.0[c] | 2.4[c] | 99.4[b] | 3.9[b] | 105.2[c] | 3.5[c] |
| 98 | 96.5[b] | 10.4[b] | 106.5[c] | 11.2[c] | 103.6[b] | 2.0[b] | 105.6[c] | 1.1[c] | 105.4[b] | 5.6[b] | 102.0[c] | 3.9[c] |
| 99 | 66.0 | 11.2 | 79.4 | 18.0 | 102.8 | 3.5 | 101.5 | 2.6 | 116.9 | 5.1 | 111.1 | 5.8 |
| 100 | 99.4 | 13.5 | 104.8 | 35.6 | 92.9 | 1.9 | 98.8 | 2.0 | 98.1 | 4.7 | 91.0 | 4.3 |
| 101 | 121.8 | 15.5 | 100.4 | 17.7 | 99.2 | 1.7 | 98.5 | 1.3 | 107.9 | 4.1 | 108.9 | 5.0 |
| 102 | 107.0 | 11.2 | 116.8 | 19.3 | 99.5 | 1.4 | 104.9 | 1.2 | 97.7 | 1.5 | 94.7 | 4.3 |
| 103 | 100.9 | 9.9 | 105.9 | 13.2 | 95.0 | 2.1 | 98.5 | 2.5 | 88.7 | 3.7 | 96.8 | 5.5 |
| 106 | 114.8 | 10.6 | 89.0 | 9.4 | 99.4 | 2.2 | 101.9 | 2.1 | 94.6 | 3.9 | 97.2 | 4.3 |
| 107 | 86.6 | 7.2 | 132.7 | 27.5 | 98.4 | 2.0 | 102.2 | 1.2 | 95.4 | 3.8 | 91.1 | 4.3 |
| 108 | 127.7 | 8.5 | 129.4 | 9.7 | 99.0 | 0.9 | 98.7 | 1.7 | 101.9 | 6.8 | 94.2 | 3.4 |
| 109 | 88.3 | 5.9 | 107.4 | 15.4 | 96.3 | 1.4 | 98.2 | 1.7 | 94.3 | 3.6 | 97.8 | 3.4 |
| 110 | 114.9 | 8.3 | 112.0 | 5.4 | 98.7 | 1.6 | 100.4 | 1.4 | 93.4 | 5.7 | 96.4 | 3.8 |
| 111 | 136.9 | 18.3 | 97.9 | 18.0 | 98.7 | 1.0 | 99.1 | 1.9 | 101.2 | 5.7 | 98.4 | 3.9 |
| 112 | 112.0 | 11.2 | 136.1 | 11.9 | 99.4 | 2.5 | 102.0 | 1.5 | 92.8 | 6.6 | 86.3 | 5.7 |
| 165 | 104.4 | 15.5 | 87.0 | 15.6 | 100.9 | 2.8 | 103.2 | 3.6 | 99.3 | 5.3 | 85.6 | 5.5 |
| 167 | 86.4 | 9.3 | 68.2 | 6.1 | 102.5 | 1.4 | 102.4 | 2.0 | 105.3 | 4.0 | 103.2 | 4.5 |
| 168 | 97.6 | 8.5 | 93.6 | 8.3 | 106.5 | 2.5 | 101.1 | 3.2 | 106.8 | 9.3 | 99.0 | 4.3 |
| 169 | 99.1 | 12.6 | 109.2 | 18.3 | 105.1 | 1.1 | 103.7 | 2.2 | 102.2 | 4.4 | 100.7 | 4.3 |
| 171 | 133.3 | 21.5 | 133.9 | 20.1 | 98.5 | 1.1 | 98.9 | 1.9 | 114.6 | 6.4 | 104.8 | 4.1 |
| 172 | 101.3 | 7.8 | 130.0 | 15.0 | 99.0 | 0.8 | 97.7 | 1.1 | 97.0 | 3.5 | 99.6 | 5.2 |
| 174 | 97.4 | 12.3 | 100.6 | 11.9 | 95.4 | 2.2 | 100.2 | 1.8 | 97.9 | 4.2 | 93.7 | 5.2 |
| 176 | 106.6 | 15.1 | 107.8 | 9.4 | 97.5 | 0.8 | 100.8 | 1.0 | 96.7 | 4.4 | 90.2 | 2.6 |
| 177 | 136.9 | 29.4 | 97.1 | 2.3 | 94.5 | 2.0 | 99.0 | 1.7 | 101.3 | 3.2 | 97.4 | 5.3 |
| 178 | 93.2 | 9.4 | 84.5 | 7.8 | 98.5 | 1.7 | 98.9 | 0.7 | 90.2 | 2.6 | 85.2 | 3.1 |
| 179 | 94.2 | 6.9 | 121.2 | 16.2 | 102.5 | 1.5 | 100.4 | 1.7 | 94.8 | 1.9 | 92.5 | 4.4 |
| 183 | 88.1 | 8.2 | 114.9 | 6.9 | 98.5 | 2.1 | 97.5 | 1.9 | 96.4 | 2.9 | 86.6 | 1.3 |
| 185 | 88.0 | 8.8 | 129.9 | 31.9 | 102.0 | 2.0 | 100.7 | 1.9 | 90.4 | 3.7 | 84.7 | 2.1 |
| 186 | 129.3 | 21.4 | 111.2 | 15.7 | 101.5 | 2.0 | 99.2 | 2.6 | 93.1 | 3.5 | 88.2 | 4.8 |
| 205 | 81.6 | 19.7 | 80.9 | 11.9 | 97.8 | 2.2 | 104.0 | 1.8 | 114.7 | 3.8 | 110.8 | 5.9 |
| 206 | 92.7 | 20.6 | 130.7 | 24.2 | 102.1 | 0.8 | 102.3 | 2.1 | 85.5 | 3.2 | 84.3 | 1.7 |
| 215 | 113.3 | 7.7 | 124.7 | 17.8 | 98.4 | 1.6 | 99.8 | 2.0 | 100.7 | 4.6 | 91.2 | 2.2 |
| 223 | 114.5 | 8.1 | 121.7 | 12.4 | 101.2 | 3.0 | 100.4 | 2.7 | 94.8 | 2.4 | 98.9 | 4.9 |
| 231 | 75.7 | 6.4 | 77.1 | 5.0 | 99.7 | 2.6 | 95.0 | 2.9 | 93.7 | 1.9 | 90.4 | 4.8 |
| 232 | 97.3 | 23.4 | 92.4 | 20.2 | 100.4 | 2.3 | 99.3 | 3.2 | 102.4 | 4.7 | 93.5 | 1.6 |
| 234 | 76.7 | 5.5 | 94.8 | 12.7 | 97.7 | 1.6 | 101.2 | 2.1 | 98.8 | 4.8 | 88.9 | 3.2 |
| 235 | 75.7 | 19.9 | 93.0 | 11.9 | 101.1 | 2.0 | 97.8 | 1.4 | 99.1 | 5.9 | 96.6 | 3.6 |
| 237 | 83.9 | 4.4 | 86.7 | 5.8 | 98.8 | 1.2 | 96.5 | 0.4 | 90.3 | 3.7 | 91.9 | 2.2 |
| 240 | 82.3 | 7.0 | 109.4 | 18.3 | 95.5 | 1.7 | 98.7 | 2.0 | 90.7 | 7.5 | 94.7 | 2.1 |
| 241 | 94.6 | 4.3 | 101.9 | 13.3 | 96.9 | 1.9 | 99.0 | 2.1 | 102.6 | 5.1 | 89.2 | 3.2 |

[a] 50 mg/kg,
[b] 1 mg/kg,
[c] 10 mg/kg

From the above results, it was clarified that the compound of the present invention reduces an influence on the white blood cell number, red blood cell number and platelet number.

Experimental Example 5

Evaluation of Hippocampal Distribution in Mouse

Experimental method

Male ICR mice (hereinafter mice) were acclimated for at least one week in a rearing facility. The mice were raised in a rearing room with controlled temperature and humidity under a 12:12 hour light-dark cycle, and allowed free ingestion of feed and water.

The compounds were suspended in 0.5% methylcellulose/0.02% citric acid/distilled water and orally administered. All compounds were administered to the mice at a dose of 10 mg/kg (body weight).

Blood samples were collected at 0.5 hr, or 1 hr, or 1.5 hr from compound administration, and the hippocampus was isolated simultaneously. The plasma concentration and hippocampus concentration of each test compound were measured by the LC/MS/MS method, the ratio (hippocampus/plasma concentration ratio) was calculated, and distribution into hippocampus was evaluated. The results are shown in Table 5.

TABLE 5

| Example No. | time after administration (hr) | concentration (ng/mL or ng/g) | | | | hippocampus/plasma concentration ratio | |
|---|---|---|---|---|---|---|---|
| | | plasma | | hippocampus | | | |
| | | mean | standard deviation | mean | standard deviation | mean | standard deviation |
| 79 | 0.5 | 759 | 82 | 569 | 70 | 0.75 | 0.07 |
| 82 | 0.5 | 5607 | 478 | 58 | 10 | 0.01 | 0.00 |
| 87 | 1 | 251 | 63 | 43 | 13 | 0.17 | 0.03 |
| 96 | 1 | 1064 | 175 | 602 | 118 | 0.56 | 0.02 |
| 99 | 1 | 143 | 51 | 283 | 109 | 1.96 | 0.14 |
| 100 | 0.5 | 889 | 94 | 207 | 20 | 0.24 | 0.05 |
| 101 | 0.5 | 907 | 80 | 181 | 15 | 0.20 | 0.03 |
| 102 | 1 | 268 | 90 | 482 | 109 | 1.84 | 0.27 |
| 103 | 1 | 375 | 65 | 1031 | 242 | 2.73 | 0.22 |
| 106 | 1 | 33 | 7 | 107 | 2 | 3.28 | 0.63 |
| 107 | 0.5 | 2564 | 114 | 242 | 46 | 0.09 | 0.01 |
| 108 | 0.5 | 684 | 153 | 983 | 333 | 1.41 | 0.24 |
| 109 | 0.5 | 1248 | 98 | 1610 | 59 | 1.29 | 0.06 |
| 110 | 0.5 | 4490 | 776 | 3297 | 1158 | 0.72 | 0.15 |
| 111 | 0.5 | 823 | 41 | 1301 | 301 | 1.59 | 0.42 |
| 112 | 0.5 | 1711 | 268 | 614 | 25 | 0.36 | 0.06 |
| 165 | 1 | 1842 | 529 | 376 | 95 | 0.21 | 0.01 |
| 167 | 1 | 1228 | 395 | 915 | 321 | 0.74 | 0.12 |
| 168 | 0.5 | 451 | 128 | 439 | 134 | 0.97 | 0.08 |
| 169 | 1 | 707 | 233 | 396 | 140 | 0.56 | 0.04 |
| 171 | 0.5 | 1312 | 91 | 266 | 23 | 0.20 | 0.00 |
| 172 | 1 | 556 | 143 | 419 | 158 | 0.74 | 0.11 |
| 174 | 1 | 1246 | 269 | 1284 | 357 | 1.02 | 0.07 |
| 176 | 1 | 515 | 196 | 642 | 322 | 1.20 | 0.20 |
| 177 | 1 | 630 | 177 | 324 | 99 | 0.51 | 0.04 |
| 178 | 0.5 | 1049 | 35 | 546 | 139 | 0.52 | 0.12 |
| 179 | 0.5 | 421 | 78 | 321 | 128 | 0.74 | 0.17 |
| 183 | 1.5 | 651 | 297 | 884 | 411 | 1.35 | 0.06 |
| 185 | 0.5 | 1020 | 155 | 581 | 122 | 0.58 | 0.17 |
| 186 | 0.5 | 1321 | 157 | 3121 | 67 | 2.38 | 0.23 |
| 205 | 1 | 920 | 116 | 437 | 84 | 0.47 | 0.04 |
| 206 | 1 | 804 | 50 | 106 | 9 | 0.13 | 0.02 |
| 215 | 0.5 | 1574 | 18 | 481 | 111 | 0.31 | 0.07 |
| 223 | 0.5 | 1401 | 235 | 2391 | 622 | 1.69 | 0.20 |
| 231 | 1 | 117 | 9 | 527 | 127 | 4.50 | 0.87 |
| 232 | 1 | 154 | 30 | 572 | 168 | 3.66 | 0.38 |
| 234 | 1 | 175 | 48 | 276 | 100 | 1.58 | 0.35 |
| 235 | 0.5 | 204 | 29 | 216 | 77 | 1.04 | 0.23 |
| 237 | 0.5 | 523 | 83 | 237 | 81 | 0.44 | 0.10 |
| 240 | 0.5 | 247 | 36 | 329 | 111 | 1.31 | 0.31 |
| 241 | 0.5 | 167 | 48 | 878 | 222 | 5.31 | 0.39 |

As shown in Table 5, the compounds of the present invention were all confirmed to have distributed into the hippocampus.

ABBREVIATION LIST

H3K4me2: dimethyiated histone H3 at lysine 4

PBS: phosphate buffered saline

EGTA: ethylene glycol tetraacetic acid

DTT: dithiothreitol

NP40: Nonidet P-40

MNase: Micrococcal Nuclease

EDTA: ethylenediaminetetraacetic acid quantitative PCR (qPCR): quantitative polymerase chain reaction Formulation Example 1

A medicament containing the compound of the present invention as an active ingredient can be produced, for example, according to the following formulation.

1. Capsule

| (1) compound obtained in Example 1 | 10 mg |
|---|---|
| (2) lactose | 90 mg |
| (3) crystalline cellulose | 70 mg |
| (4) magnesium stearate | 10 mg |
| 1 capsule | 180 mg |

The total amount of the above-mentioned (1), (2) and (3) and 5 mg of (4) are blended, and the mixture is granulated. Thereto is added the remaining 5 mg of (4), and the whole is sealed in a gelatin capsule.

2. Tablet

| (1) compound obtained in Example 1 | 10 mg |
|---|---|
| (2) lactose | 35 mg |
| (3) cornstarch | 150 mg |
| (4) crystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended, and the mixture is granulated. Thereto are added the remaining 10 mg of (4) and 2.5 mg of (5), and the mixture is compression-molded to give a tablet.

INDUSTRIAL APPLICABILITY

The compound of the present invention has a superior LSD1 inhibitory action, and is useful as a medicament such as a prophylactic or therapeutic agent for cancer, schizophrenia, Alzheimer's disease, Parkinson's disease or Huntington's disease, and the like.

This application is based on patent application Nos. 2012-227243 and 2013-22534 filed in Japan, the entire contents of which are incorporated by reference herein.

The invention claimed is:

1. A compound represented by the formula

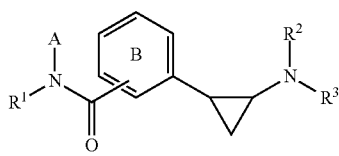

(I)

wherein A is
(1) a cyclobutyl group, a cyclopentyl group, or a cyclohexyl group, each optionally having 1 or 2 fluorine atoms,
(2) a phenyl group optionally having one pyrimidinyl group, or
(3) a piperidinyl group, a pyrazolyl group, an isoxazolyl group, a thiazolyl group, a thiadiazolyl group, or a tetrahydropyranyl group, each optionally having 1 or 2 substituents selected from $C_{1-6}$ alkyl groups optionally having 1 to 3 substituents selected from a fluorine atom and a cyclopropyl group;

B is a benzene ring optionally further having one substituent selected from
(1) a halogen atom,
(2) a $C_{1-6}$ alkyl group, and
(3) a $C_{1-6}$ alkoxy group;

$R^1$ is a hydrogen atom;

$R^2$ is a hydrogen atom; and $R^3$ is
(1) a cyclohexyl group, a cyclopentyl group, or a cyclobutyl group, each optionally having 1 or 2 fluorine atoms,
(2) a cyclopropylmethyl group,
(3) a $C_{1-6}$ alkyl group having one tetrahydropyranyl group, or
(4) a piperidinyl group or a tetrahydropyranyl group, each optionally having one substituent selected from
   (a) a $C_{1-6}$ alkyl group optionally having 1 to 3 fluorine atoms, and
   (b) a cyclopropyl group, or a salt thereof.

2. The compound according to claim 1, wherein A is
(1) a cyclopentyl group or a cyclohexyl group, each optionally having 1 or 2 fluorine atoms, or
(2) a piperidinyl group, an isoxazolyl group, a thiadiazolyl group, or a tetrahydropyranyl group, each optionally having one $C_{1-6}$ alkyl group optionally having 1 to 3 fluorine atoms;

B is a benzene ring;

$R^1$ is a hydrogen atom;

$R^2$ is a hydrogen atom; and $R^3$ is
(1) a cyclohexyl group or a cyclobutyl group, each optionally having 1 or 2 fluorine atoms,
(2) a cyclopropylmethyl group, or
(3) a piperidinyl group or a tetrahydropyranyl group, each optionally having one cyclopropyl group, or a salt thereof.

3. 3-(trans-2-((Cyclopropylmethyl)amino)cyclopropyl)-N-(5-methyl-1,2-oxazol-3-yl)benzamide or a salt thereof.

4. 3-(trans-2((1-Cyclopropylpiperidin-4-yl)amino)cyclopropyl)-N-(5-methyl-1,3,4-thiadiazol-2-yl)benzamide or a salt thereof.

5. 3-(trans-2-(Cyclobutylamino)cyclopropyl)-N-(tetrahydro-2H-pyran-4-yl)benzamide or a salt thereof.

6. A pharmaceutical composition comprising an effective amount of the compound according to claim 1 or a salt thereof, and a pharmaceutically acceptable carrier.

7. The pharmaceutical composition according to claim 6, wherein the compound according to claim 1 or a salt thereof is an LSD1 inhibitor.

8. The pharmaceutical composition according to claim 6, wherein the compound according to claim 1 or a salt thereof is a therapeutic agent for at least one selected from the group consisting of schizophrenia, Alzheimer's disease, Parkinson's disease and Huntington's disease.

9. A method of inhibiting LSD1 in a mammal, comprising administering an effective amount of the compound according to claim 1 or a salt thereof to the mammal.

10. A method for the treatment of schizophrenia, Alzheimer's disease, Parkinson's disease or Huntington's disease in a mammal, comprising administering an effective amount of the compound according to claim 1 or a salt thereof to the mammal.

* * * * *

```
                       SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
agaatcattt aaatggtgat catgtaaccc atcct                                35

<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
cgccctgaaa gtacaggttc tcatccgatt ttggaggatg gtcg                      44

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ataataggat ccgccctgaa agtacaggtt ctc                                  33

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
tattatgcta gcgccaccat gttatctggg aagaaggcgg cagc                      44

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
tattatgcgg ccgctcacat gcttggggac tgctgtgc                             38

<210> SEQ ID NO 6
<211> LENGTH: 34
<212> TYPE: DNA
<213> ORGANISM: Artificial Sequence
<220> FEATURE:
<223> OTHER INFORMATION: primer
```

```
<400> SEQUENCE: 6
ataataagat cttcgggtgt ggagggcgca gctt                              34

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
ataatagcgg ccgccatggc ccccaaaaac tggtctgca                         39

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgatcttttc cctgctgtca                                              20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tcccatgagt aatccagaac g                                            21
```